(12) United States Patent
Zipnick

(10) Patent No.: US 9,005,296 B2
(45) Date of Patent: Apr. 14, 2015

(54) TAPERED ARCUATE INTERVERTEBRAL IMPLANT

(75) Inventor: Richard I. Zipnick, Park City, UT (US)

(73) Assignee: Arthrodisc, L.L.C., Park City, UT (US)

( * ) Notice: Subject to any disclaimer, the term of this patent is extended or adjusted under 35 U.S.C. 154(b) by 111 days.

(21) Appl. No.: 13/605,756

(22) Filed: Sep. 6, 2012

(65) Prior Publication Data

US 2012/0330417 A1    Dec. 27, 2012

Related U.S. Application Data

(63) Continuation-in-part of application No. 13/370,925, filed on Feb. 10, 2012, and a continuation-in-part of
(Continued)

(51) Int. Cl.
*A61F 2/44*      (2006.01)
*A61B 17/32*      (2006.01)
(Continued)

(52) U.S. Cl.
CPC ....... *A61B 17/320016* (2013.01); *A61B 1/3135* (2013.01); *A61B 17/32002* (2013.01); *A61B 17/320068* (2013.01); *A61B 17/3421* (2013.01); *A61B 17/3468* (2013.01); *A61B 17/3476* (2013.01); *A61B 17/7059* (2013.01); *A61B 17/7065* (2013.01); *A61B 17/7067* (2013.01); *A61B 2017/00261* (2013.01); *A61B 2017/320044* (2013.01); *A61B 2017/32113* (2013.01); *A61B 2019/4805* (2013.01); *A61F 2/30771* (2013.01); *A61F 2/3094* (2013.01); *A61F 2/442* (2013.01); *A61F 2/4425* (2013.01); *A61F 2/4455* (2013.01); *A61F 2/446* (2013.01); *A61F 2/447* (2013.01); *A61F 2/4611* (2013.01); *A61F 2002/30112* (2013.01); *A61F 2002/30131* (2013.01); *A61F 2002/30136* (2013.01); *A61F 2002/30153* (2013.01); *A61F 2002/30172* (2013.01); *A61F 2002/30205* (2013.01); *A61F 2002/30224* (2013.01); *A61F 2002/30233* (2013.01); *A61F 2002/30253* (2013.01); *A61F 2002/30271* (2013.01); *A61F 2002/30285* (2013.01); *A61F 2002/30286* (2013.01); *A61F 2002/30293* (2013.01);
(Continued)

(58) Field of Classification Search
CPC .......... A61F 2/44; A61F 2/442; A61F 2/4425
USPC ................................ 623/17.11, 17.14, 17.16
See application file for complete search history.

(56) References Cited

U.S. PATENT DOCUMENTS 4,714,469 A * 12/1987 Kenna .......................... 606/86 A
5,645,599 A * 7/1997 Samani ...................... 623/17.16
(Continued)

*Primary Examiner* — Andrew Yang
(74) *Attorney, Agent, or Firm* — Maschoff Brennan, PLLC

(57) ABSTRACT

An intervertebral implant can include: a tapered arcuate shape. The implant can include a solid non-elastic portion. The implant can include an implant-suitable material. The implant can be at least partially porous, and optionally, the pores can be filed with a biodegradable material that can include one or more active agents, such as growth factors. The implant can be formed from a hybrid of at least two implant-suitable materials. The implant can include a body having a rounded surface and a substantially flat surface. Optionally, the substantially flat surface can be opposite of the rounded surface. The rounded surface and substantially flat surface can extend from a base to a tip of the tapered arcuate shape. The base may be substantially flat, where the tip can be rounded. The tapered arcuate shape can extend from a substantially flat base and curve to a tip of the arc.

31 Claims, 118 Drawing Sheets

Related U.S. Application Data application No. 13/478,870, filed on May 23, 2012, which is a continuation-in-part of application No. 13/199,324, filed on Aug. 26, 2011, which is a continuation-in-part of application No. 13/065,291, filed on Mar. 18, 2011, which is a continuation-in-part of application No. 11/804,838, filed on May 21, 2007, now Pat. No. 7,909,872, which is a continuation-in-part of application No. 11/638,652, filed on Dec. 12, 2006, now Pat. No. 7,883,542, which is a continuation-in-part of application No. 11/472,060, filed on Jun. 21, 2006, now Pat. No. 7,879,099, which is a continuation-in-part of application No. 11/404,938, filed on Apr. 14, 2006, now Pat. No. 7,727,279, which is a continuation-in-part of application No. 11/351,665, filed on Feb. 10, 2006, now abandoned, which is a continuation-in-part of application No. 11/299,395, filed on Dec. 12, 2005, now abandoned, which is a continuation-in-part of application No. 11/241,143, filed on Sep. 30, 2005, now abandoned.

(51) Int. Cl.

| | | |
|---|---|---|
| *A61B 17/34* | (2006.01) | |
| *A61F 2/46* | (2006.01) | |
| *A61B 17/16* | (2006.01) | |
| *A61B 1/313* | (2006.01) | |
| *A61B 17/70* | (2006.01) | |
| *A61B 17/00* | (2006.01) | |
| *A61B 17/3211* | (2006.01) | |
| *A61B 19/00* | (2006.01) | |
| *A61F 2/30* | (2006.01) | |
| *A61B 17/88* | (2006.01) | |

(52) U.S. Cl.
CPC ............ *A61F 2002/30294* (2013.01); *A61F 2002/30331* (2013.01); *A61F 2002/30393* (2013.01); *A61F 2002/30398* (2013.01); *A61F 2002/30401* (2013.01); *A61F 2002/30428* (2013.01); *A61F 2002/30471* (2013.01); *A61F 2002/30507* (2013.01); *A61F 2002/30517* (2013.01); *A61F 2002/30528* (2013.01); *A61F 2002/30545* (2013.01); *A61F 2002/3055* (2013.01); *A61F 2002/30553* (2013.01); *A61F 2002/30566* (2013.01); *A61F 2002/30571* (2013.01); *A61F 2002/30573* (2013.01); *A61F 2002/30579* (2013.01); *A61F 2002/30594* (2013.01); *A61F 2002/30601* (2013.01); *A61F 2002/30604* (2013.01); *A61F 2002/30624* (2013.01); *A61F 2002/30634* (2013.01); *A61F 2002/30649* (2013.01); *A61F 2002/30662* (2013.01); *A61F 2002/30772* (2013.01); *A61F 2002/30818* (2013.01); *A61F 2002/30822* (2013.01); *A61F 2002/30823* (2013.01); *A61F 2002/30831* (2013.01); *A61F 2002/30841* (2013.01); *A61F 2002/30881* (2013.01); *A61F 2002/30883* (2013.01); *A61F 2002/30884* (2013.01); *A61F 2002/4415* (2013.01); *A61F 2002/443* (2013.01); *A61F 2002/444* (2013.01); *A61F 2002/4475* (2013.01); *A61F 2002/4627* (2013.01); *A61F 2002/4629* (2013.01); *A61F 2002/4677* (2013.01); *A61F 2220/0025* (2013.01); *A61F 2220/0033* (2013.01); *A61F 2220/0091* (2013.01); *A61F 2230/0004* (2013.01); *A61F 2230/0013* (2013.01); *A61F 2230/0019* (2013.01); *A61F 2230/0052* (2013.01); *A61F 2230/0063* (2013.01); *A61F 2230/0067* (2013.01); *A61F 2230/0069* (2013.01); *A61F 2230/0071* (2013.01); *A61F 2230/0076* (2013.01); *A61F 2230/0082* (2013.01); *A61F 2230/0091* (2013.01); *A61F 2250/0008* (2013.01); *A61F 2250/001* (2013.01); *A61F 2310/00011* (2013.01); *A61F 2310/00179* (2013.01); *A61B 17/1671* (2013.01); *A61B 17/7064* (2013.01); *A61B 17/888* (2013.01)

(56) References Cited

U.S. PATENT DOCUMENTS

| | | | | |
|---|---|---|---|---|
| 2003/0176921 | A1* | 9/2003 | Lawson .................... | 623/17.11 |
| 2004/0230309 | A1* | 11/2004 | DiMauro et al. ........... | 623/17.12 |

* cited by examiner

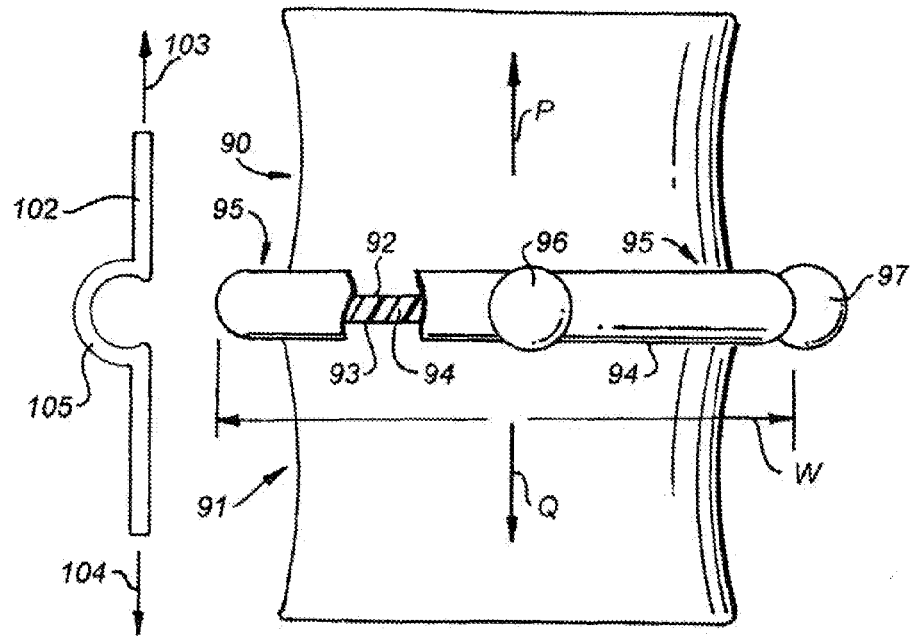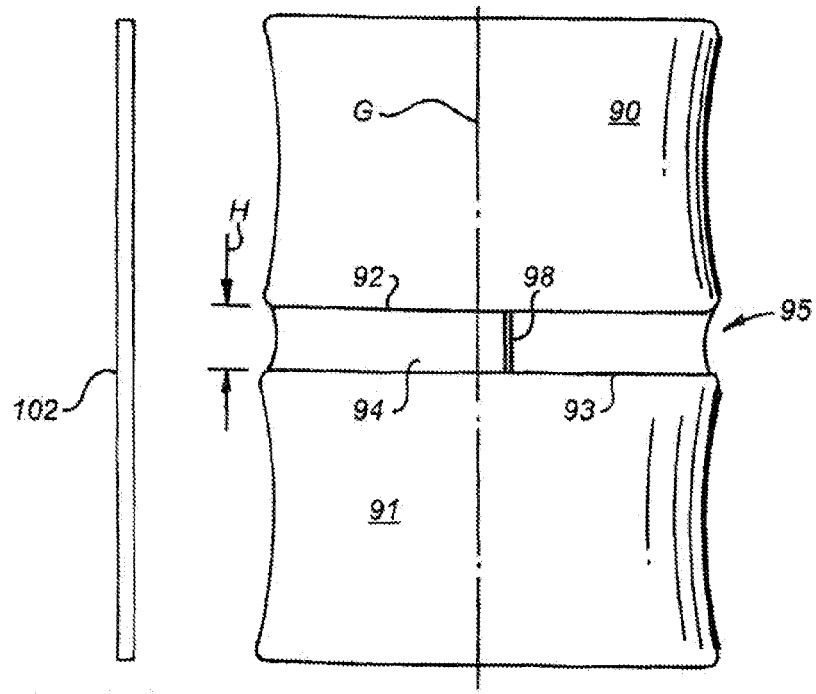

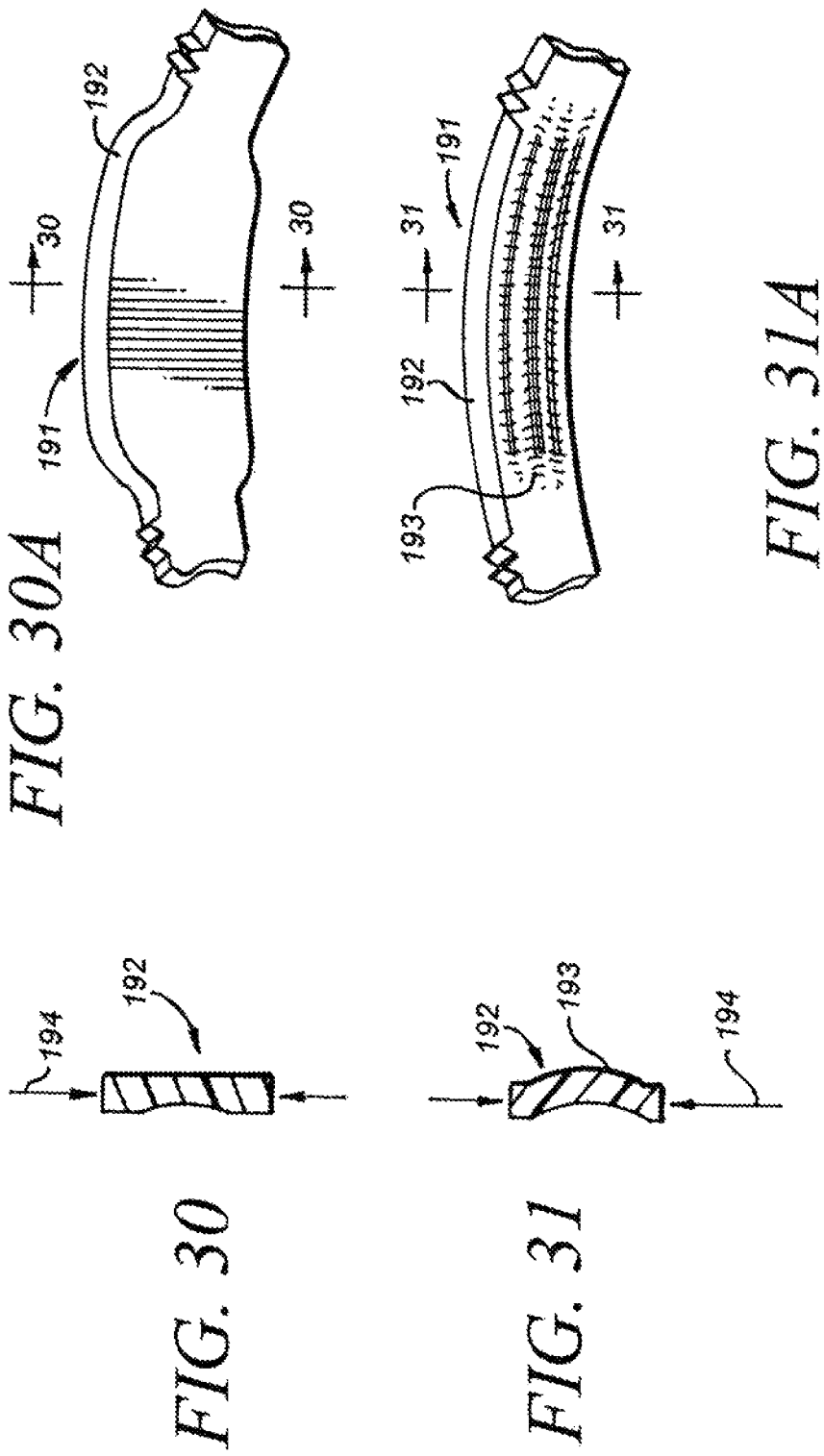

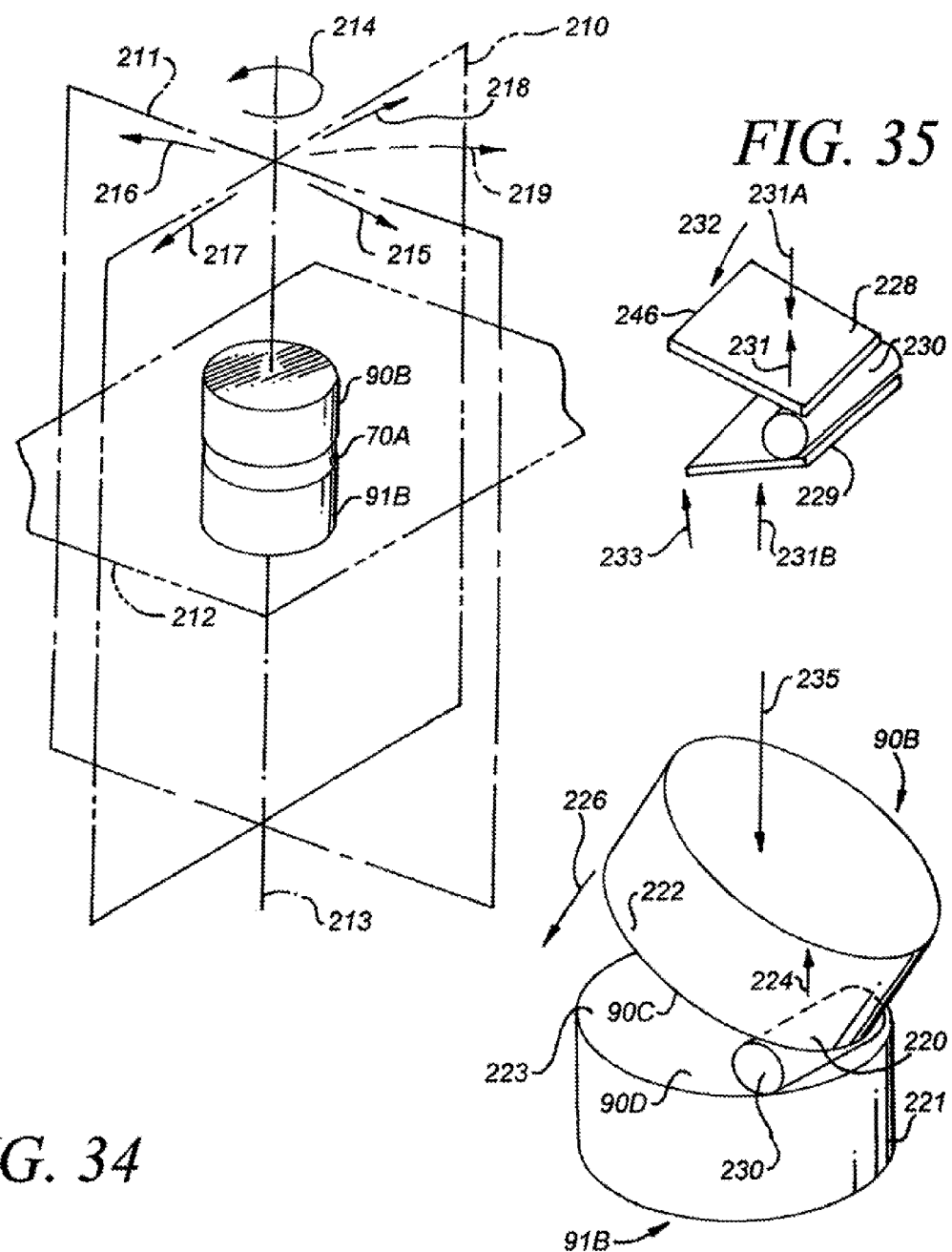

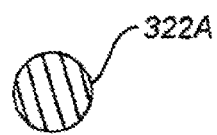
FIG. 46A  FIG. 47A

FIG. 48A  FIG. 49A
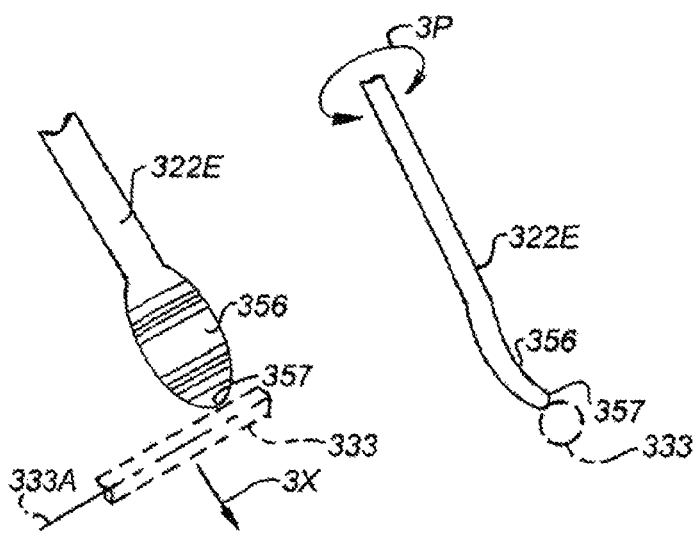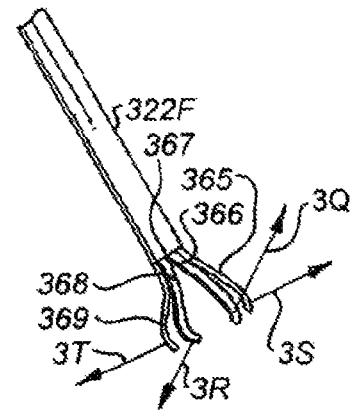
FIG. 47B  FIG. 47C  FIG. 47D

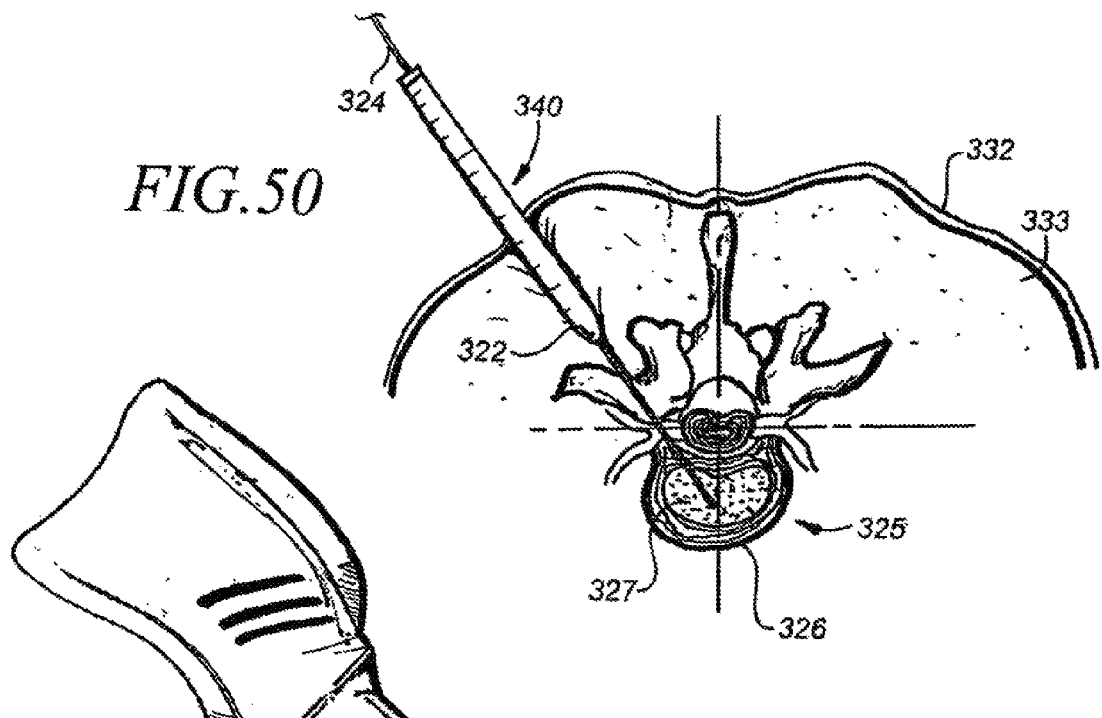
FIG. 50
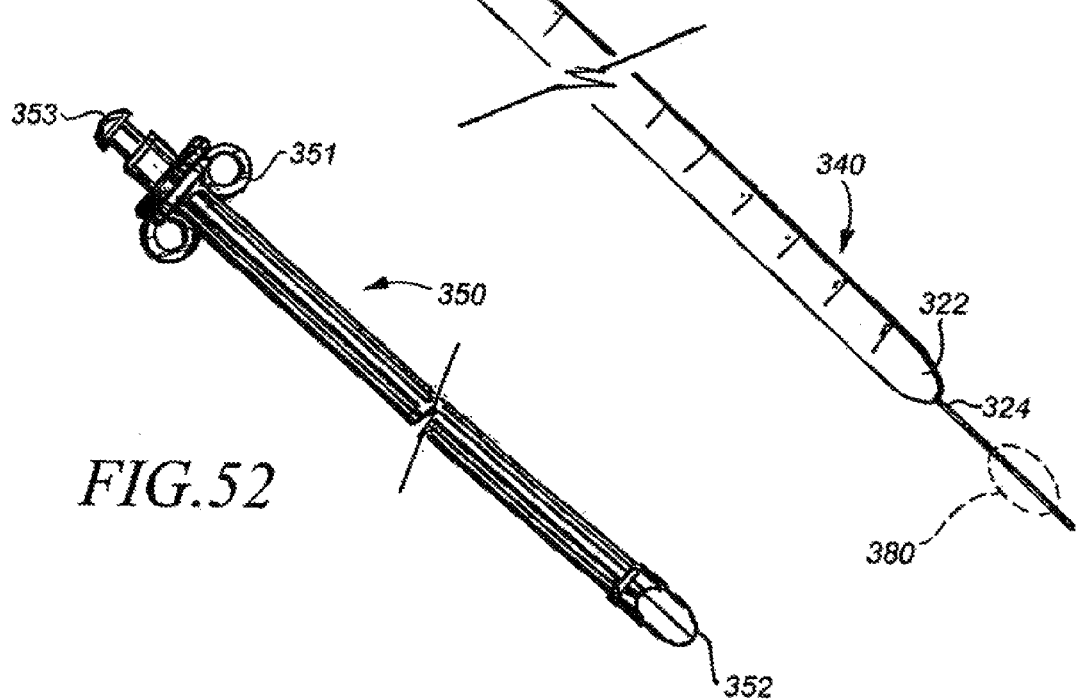
FIG. 51
FIG. 52

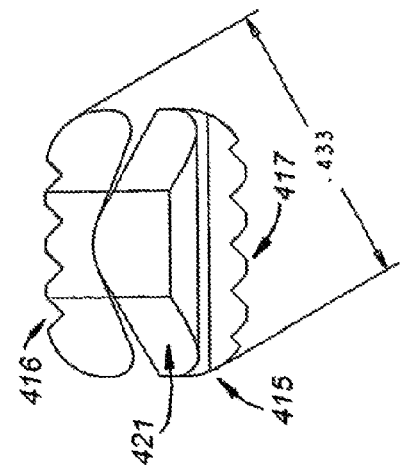
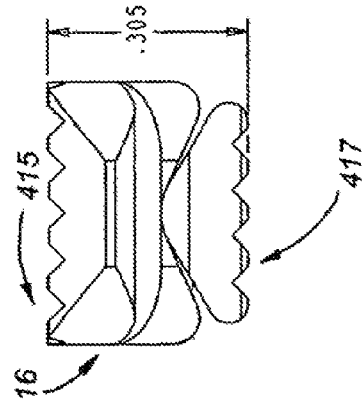
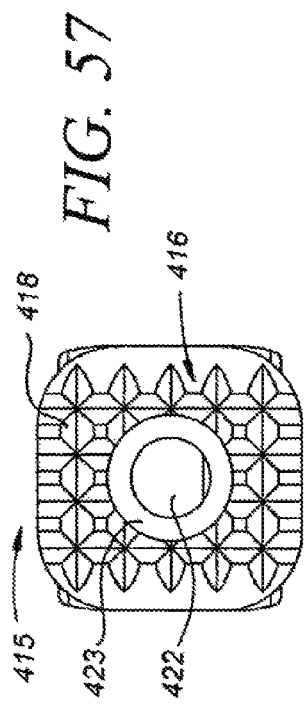
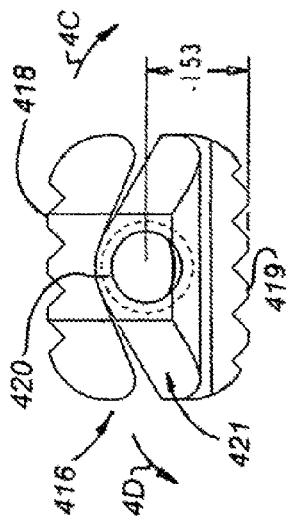

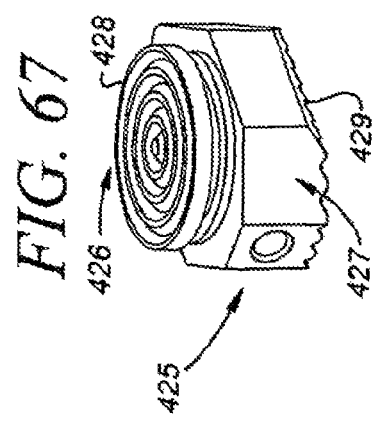
FIG. 62
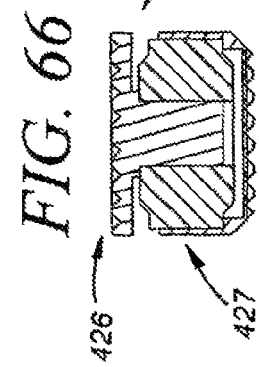
FIG. 66
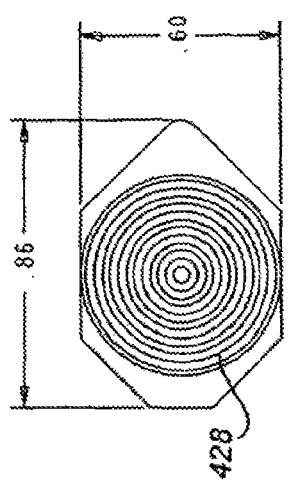
FIG. 63
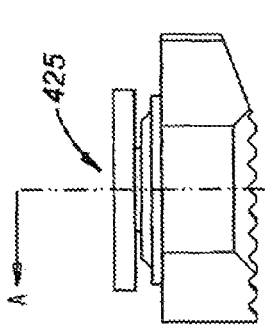
FIG. 65
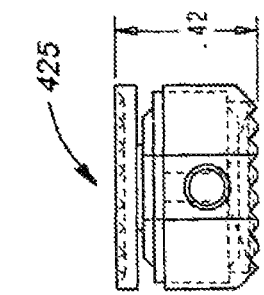
FIG. 64
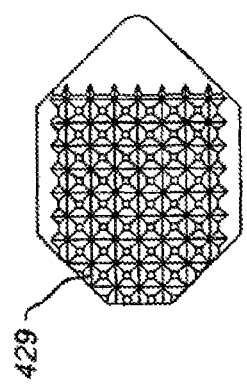
FIG. 67
FIG. 68

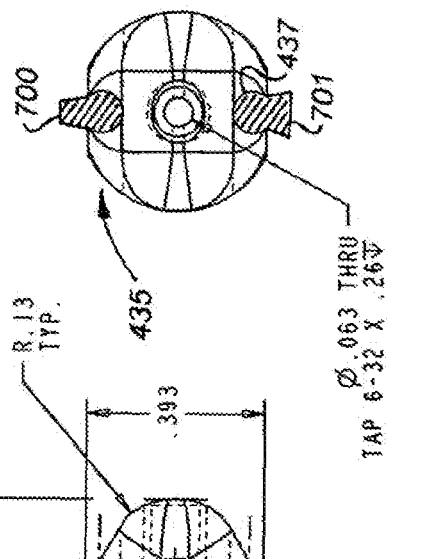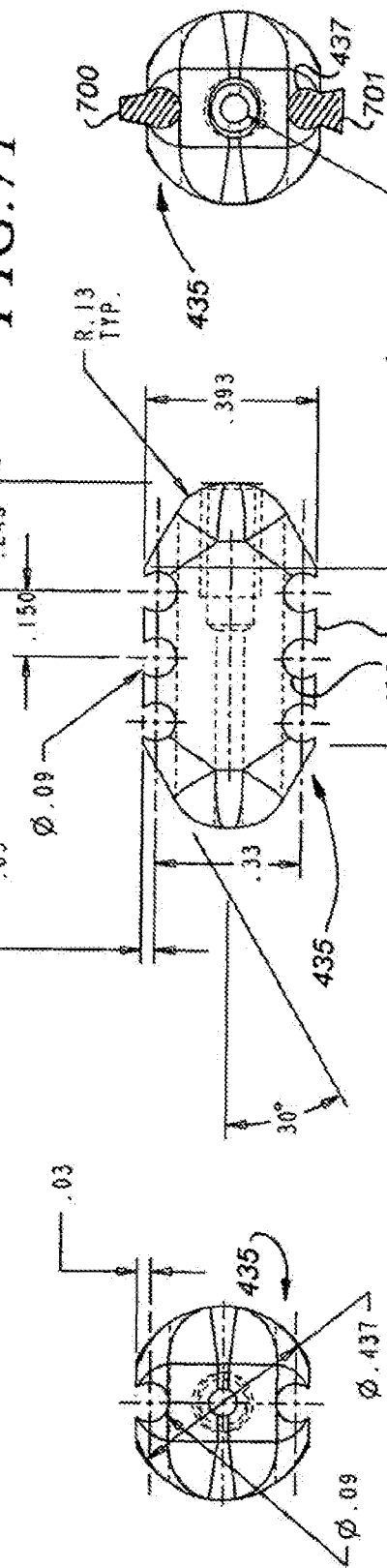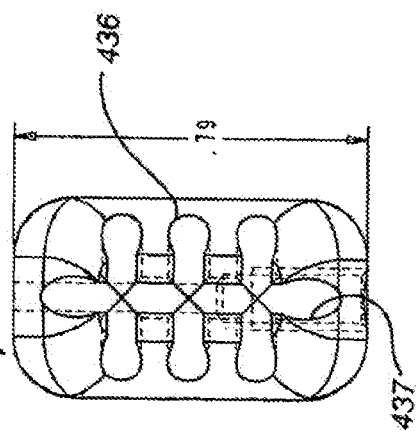

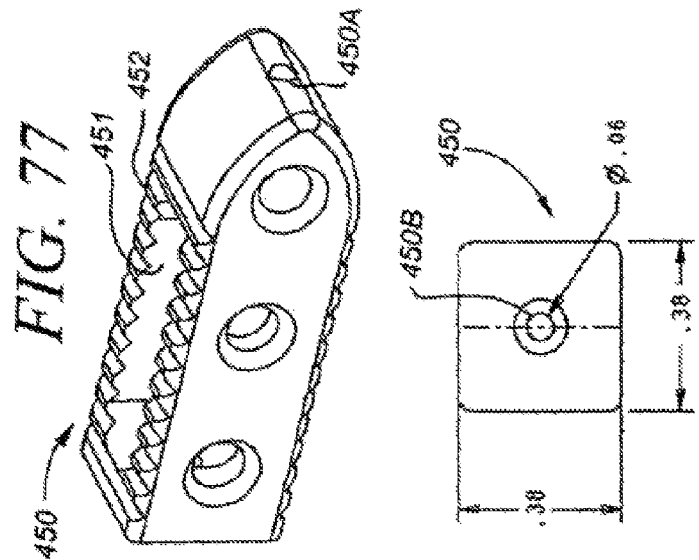
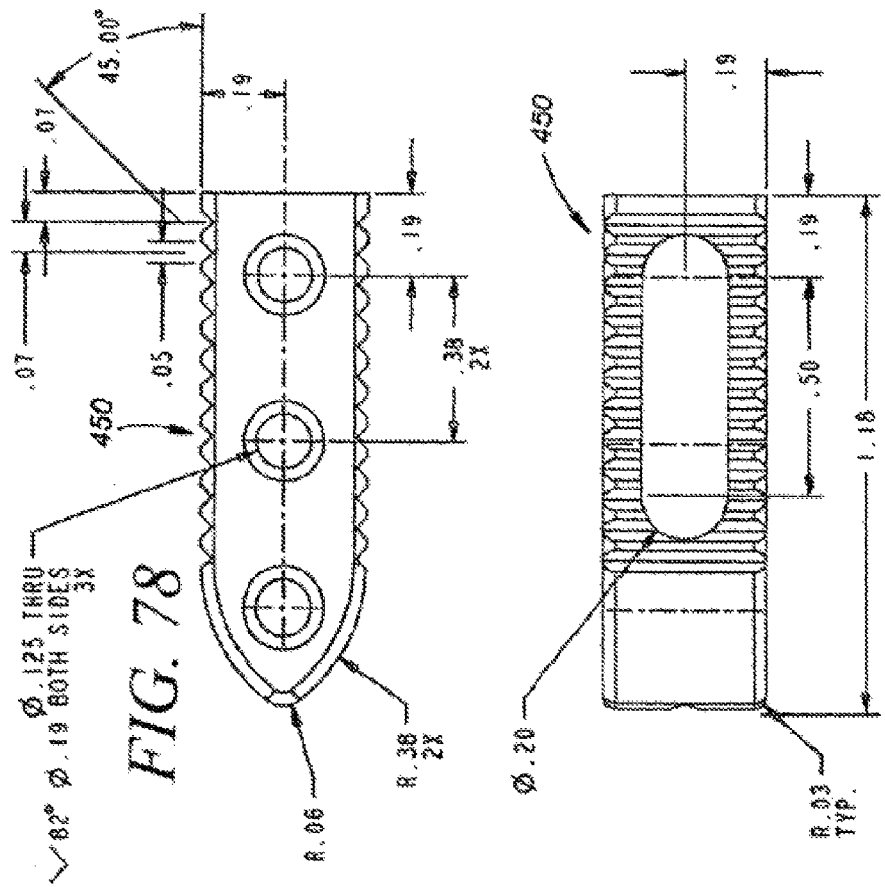

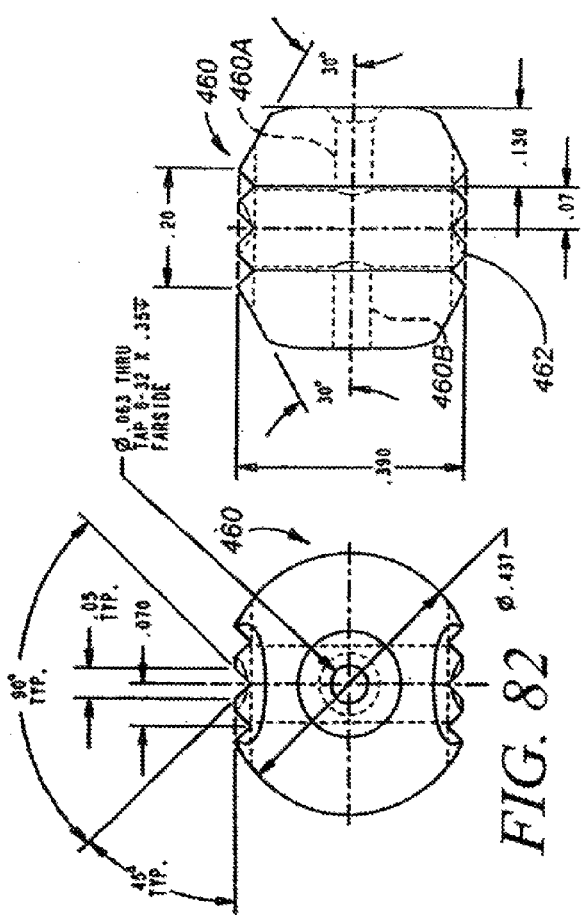
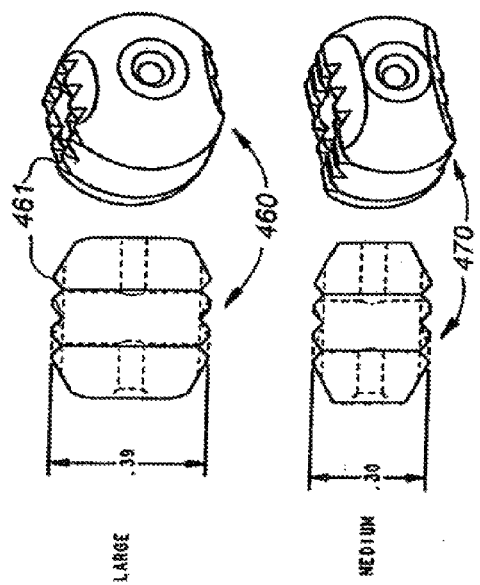
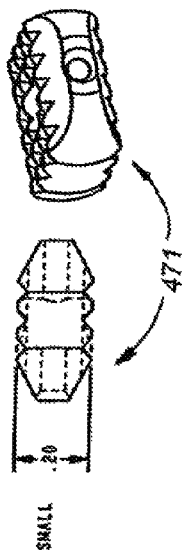
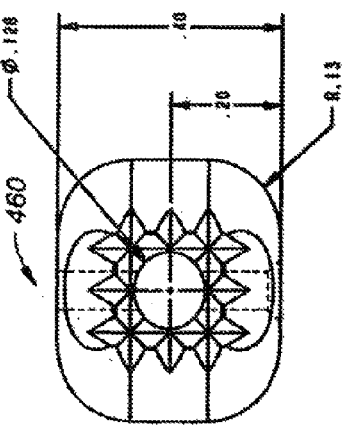
FIG. 84  FIG. 85  FIG. 86  FIG. 87  FIG. 88  FIG. 89
FIG. 81  FIG. 82  FIG. 83

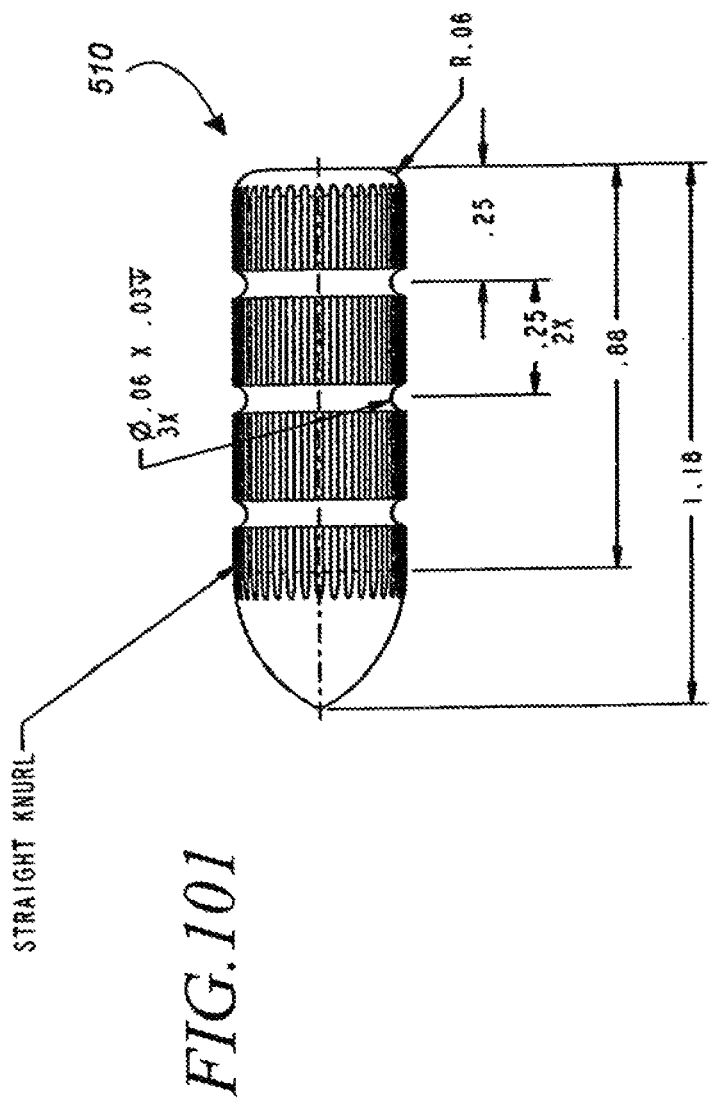
FIG. 101
FIG. 102
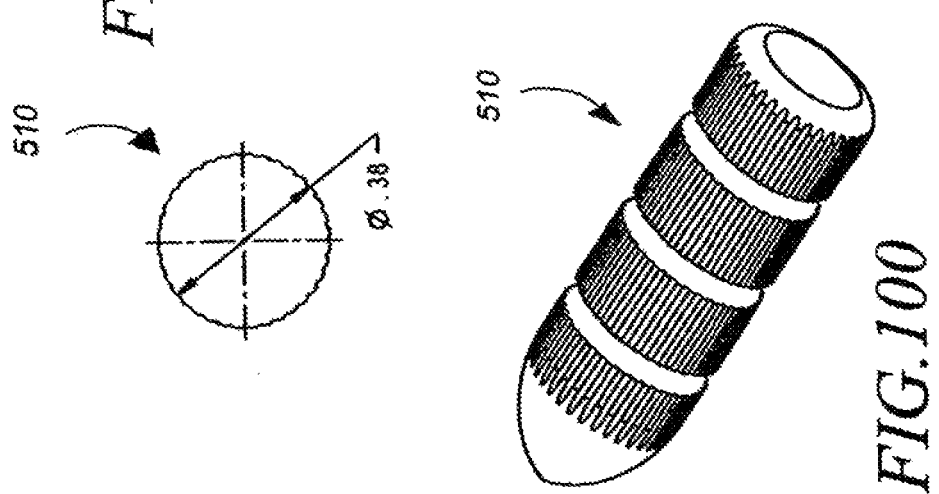
FIG. 100

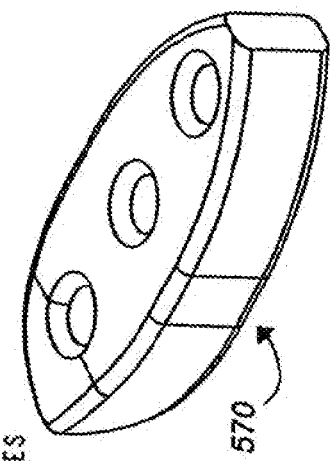
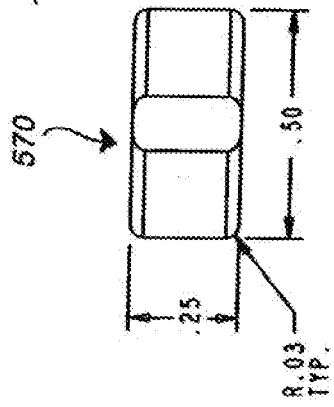
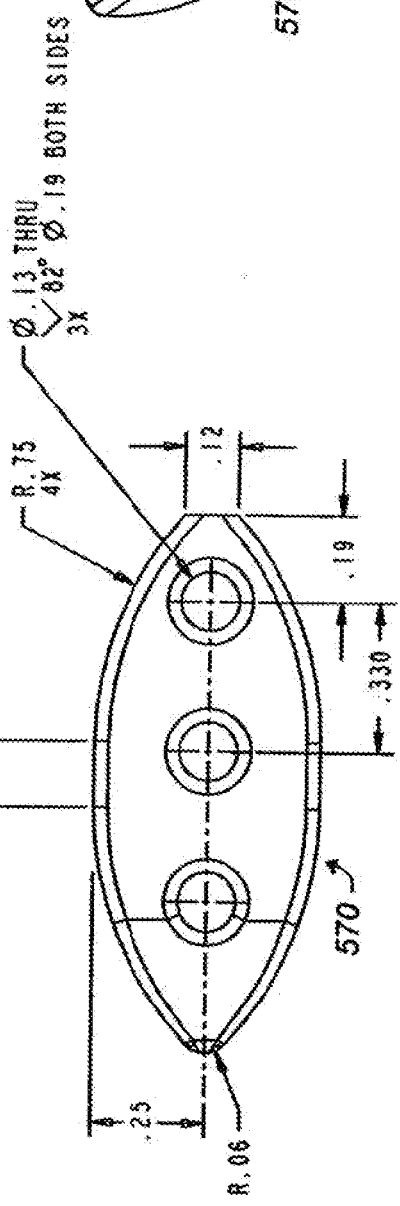
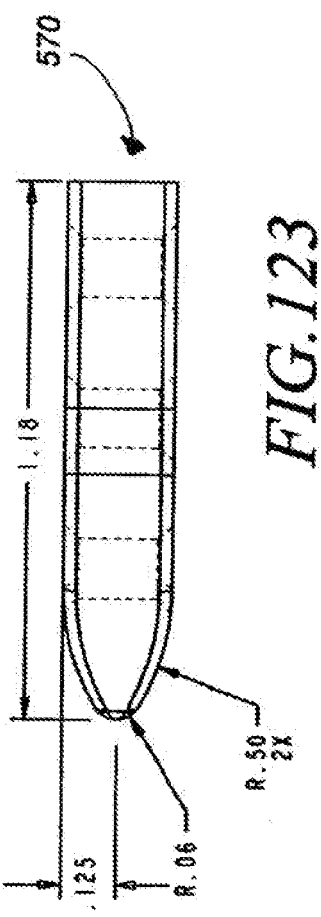

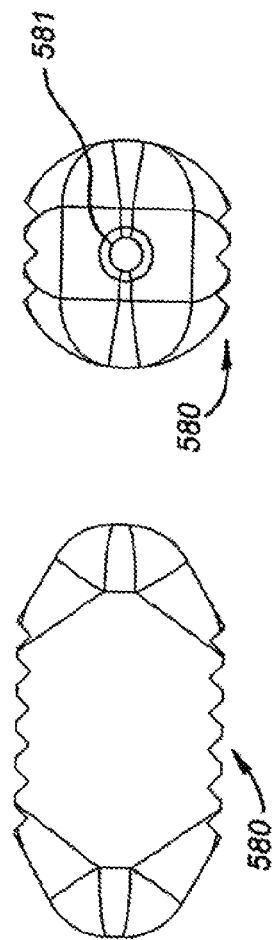
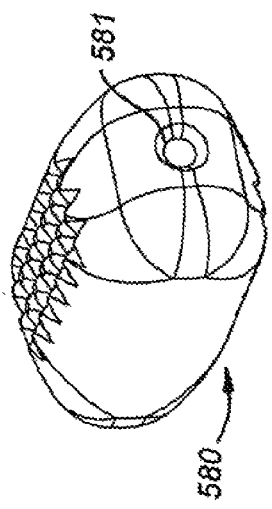
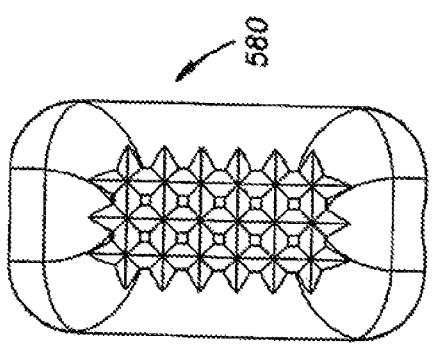
FIG. 129
FIG. 126
FIG. 127
FIG. 128
FIG. 125

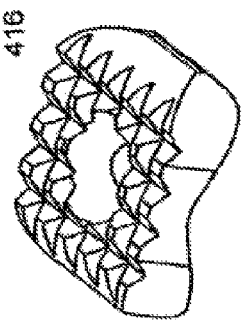
FIG.131
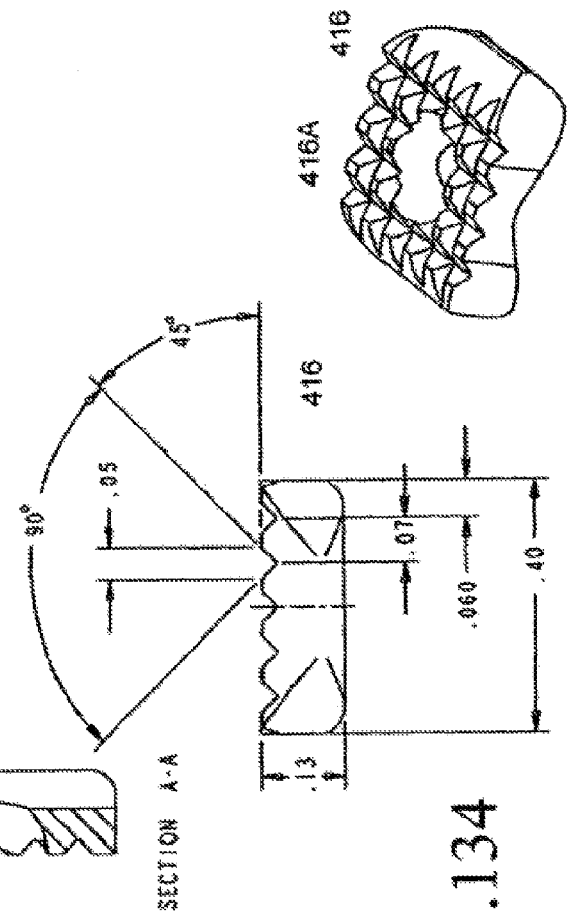
FIG.133
FIG.135
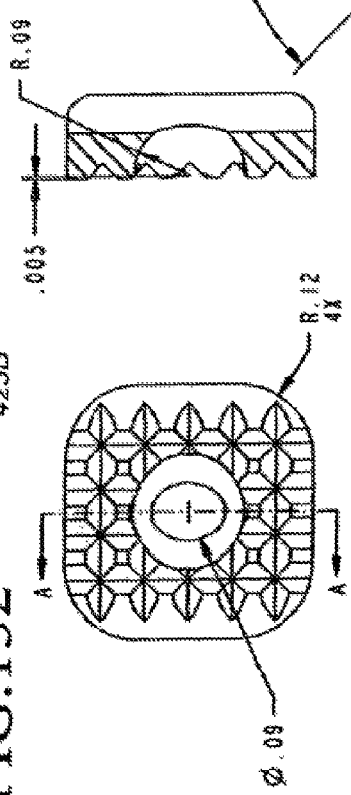
FIG.132
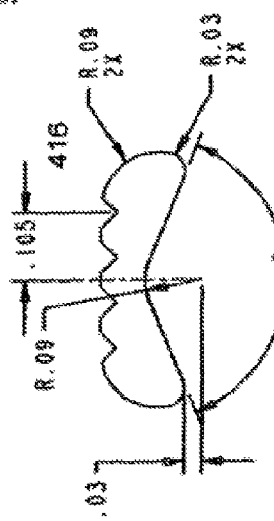
FIG.134
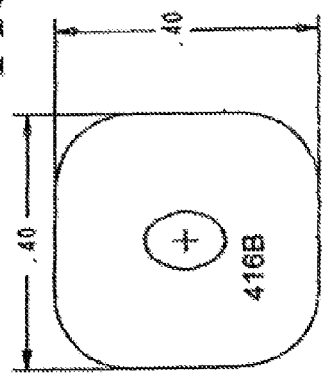
FIG.136

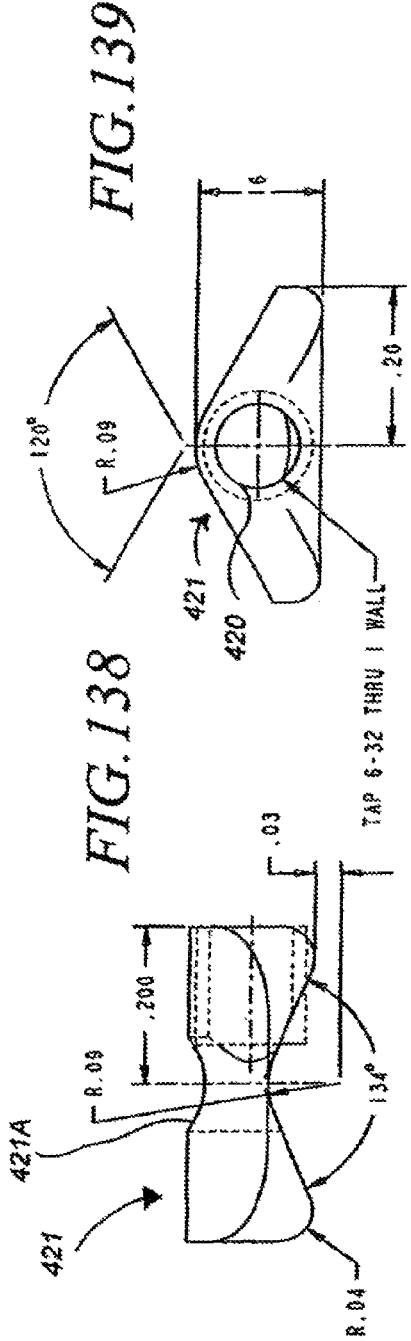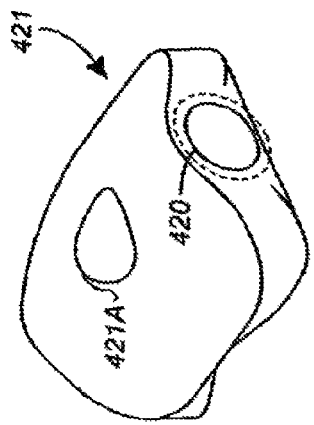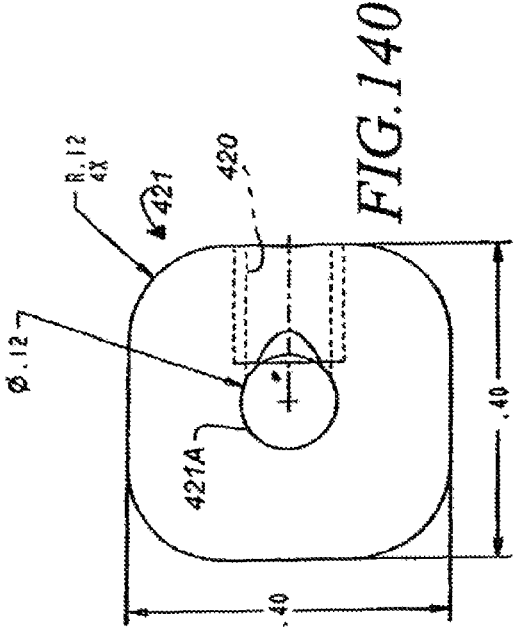

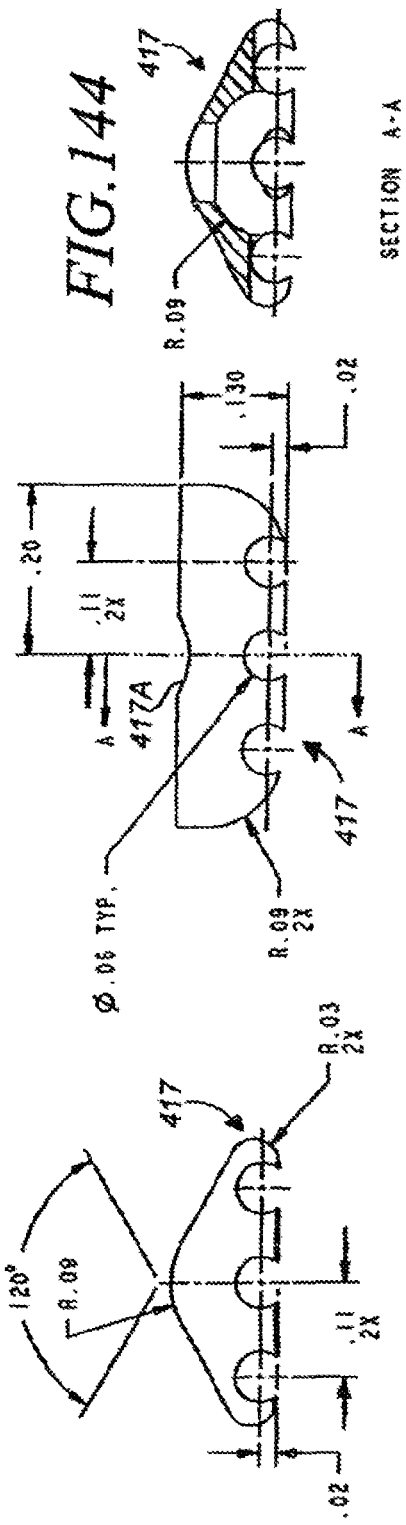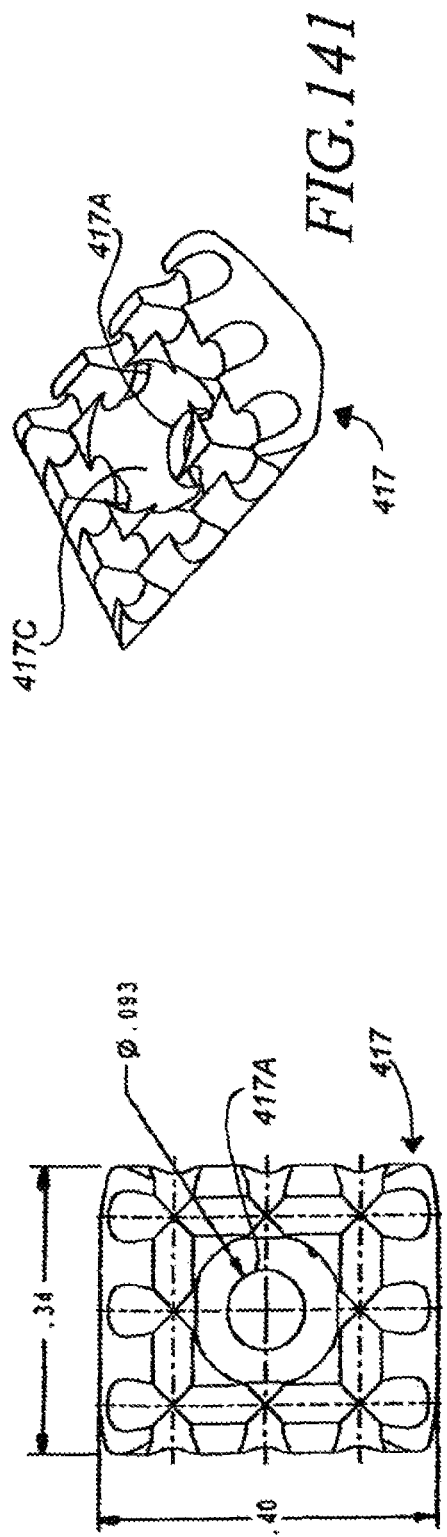

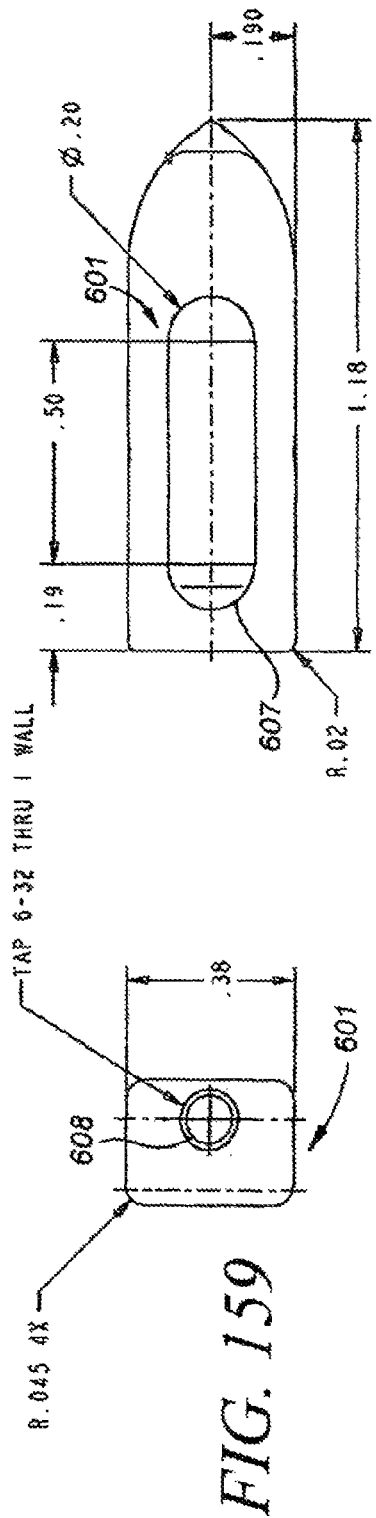
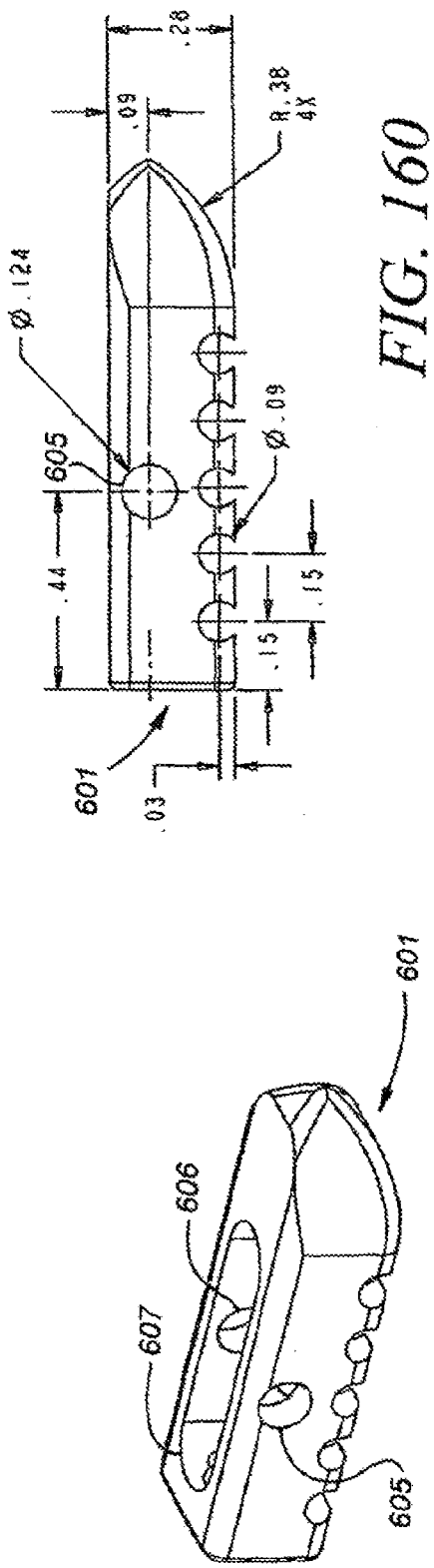
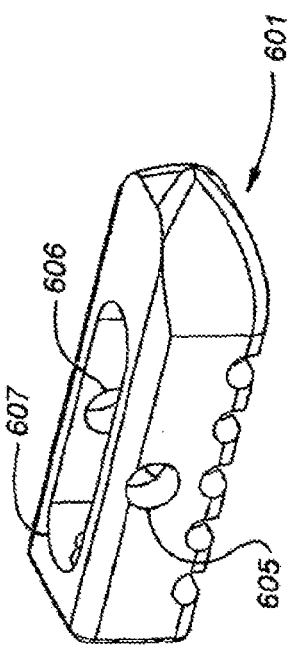

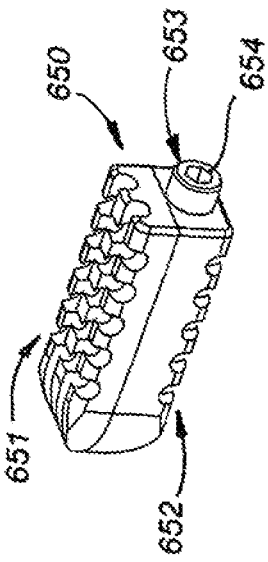
FIG. 166
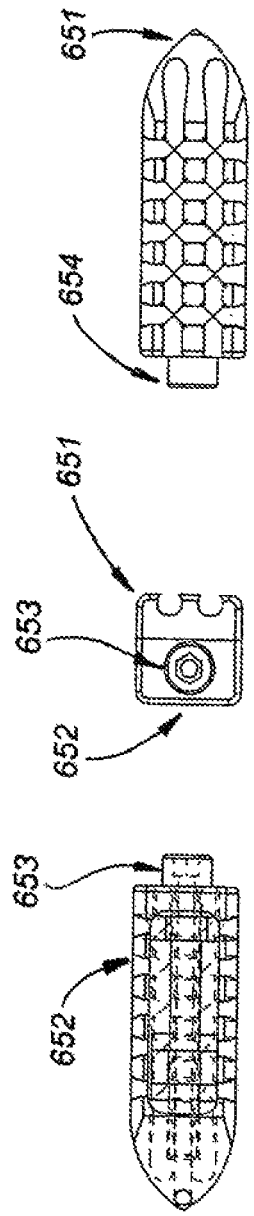
FIG. 167
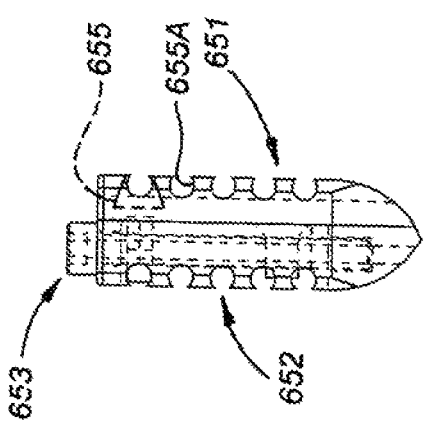
FIG. 168
FIG. 165
FIG. 169

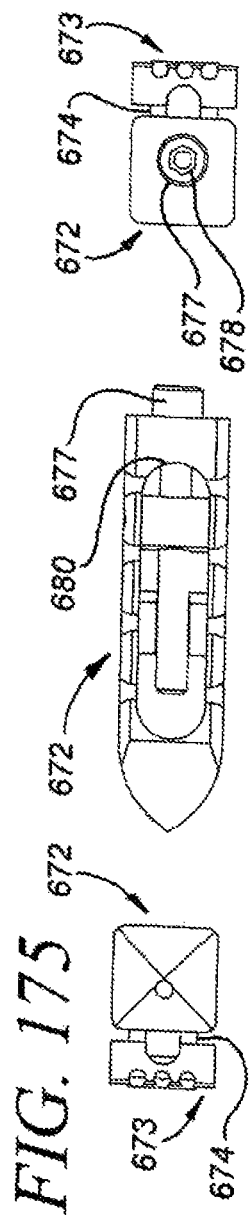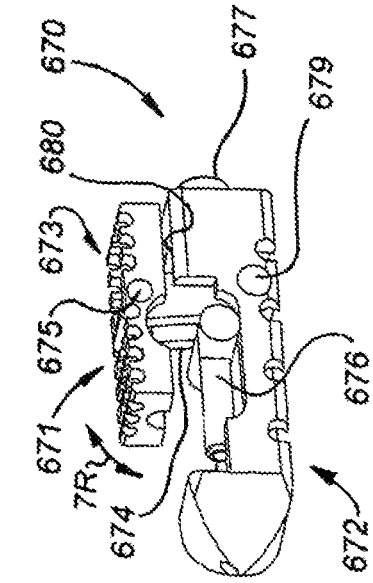

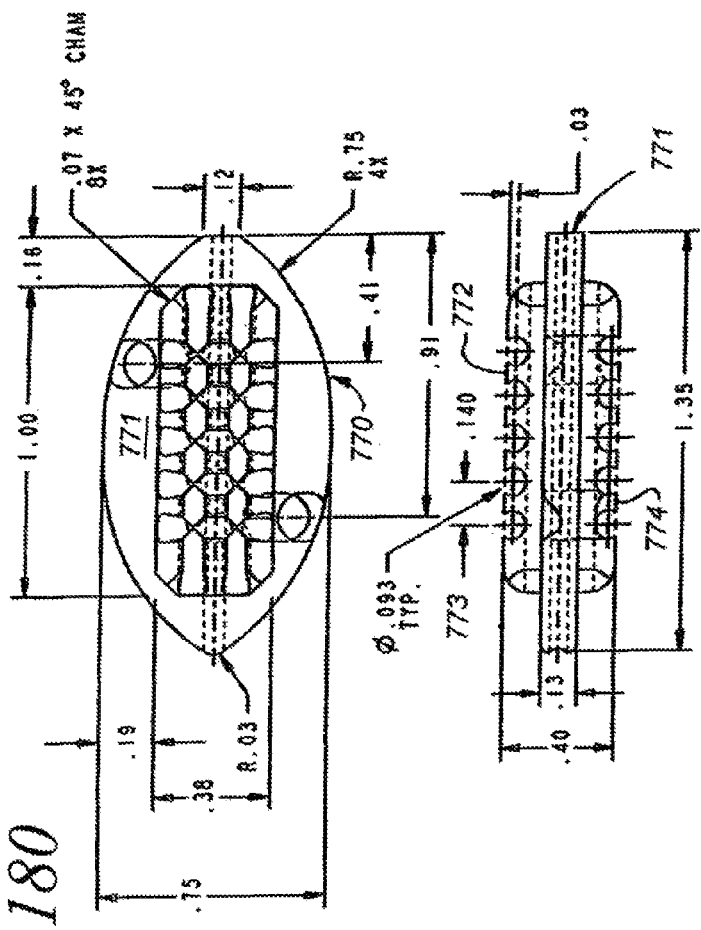
FIG. 182
FIG. 183
FIG. 180
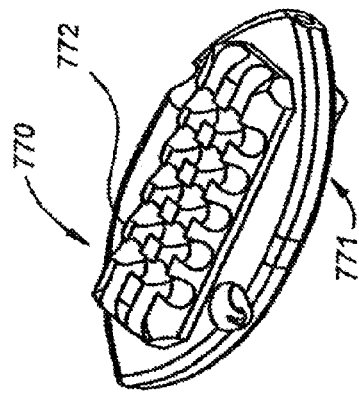
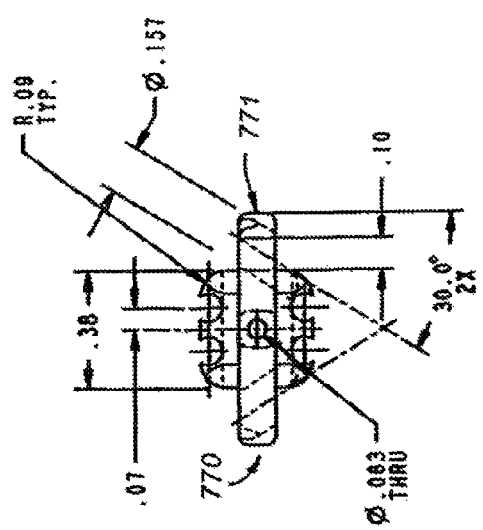
FIG. 181

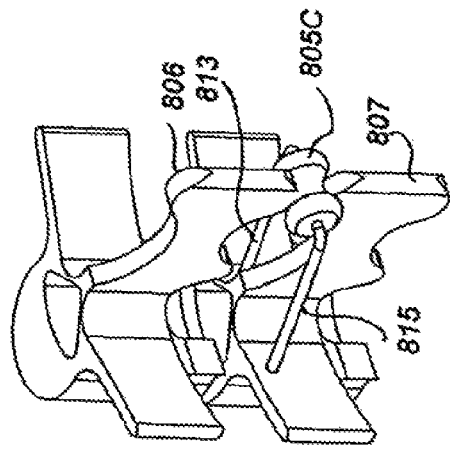
FIG. 193
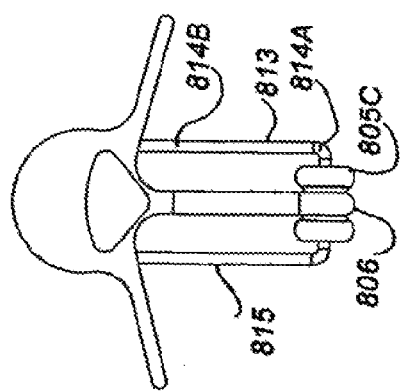
FIG. 194
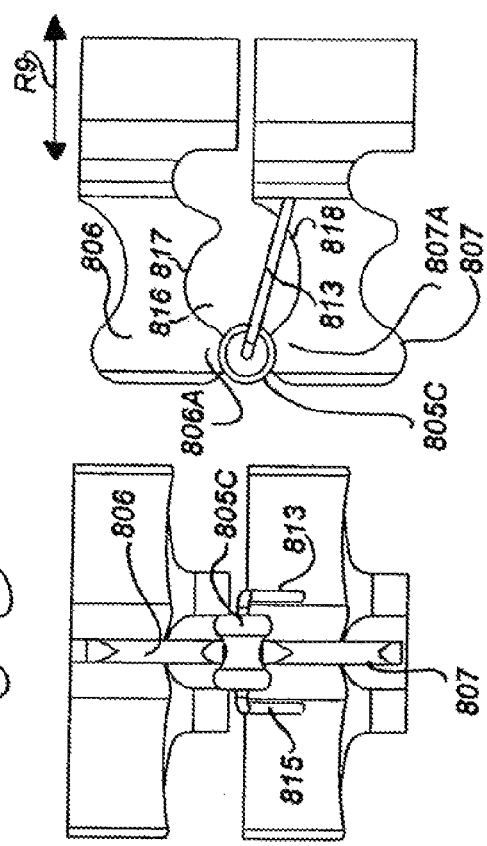
FIG. 195
FIG. 196

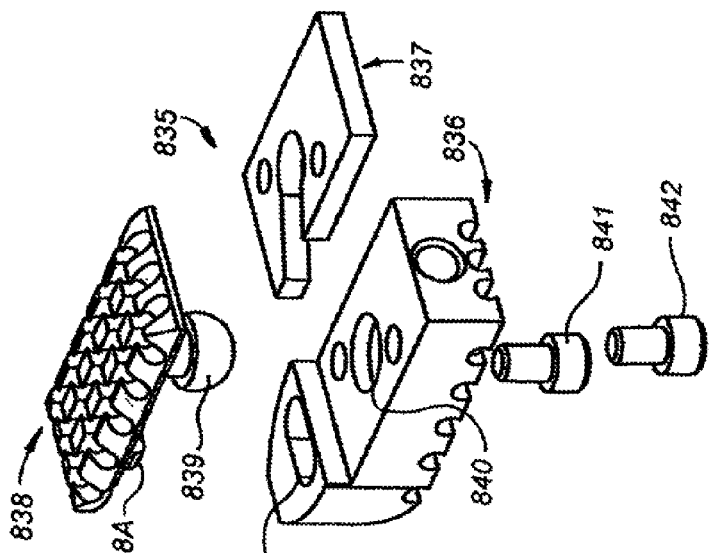
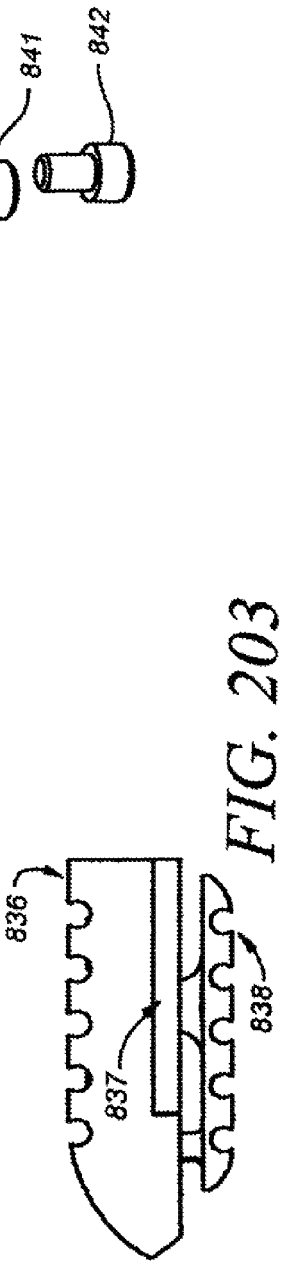
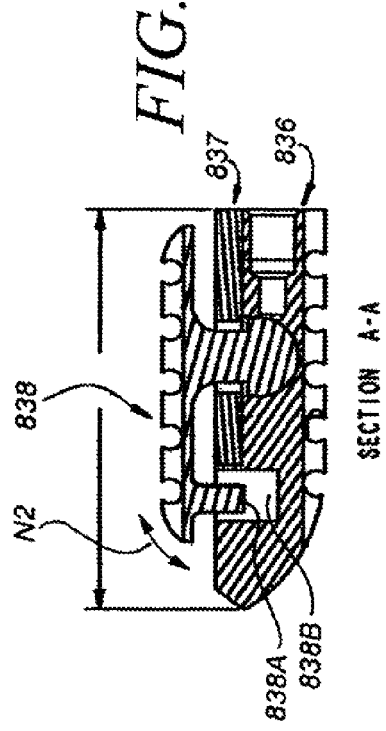
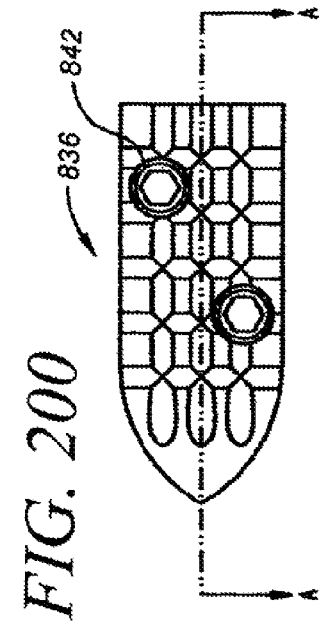

FIG. 206
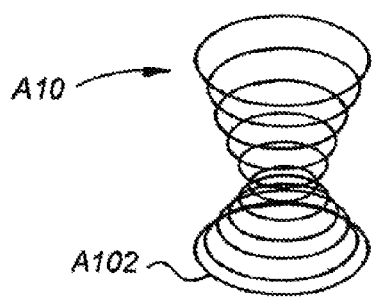
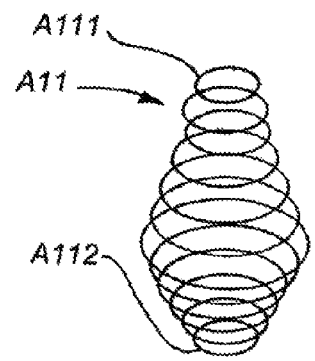
FIG. 207
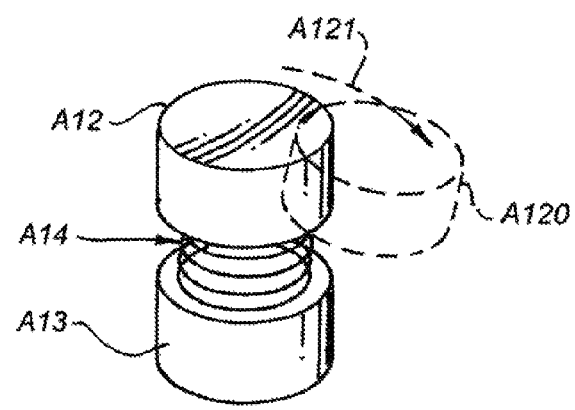
FIG. 209
FIG. 208
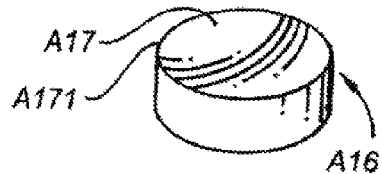
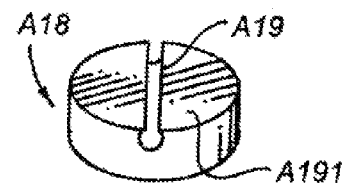
FIG. 210
FIG. 211

FIG. 212
FIG. 213
FIG. 214
FIG. 212A
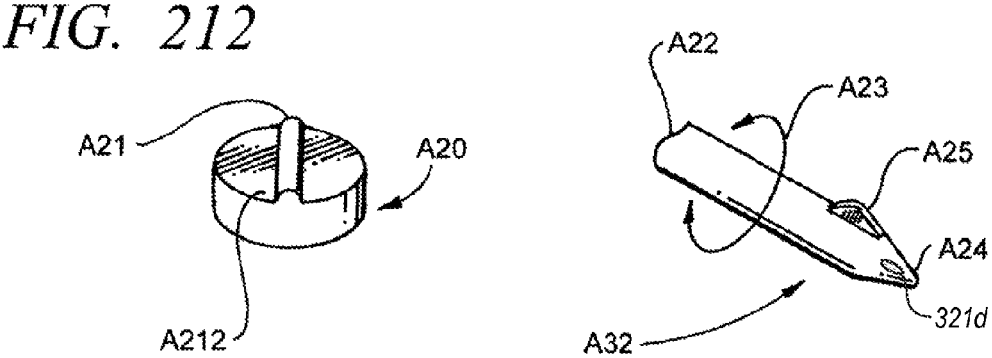
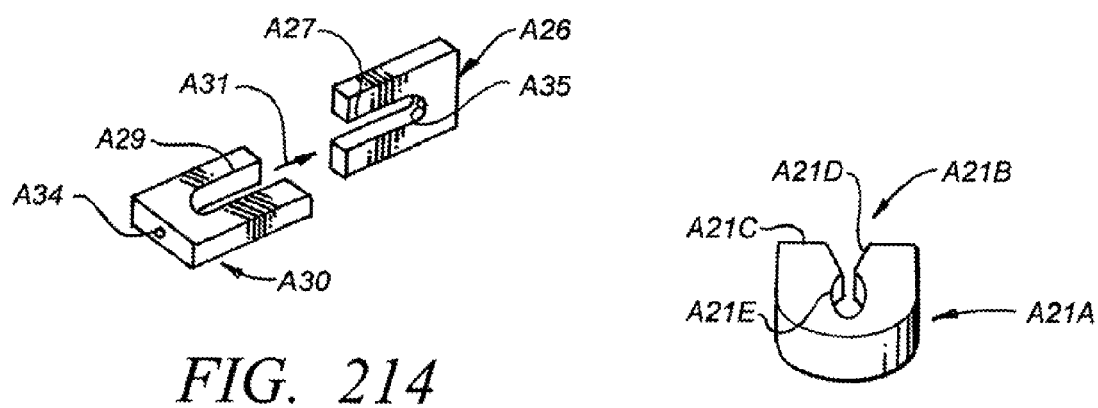
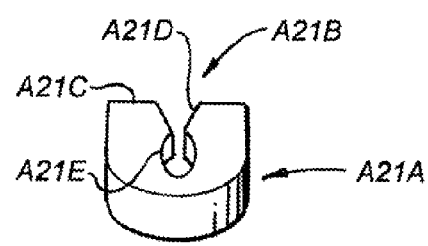

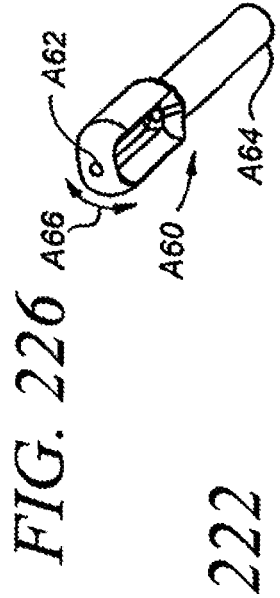
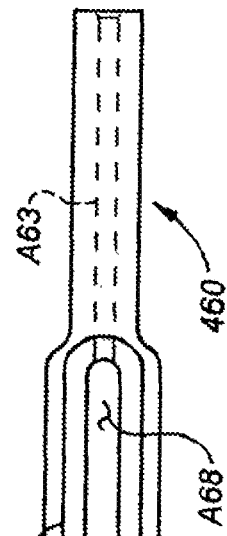
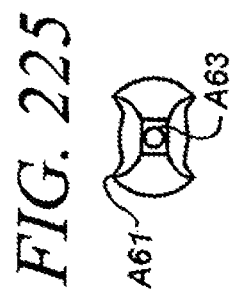
FIG. 222
FIG. 223
FIG. 224
FIG. 225
FIG. 226
FIG. 227

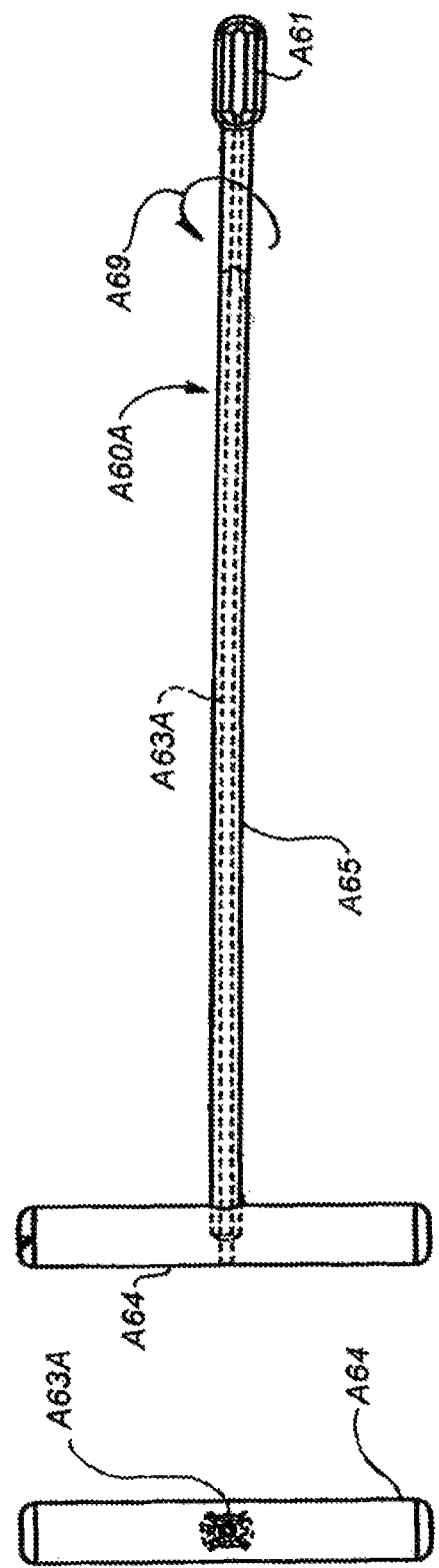

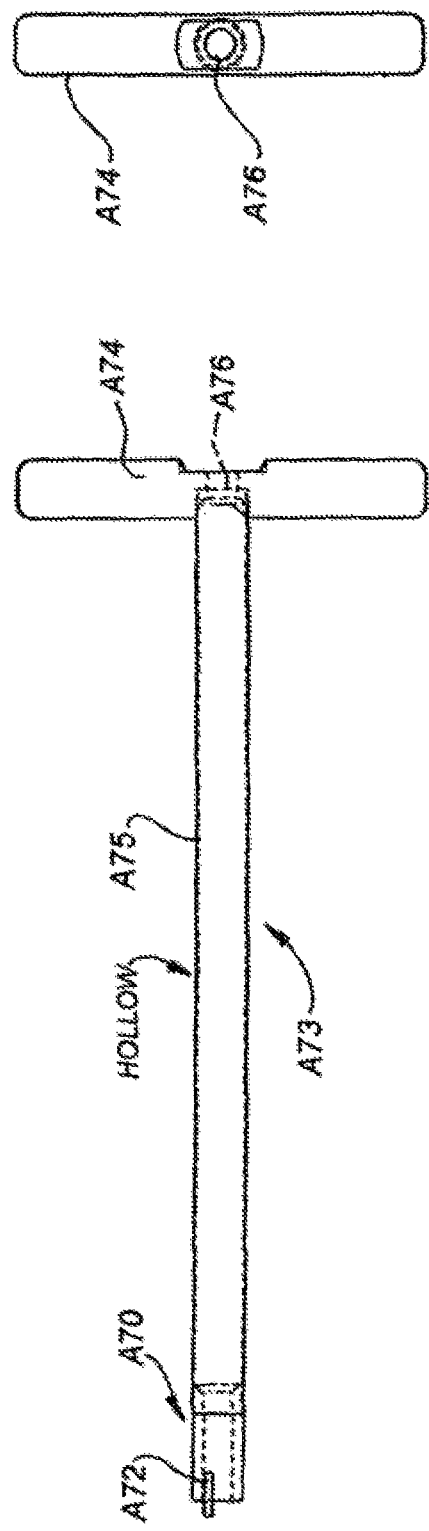

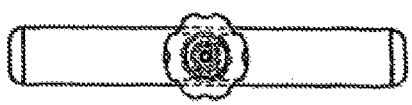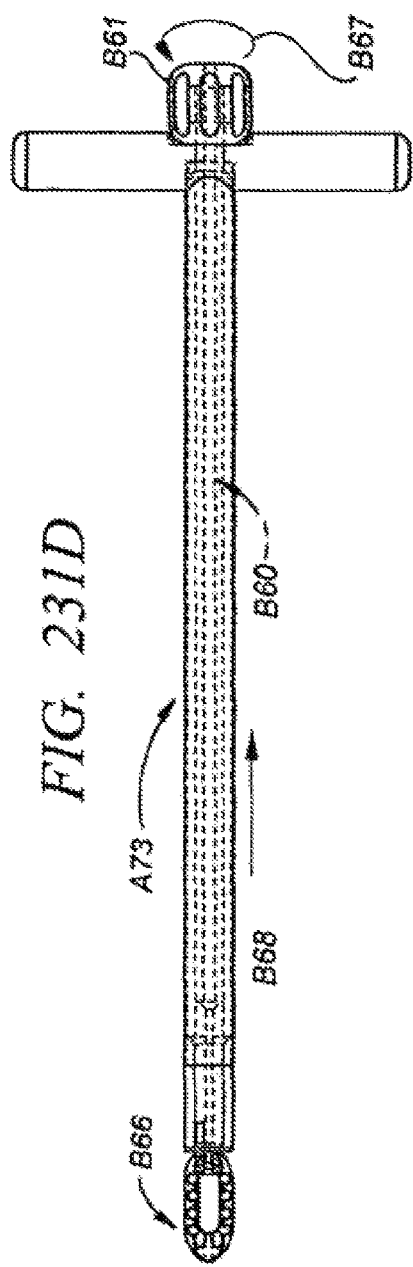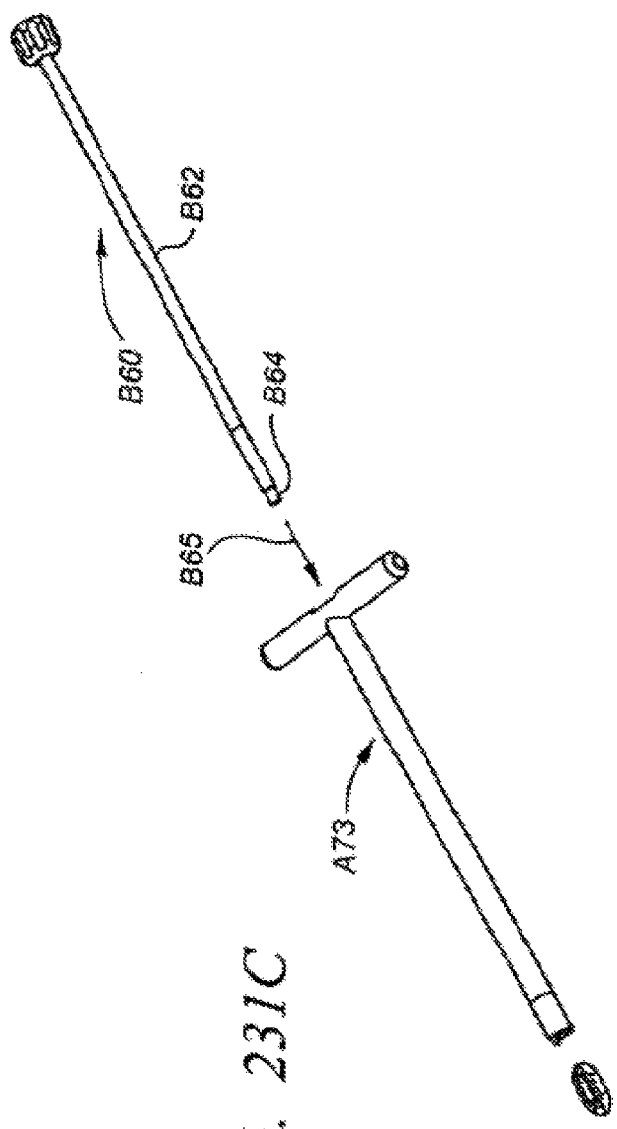

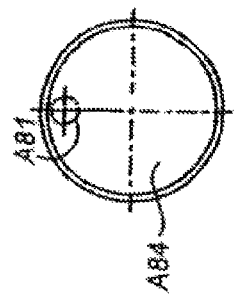
FIG. 234
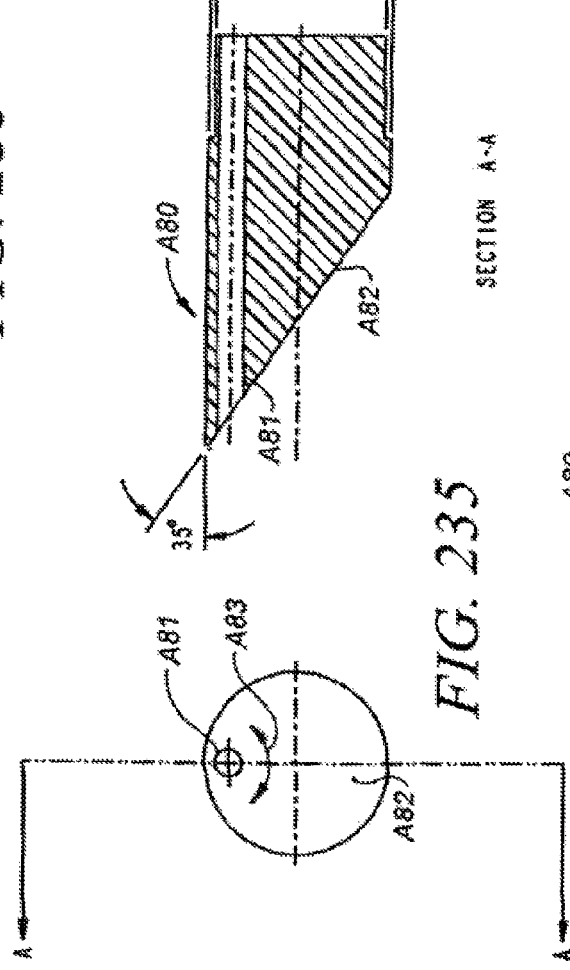
FIG. 233
FIG. 235
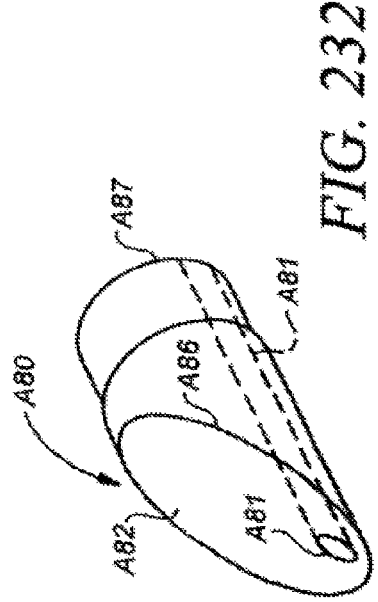
FIG. 232

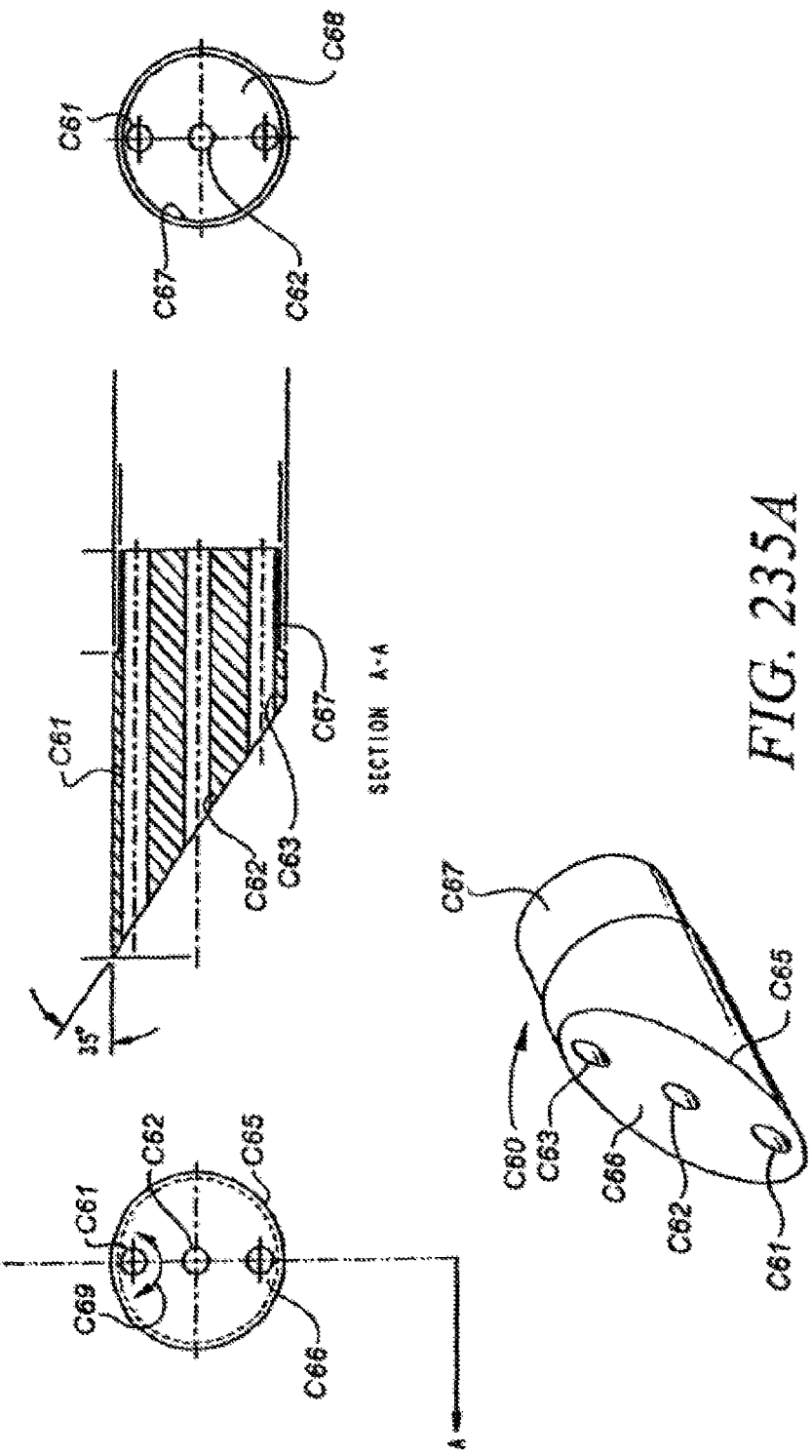

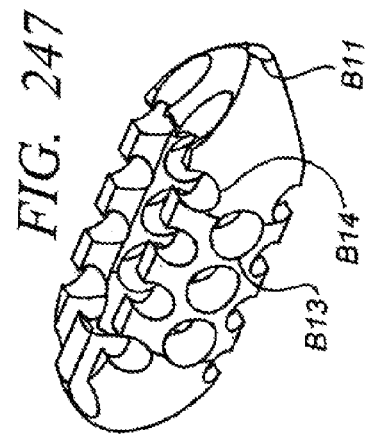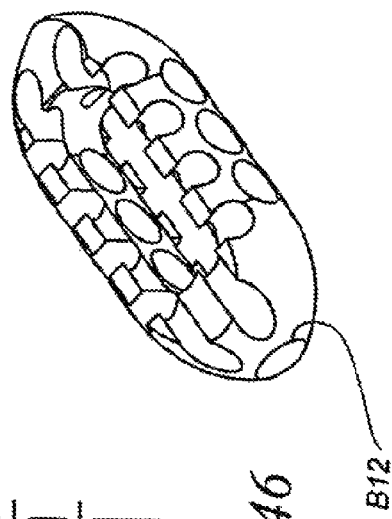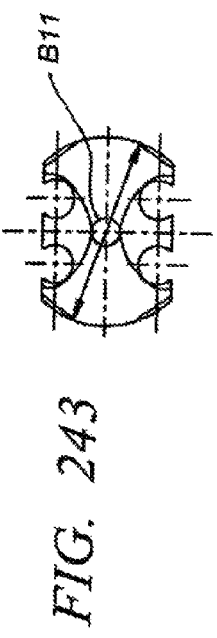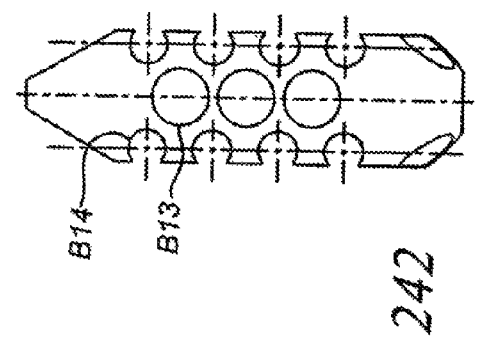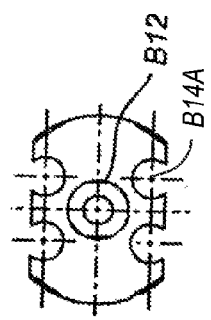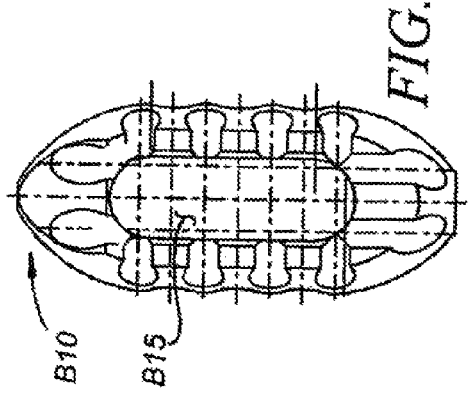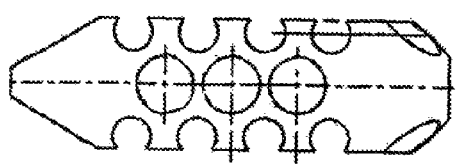

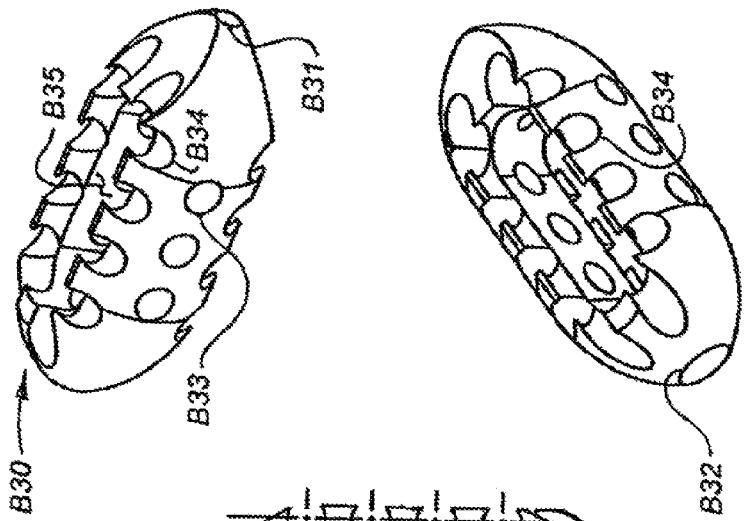
FIG. 258
FIG. 259
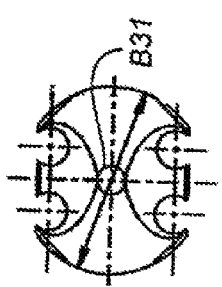
FIG. 253
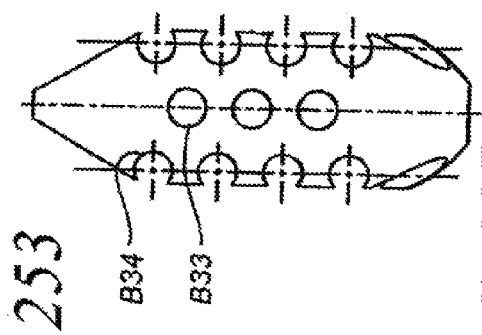
FIG. 257
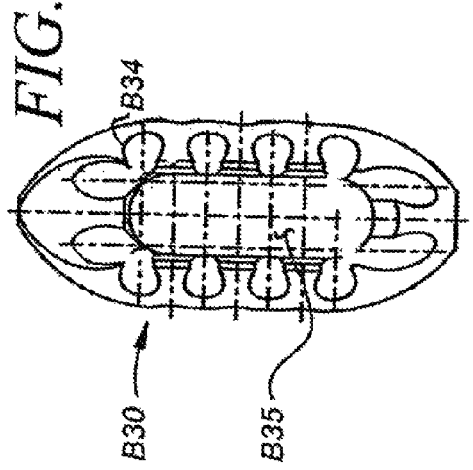
FIG. 255
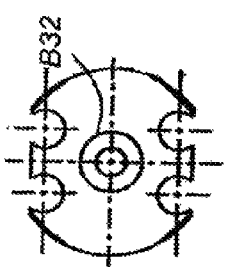
FIG. 256
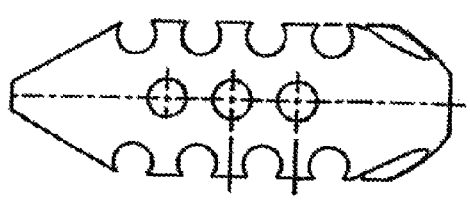
FIG. 254

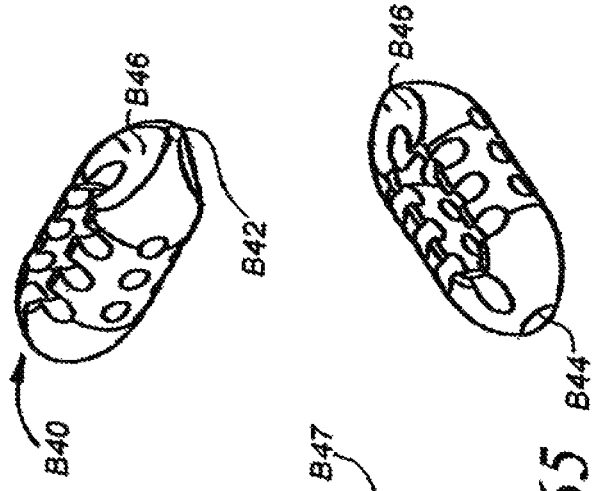
FIG. 266  FIG. 267
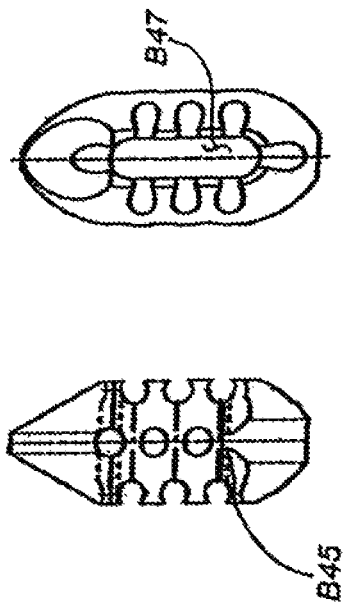
FIG. 262  FIG. 265
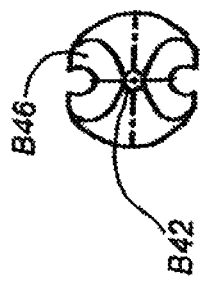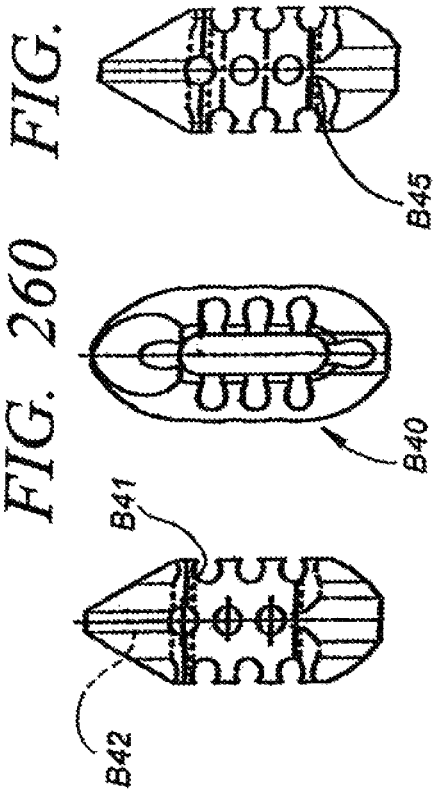
FIG. 264  FIG. 260  FIG. 263
FIG. 261

FIG. 271
FIG. 272
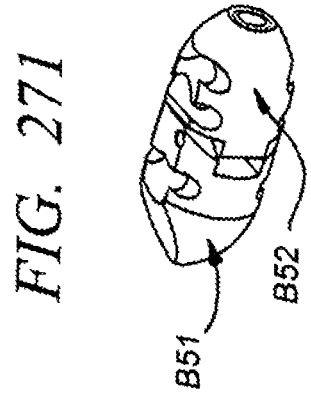
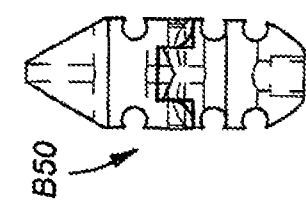
FIG. 270
FIG. 268
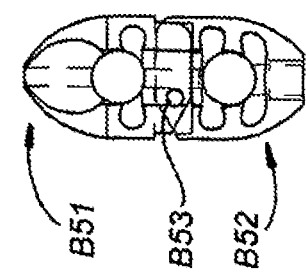
FIG. 269

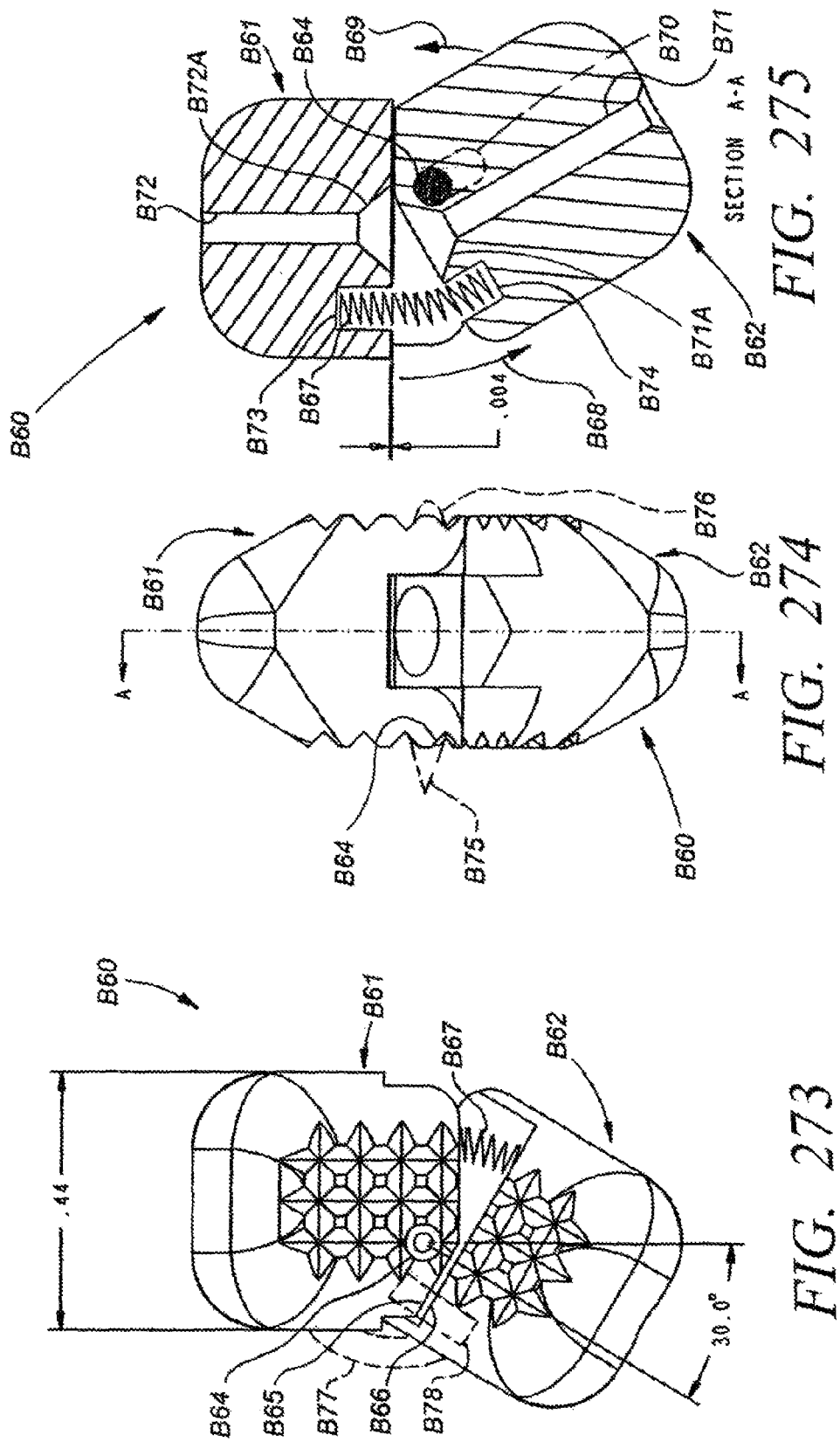

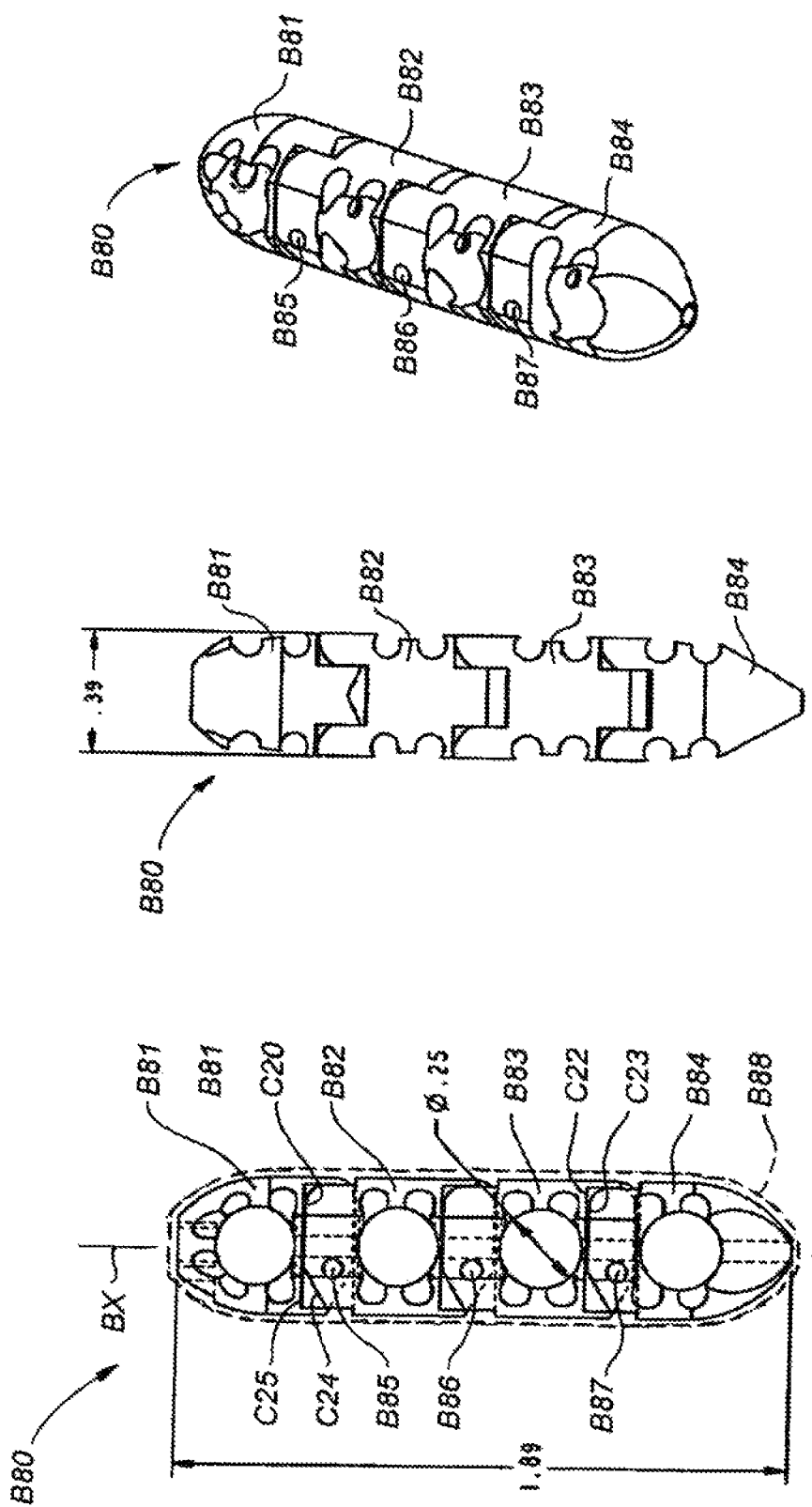

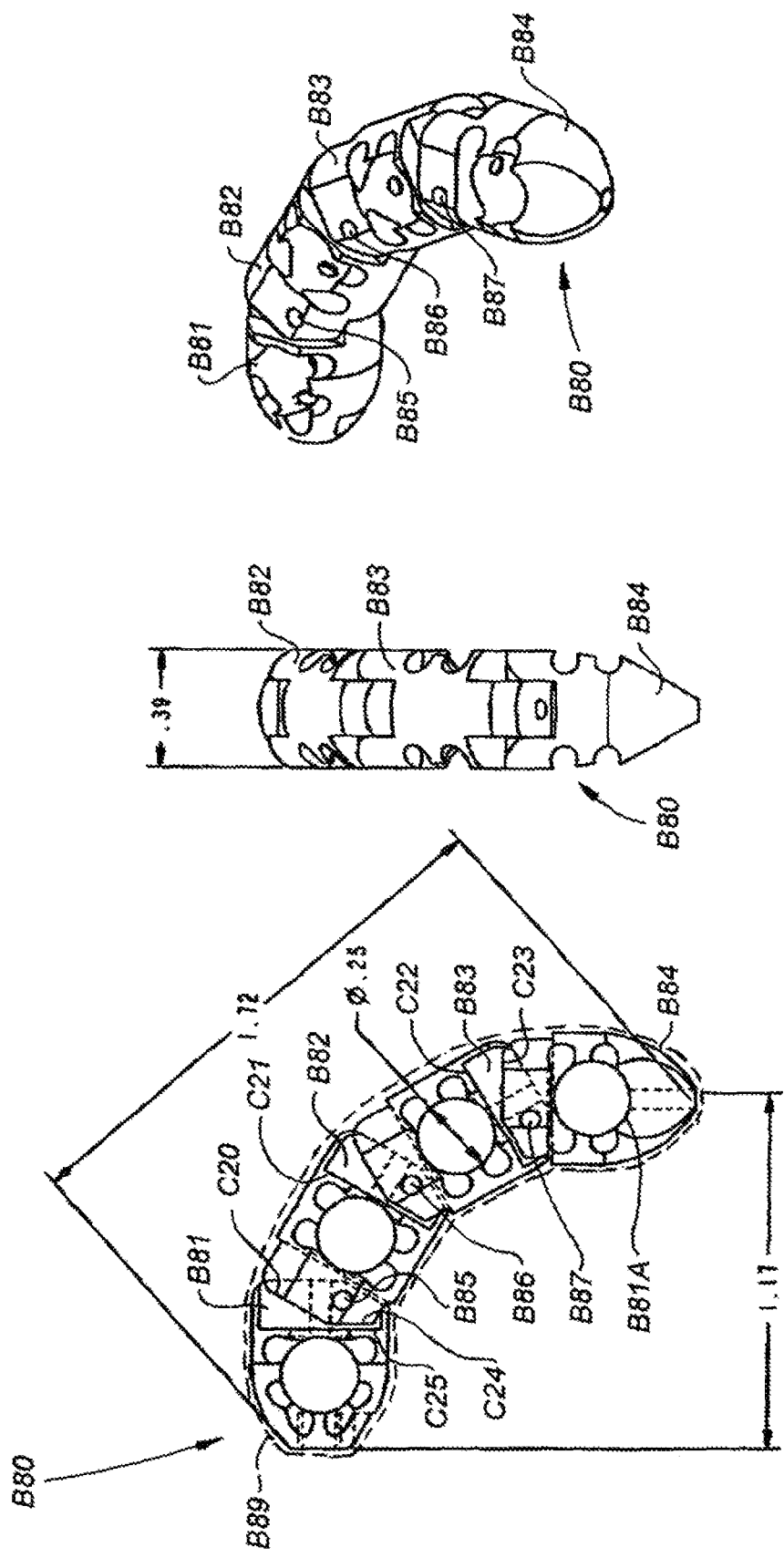

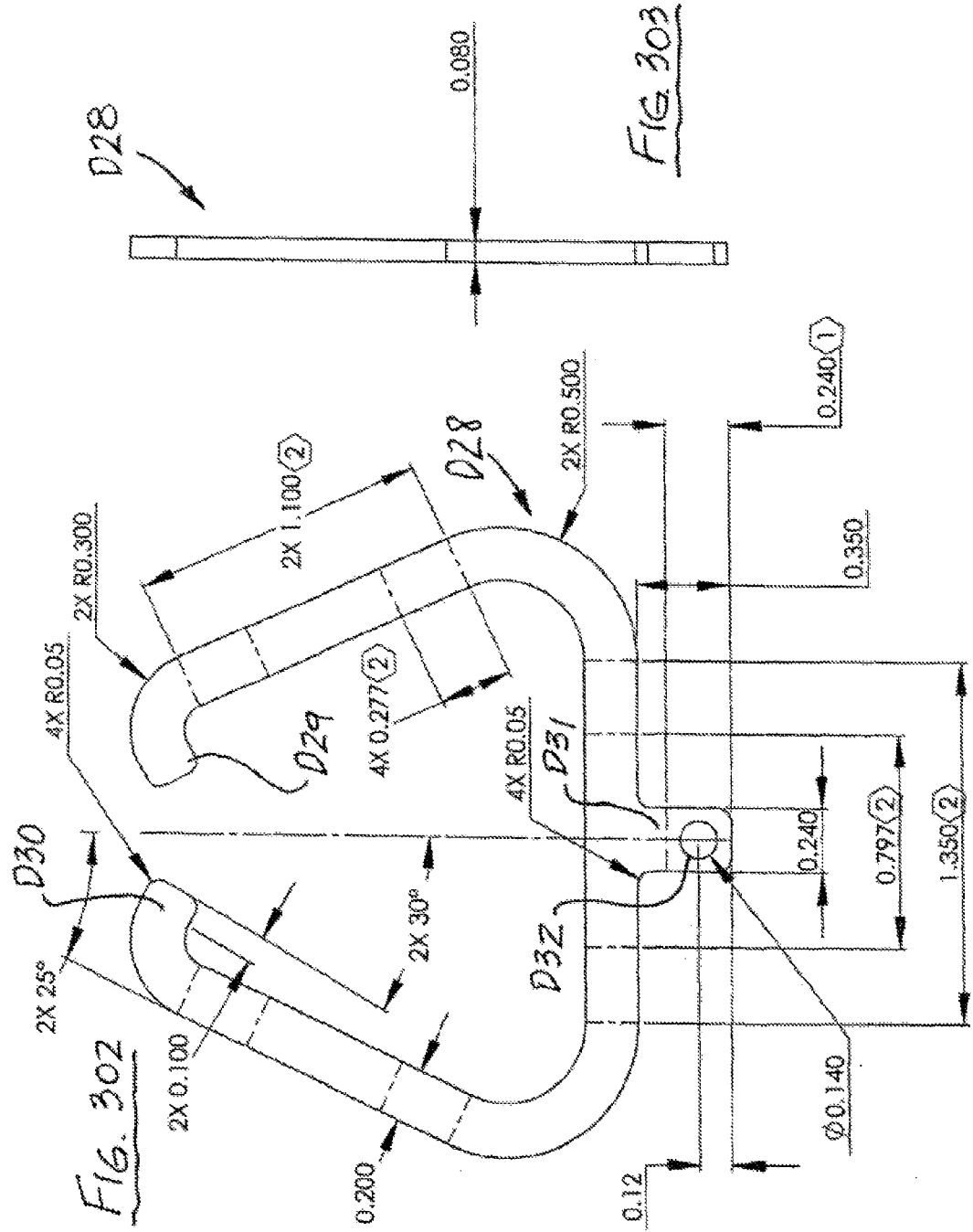

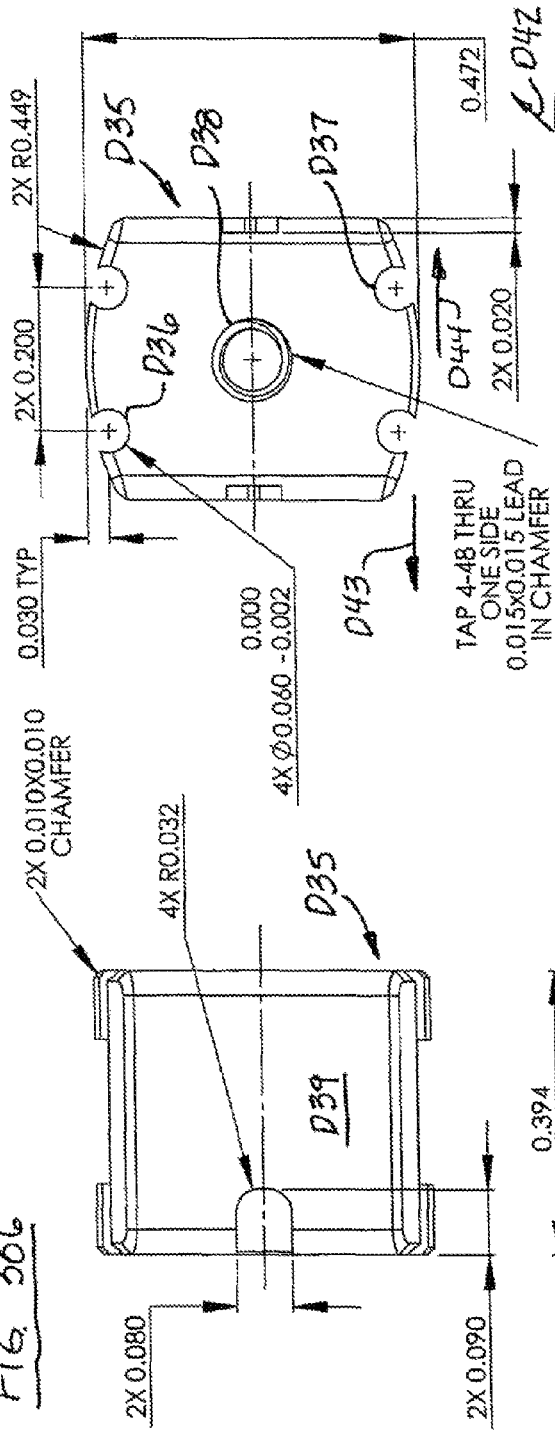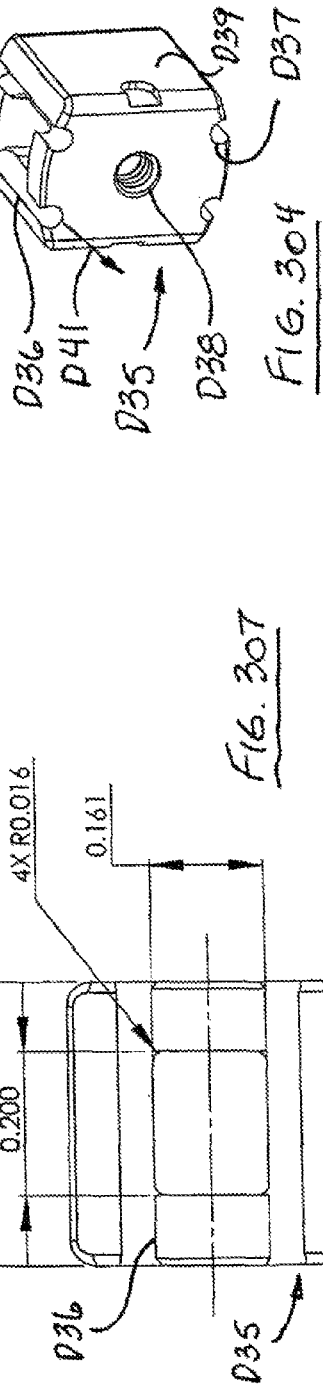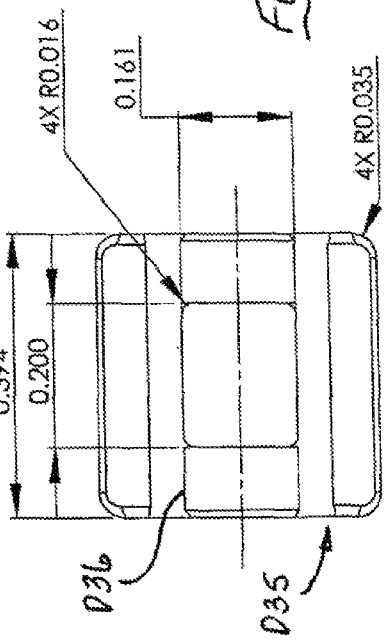

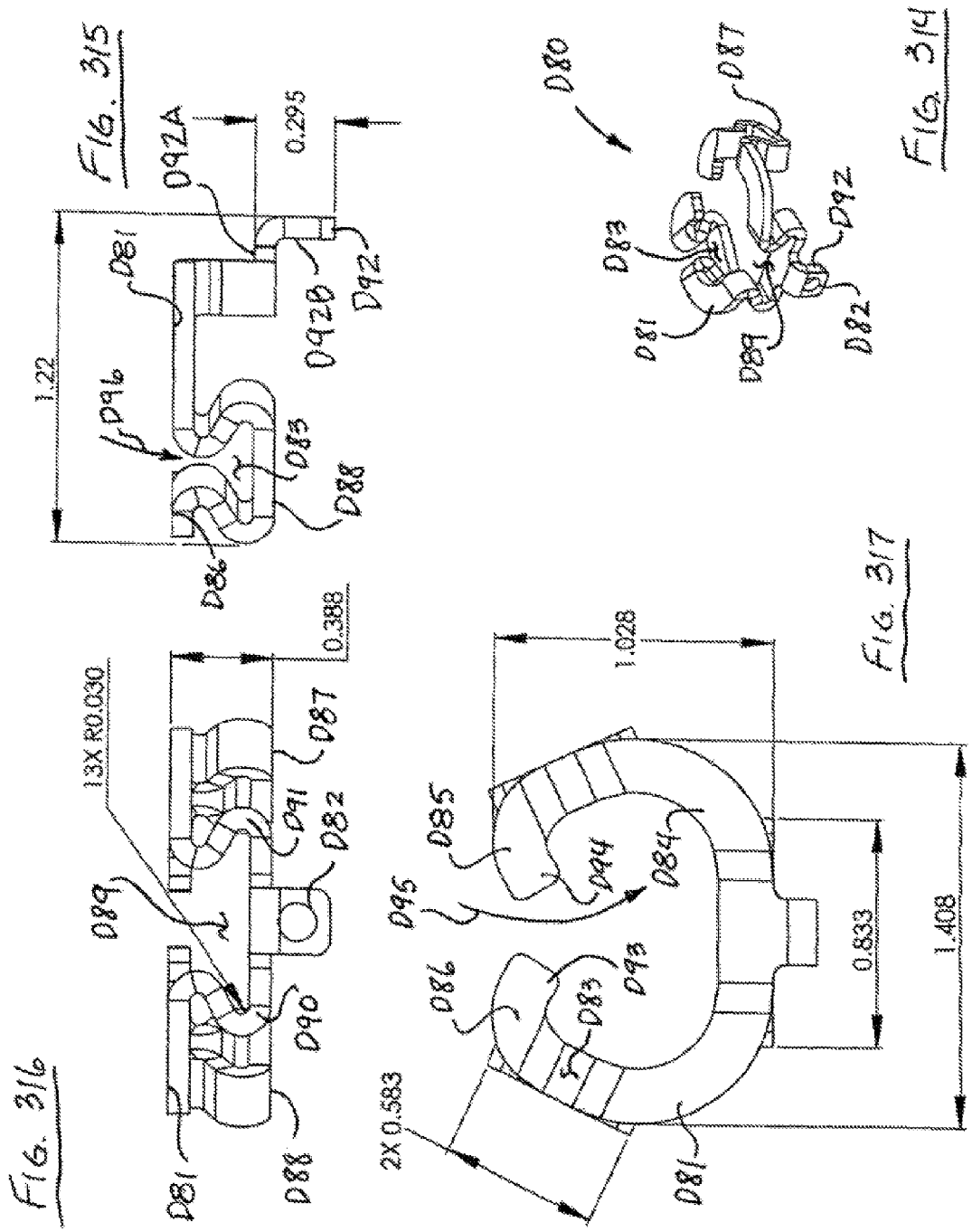

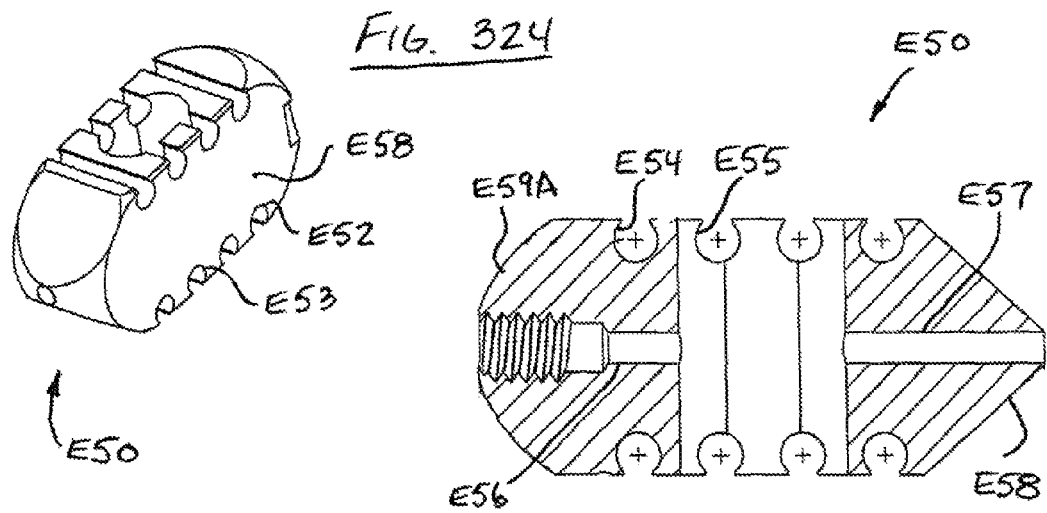
FIG. 324
FIG. 325
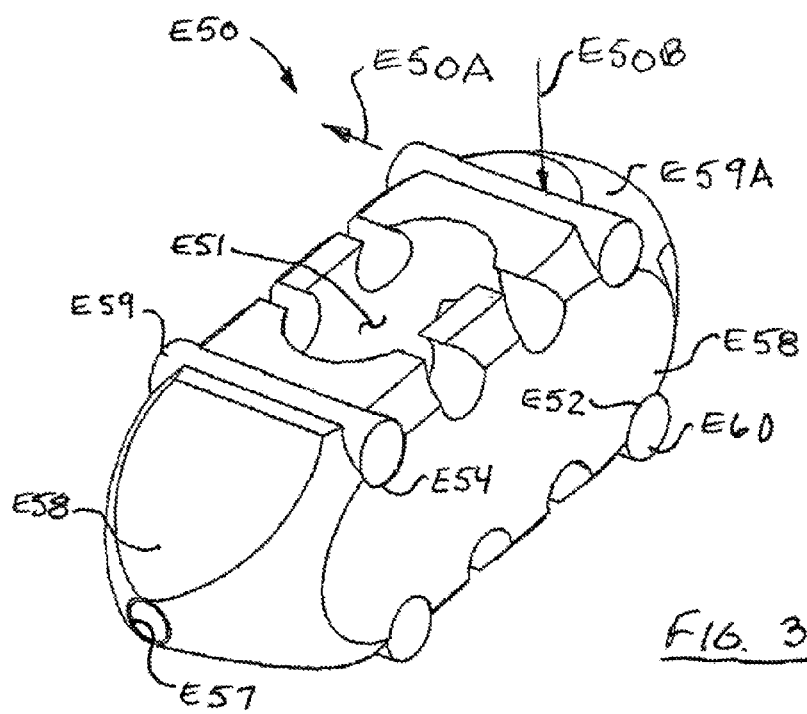
FIG. 326

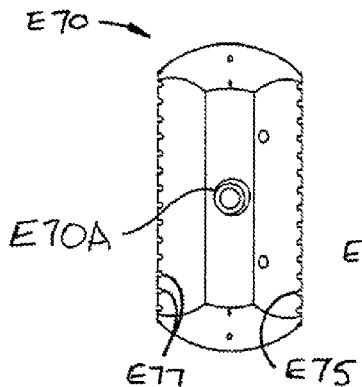
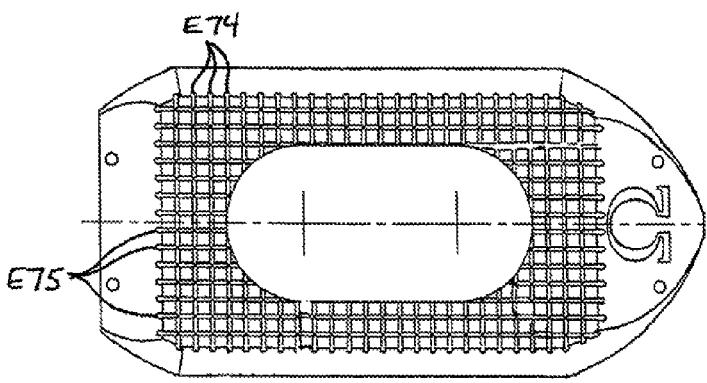
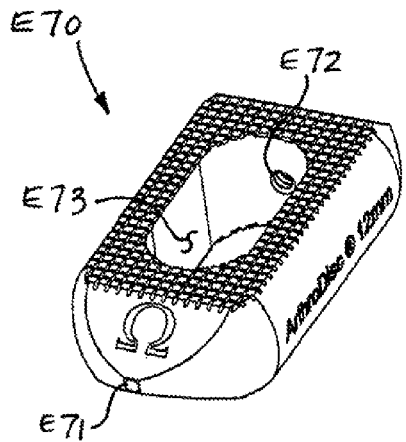

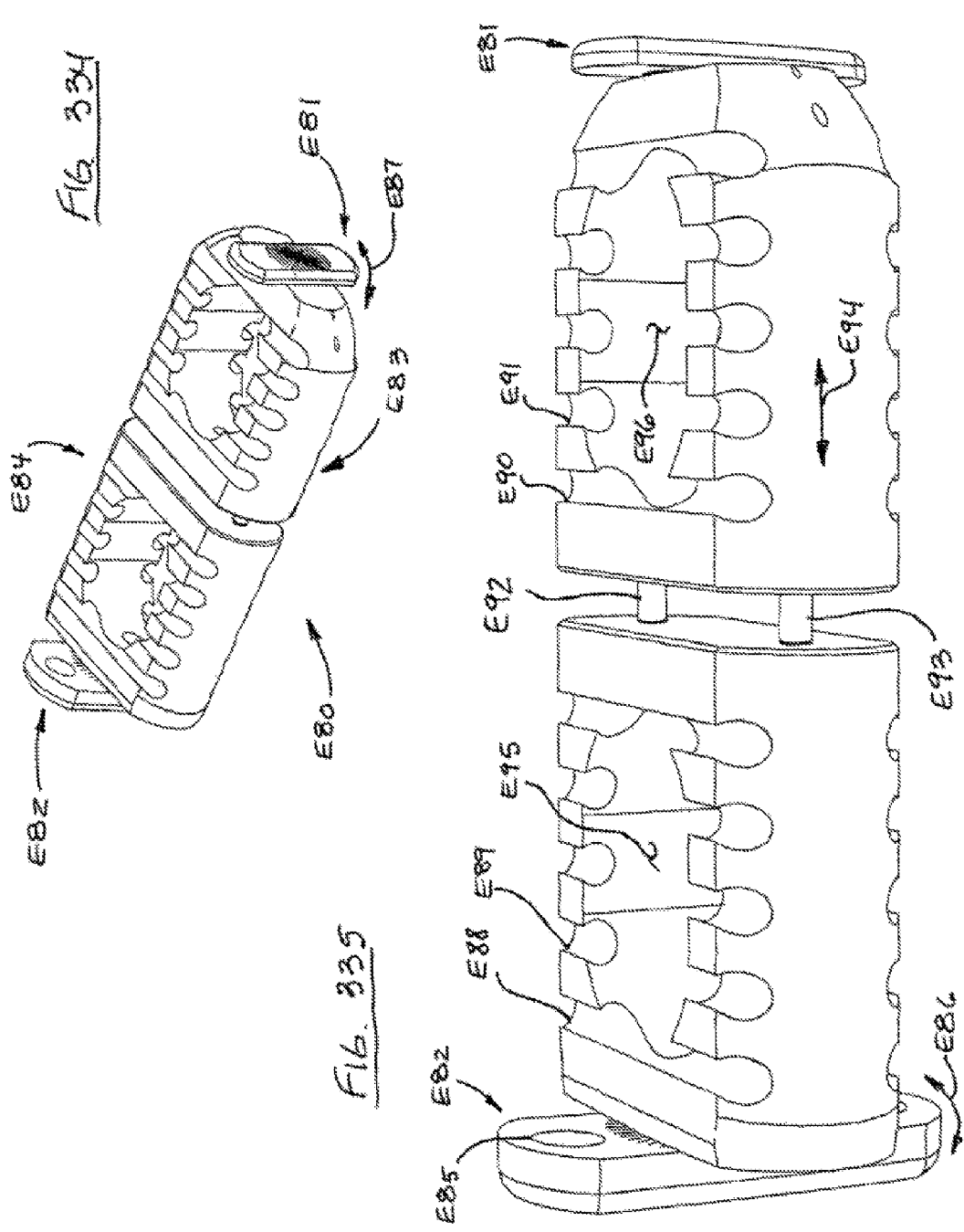

TAPERED ARCUATE INTERVERTEBRAL IMPLANT

CROSS-REFERENCE TO RELATED APPLICATIONS

This application is a continuation-in-part of U.S. patent application Ser. No. 13/370,925 filed Feb. 10, 2012 and continuation-in-part of U.S. patent application Ser. No. 13/478,870 filed May 23, 2012, which are continuation-in-parts of U.S. patent application Ser. No. 13/199,324 filed Aug. 26, 2011 [P12], which is a continuation-in-part of U.S. patent application Ser. No. 13/065,291, filed Mar. 18, 2011 [P11], which is a continuation-in-part of U.S. patent application Ser. No. 11/804,838, filed May 21, 2007 [P8], now U.S. Pat. No. 7,909,878, which is a continuation-in-part of U.S. patent application Ser. No. 11/638,652 [P7], now U.S. Pat. No. 7,883,542 filed Dec. 12, 2006, which is a continuation-in-part of U.S. patent application Ser. No. 11/472,060 [P6] now U.S. Pat. No. 7,879,099, filed Jun. 21, 2006, which is a continuation-in-part of U.S. patent application Ser. No. 11/404,938 [P5] now U.S. Pat. No. 7,727,279 filed Apr. 14, 2006, which is a continuation-in-part of U.S. patent application Ser. No. 11/351,665 [P4] filed Feb. 10, 2006 now abandoned, which is a continuation-in-part of U.S. patent application Ser. No. 11/299,395 [P3] filed Dec. 12, 2005 now abandoned, which is a continuation-in-part of U.S. patent application Ser. No. 11/241,143 [P2] filed Sep. 30, 2005 now abandoned, which applications and patents are incorporated herein by specific reference.

BACKGROUND

An intervertebral disc is a soft tissue compartment connecting the vertebra bones in a spinal column. Each healthy disc consists of two parts, an outer annulus fibrosis (hereinafter "the annulus") and an inner nucleus pulposes (hereinafter "the nucleus"). The annulus completely circumscribes and encloses the nucleus. The annulus is connected to its adjacent associated pair of vertebrae by collagen fibers. The intervertebral disc is an example of a soft tissue compartment adjoining first and second bones (vertebra) having an initial height and an initial width. Other joints consisting of a soft tissue compartment adjoining at least first and second bones having an initial height and an initial width include the joints of the hand, wrist, elbow, shoulder, foot, ankle, knee, hip, and the like.

Typically, when a disc is damaged, the annulus ruptures and the nucleus herniates. Discectomy surgery removes the extruded nucleus, leaving behind the ruptured annulus. The ruptured annulus is, by itself, ineffective in controlling motion and supporting the loads applied by the adjacent pair of vertebrae. With time, the disc flattens, widens, and bulges, compressing nerves and producing pain. Uncontrolled loads are transmitted to each vertebra. Each vertebra tends to grow wider in an attempt to distribute and compensate for higher loads. When a vertebra grows, bone spurs form. The bone spurs further compress nerves, producing pain. In response to damaged discs, especially herniated disks, a variety of intervertebral devices are disclosed in the art to replace the intervertebral disc. Such devices are implanted intermediate an adjacent pair of vertebra, and function to assist the vertebra. These devices do not assist the intervertebral disc. In fact, in many cases the disc is removed. Insertion of these devices has heretofore been complicated, problematic, and usually performed blindly or with only fluoroscopy or other radioimaging techniques.

In view of the foregoing, it would be advantageous to have implantation devices, systems, and methods that allow for visualization of the disc as well as the implantation of a medical device between adjacent vertebra using endoscopy.

SUMMARY

In one embodiment, an intervertebral implant can include: a tapered arcuate shape. The implant can include a solid non-elastic portion. The implant can include an implant-suitable material, such as a biocompatible metal or polymer or ceramic or composite or combination thereof. The implant can be at least partially porous, and optionally, the pores can be filed with a biodegradable material that can include one or more active agents, such as growth factors. Also, the implant can be formed from a hybrid of at least two implant-suitable materials. The implant can include a body having a rounded surface and a substantially flat surface. Optionally, the substantially flat surface can be opposite of the rounded surface. The rounded surface and substantially flat surface can extend from a base to a tip of the tapered arcuate shape. The base may also be substantially flat, where the tip can be rounded. The tapered arcuate shape can extend from a substantially flat base and curve to a tip of the arc.

In one embodiment, the implant can be configured in accordance with one or more of the following: the substantially flat surface can be configured to be mounted on a surface of a vertebra of two adjacent vertebras; the rounded surface can be configured to contact a surface of a vertebra of two adjacent vertebras; the implant can be configured to be secured to and only contact the surface of the vertebra; the substantially flat surface can be configured to be secured to a surface of a vertebra of two adjacent vertebras such that the other vertebra is capable of pivoting and rotating about the rounded surface; or a body having the tapered arcuate shape extending from a substantially flat base to a tip, the body having a rounded surface and a substantially flat surface opposite of the rounded surface, the surfaces extending between the base and tip of a body having the tapered arcuate shape extending from a substantially flat base to a tip, the body having a rounded surface and a substantially flat surface opposite of the rounded surface, the surfaces extending between the base and tip.

In one embodiment, an implant can include a spring that is configured to generate force between two adjacent vertebras when the spring is loaded.

In one embodiment, the implant can be configured for implantation between two adjacent vertebras. That is, the implant can be configured to be implanted between the facing surfaces of two adjacent vertebras. This can include the implant being completely within a peripheral edge of one of the facing surfaces of the adjacent vertebras. Also, the implant can be dimensioned to be implanted between and edge portion (e.g., periphery) and center of the two adjacent vertebras.

In one embodiment, the tapered arcuate shape can be configured to align two adjacent vertebras. The alignment can be performed by the implant rotating the two adjacent vertebras around the tapered arcuate shaped implant in three axes of rotation. At least two axes of rotation can be relative to the sagittal and coronal planes and one of the axes is the vertical axis of rotation. In one aspect, the tapered arcuate shape is configured to align two adjacent vertebras by: rotating surfaces of the two adjacent vertebras around the tapered arcuate implant in at least one axis of rotation; and/or rotating the surfaces of the two adjacent vertebras around a vertical axis of rotation. In one aspect, the tapered arcuate shape can be configured to provide rotation about a vertical axis of rotation from a wide portion to a tip of the tapered arcuate shape in the direction of its arc. In one aspect, the tapered arcuate shape can include a surface configured to be secured to a surface of a vertebra between two adjacent vertebras. In one aspect, the tapered arcuate shape can include a surface configured to pivotally contact a surface of a vertebra between two adjacent vertebras. In one aspect, the tapered arcuate shape includes a surface configured to pivotally and rotatably contact a surface of a vertebra between two adjacent vertebras.

In one embodiment, mechanically aligned adjacent vertebras can include the tapered arcuate implant located between the adjacent vertebras. The tapered arcuate implant can be configured as described herein. The implant can be in the disc between the two adjacent vertebras. The implant can align the two adjacent vertebras by imparting a mechanical action. The mechanically aligned adjacent vertebras that contain the implant can be from a spine having scoliosis, lordosis, and/or kyphosis without the implanted tapered arcuate implant between the adjacent vertebras. The tapered arcuate implant can provide a therapy for these ailments.

In one embodiment, a method of treating adjacent vertebras can include: providing the implant as described herein; and inserting the implant between two adjacent and misaligned vertebras so as to align the two adjacent vertebras. The two adjacent vertebras can include a vertical axis of rotation, a first vertebra having a bottom surface, and a second vertebra having a top surface. Optionally, the adjacent vertebras can include a vertical axis of rotation, a first vertebra having a bottom surface that faces a top surface of a second vertebra.

In one embodiment, the method can include at least one or only one of the following: contacting the implant with the top surface of the second vertebra, and securing the implant to the top surface of the second vertebra; contacting the implant with the top surface of the second vertebra without contacting the bottom surface of the first vertebra, and securing the implant to the top surface of the second vertebra; or contacting the implant with the top surface of the second vertebra without contacting the bottom surface of the first vertebra or securing the implant to the top surface of the second vertebra; or contacting the implant with the top surface of the second vertebra without securing the implant to the top surface of the second vertebra; or contacting the implant with the bottom surface of the first vertebra, and securing the implant to the bottom surface of the first vertebra; or contacting the implant with the bottom surface of the first vertebra without contacting the top surface of the second vertebra, and securing the implant to the bottom surface of the first vertebra; or contacting the implant with the bottom surface of the first vertebra without contacting the top surface of the second vertebra or securing the implant to the bottom surface of the first vertebra; or contacting the implant with the bottom surface of the first vertebra without securing the implant to the bottom surface of the first vertebra; or contacting the implant with the bottom surface of the first vertebra and top surface of the second vertebra.

In one embodiment, a method of treating adjacent vertebras can include: selecting the tapered arcuate implant as described herein; identifying two adjacent vertebras having a vertical axis of rotation and adjacent surfaces being nonparallel; and inserting the tapered arcuate implant between the vertebras at a location between the vertical axis of rotation and edge portions of the two adjacent vertebras; and rotating the two adjacent vertebras around the tapered arcuate implant in at least one axis of rotation. The method can also include rotating the two adjacent vertebras so as to be about parallel. In one aspect, the method can include rotating the two adjacent vertebras around the implant in at least two axes of rotation, wherein the at least two axes of rotation are relative to at least one of the sagittal, coronal planes, and vertical axis of rotation. In one aspect, the method can include rotating the two adjacent vertebras around the implant in at least three axes of rotation.

In one embodiment, the method of treating adjacent vertebras can include locating the implant to be closer to the edge portions of the two adjacent vertebras than the vertical axis of rotation. Alternatively, the method of treating adjacent vertebras can include locating the implant to be closer to the vertical axis of rotation than the edge portions.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 12 is a side elevation view illustrating a bulging disc intermediate a pair of vertebrae;

FIG. 13 is a side elevation view illustrating the disc and vertebrae of FIG. 12 after internal traction;

FIG. 14 is a side elevation view illustrating a rubber band or string that has a bulge similar to the bulge formed in a intervertebral disc;

FIG. 15 is a side elevation view illustrating the rubber band of FIG. 14 after it has been tensioned to remove the bulge;

FIG. 31 is a side section view illustrating the mode of operation of the spring apparatus of FIG. 30;

FIG. 31A is a front perspective view of the spring apparatus of FIG. 31;

FIG. 34 is a perspective view illustrating the general relationship of the spine and anatomical planes of the body;

FIG. 35 is a perspective view illustrating the use of an apparatus to pivot in one rotational direction one member with respect to another adjacent member;

FIG. 36 is a perspective view illustrating the use of the apparatus of FIG. 35 to pivot in one rotational direction one vertebra with respect to an adjacent vertebra;

FIG. 46A is a section view illustrating the instrument of FIG. 46 and taken along section line 46A-46A;

FIG. 47A is a section view illustrating the instrument of FIG. 47 and taken along section line 47A-47A;

FIG. 47B is a top view illustrating another instrument constructed in accordance with the invention;

FIG. 47C is a side view illustrating the instrument of FIG. 47B;

FIG. 47D is a top view illustrating a further instrument constructed in accordance with the invention;

FIG. 48A is a section view illustrating the instrument of FIG. 48 and taken along section line 48A-48A;

FIG. 49A is a section view illustrating the instrument of FIG. 49 and taken along section line 49A-49A;

FIG. 50 is a top view further illustrating the insertion of the instrument of FIG. 43 in an intervertebral disc along a wire;

FIG. 51 is a side view further illustrating the instrument of FIG. 43;

FIG. 52 is a side view of an instrument that functions both to produce an opening in the tissue and to insert an implant once the opening has been produced;

FIG. 57 is a top view illustrating an intervertebral implant;

FIG. 58 is a front view illustrating the implant of FIG. 57;

FIG. 59 is a bottom view illustrating the implant of FIG. 57;

FIG. 60 is a side view illustrating the implant of FIG. 57;

FIG. 61 is a back view of the implant of FIG. 57;

FIG. 62 is a top view illustrating an intervertebral implant;

FIG. 63 is a side view illustrating the implant of FIG. 62;

FIG. 64 is a bottom view illustrating the implant of FIG. 62;

FIG. 65 is a back view illustrating the implant of FIG. 62;

FIG. 66 is a section view illustrating the implant of FIG. 63 and taken along section line a-a in FIG. 63;

FIG. 67 is a top perspective view illustrating the implant of FIG. 62;

FIG. 68 is a bottom perspective view illustrating the implant of FIG. 62;

FIG. 69 is a bottom view illustrating an intervertebral implant;

FIG. 70 is a left hand side view illustrating the implant of FIG. 69;

FIG. 71 is a right hand side view illustrating the implant of FIG. 69;

FIG. 72 is a top view illustrating the implant of FIG. 69;

FIG. 77 is a perspective view illustrating an intervertebral implant;

FIG. 78 is a side view illustrating the implant of FIG. 77;

FIG. 79 is a top view illustrating the implant of FIG. 77;

FIG. 80 is an end view illustrating the implant of FIG. 77;

FIG. 81 is a side view illustrating an intervertebral implant;

FIG. 82 is an end view illustrating the implant of FIG. 81;

FIG. 83 is a top view illustrating the implant of FIG. 81;

FIG. 84 is a perspective view illustrating the implant of FIG. 81;

FIG. 85 is a back view illustrating the implant of FIG. 81;

FIG. 86 is a perspective view illustrating an intervertebral implant;

FIG. 87 is a side view of the implant of FIG. 86;

FIG. 88 is a perspective view illustrating an intervertebral implant;

FIG. 89 is a side view of the implant of FIG. 88;

FIG. 100 is a perspective view illustrating a unitary intervertebral implant;

FIG. 101 is an end view illustrating the implant of FIG. 100;

FIG. 102 is a side view illustrating the implant of FIG. 100;

FIG. 108 is an end view illustrating the implant of FIG. 105;

FIG. 109 is a front view illustrating the implant of FIG. 105;

FIG. 110 is a top view illustrating an articulating intervertebral implant;

FIG. 111 is a side view illustrating the implant of FIG. 110 in alignment to slide down a guide wire;

FIG. 112 is a top section view of the implant of FIG. 110 illustrating internal construction details thereof;

FIG. 113 is perspective view illustrating a unitary intervertebral implant;

FIG. 114 is a side view illustrating the implant of FIG. 113;

FIG. 115 is a top view illustrating the implant of FIG. 113;

FIG. 116 is an end view illustrating the implant of FIG. 113;

FIG. 117 is a perspective view illustrating a unitary intervertebral implant;

FIG. 118 is a side view illustrating the implant of FIG. 117;

FIG. 119 is a top view illustrating the implant of FIG. 117;

Figure 117:
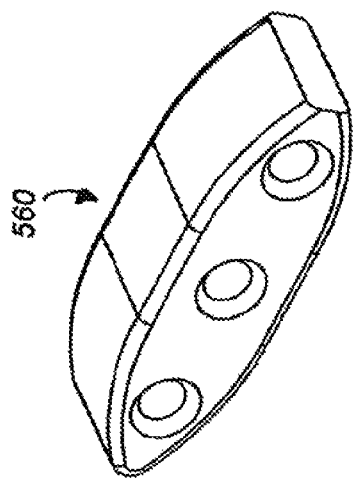
Figure 118:
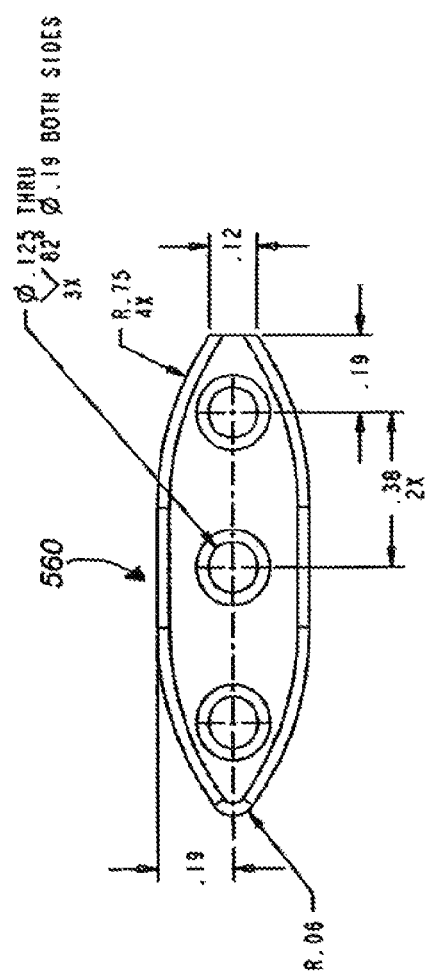
Figure 120:
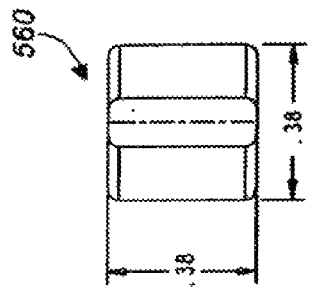
Figure 119:
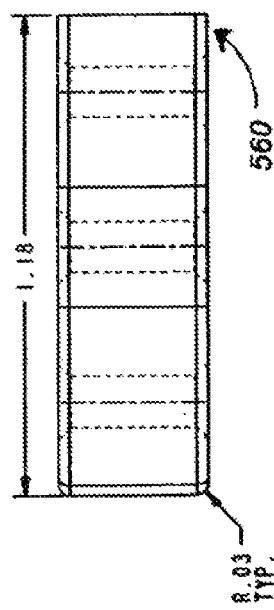
Figure 130:
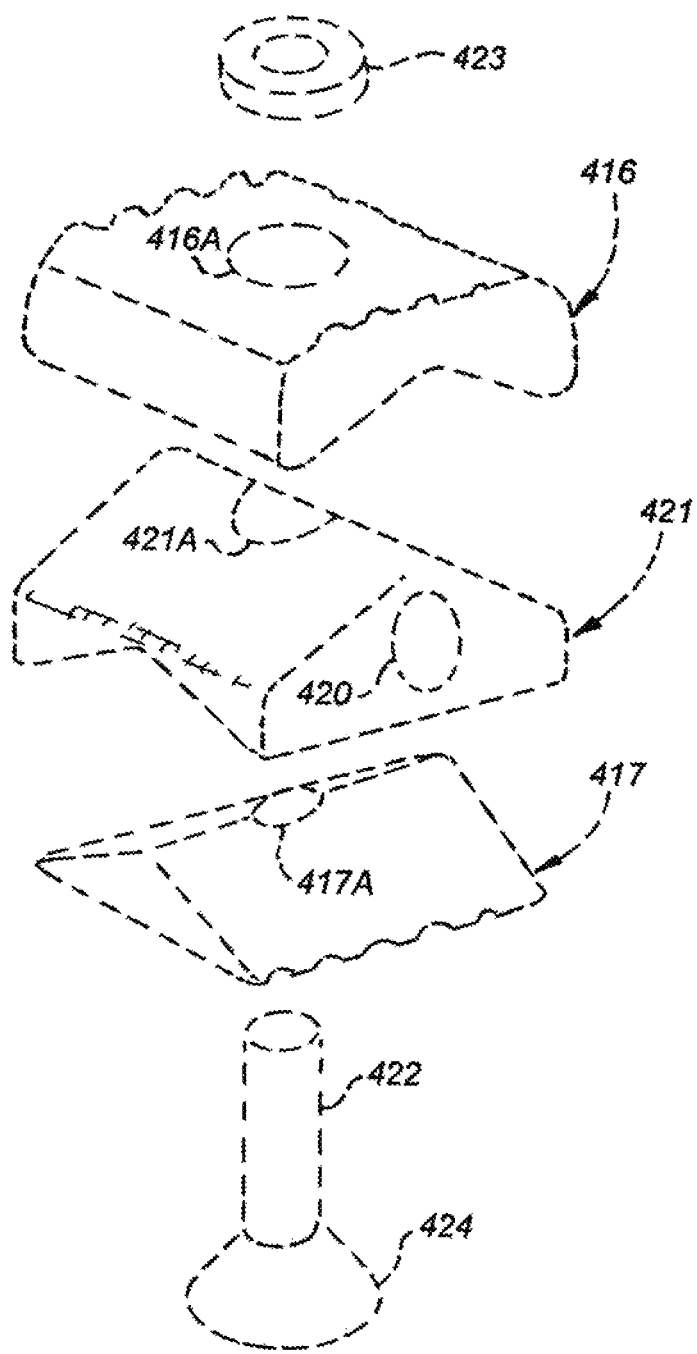
Figure 148:
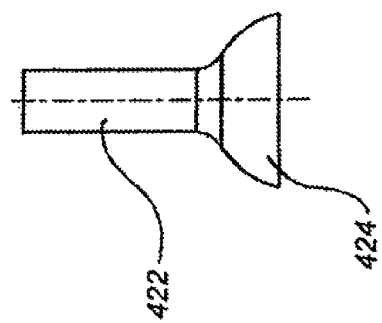
Figure 147:
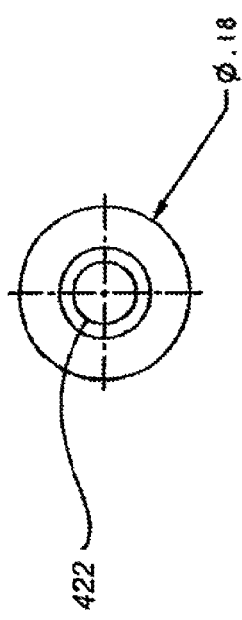
Figure 146:
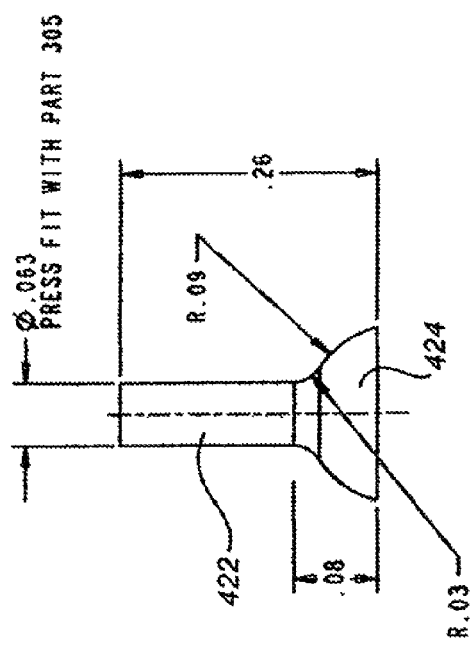
Figure 149:
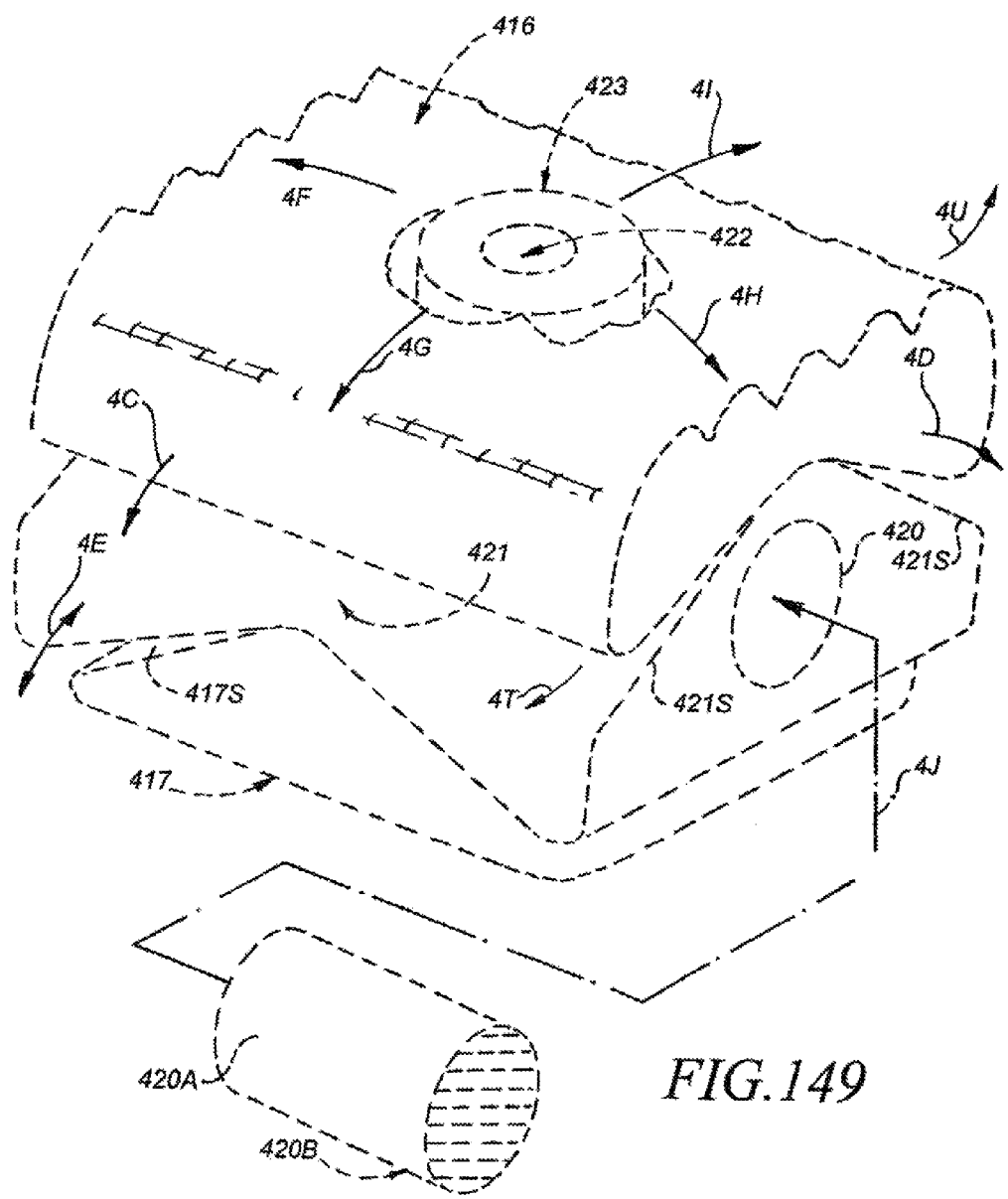
Figure 150:
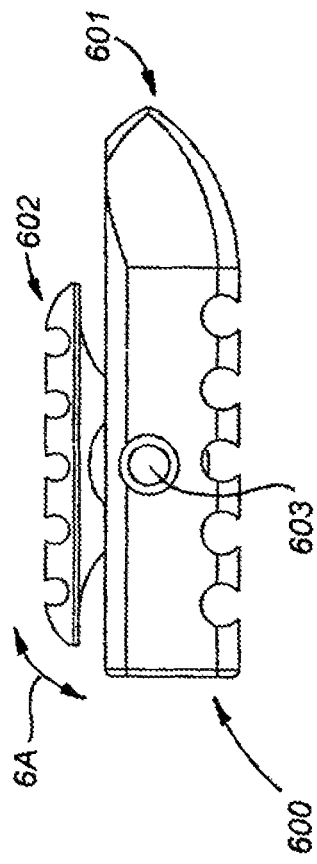
Figure 151:
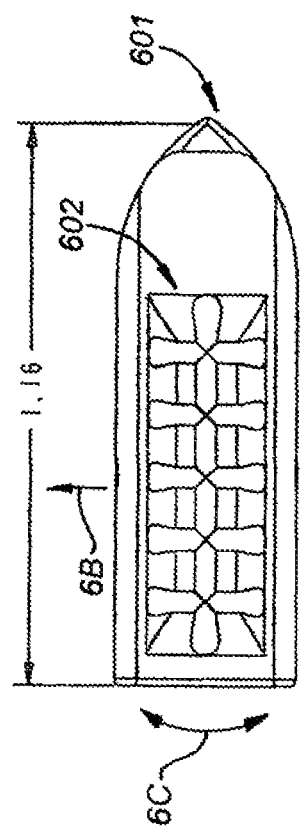
Figure 152:
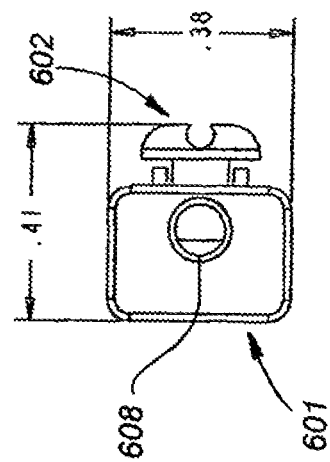
Figures 153, 154, 155, 156:
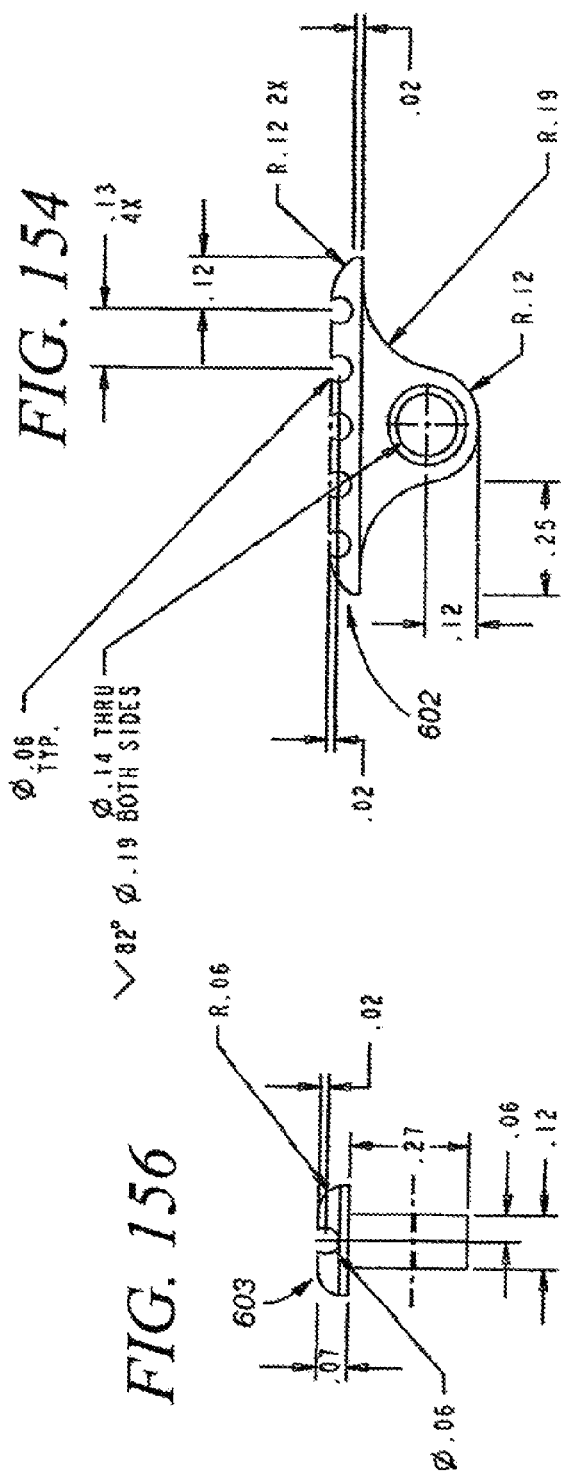
Figure 161:
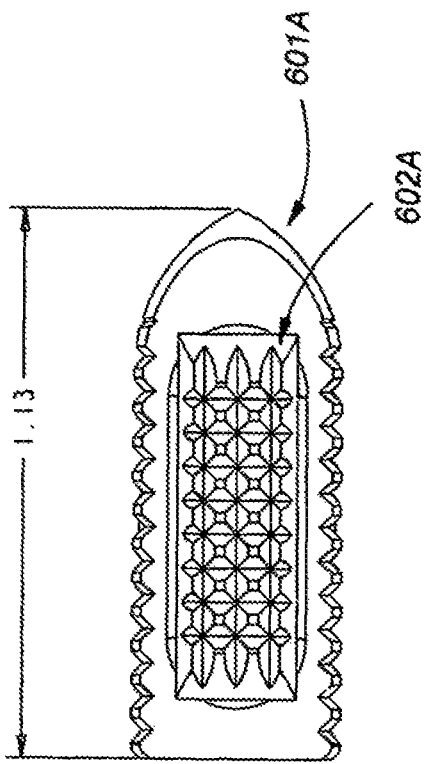
Figure 162:
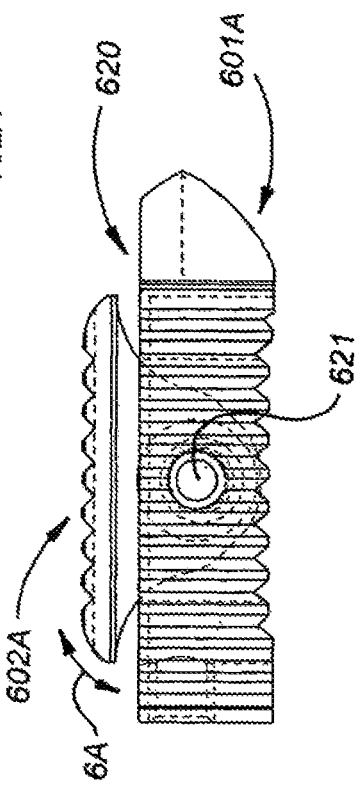
Figure 163:
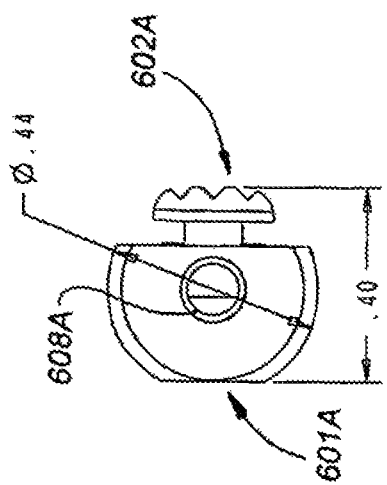
Figure 164:
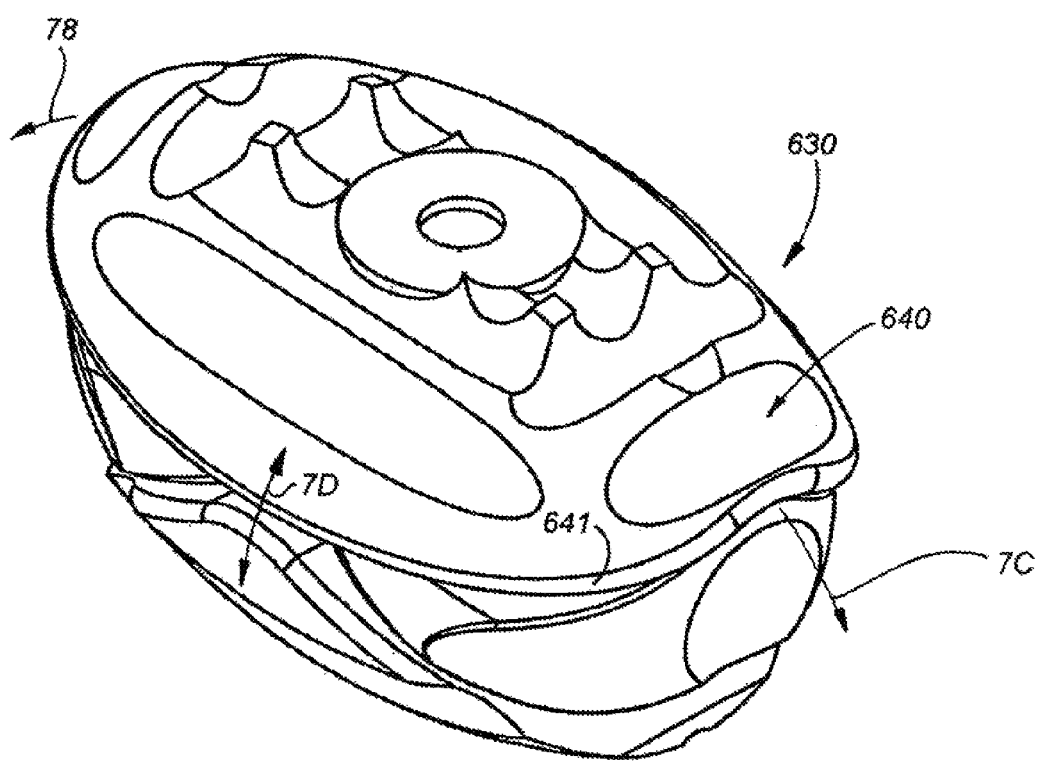
Figure 170:
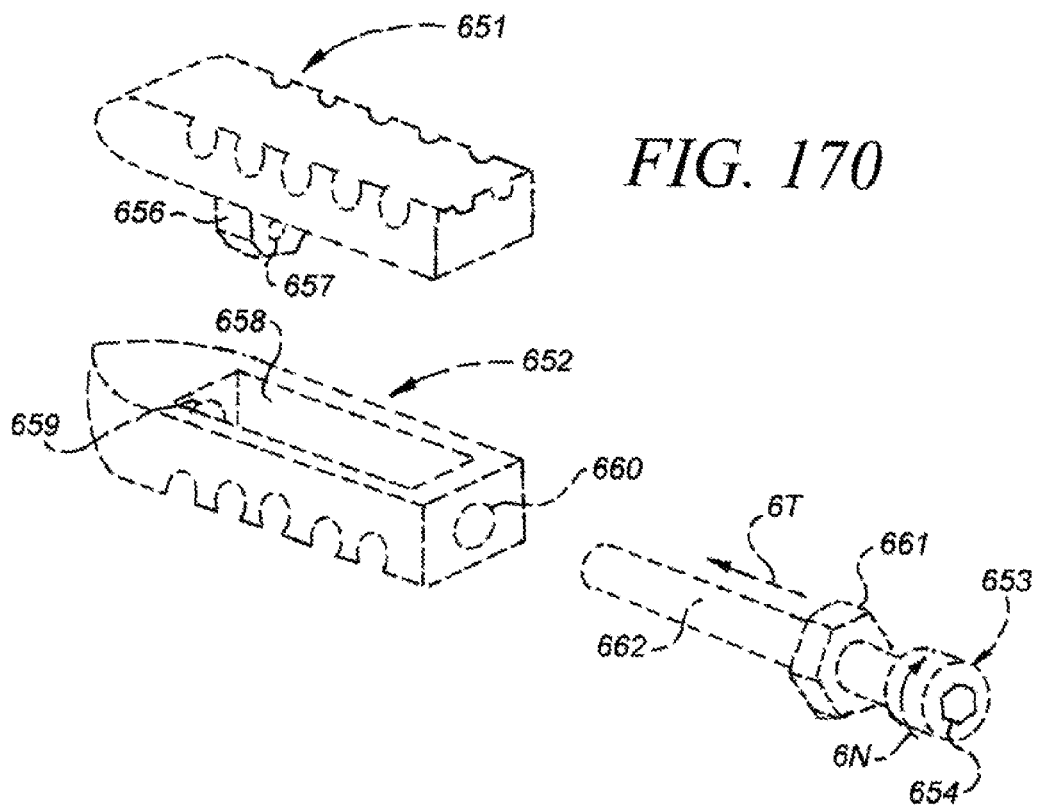
Figure 171:
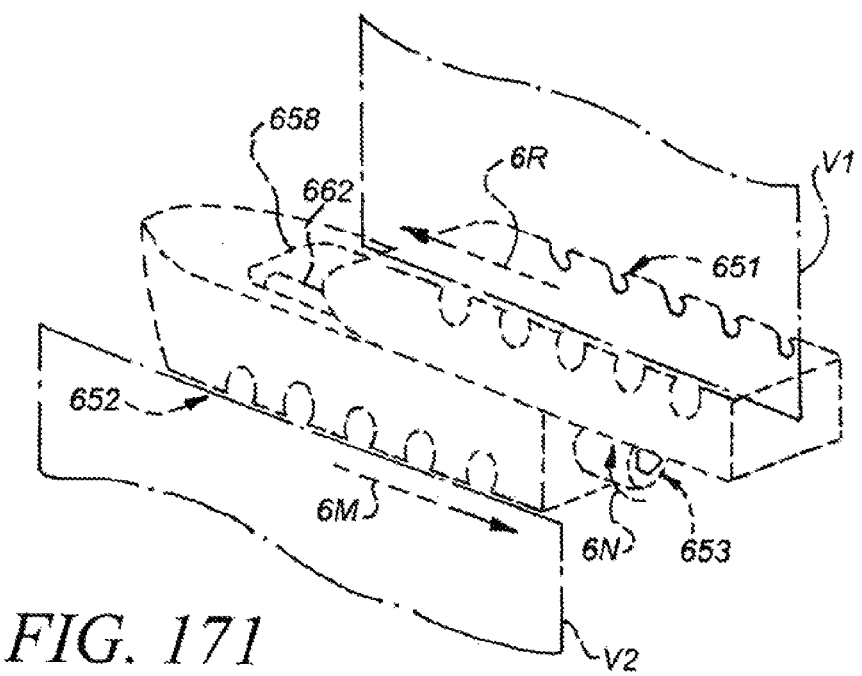
Figure 177:
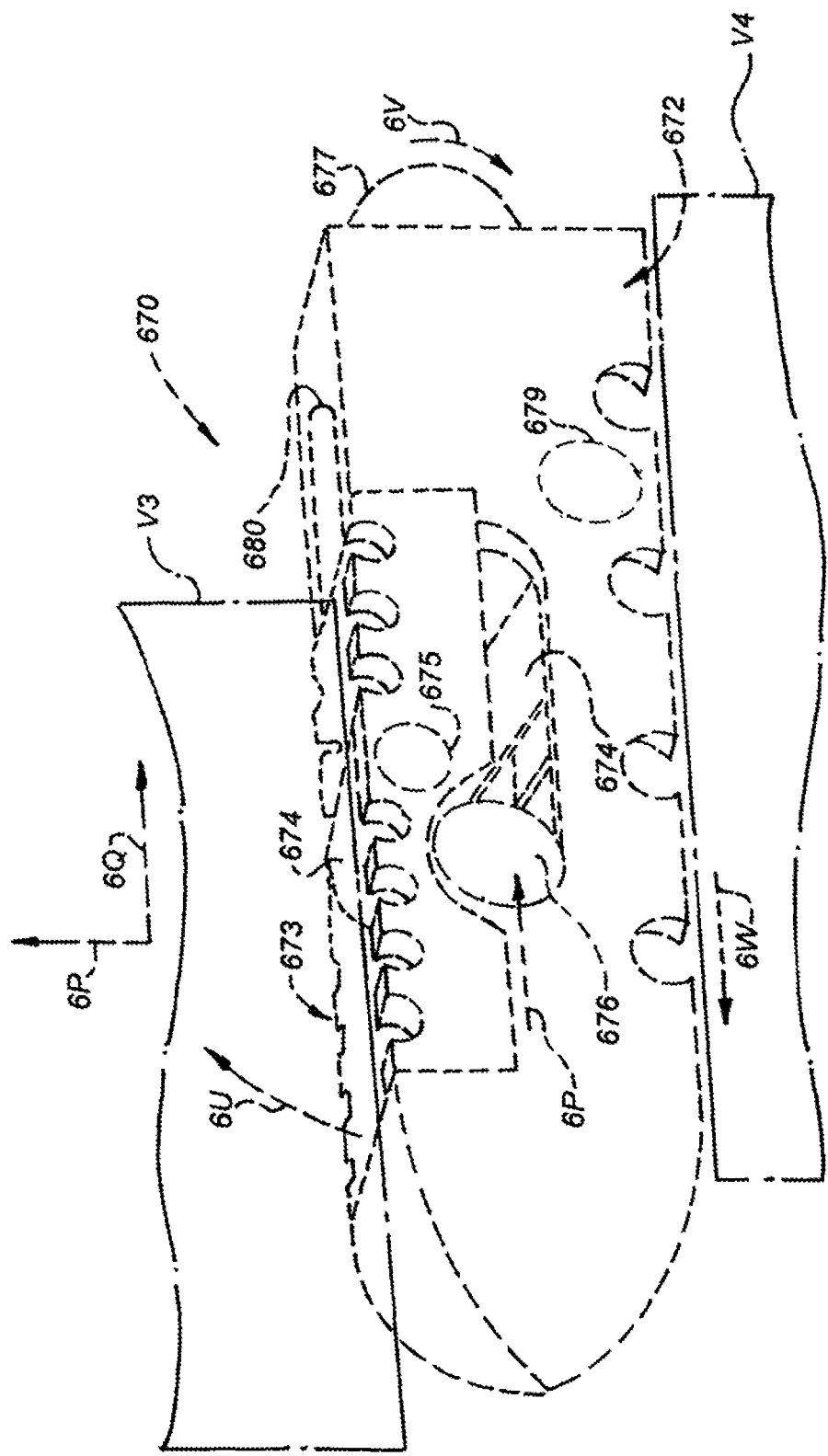
Figure 178:
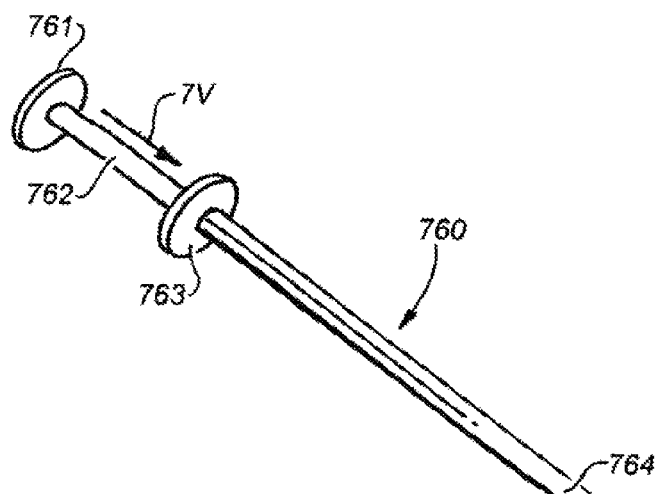
Figure 179:
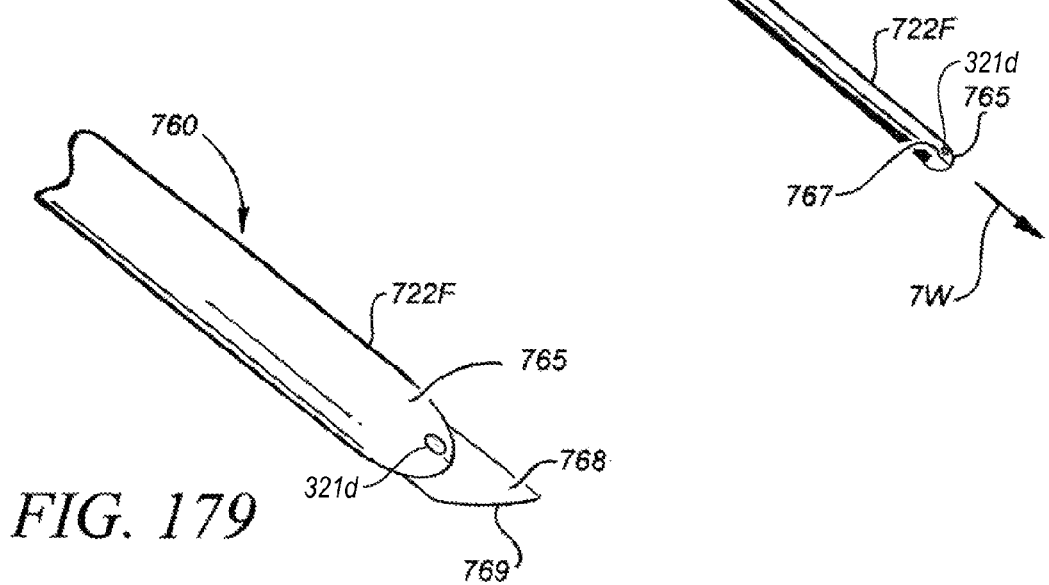
Figure 184:
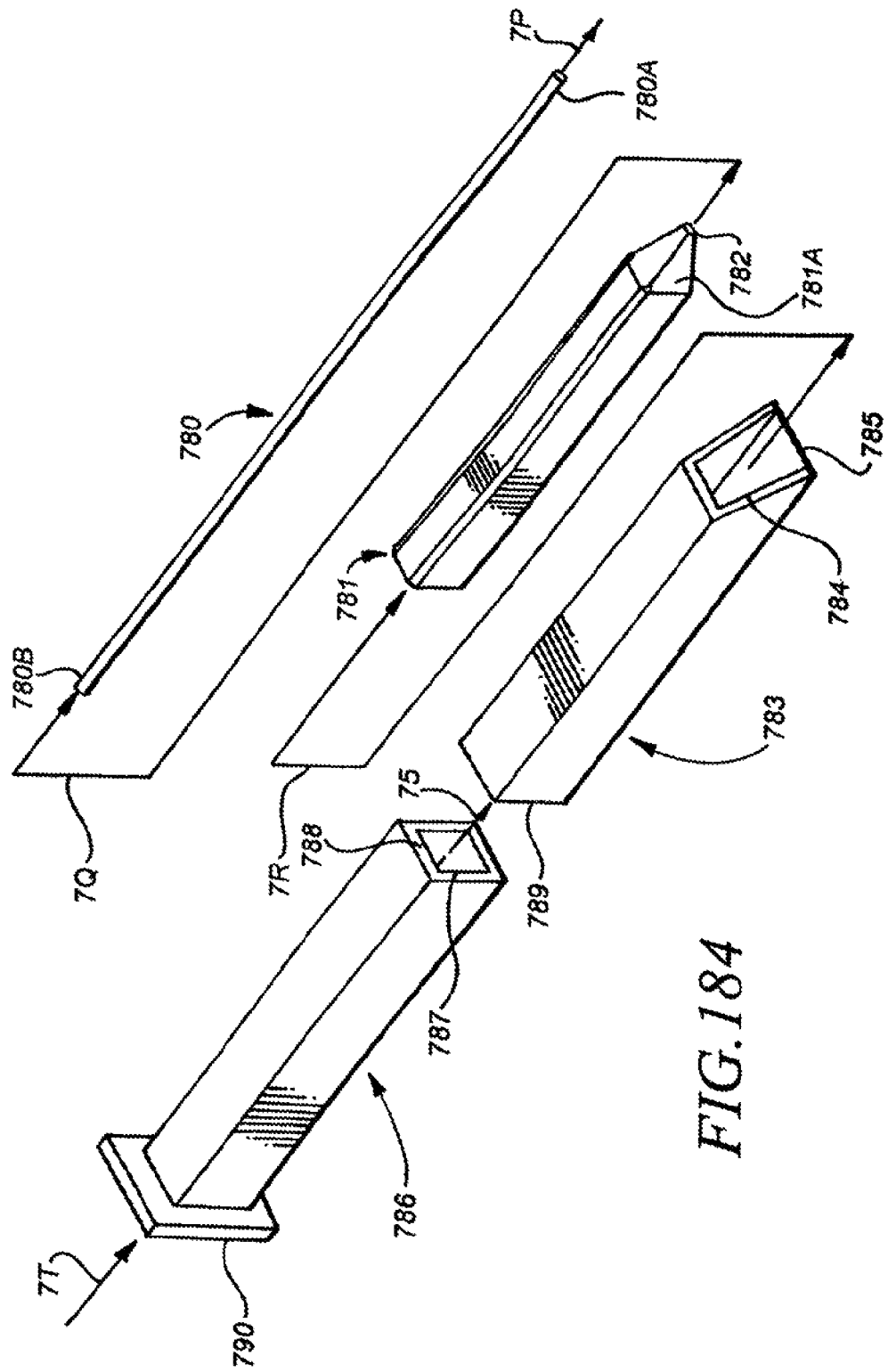
Figure 185:
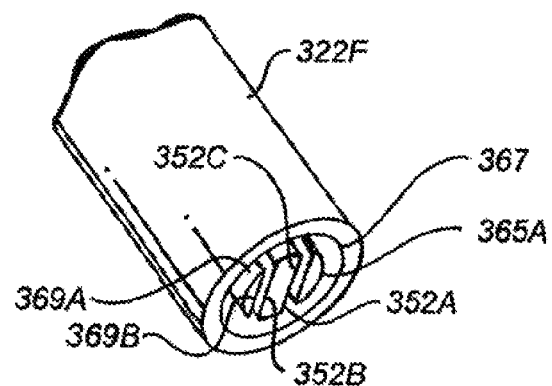
Figure 186:
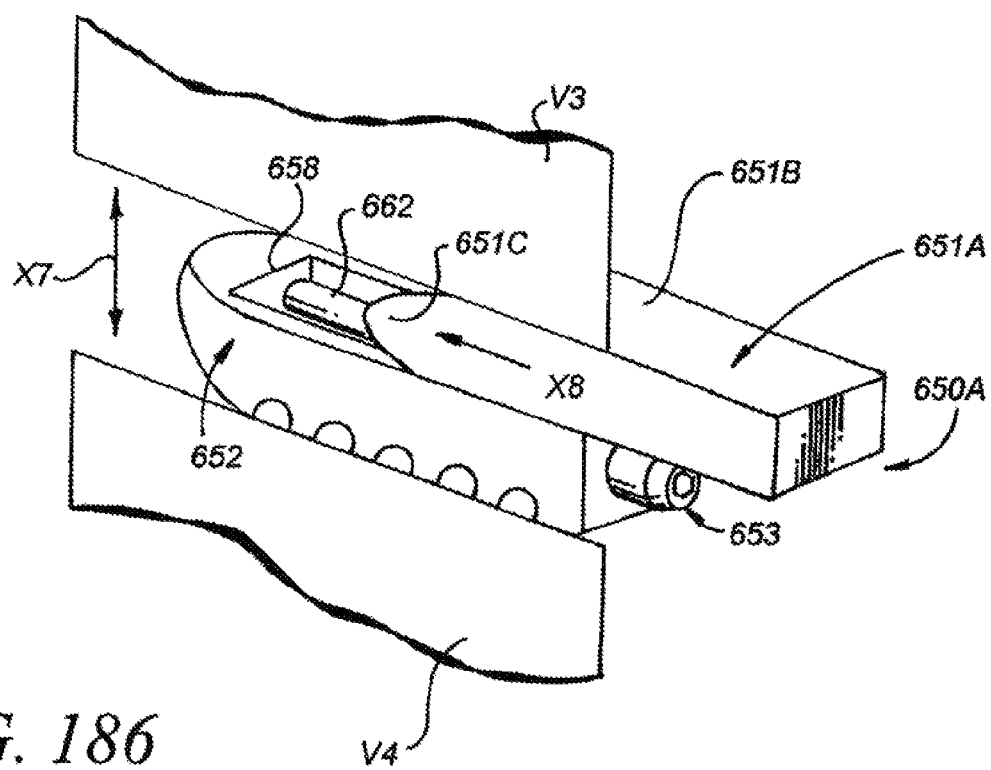
Figure 187:
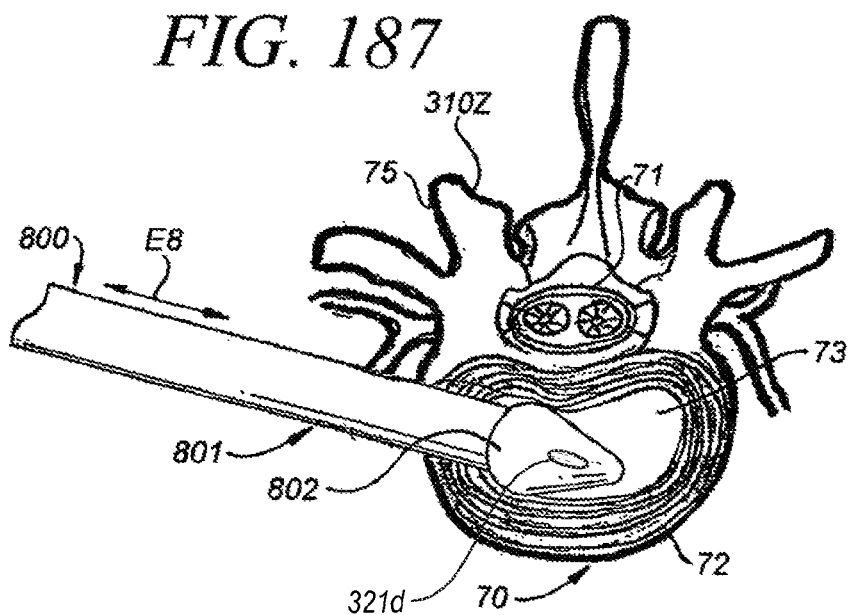
Figure 188:
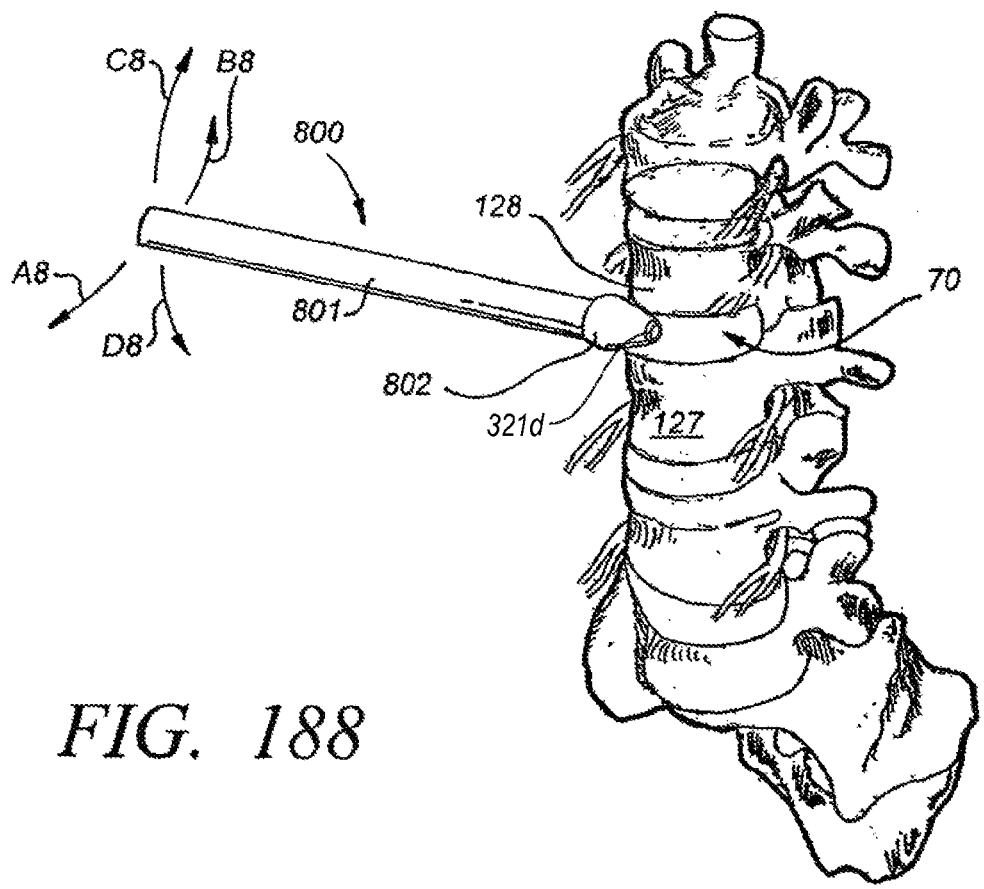
Figure 189:
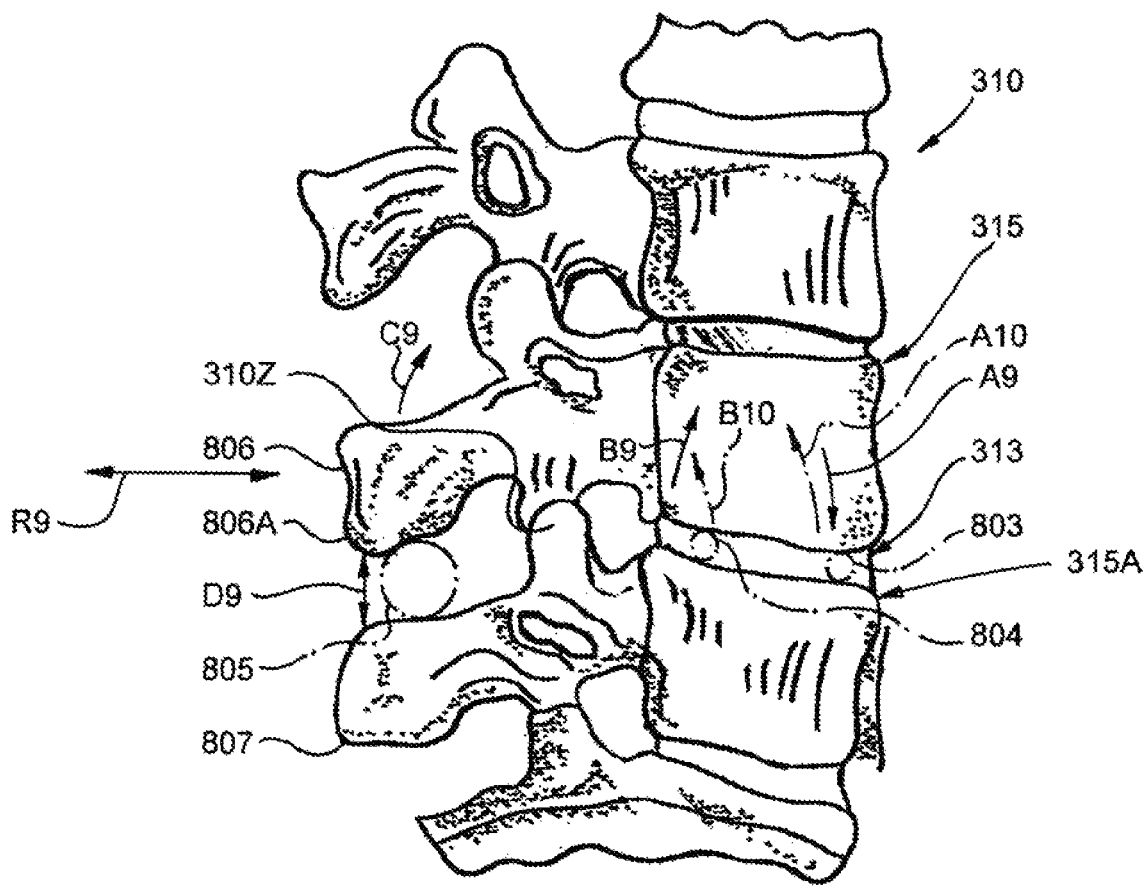
Figure 190:
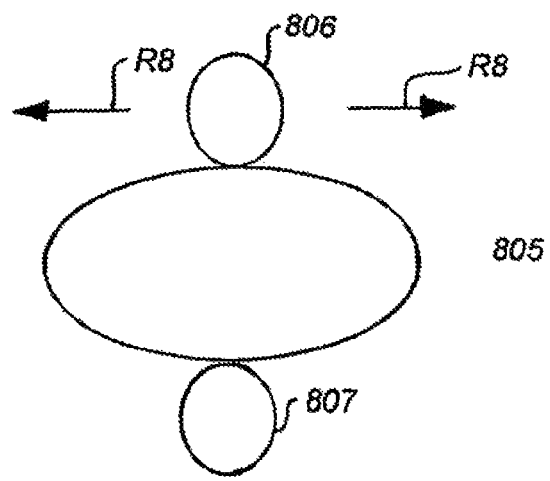
Figure 191:
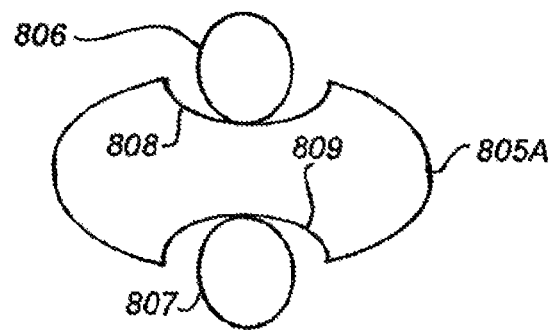
Figure 192:
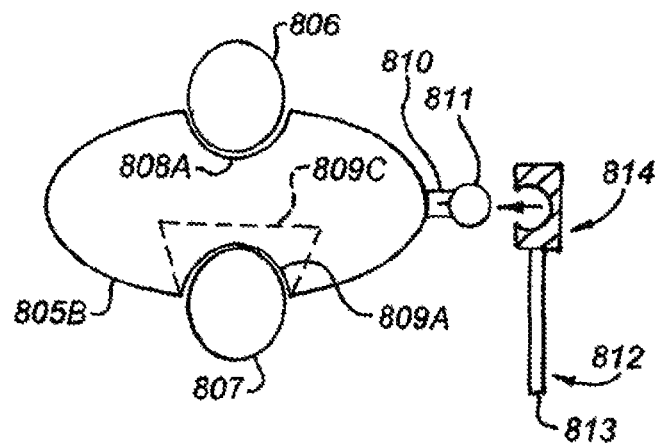
Figures 197, 198:
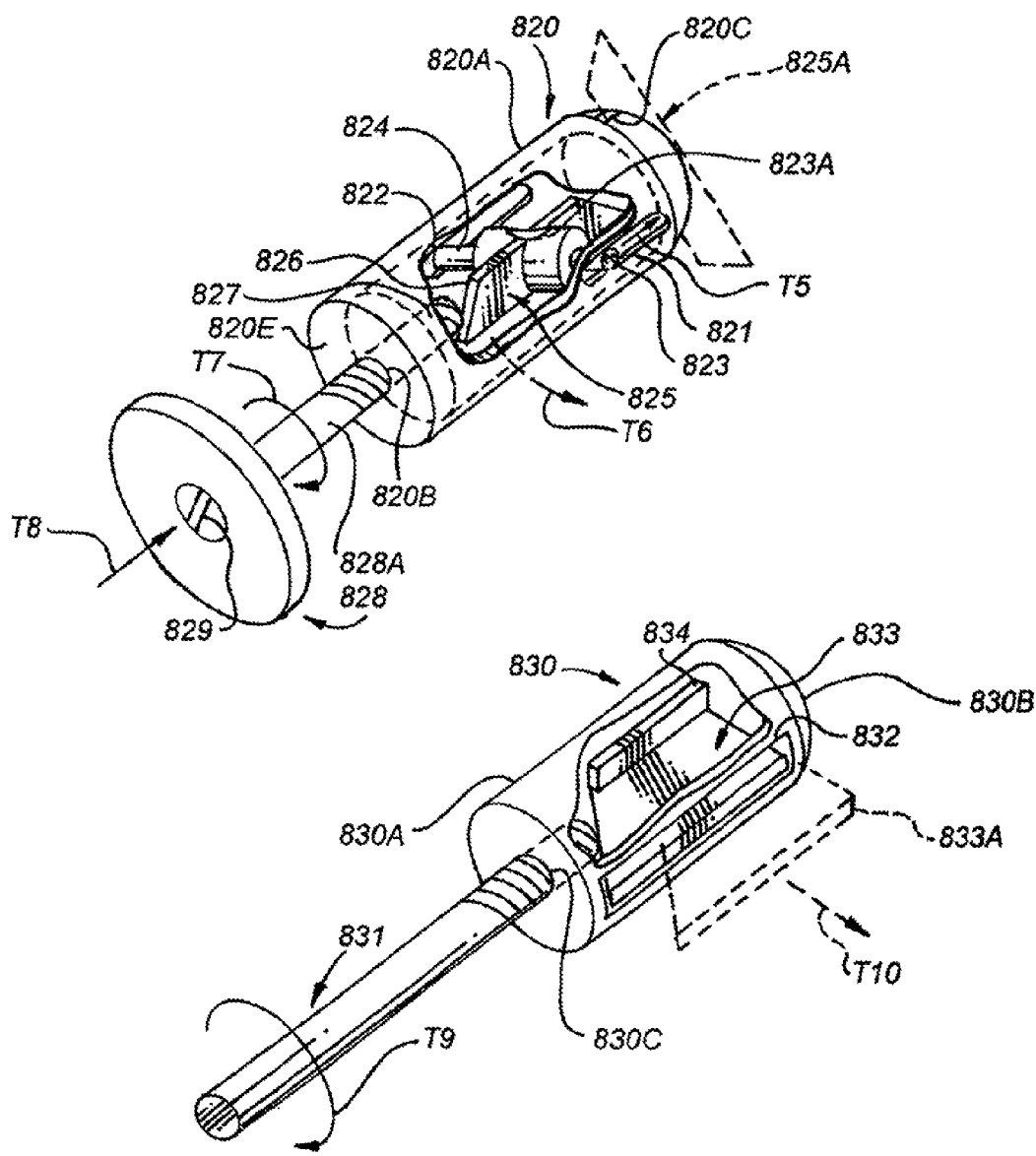
Figure 204:
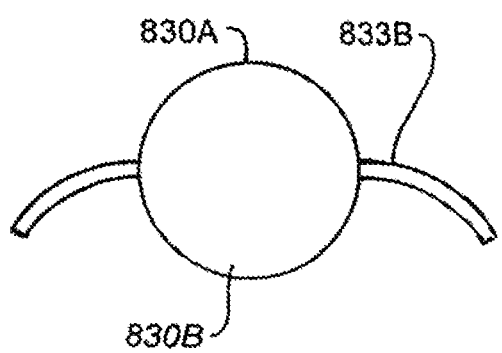
Figure 205:
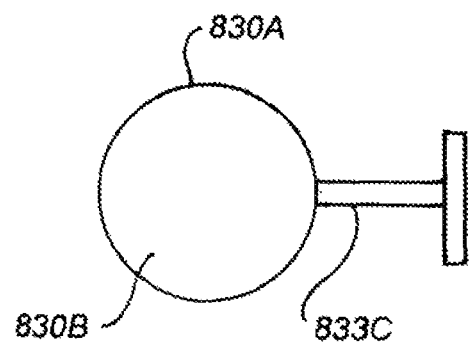
Figure 217:
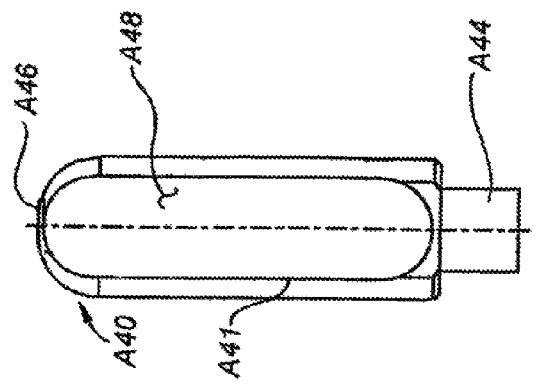
Figure 216:
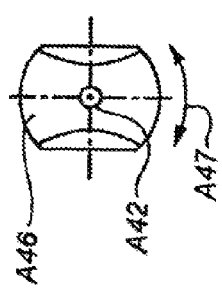
Figure 215:
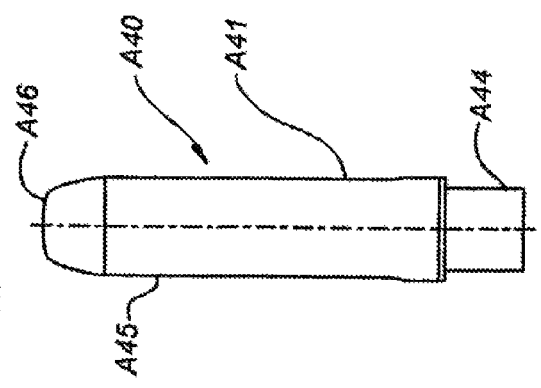
Figure 215A:
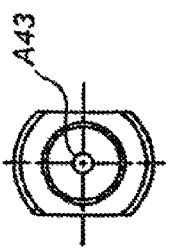
Figure 218:
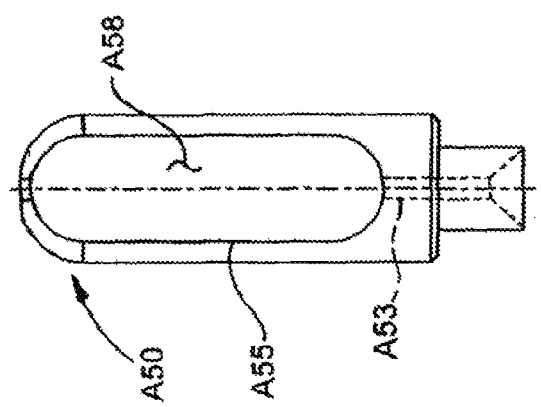
Figure 219:
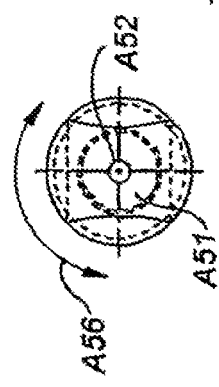
Figure 220:
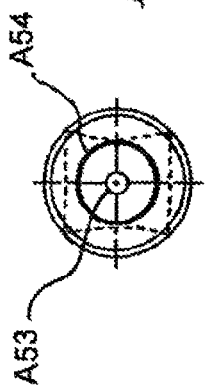
Figure 221:
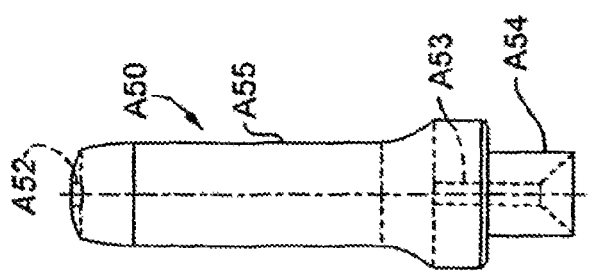
Figure 228:
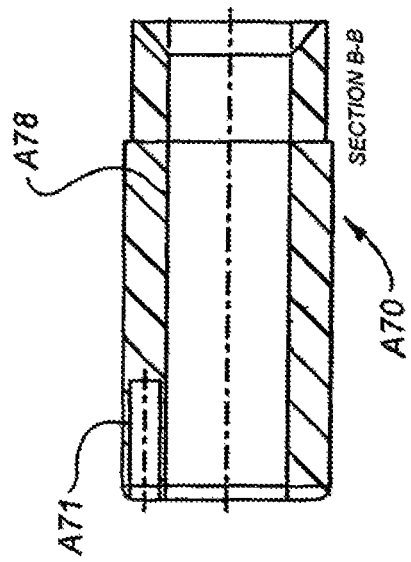
Figure 229:
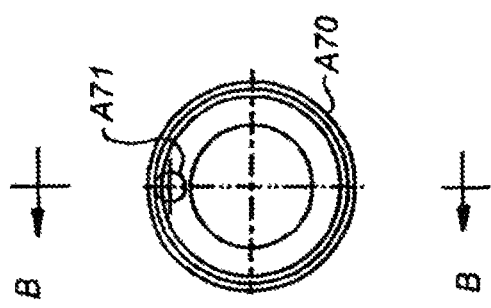
Figures 231A, 231B:
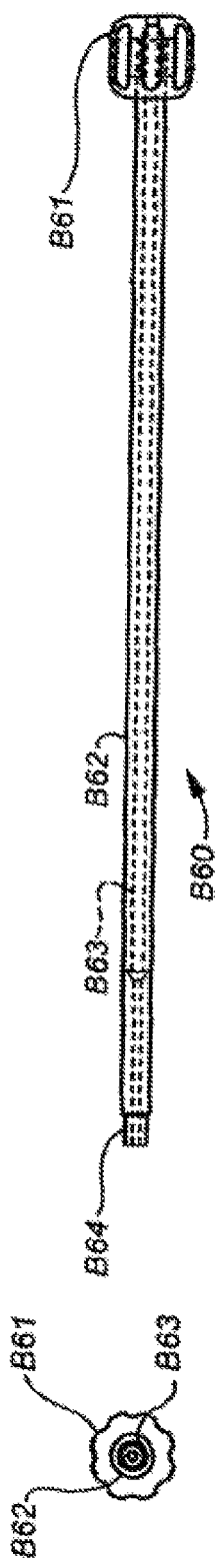
Figure 235E:
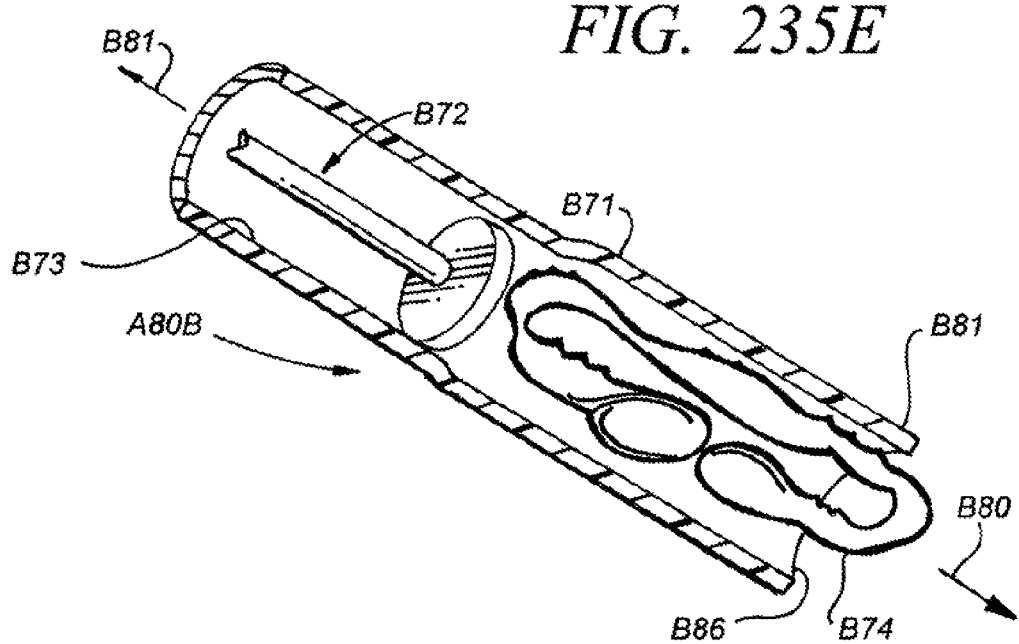
Figure 235F:
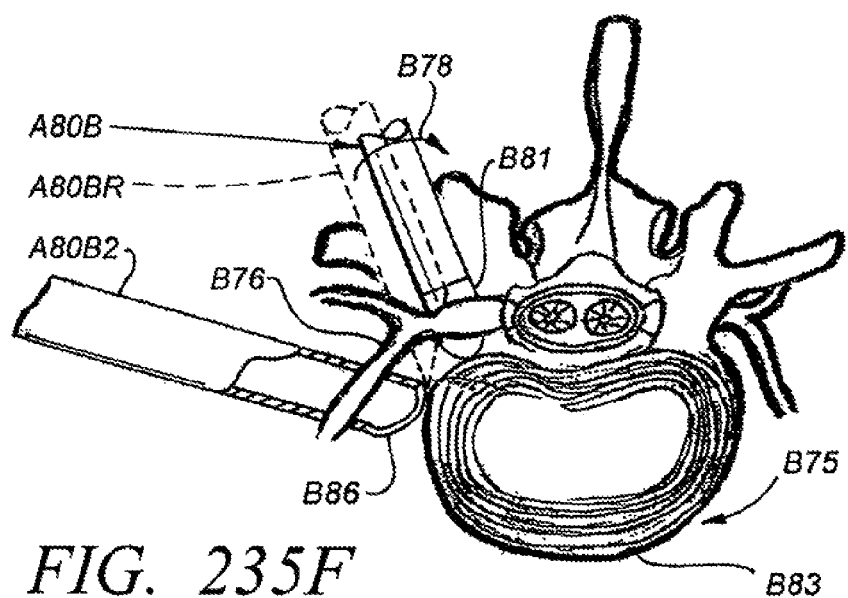
Figure 235G:
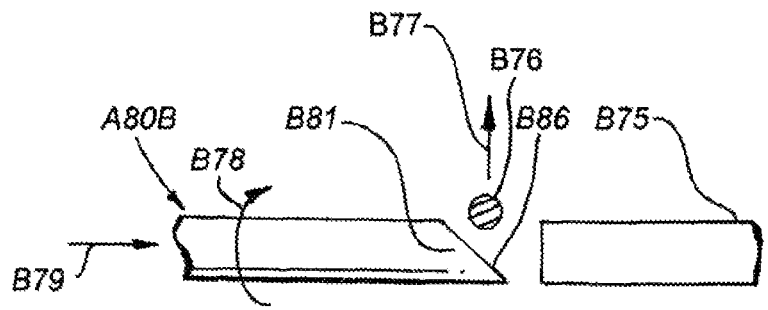
Figure 235H:
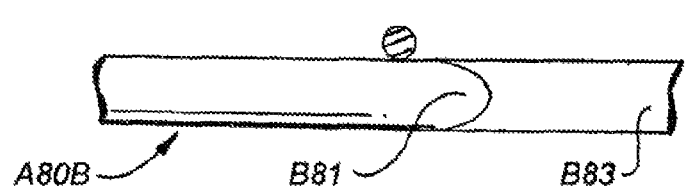
Figure 235I:
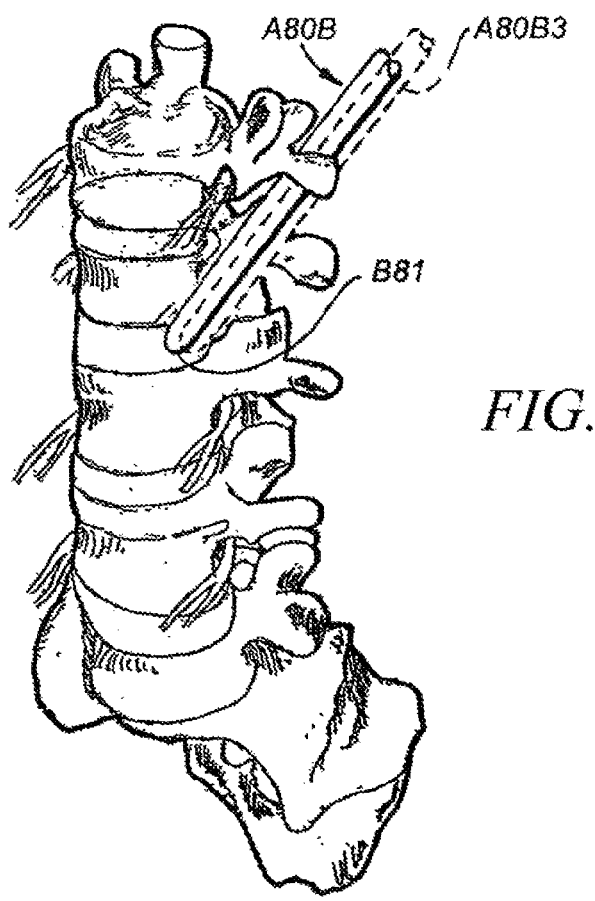
Figure 240:
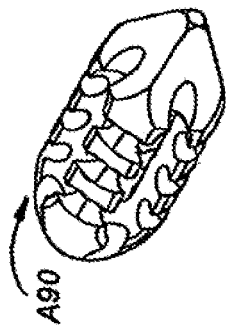
Figure 241:
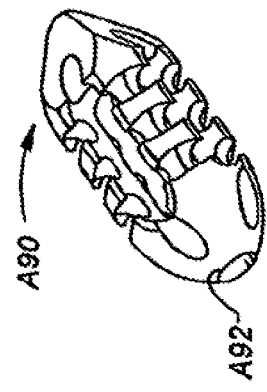
Figure 236:
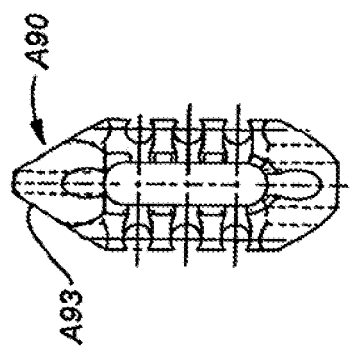
Figure 238:
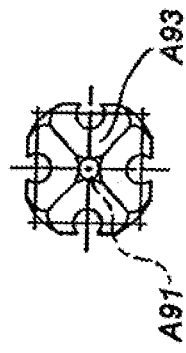
Figure 237:
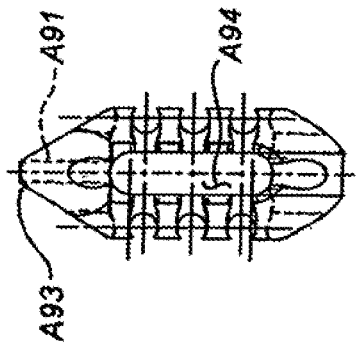
Figure 239:
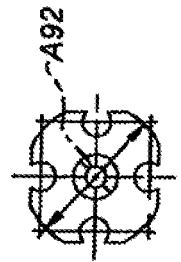
Figure 251:
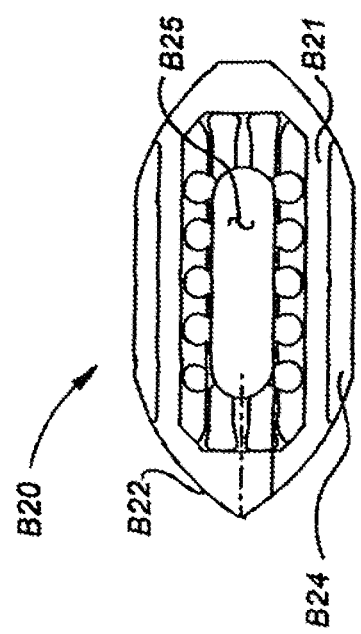
Figure 252:
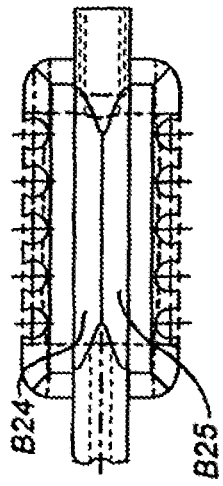
Figure 249:
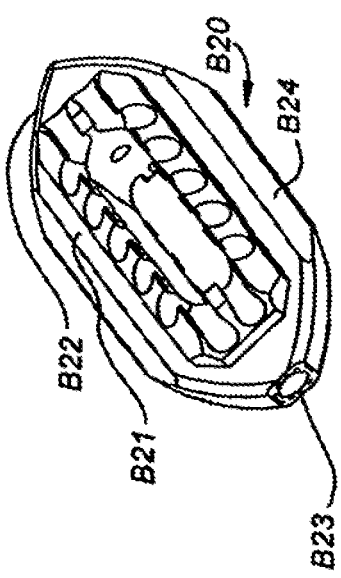
Figure 250:
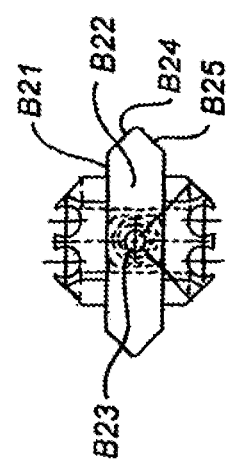
Figure 282:
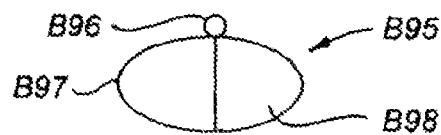
Figure 283:
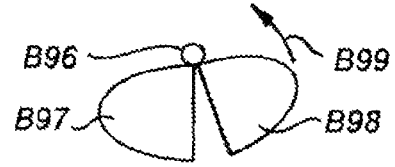
Figure 284:
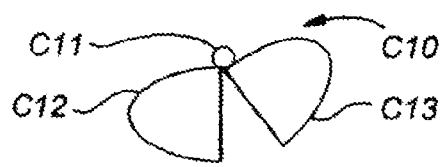
Figure 285:
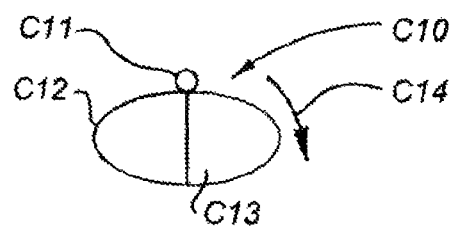
Figure 286:
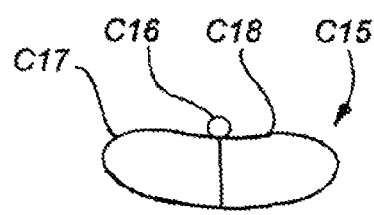
Figure 287:
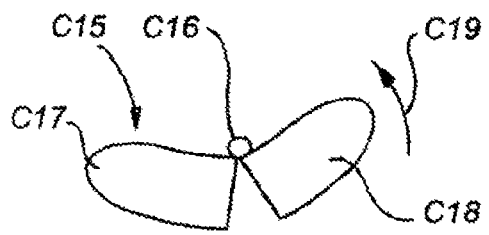
Figure 288:
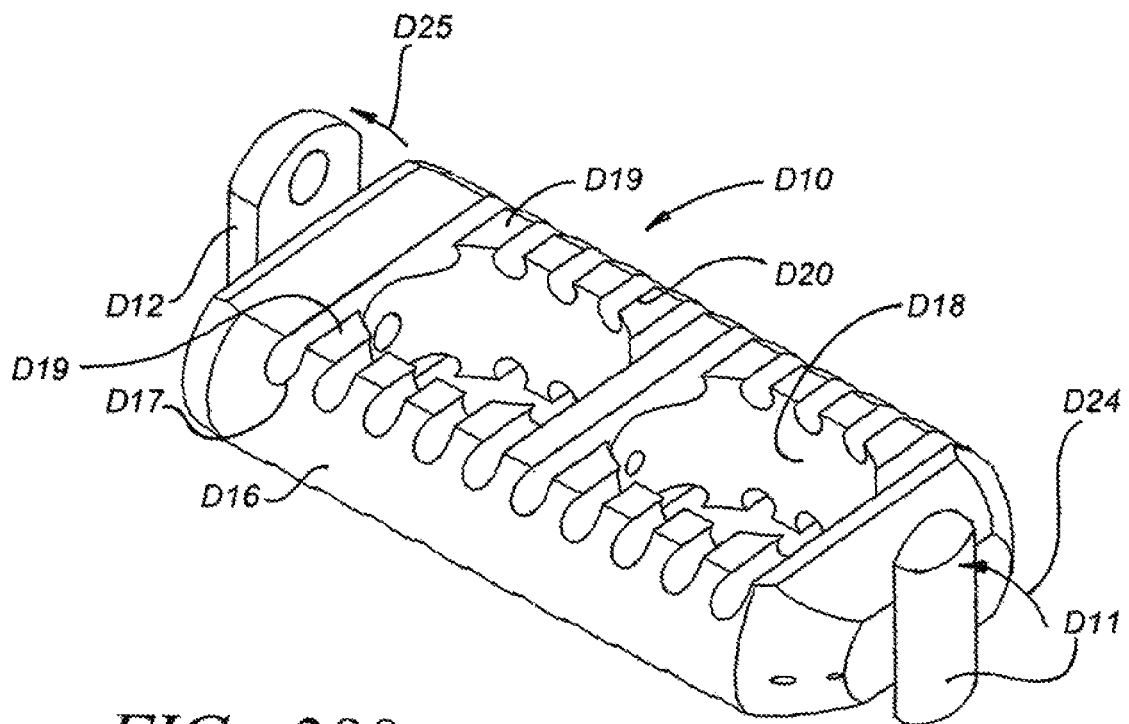
Figure 289:
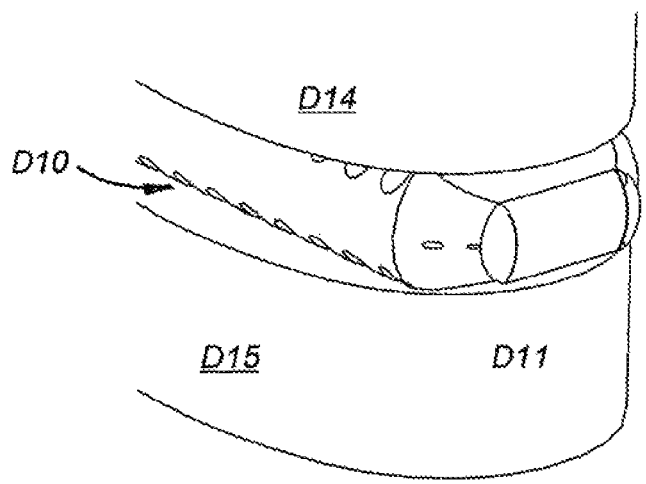
Figure 290:
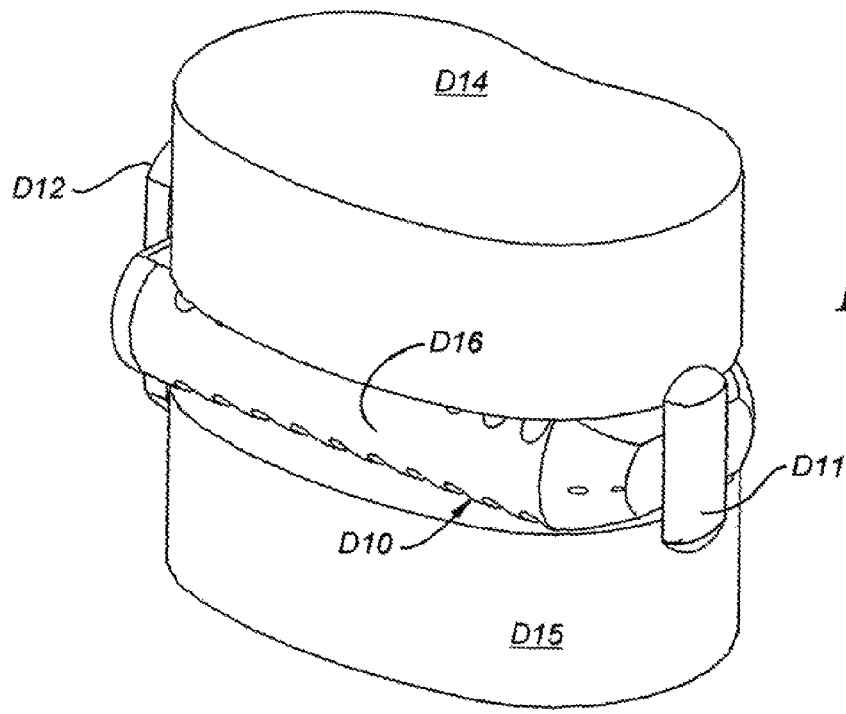
Figure 291:
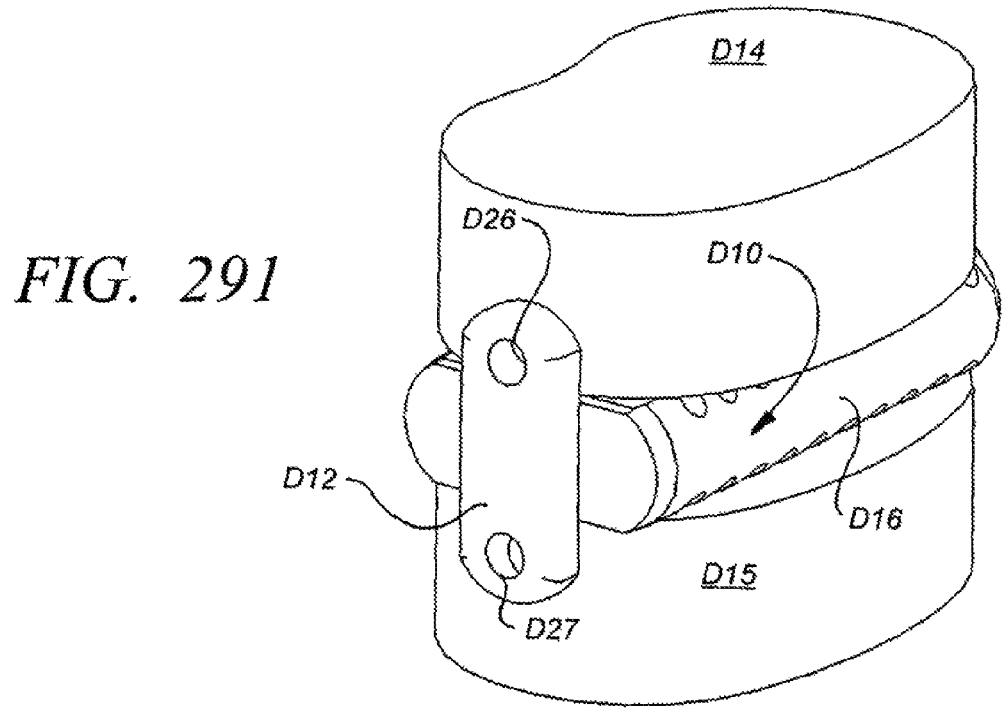
Figure 292:
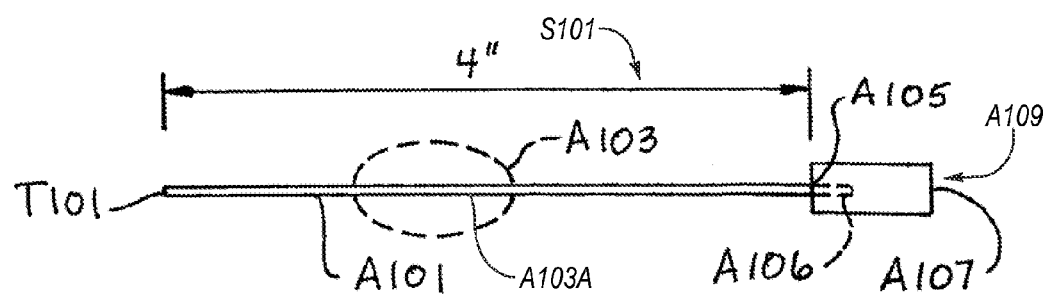
Figure 293:
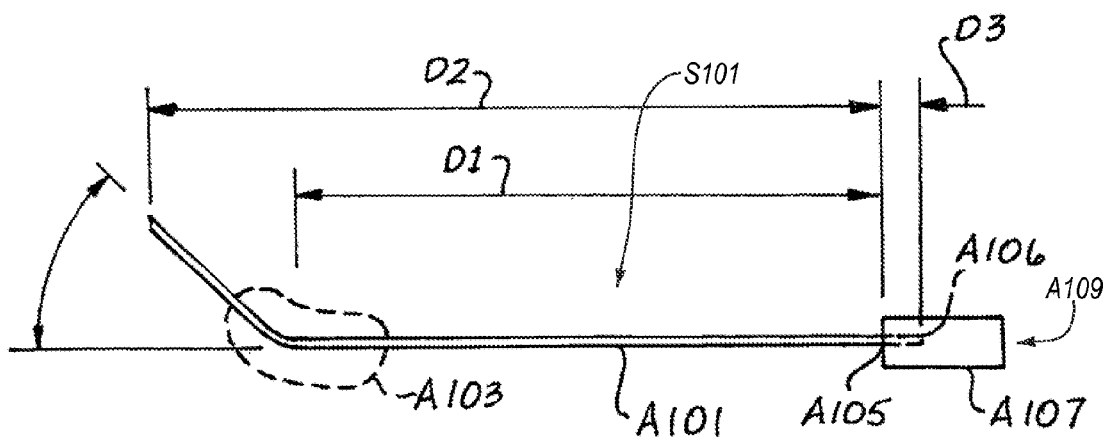
Figure 294:
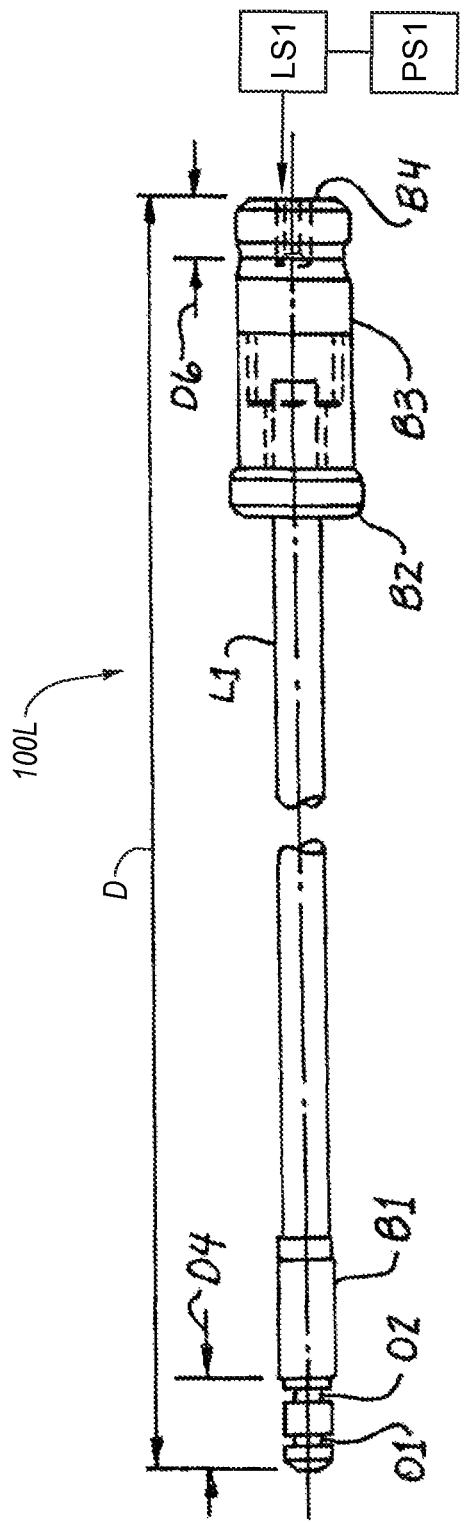
Figure 295:
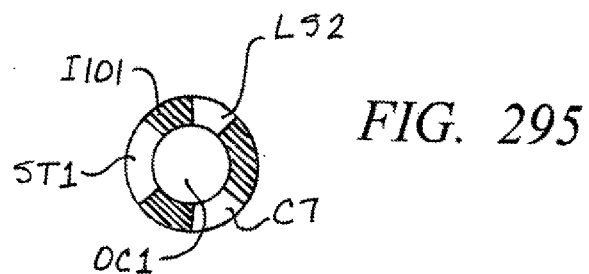
Figure 295A:
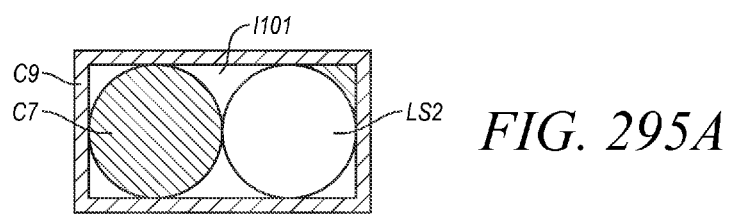
Figure 295B:
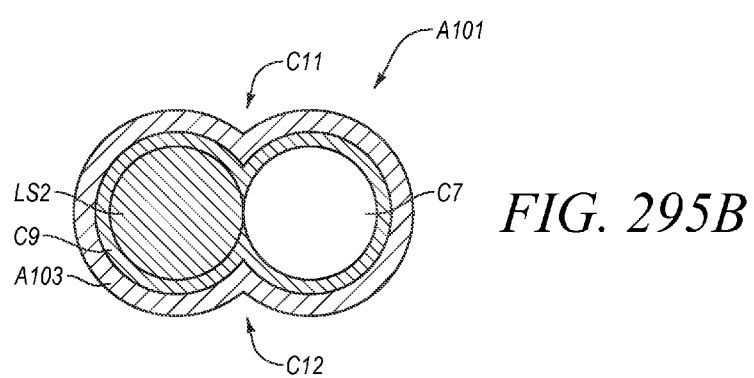

FIG. 120 is an end view illustrating the implant of FIG. 117;

FIG. 121 is a perspective view illustrating a unitary intervertebral implant;

FIG. 122 is a top view illustrating the implant of FIG. 121;

FIG. 123 is a side view of the implant of FIG. 122;

FIG. 124 is an end view illustrating the implant of FIG. 123;

FIG. 125 is a perspective view illustrating an intervertebral implant;

FIG. 126 is a top view illustrating the implant of FIG. 125;

FIG. 127 is a side view illustrating the implant of FIG. 125;

FIG. 128 is a left hand side view illustrating the implant of FIG. 127;

FIG. 129 is a right hand side view illustrating the implant of FIG. 127;

FIG. 130 is an exploded ghost view further illustrating the implant of FIGS. 57 to 61;

FIG. 131 is a perspective view illustrating a component of the implant of FIG. 130;

FIG. 132 is a top view illustrating the component of FIG. 131;

FIG. 133 is a section view further illustrating the component of FIG. 132 and taken along section line A-A thereof;

FIG. 134 is a front view illustrating the component of FIG. 132;

FIG. 135 is a side view illustrating the component of FIG. 134;

FIG. 136 is a bottom view of the component of FIG. 134;

FIG. 137 is a perspective view illustrating a component of the implant of FIG. 130;

FIG. 138 is a side view illustrating the component of FIG. 137;

FIG. 139 is a front view illustrating the component of FIG. 138;

FIG. 140 is a bottom view illustrating the component of FIG. 138;

FIG. 141 is a bottom perspective view illustrating a component of the implant of FIG. 130;

FIG. 142 front view illustrating the component of FIG. 141 inverted;

FIG. 143 is a side view illustrating the component of FIG. 142;

FIG. 144 is a section view illustrating the component of FIG. 143 and taken along section line A-A thereof;

FIG. 145 is a bottom view illustrating the component of FIG. 142;

FIG. 146 is a front view illustrating a component of the implant of FIG. 130;

FIG. 147 is a top view illustrating the component of FIG. 146;

FIG. 148 is a side view illustrating the component of FIG. 146;

FIG. 149 is a perspective view illustrating the implant of FIG. 130 assembled and illustrating the mode of operation thereof;

FIG. 150 is a side view illustrating another implant constructed in accordance with the invention;

FIG. 151 is a top view illustrating the implant of FIG. 150;

FIG. 152 is an end view illustrating the implant of FIG. 151;

FIG. 153 is a perspective view illustrating the rocker component of the implant of FIG. 150;

FIG. 154 is a side view illustrating the rocker component of FIG. 153;

FIG. 155 is a bottom view illustrating the rocker component of FIG. 154;

FIG. 156 is a front view illustrating the rocker component of FIG. 154;

FIG. 157 is a perspective view illustrating the base component of the implant of FIG. 150;

FIG. 158 is a top view illustrating the base component of FIG. 150;

FIG. 159 is an end view illustrating the base component of FIG. 158;

FIG. 160 is a side view illustrating the base component of FIG. 158;

FIG. 161 is a top view illustrating a further implant, which implant is similar to the implant of FIG. 150;

FIG. 162 is a side view of the implant of FIG. 161;

FIG. 163 is a side view rotated ninety degrees clockwise of the implant of FIG. 161;

FIG. 164 is a perspective view illustrating still another intervertebral implant;

FIG. 165 is a perspective view illustrating still a further intervertebral implant constructed in accordance with the invention to displace transversely one spinal vertebra with respect to an adjacent spinal vertebra;

FIG. 166 is a top view illustrating the implant of FIG. 165;

FIG. 167 is an end view rotated ninety degrees clockwise illustrating the implant of FIG. 166;

FIG. 168 is a side view illustrating the implant of FIG. 167;

FIG. 169 is a bottom view illustrating the implant of FIG. 167;

FIG. 170 is an exploded ghost view illustrating further construction details of the implant of FIG. 165;

FIG. 171 is a perspective ghost view illustrating the implant of FIG. 165 and the mode of operation thereof;

FIG. 172 is a perspective view illustrating yet another implant;

FIG. 173 is bottom view illustrating the implant of FIG. 172;

FIG. 174 is a back or rear view rotated ninety degrees clockwise illustrating the implant of FIG. 173;

FIG. 175 is a front end view rotated ninety degrees counterclockwise illustrating the implant of FIG. 173;

FIG. 176 is a side view illustrating the implant of FIG. 173;

FIG. 177 is a perspective view illustrating the mode of operation of the implant of FIG. 173;

FIG. 178 is a perspective view illustrating an instrument constructed in accordance with the invention;

FIG. 179 is a perspective view illustrating the mode of operation of the instrument;

FIG. 180 is a perspective view illustrating a floating implant constructed in accordance with the invention;

FIG. 181 is an end view further illustrating the implant of FIG. 180;

FIG. 182 is a top view further illustrating the implant of FIG. 180;

FIG. 183 is a side view of the implant of FIG. 180 illustrating additional construction details thereof;

FIG. 184 is a perspective exploded view illustrating an orthogonal implant system constructed in accordance with the invention;

FIG. 185 is a perspective view illustrating an implant insertion instrument;

FIG. 186 is a perspective view illustrating an implant utilized to separate a pair of opposing vertebrae;

FIG. 187 is a top view illustrating the mode of operation of an instrument constructed in accordance with another embodiment of the invention;

FIG. 188 is a perspective view further illustrating the use of the instrument of FIG. 187;

FIG. 189 is a side view of a portion of a spine illustrating the use of implants to pivotally adjust vertebrae;

FIG. 190 is a front view illustrating an implant inserted between a pair of opposing spinous processes;

FIG. 191 is a front view illustrating another implant inserted between a pair of opposing spinous processes;

FIG. 192 is a front view illustrating a further implant inserted between a pair of opposing spinous processes;

FIG. 193 is a perspective view illustrating an implant inserted between a pair of opposed, adjacent spinous processes;

FIG. 194 is a top view of the spinous processes/implant of FIG. 193 illustrating further details thereof;

FIG. 195 is a front view of the spinous processes/implant of FIG. 193 illustrating additional construction details thereof;

FIG. 196 is a side view of the spinous processes/implant of FIG. 193 illustrating additional construction details thereof;

FIG. 197 is a perspective view illustrating an implant including a deployable wing component;

FIG. 198 is a perspective view illustrating an alternate embodiment of an implant with a deployable wing component;

FIG. 199 is an exploded perspective view illustrating an alternate embodiment of an implant constructed in accordance with the invention;

FIG. 200 is a bottom view further illustrating the implant of FIG. 199;

FIG. 201 is a side section view taken along section line A-A and further illustrating the implant of FIG. 200;

FIG. 202 is an end view further illustrating the implant of FIG. 200;

FIG. 203 is a side view further illustrating the implant of FIG. 200;

FIG. 204 is a front view illustrating an implant with deployed wings that have an arcuate configuration;

FIG. 205 is a front view illustrating an implant having a T-shaped deployed wing;

FIG. 206 is a perspective view illustrating a resilient spring implant;

FIG. 207 is a perspective view illustrating another resilient spring implant;

FIG. 208 is a perspective view illustrating a resilient implant interposed between a pair of adjacent vertebra;

FIG. 209 is a perspective view illustrating an ovate resilient implant;

FIG. 210 is a perspective view illustrating a resilient implant with a concave upper surface;

FIG. 211 is a perspective view illustrating a resilient implant with an expanding groove formed therein;

FIG. 212 is a perspective view illustrating a resilient implant with a tooth extending outwardly from the upper surface thereof;

FIG. 212A is a perspective view illustrating a resilient implant with a toothed opening than initially narrows and then widens;

FIG. 213 is a perspective view illustrating an instrument including a distal end having a cam surface usable to separate, penetrate, or cut tissue;

FIG. 214 is a perspective exploded view illustrating an implant comprised of a pair of interlocking members;

FIG. 215 is a side view illustrating an instrument utilized to cut tissue;

FIG. 215A is a back view illustrating the instrument of FIG. 215;

FIG. 216 is a front view further illustrating the instrument of FIG. 215;

FIG. 217 is a top view illustrating the instrument of FIG. 215;

FIG. 218 is a front view illustrating an instrument utilized to cut tissue;

FIG. 219 is a side view illustrating the instrument of FIG. 218;

FIG. 220 is a back end view illustrating the instrument of FIG. 218;

FIG. 221 is a top view illustrating the instrument of FIG. 218;

FIG. 222 is a top view illustrating an instrument utilized to cut tissue;

FIG. 223 is a side view illustrating the instrument of FIG. 222;

FIG. 224 is a front view illustrating the instrument of FIG. 222;

FIG. 225 is a section view further illustrating construction details of the instrument of FIG. 223 and taken along section line V-V thereof;

FIG. 226 is a perspective view illustrating the instrument of FIG. 222;

FIG. 227 is a back view illustrating the instrument of FIG. 226;

FIG. 227A is a top view illustrating an instrument that can be slid along a wire to separate, pass through, cut, or resect tissue;

FIG. 227B is a left hand end view further illustrating the instrument of FIG. 227A;

FIG. 228 is a section view illustrating the distal implant delivery end of the instrument illustrated in FIGS. 230 and 231;

FIG. 229 is a front view illustrating the instrument delivery end of FIG. 228;

FIG. 230 is a side view illustrating an instrument utilized to insert implants in accordance with the invention;

FIG. 231 is a back view illustrating the instrument of FIG. 230;

FIG. 231A is a side view of an instrument that can be utilized alone or in conjunction with the instrument illustrated in FIG. 230;

FIG. 231B is a left hand end view of the instrument of FIG. 231A;

FIG. 231C is an exploded view illustrating the instrument of FIG. 231A utilized in conjunction with the instrument of FIG. 230;

FIG. 231D is a top view illustrating the instrument of FIG. 231A assembly with the instrument of FIG. 230;

FIG. 231E is a right hand side view illustrating the assembled instruments of FIG. 231D;

FIG. 232 is a perspective view illustrating an instrument utilized to separate tissue, cut tissue, or penetrate tissue;

FIG. 233 is a side section view illustrating the instrument of FIG. 232 and taken along section line A-A of FIG. 235;

FIG. 234 is a back view illustrating the instrument of FIG. 232;

FIG. 235 is a front view illustrating the instrument of FIG. 233;

FIG. 235A is a perspective view illustrating an instrument utilized to separate tissue, cut tissue, or penetrate tissue;

FIG. 235B is an inverted left hand end view illustrating the instrument of FIG. 235A;

FIG. 235C is a section view illustrating the instrument of FIG. 235B and taken along section line A-A thereof;

FIG. 235D is a right hand end view illustrating the instrument of FIG. 235C;

FIG. 235E is a perspective partial section view illustrating a hollow instrument including a plunger mounted slidably therein to eject an implant or to create suction to draw an implant or tissue into the instrument;

FIG. 235F is a top view illustrating the positioning of an instrument relative to a nerve prior to using the instrument to laterally displace the nerve in cam-like fashion to safely advance the instrument past the nerve toward a spinal disc;

FIG. 235G is a side view illustrating the instrument, nerve, and disc of FIG. 235F;

FIG. 235H is a side view illustrating the instrument, nerve, and disc of FIG. 235H after the instrument has been rotated to laterally displace the nerve and has been advanced to a position where the tip of the instrument is adjacent and generally conforms to the periphery of the disc;

FIG. 235I is a perspective view illustrating the positioning of an instrument adjacent a nerve prior to rotating the instrument to displace the nerve in cam-like fashion;

FIG. 236 is a top view illustrating an implant constructed in accordance with the invention to slide along a guide wire and/or along a hollow guide unit;

FIG. 237 is a side view illustrating the implant of FIG. 236;

FIG. 238 is a front view illustrating the implant of FIG. 236;

FIG. 239 is a back end view illustrating the implant of FIG. 237;

FIG. 240 is a perspective view illustrating the implant of FIG. 236;

FIG. 241 is a perspective view illustrating the implant of FIG. 236;

FIG. 242 is a top view illustrating an implant constructed to slide along a guide wire and/or along a hollow guide unit;

FIG. 243 is a front end view illustrating the implant of FIG. 242;

FIG. 244 is a left-hand side view illustrating the implant of FIG. 242;

FIG. 245 is a back end view illustrating the implant of FIG. 242;

FIG. 246 is a right-hand side view illustrating the implant of FIG. 242;

FIG. 247 is a perspective view illustrating the implant of FIG. 242;

FIG. 248 is a perspective view illustrating the implant of FIG. 242;

FIG. 249 is a perspective view illustrating an implant constructed to slide along a guide wire and/or along a hollow guide unit;

FIG. 250 is a front end view illustrating the implant of FIG. 249;

FIG. 251 is a top view illustrating the implant of FIG. 249;

FIG. 252 is a side view illustrating the implant of FIG. 251;

FIG. 253 is a top view illustrating an implant constructed to slide along a guide wire and/or along a hollow guide unit;

FIG. 254 is a left-hand side view illustrating the implant of FIG. 253;

FIG. 255 is a front end view illustrating the implant of FIG. 253;

FIG. 256 is a back end view illustrating the implant of FIG. 253;

FIG. 257 is a right-hand side view illustrating the implant of FIG. 253;

FIG. 258 is a perspective view illustrating the implant of FIG. 253;

FIG. 259 is a perspective view illustrating the implant of FIG. 253;

FIG. 260 is a top view illustrating an implant constructed to slide along a guide wire and/or along a hollow guide unit;

FIG. 261 is a left-hand side view illustrating the implant of FIG. 260;

FIG. 262 is a right-hand side view illustrating the implant of FIG. 260;

FIG. 263 is a back end view illustrating the implant of FIG. 260;

FIG. 264 is a front end view illustrating the implant of FIG. 260;

FIG. 265 is a bottom view illustrating the implant of FIG. 260;

FIG. 266 is a perspective view illustrating the implant of FIG. 260;

FIG. 267 is a perspective view illustrating the implant of FIG. 260;

FIG. 268 is a top view illustrating an articulating implant constructed to slide along a guide wire and/or along a hollow guide unit;

FIG. 269 is a back end view illustrating the implant of FIG. 268;

FIG. 270 is a side view illustrating the implant of FIG. 268;

FIG. 271 is a perspective view illustrating the implant of FIG. 268;

FIG. 272 is a perspective view illustrating the implant of FIG. 268;

FIG. 273 is a top view illustrating a hinged spring-loaded implant constructed in accordance with another embodiment of the invention;

FIG. 274 is a bottom view further illustrating the implant of FIG. 273;

FIG. 275 is a section view of the implant of FIG. 274 taken along section line A-A and further illustrating construction details of the implant;

FIG. 276 is a top view illustrating a hinged implant constructed in accordance with another embodiment of the invention;

FIG. 277 is a side view of the implant of FIG. 276 illustrating further construction details thereof;

FIG. 278 is a perspective view further illustrating the implant of FIG. 276;

FIG. 279 is a top view of the implant of FIG. 276 illustrating the mode of operation thereof;

FIG. 280 is a side view of the implant of FIG. 279;

FIG. 281 is a perspective view of the implant of FIG. 279;

FIG. 282 is a top view illustrating an alternate hinged implant of the invention;

FIG. 283 is a top view of the implant of FIG. 282 illustrating the mode of operation thereof;

FIG. 284 is a top view illustrating still another hinged implant of the invention;

FIG. 285 is a top view of the implant of FIG. 284 illustrating the mode of operation thereof;

FIG. 286 is a top view illustrating yet another hinged implant of the invention;

FIG. 287 is a top view of the implant of FIG. 286 illustrating the mode of operation thereof;

FIG. 288 is a perspective view illustrating an implant constructed in accordance with an alternate embodiment of the invention;

FIG. 289 is a partial perspective view illustrating the implant of FIG. 288 inserted between a pair of vertebra;

FIG. 290 is a perspective view illustrating the mode of operation of the implant of FIG. 288;

FIG. 291 is a rear view of the implant and vertebra of FIG. 290 further illustrating the mode of operation of the implant;

FIG. 292 is a side view of a light source operable to illuminate a surgical site and configured to deliver a perforated implant;

FIG. 293 an exploded side view of another light source operable to illuminate a surgical site and configured to deliver a perforated implant;

FIG. 294 is a exploded side view of an optical guide unit system operable to illuminate a surgical site and configured to deliver a perforated implant;

FIGS. 295, 295A, and 295B include end cross sectional views of distal tip T101 of shaft A101 illustrated in FIG. 292-293.

Figure 296:
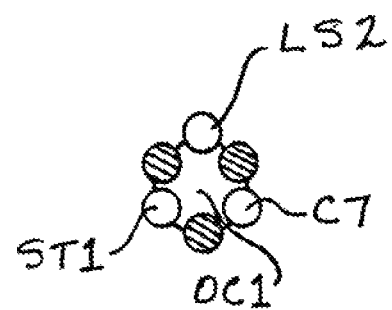
Figure 296A:
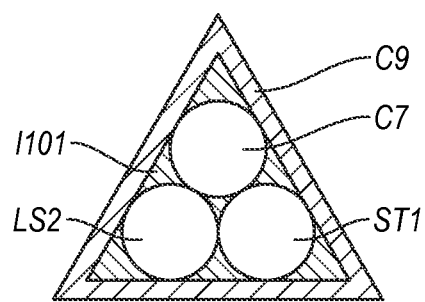
Figure 297:
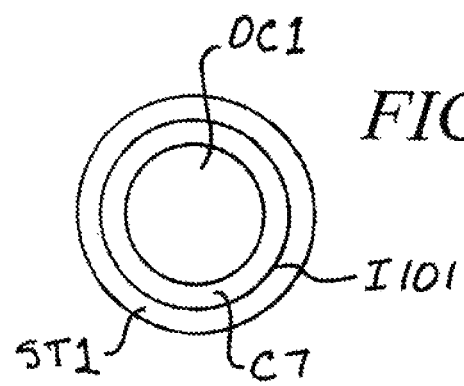
Figure 297A:
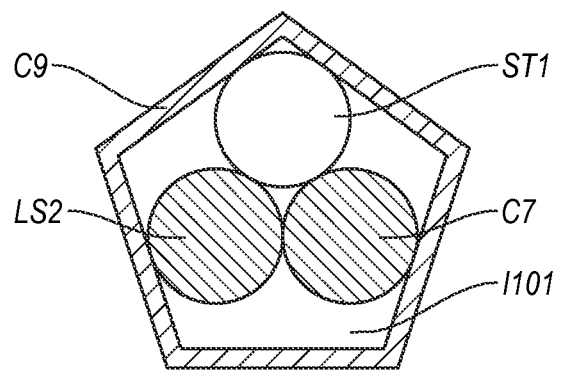
Figures 298, 299:
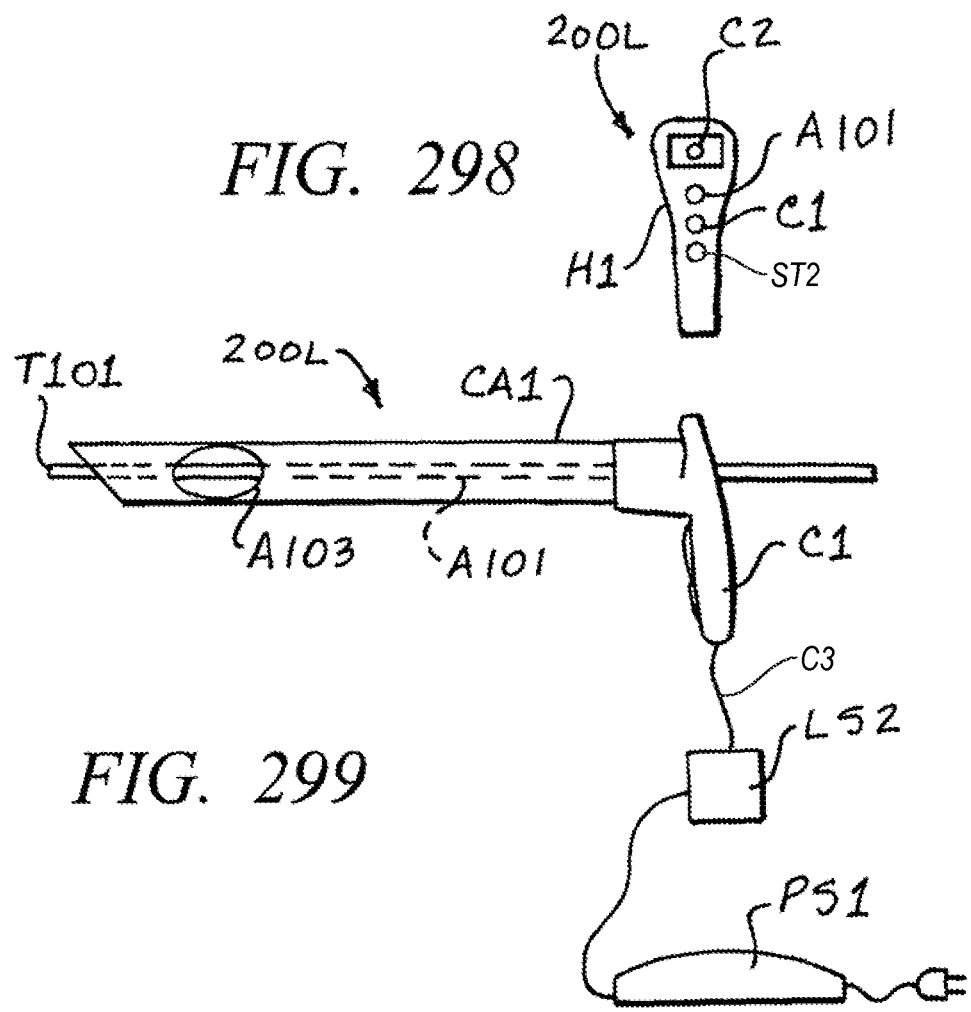
Figure 299A:
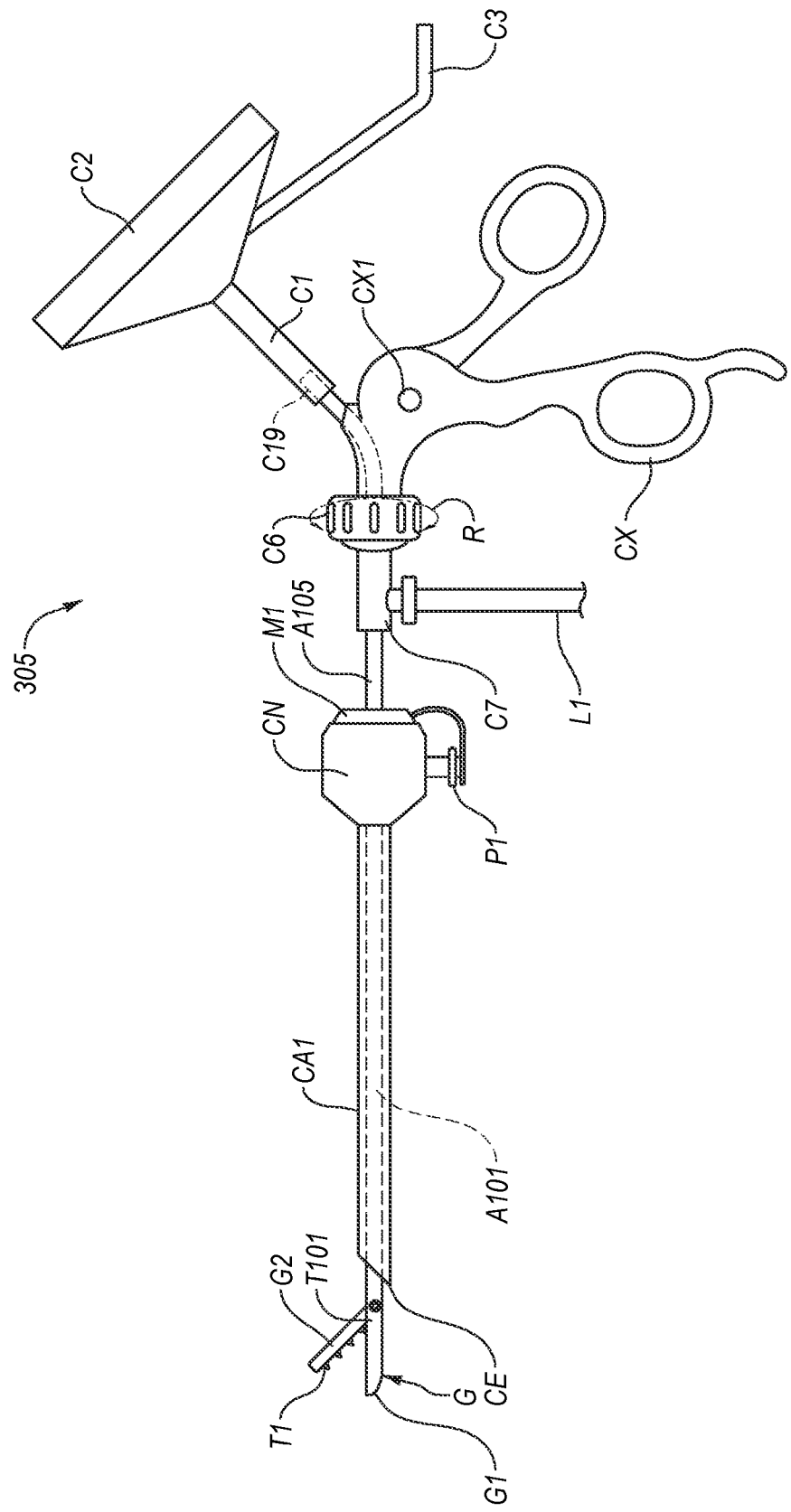
Figure 300:
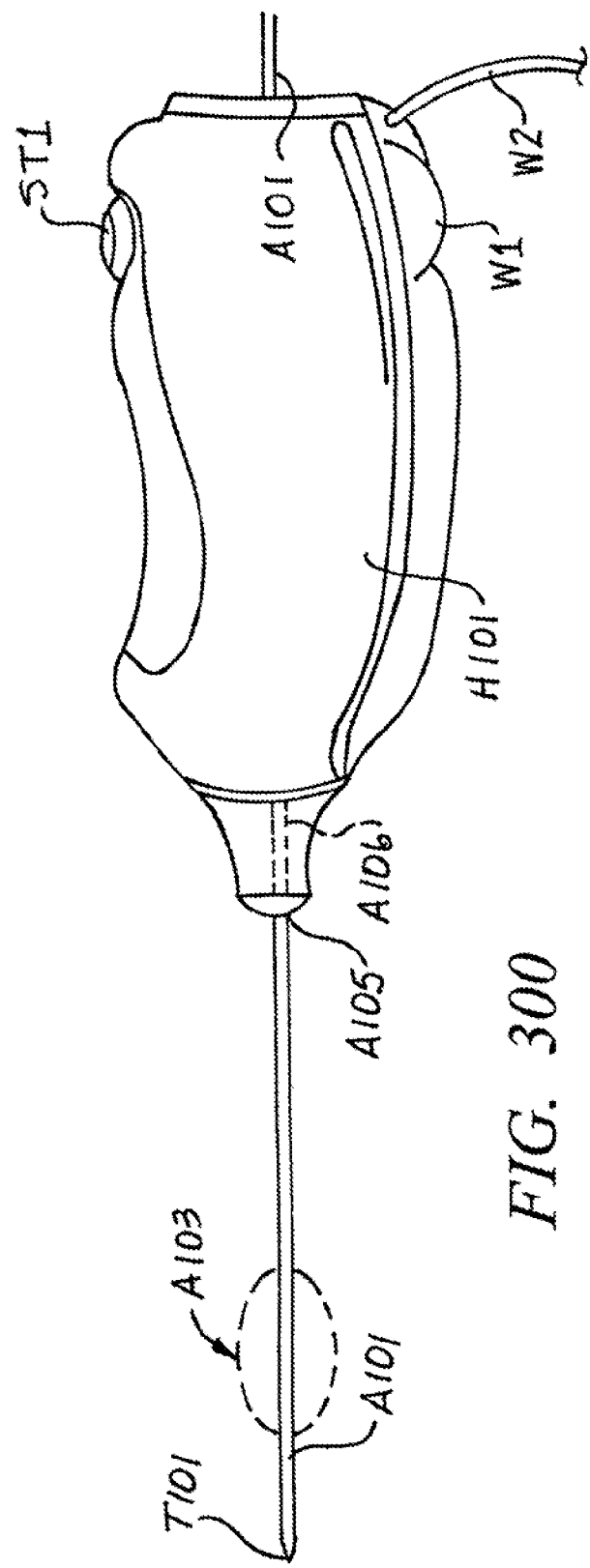
Figure 308:
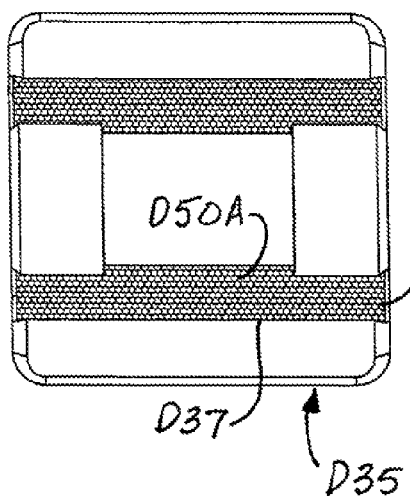
Figure 309:
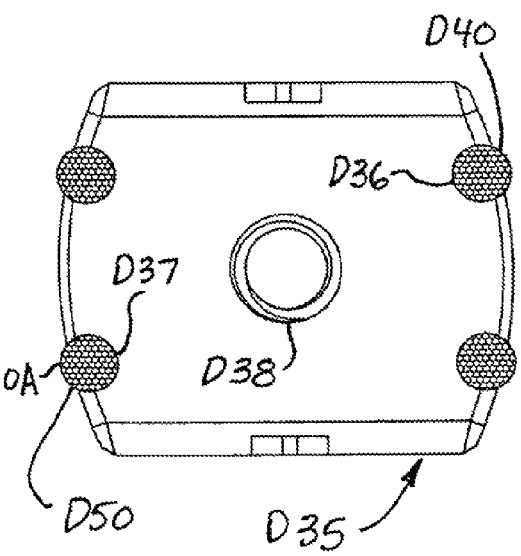
Figure 311:
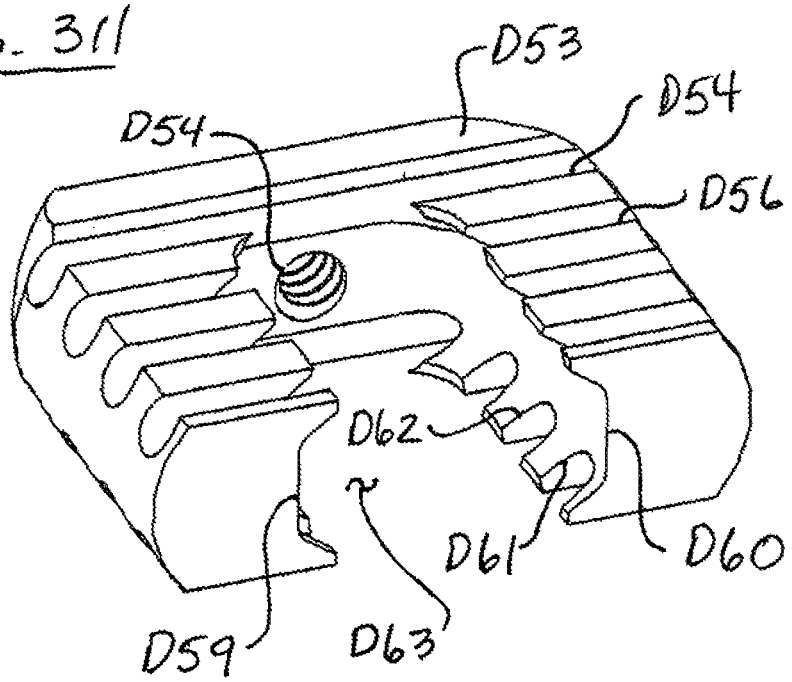
Figure 310:
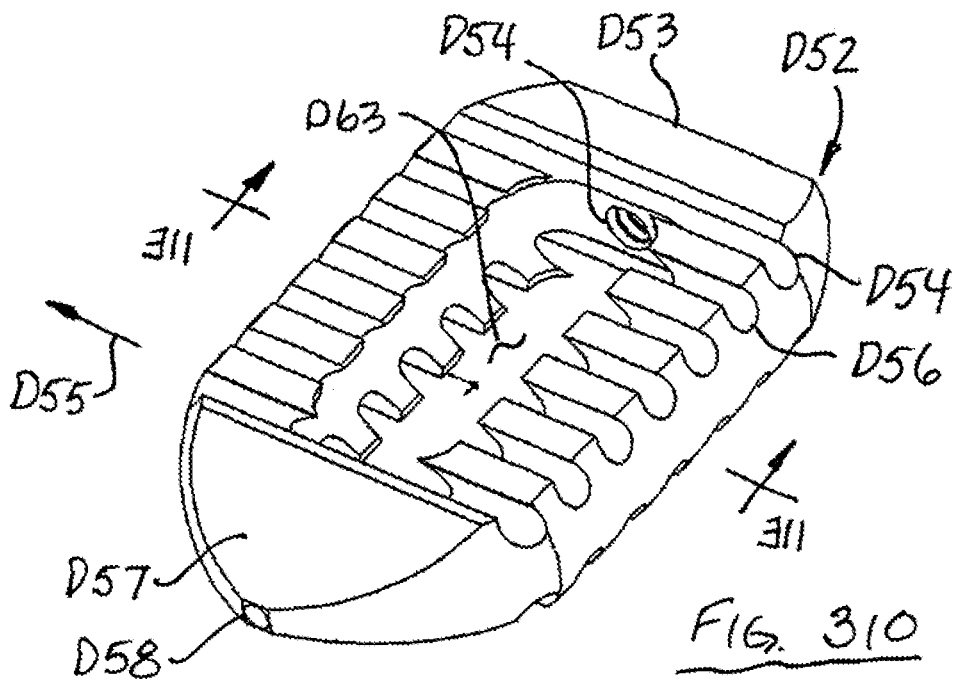
Figure 312:
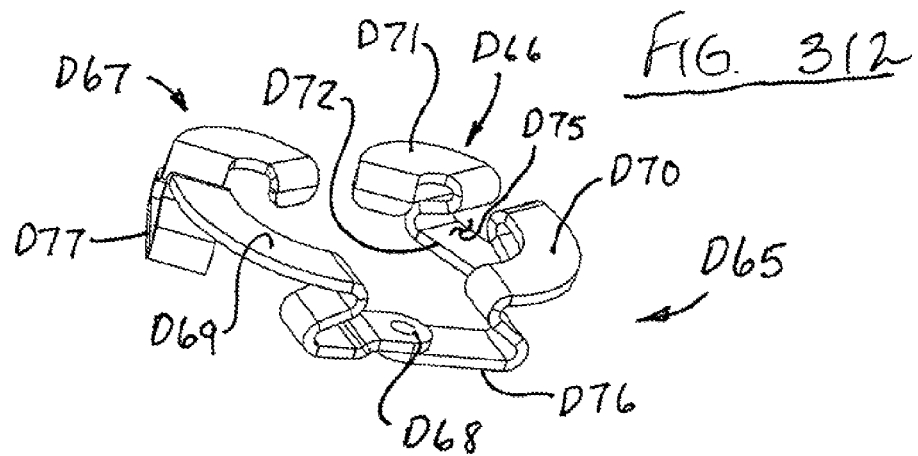
Figure 313:
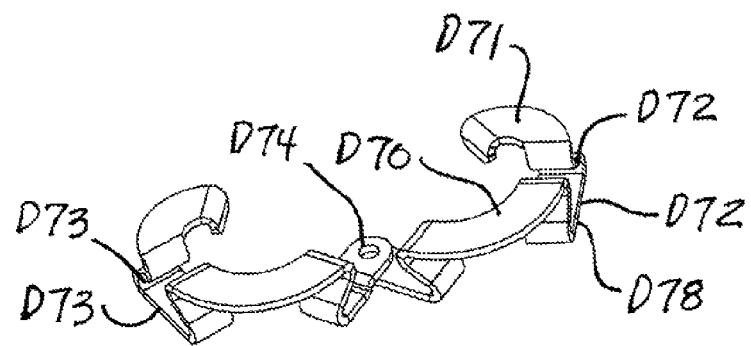
Figure 319:
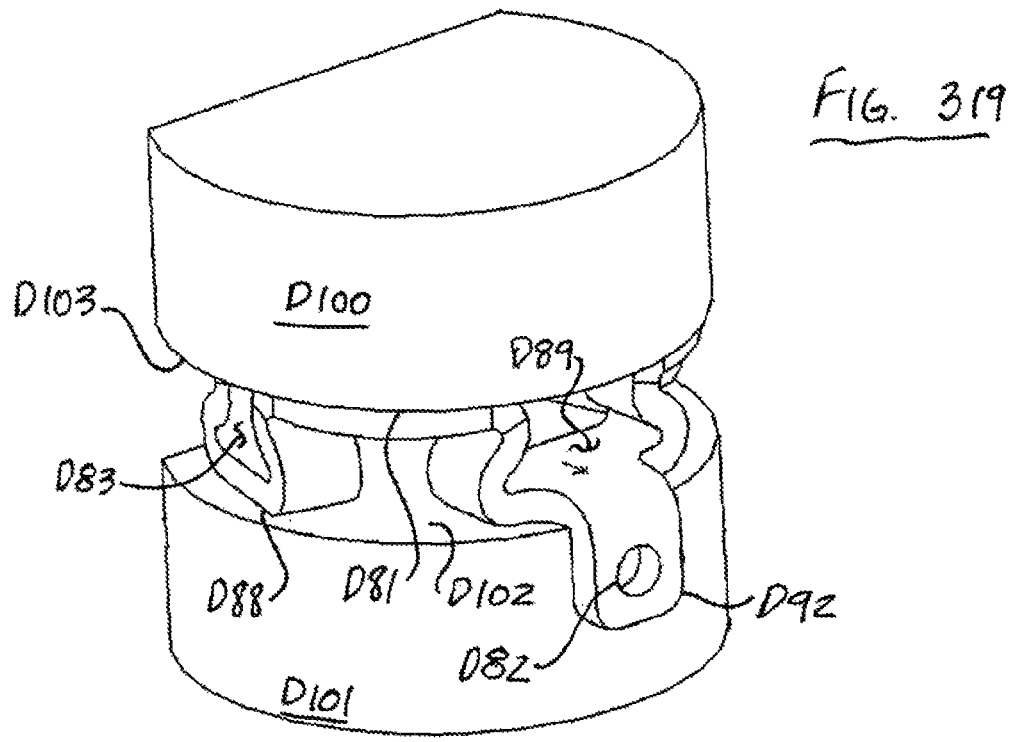
Figure 318:
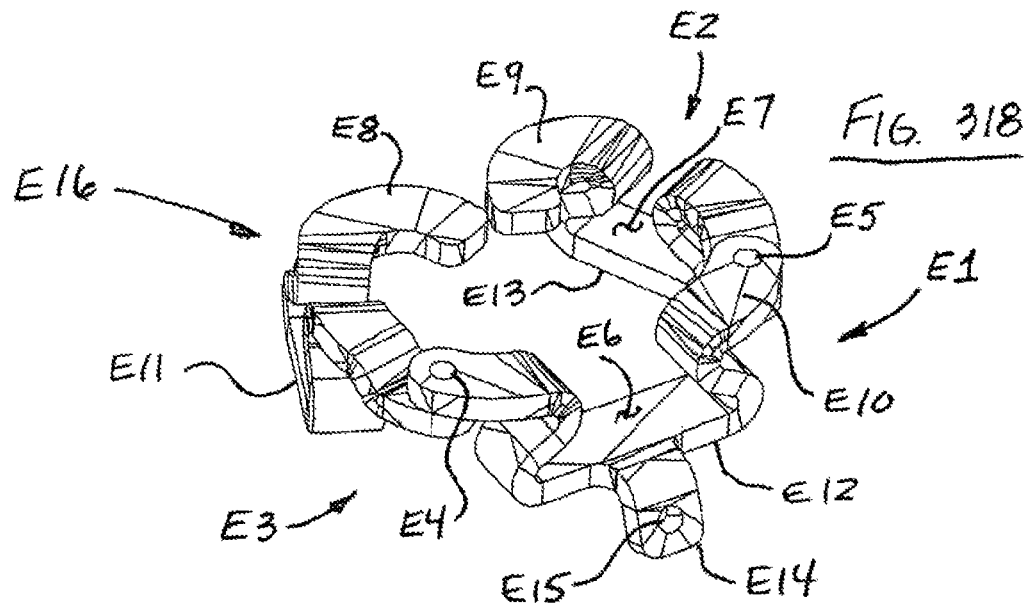
Figure 320:
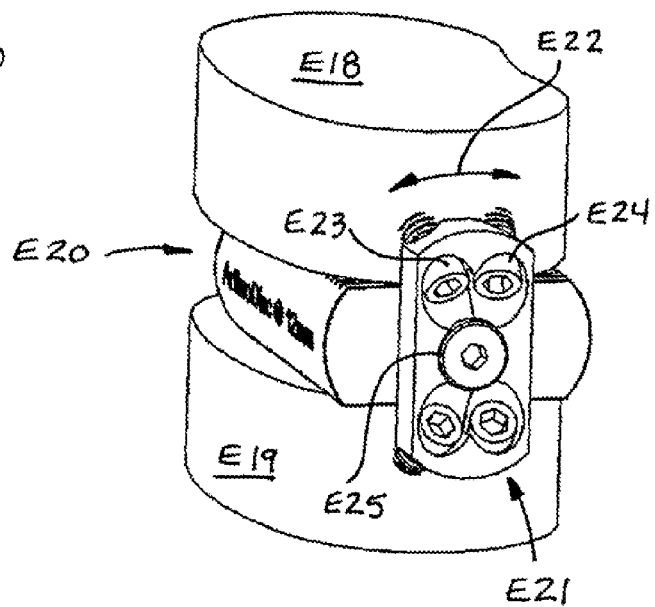
Figure 321:
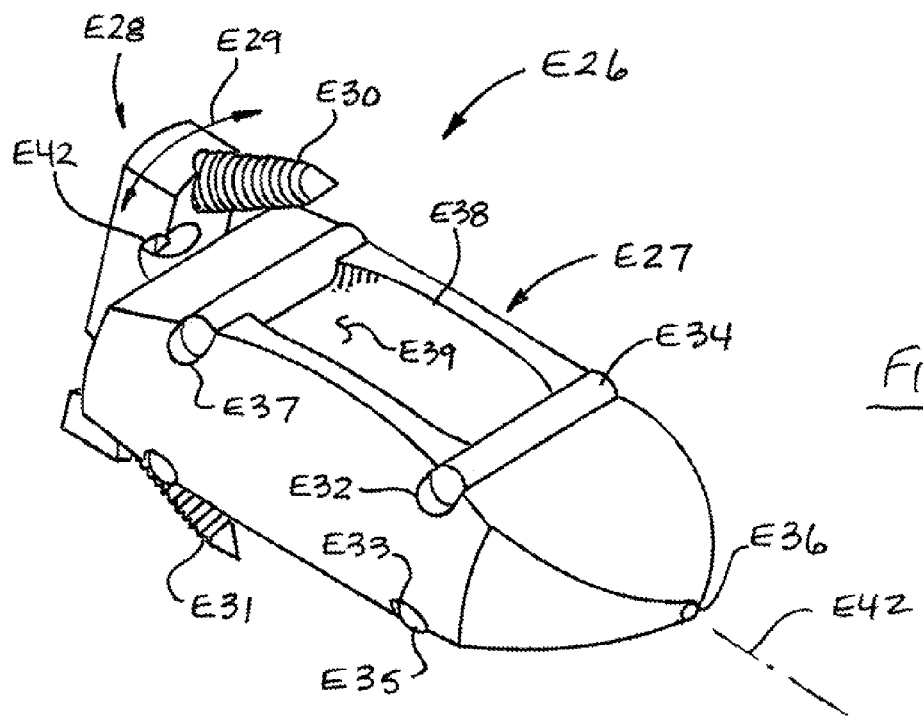
Figure 322:
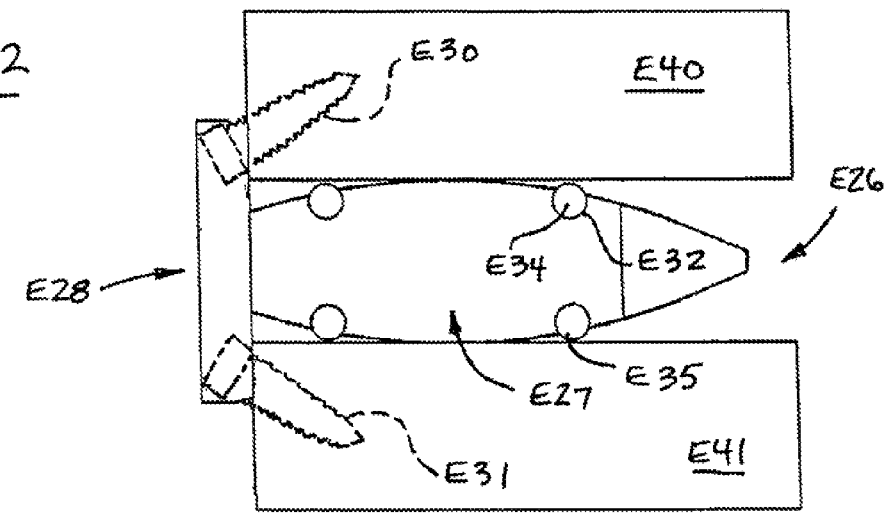
Figure 323:
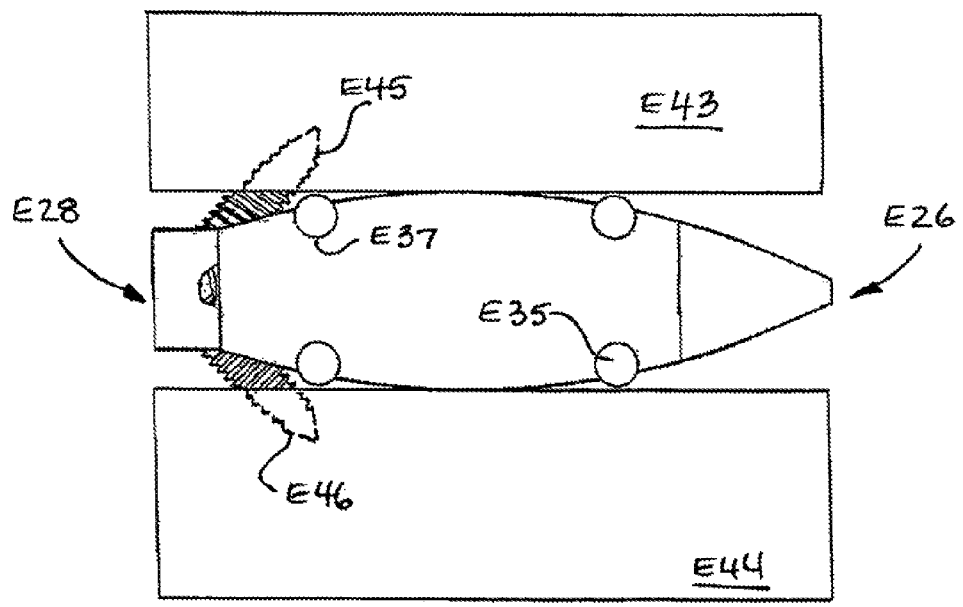
Figure 327:
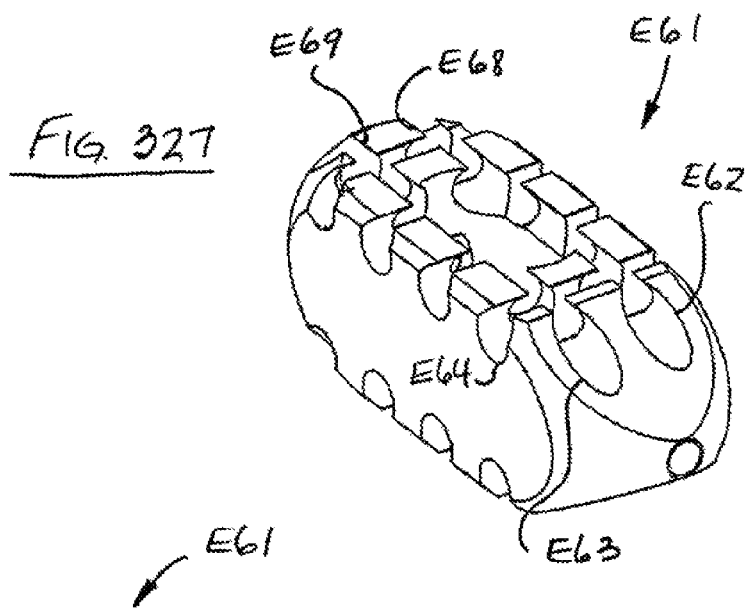
Figure 328:
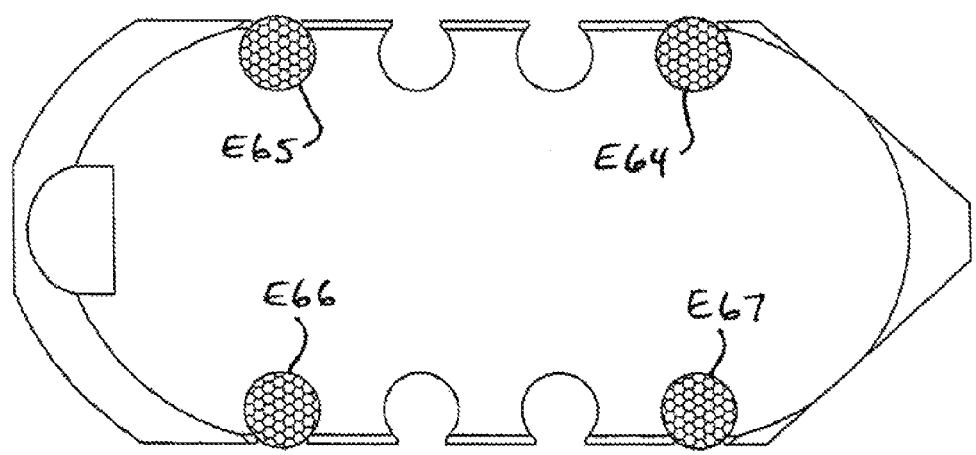
Figure 329:
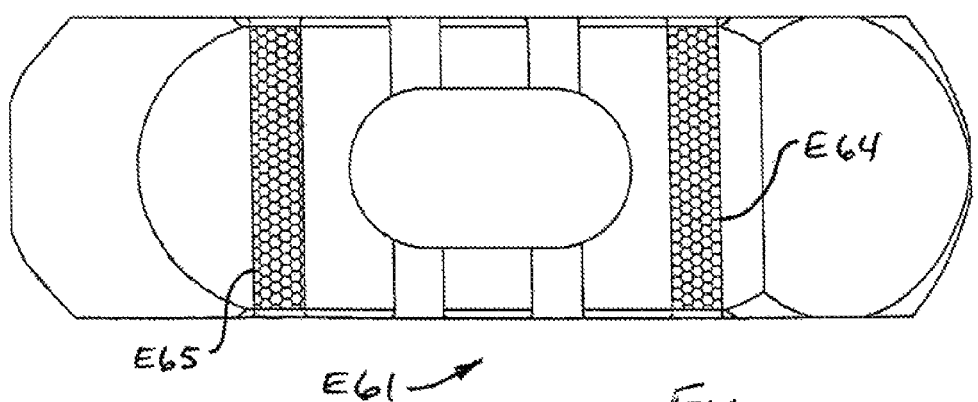

FIGS. 296 and 296A include additional end cross sectional views of distal tip T101 of shaft A101 illustrated in FIG. 292-293;

FIGS. 297 and 297A include additional end cross sectional views of distal tip T101 of shaft A101 illustrated in FIG. 292-293;

FIG. 298 is an end view of another optical guide unit system operable to illuminate a surgical site, transmit or detect current, and configured to deliver a perforated implant;

FIG. 299 is a transparent side view of optical guide unit system illustrated in FIG. 294 operable to illuminate a surgical site, transmit or detect current, and configured to deliver a perforated implant;

FIG. 299A is a transparent side view of an elongate guide member having a grabbing tip, and which is located within a cannula and operably coupled to a handle that actuates the grabbing tip, and operably coupled to a camera and monitor;

FIG. 300 is a side view of an electrical guide unit system operable to conduct an electrical current to a surgical site and configured to deliver a perforated implant;

FIG. 301 is a profile view of an implant configured to revitalize an intervertebral disc by tilting when compressed intermediate two vertebra after sliding along an elongate guide unit;

FIG. 302 is a top view illustrating an intervertebral plate constructed in accordance with another embodiment of the invention;

FIG. 303 is a side view further illustrating the plate of FIG. 302;

FIG. 304 is a perspective view illustrating an implant constructed in accordance with another embodiment of the invention;

FIG. 305 is a front view of the implant of FIG. 304 illustrating further construction details thereof;

FIG. 306 is a side view of the implant of FIG. 304 further illustrating details thereof;

FIG. 307 is a top view of the implant of FIG. 304 further illustrating details thereof;

FIG. 308 is a bottom view of the implant of FIG. 304 illustrating marker rods inserted therein;

FIG. 309 is a front view of the implant of FIG. 308 further illustrating marker rods inserted therein;

FIG. 310 is a perspective view illustrating an implant constructed in accordance with another embodiment of the invention;

FIG. 311 is a perspective section view of the implant of FIG. 310 taken along section lines 311-311 and illustrating further details thereof;

FIG. 312 is a perspective view of an implant constructed in accordance with another embodiment of the invention;

FIG. 313 is a perspective view of the implant of FIG. 312 illustrating the mode of operation thereof;

FIG. 314 is a perspective view illustrating an implant constructed in accordance with another embodiment of the invention;

FIG. 315 is a side view of the implant of FIG. 314 illustrating additional construction details thereof;

FIG. 316 is a front view of the implant of FIG. 314 illustrating additional details thereof;

FIG. 317 is a top view of the implant of FIG. 314 illustrating additional details thereof;

FIG. 318 is a perspective view illustrating an implant constructed in accordance with another embodiment of the invention;

FIG. 319 is a perspective view illustrating the implant of FIG. 314 inserted between a pair of vertebra;

FIG. 320 is a perspective view illustrating an implant constructed in accordance with another embodiment of the invention inserted between a pair of vertebra;

FIG. 321 is a perspective view illustrating an implant constructed in accordance with another embodiment of the invention;

FIG. 322 is a side view illustrating the implant of FIG. 321 inserted between a pair of vertebra;

FIG. 323 is a side view illustrating the implant of FIG. 321 in a different configuration and inserted between a pair of vertebra;

FIG. 324 is a perspective view illustrating an implant constructed in accordance with another embodiment of the invention;

FIG. 325 is a side section view of the implant of FIG. 324 illustrating additional construction details thereof;

FIG. 326 is a perspective view of the implant of FIG. 324 illustrating marker rods inserted therein;

FIG. 327 is a perspective view illustrating an implant constructed in accordance with another embodiment of the invention;

FIG. 328 is side view of the implant of FIG. 327 illustrating marker rods inserted therein;

FIG. 329 is a top view of the implant of FIG. 328 illustrating details thereof;

FIG. 330 is a perspective view of an implant constructed in accordance with another embodiment of the invention;

FIG. 331 is a side view of the implant of FIG. 330 illustrating details thereof;

FIG. 332 is a top view of the implant of FIG. 330 illustrating details thereof;

FIG. 333 is an end view of the implant of FIG. 330 illustrating details thereof;

FIG. 334 is a perspective view illustrating an implant constructed in accordance with another embodiment of the invention; and, FIG. 335 is a perspective view of the implant of FIG. 334 illustrating the mode of operation thereof;

all arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention includes devices, systems, and methods for performing medical protocols with adjacent vertebras and the intervertebral discs between adjacent vertebras. The medical procedure can range from observing an intervertebral disc, resection of a herniated disc, forming a delivery pathway for to and into a disc, and for delivering an implant between adjacent vertebras as well as any medical procedure described herein that can be performed using endoscopic techniques with a miniaturized endoscope device as described herein. The miniaturized endoscope device can include an elongate light guide for use in visualizing and observing the anatomical space in, between, around and associated with adjacent vertebras and intervertebral discs. In one example, the elongate light guide can be used as the guide for delivering the implant, and thereby any of the guide wires, guide members, or the like can be configured as one of the embodiments of the elongate light guide as described.

In one embodiment, the elongate light guide can be used to deliver the implant by the implant passing over, on, around, or through the elongate light guide. For example: the implant can include an aperture to slide over or around an outer surface of the elongate light guide; the implant can include a slot to slide on over or on an outer surface of the elongate light guide; the implant can be slide through a conduit or internal lumen of the elongate light guide. While being delivered, the elongate light guide can observe the location of implantation and monitor the implantation of the implant as well as facilitate implantation into a particular location between the adjacent vertebras. The devices, systems, and methods can include any of the embodiments described herein as well as combinations thereof that are configured and operated in a manner suitable for delivery of an implant with an elongate light guide. Accordingly, any of the implants described herein can include an aperture, conduit, slot, groove, or other feature that cooperates with the elongate light guide for delivery, steering (along an arcuate or linear path), and implantation between adjacent vertebra, where such modification of the figures shown to include these features that facilitate delivery and implantation can be made in view of the implants shown and described that have these features.

In one embodiment, the elongate light guide can be used for visualizing and observing the anatomical space and tissues in, between, around and associated with adjacent vertebras, nerves, facets, ligaments, and intervertebral discs during a medical procedure. The visualizing and observing can be conducted using light of one or more wavelengths for illumination (e.g., transmission) and viewing (e.g., reception). Accordingly, the light can be monochromatic or broad spectrum light (e.g., white light) to illuminate the adjacent vertebras and intervertebral disc as well as surrounding tissue, such as nerves. facets, ligaments, etc. Additionally, one or more dyes can be used to dye the tissue associated with the intervertebral disc and surrounding tissues so that different tissues can be easily differentiated from teach other. In one example, the dye can be used to contrast between an intact portion of a disc from a ruptured or otherwise compromised portion of the disc. In another example, the dye can be used to contrast between different tissues that are similarly colored or otherwise visually similar, which can include contrasting between a disc (e.g., intact or ruptured) and a nerve.

Briefly, in accordance with the invention, provided is an improved method to manipulate a damaged intervertebral disc to improve the functioning of the disc. The disc includes an annulus. The method comprises the steps of providing a device to alter, when inserted in the disc, the shape and dimension of the disc; and, inserting the device in the disc to alter said shape and dimension of the disc. The disc is intermediate a first and a second vertebra. The first vertebra has a bottom adjacent the disc and the second vertebra has a top adjacent the disc. The device alters the shape and dimension of the disc by internal traction to increase the height (H) of the disc along an axis (G) generally normal to the bottom of the first vertebra and the top of the second vertebra. The device can also alter the shape and dimension of the disc by internal traction to decrease the width (W) of the disc. The device can further alter the shape and dimension of the disc by internal traction changing the pressure in the disc. This method can include using an elongate light guide for visualizing or imaging the disc, adjacent vertebras as well as any tissues, such as the annulus, ligaments, facets, and/or nerves, associated therewith or adjacent thereto. Also, this method can include the use of one or more light wavelengths or one or more dyes for coloring or contrasting of one or more tissues for visual differentiation.

In another embodiment of the invention, provided is an improved method for inserting a device to improve in an individual's body the functioning of a damaged intervertebral disc, including an annulus, between a pair of vertebra, the body having a front, a first side, a second side, and a back. The disc includes a front portion facing the front of the body, side portions each facing a side of the body, and a back portion facing the back of the body. The vertebrae are in a pre-existing spaced apart configuration with respect to each other. The improved method comprises the steps of forming an opening in the disc between the pair of vertebrae, and in one of a group consisting of the side portions of the disc, the front portion of the disc, and the back portion of the disc; providing a support device shaped and dimensioned to fit through the opening in the disc; and, inserting the support device through the opening in the disc without enlarging the pre-existing spaced apart configuration of the pair of vertebrae. This method can include using an elongate light guide for visualizing or imaging the disc, adjacent vertebras as well as any tissues, such as the annulus, ligaments, facets and/or nerves, associated therewith or adjacent thereto, especially during the forming, providing, and/or inserting steps. Also, this method can include the use of one or more light wavelengths or one or more dyes for coloring or contrasting of one or more tissues for visual differentiation during these steps.

In a further embodiment of the invention, provided is an improved method inserting a device to improve in an individual's body the functioning of a damaged intervertebral disc, including an annulus, between a pair of vertebrae. The individual's body has a front, a first side, a second side, and a back. The disc includes a front portion facing the front of the body, side portions each facing a side of the body, a back portion facing the back of the body, and a pre-existing rupture. The vertebrae are in a pre-existing spaced apart configuration with respect to each other. The method comprises the steps of providing a support device shaped and dimensioned to fit through the pre-existing rupture in the disc; and, inserting the support device through the pre-existing rupture in the disc without enlarging the pre-existing spaced apart configuration of the pair of vertebrae. This method can include using an elongate light guide for visualizing or imaging the disc, ligaments, facets, etc., adjacent vertebras as well as any tissues, such as the annulus and/or nerves, ligaments, facets, etc., associated therewith or adjacent thereto as well as ruptures of the tissue before, during, and after the inserting. Also, this method can include the use of one or more light wavelengths or one or more dyes for coloring or contrasting of one or more tissues for visual differentiation.

In a still further embodiment of the invention, provided is an improved method to manipulate a damaged intervertebral disc to improve the functioning of the disc. The disc includes an annulus. The improved method comprises the step of inserting a device in the disc, the device operable to apply a force to the disc. The method also comprises the step of operating the device to apply a force to the disc. This method can include using an elongate light guide for visualizing or imaging the disc, adjacent vertebras as well as any tissues, such as the annulus and/or nerves, ligaments, facets, etc., associated therewith or adjacent thereto before, during, or after the inserting and application of force. Also, this method can include the use of one or more light wavelengths or one or more dyes for coloring or contrasting of one or more tissues for visual differentiation.

In still another embodiment of the invention, provided is an improved method to improve the functioning of a damaged intervertebral disc positioned between, contacting, and separating a pair of vertebrae. The disc includes an annulus. The method comprises the steps of providing a device shaped and dimensioned when inserted in the disc to contact each of the vertebrae, and operable in response to movement of the vertebrae to permit simultaneous polyaxial movement of the vertebrae and said device; and, inserting the device in the disc to contact each of the vertebrae. This method can include using an elongate light guide for visualizing or imaging the disc, adjacent vertebras as well as any tissues, such as the annulus and/or nerves, ligaments, facets, etc., associated therewith or adjacent thereto before, during, and after the inserting step or polyaxial movement of the vertebrae. Also, this method can include the use of one or more light wavelengths or one or more dyes for coloring or contrasting of one or more tissues for visual differentiation.

In a further embodiment of the invention, provided is an improved apparatus for disposition between first and second opposing vertebrae. The first vertebra is canted with respect to the second vertebra. The apparatus is shaped and dimensioned to generate a force to change the cant of the first vertebra with respect to the second vertebra.

In another embodiment of the invention, provided is improved apparatus for disposition between first and second opposing vertebrae. The first vertebra is rotated about a vertical axis from a first desired position to a second misaligned position. The apparatus is shaped and dimensioned to generate a force to rotate said first vertebra from the second misaligned position toward the first desired position.

In another embodiment of the invention, provided is an apparatus to manipulate an intervertebral disc to improve the functioning of the disc, the disc including an annulus, between a pair of vertebra, comprising a device configured when inserted in the disc to contact the vertebra, and operable in response to movement of the vertebra to change the shape of the disc.

In another embodiment of the invention, provided is an apparatus to manipulate an intervertebral disc to improve the functioning of the disc, said apparatus shaped and dimensioned such that when said apparatus is inserted in the disc and compressed between a pair of vertebra, said apparatus gathers at least a portion of the disc to offset at least in part expansive forces acting on the disc. The apparatus can be unitary; can roll over at least one of the vertebra when compressed between the vertebra; can slide over at least a portion of one of the vertebra when compressed between the vertebra; can lengthen inwardly when compressed between the vertebra; can coil inwardly when compressed between the vertebra; and, can fixedly engage at least one of the vertebra when compressed.

In another embodiment of the invention, provide is an apparatus to manipulate an intervertebral disc to improve the functioning of the disc, said apparatus shaped and dimensioned such that when said apparatus is inserted in the disc and compressed between a pair of vertebra, at least a portion of said apparatus moves away from the periphery of the disc.

In another embodiment of the invention, provided is an improved method to manipulate an intervertebral disc to improve the functioning of the disc, the disc including an annulus, between a pair of vertebra. The method comprises the steps of providing a device shaped and dimensioned when inserted in the disc to contact the vertebra, and operable in response to movement of the vertebra to change the shape of the disc; and, inserting said device in the disc to change the shape of the disc. This method can include using an elongate light guide for visualizing or imaging the disc, adjacent vertebras as well as any tissues, such as the annulus and/or nerves, associated therewith or adjacent thereto, such as during the insertion, steering (along an arcuate or linear path), and positioning of the device and inspection thereof. Also, this method can include the use of one or more light wavelengths or one or more dyes for coloring or contrasting of one or more tissues for visual differentiation.

In another embodiment of the invention, provided is an improved method to manipulate an intervertebral disc to improve the functioning of the disc. The method comprises the steps of providing an apparatus shaped and dimensioned when inserted in the disc and compressed between a pair of vertebra to gather at least a portion of the disc to offset at least in part expansive forces acting on the disc; and, inserting the apparatus in the disc to gather said portion of the disc when the apparatus is compressed between a pair of the vertebra. This method can include using an elongate light guide for visualizing or imaging the disc, adjacent vertebras as well as any tissues, such as the annulus and/or nerves, associated therewith or adjacent thereto before, during, and/or after the insertion step as well as inspection of implantation. Also, this method can include the use of one or more light wavelengths (including but not limited to infrared), or one or more dyes for coloring or contrasting of one or more tissues for visual differentiation. The apparatus can be unitary; can roll over at least one of the vertebra when compressed between the vertebra; can slide over at least a portion of one of the vertebra when compressed between the vertebra; can lengthen inwardly when compressed between the vertebra; can coil inwardly when compressed between the vertebra; and, can fixedly engage at least one of the vertebra when compressed.

In a further embodiment of the invention, provided is an improved method to manipulate an intervertebral disc to improve the functioning of the disc. The disc includes a periphery. The method comprises the steps of providing an apparatus shaped and dimensioned when inserted in the disc and compressed between a pair of vertebra to move at least a portion of the apparatus away from the periphery of the disc; and, inserting the apparatus in the disc to move said portion of said apparatus when the apparatus is compressed between a pair of said vertebra. This method can include using an elongate light guide for visualizing or imaging the disc, adjacent vertebras as well as any tissues, such as the annulus and/or nerves, associated therewith or adjacent thereto before, during, or after the inserting step and inspection thereof. Also, this method can include the use of one or more light wavelengths or one or more dyes for coloring or contrasting of one or more tissues for visual differentiation.

In another embodiment of the invention, provided is an improved method for inserting a device to improve in an individual's body the functioning of an intervertebral disc, including an annulus, between a pair of vertebra, the body having a front, a first side, a second side, and a back. The disc includes a front portion facing the front of the body, side portions each facing a side of the body, and a back portion facing the back of the body. The improved method comprises the steps of forming an opening in the disc between the pair of vertebrae, and in one of a group consisting of the side portions of the disc, the front portion of the disc, and the back portion of the disc; providing a device shaped and dimensioned to fit through the opening in the disc; and, inserting the device through the opening in the disc and retaining substantially all of the disc. This method can include using an elongate light guide for visualizing or imaging the disc, adjacent vertebras as well as any tissues, such as the annulus and/or nerves, associated therewith or adjacent thereto before, during, or after the opening forming or inserting steps and inspection thereof. Also, this method can include the use of one or more light wavelengths or one or more dyes for coloring or contrasting of one or more tissues for visual differentiation.

In a further embodiment of the invention, provided is an improved method for inserting a device to improve in an individual's body the functioning of an intervertebral disc, including an annulus, between a pair of vertebrae. The individual's body has a front, a first side, a second side, and a back. The disc includes a front portion facing the front of the body, side portions each facing a side of the body, a back portion facing the back of the body, and a pre-existing rupture. The method comprises the steps of providing a device shaped and dimensioned to fit through the pre-existing rupture in the disc; and, inserting the device through the pre-existing rupture in the disc and retaining substantially all of the disc. This method can include using an elongate light guide for visualizing or imaging the disc, adjacent vertebras as well as any tissues, such as the annulus and/or nerves, associated therewith or adjacent thereto before, during, or after inspection of the pre-existing rupture and inserting step and inspection thereof. Also, this method can include the use of one or more light wavelengths or one or more dyes for coloring or contrasting of one or more tissues for visual differentiation.

Provided in another embodiment of the invention is an improved method to separate tissue. The improved method comprises the steps of providing an instrument shaped and dimensioned to oscillate within tissue around nerves and vasculature; and, oscillating the instrument within tissue around nerves and vasculature. This method can include using an elongate light guide for visualizing or imaging the disc, adjacent vertebras as well as any tissues, such as the annulus and/or nerves, associated therewith or adjacent thereto before, during, or after the oscillating step and inspection thereof. Also, this method can include the use of one or more light wavelengths or one or more dyes for coloring or contrasting of one or more tissues for visual differentiation.

In another embodiment of the invention, provided is an improved method to form an opening in an intervertebral disc. The method comprises the steps of providing an instrument shaped and dimensioned to oscillate within the intervertebral disc; and, oscillating the instrument within an intervertebral disc. This method can include using an elongate light guide for visualizing or imaging the disc, adjacent vertebras as well as any tissues, such as the annulus and/or nerves, associated therewith or adjacent thereto before, during, or after the oscillating step and inspection thereof. Also, this method can include the use of one or more light wavelengths or one or more dyes for coloring or contrasting of one or more tissues for visual differentiation.

In a further embodiment of the invention, provided is an improved method to widen an opening in an intervertebral disc. The method comprises the steps of providing an instrument shaped and dimensioned to oscillate within the intervertebral disc; and, oscillating the instrument within the intervertebral disc. This method can include using an elongate light guide for visualizing or imaging the disc, adjacent vertebras as well as any tissues, such as the annulus and/or nerves, associated therewith or adjacent thereto before, during, or after the oscillating step and inspection thereof. Also, this method can include the use of one or more light wavelengths or one or more dyes for coloring or contrasting of one or more tissues for visual differentiation.

In still another embodiment of the invention, provided is an improved method for forming an opening in hard tissue while minimizing the risk of injury to principal vasculature and nerves. The method comprises the steps of providing an instrument with a distal end shaped and dimensioned to penetrate, when oscillated in and out, soft tissue; and, shaped and dimensioned, when contacting a principal vasculature or nerve, to prevent said distal end from cutting or piercing the principal vasculature or nerve, and to enable the distal end to move past the principal vasculature or nerve. The distal end moves past the principal vasculature or nerve by being oscillated in directions toward and away from the vessel, and by being laterally displaced. When the distal end contacts and is impeded by the principal vasculature or nerve, a resistance to movement of the distal end is generated that, along with the location of the distal end, indicates that the distal end has contacted the principal vasculature or nerve. The method also comprises the steps of oscillating the distal end to pass through the soft tissue; of, when contacting the principal vasculature or nerve, laterally displacing and oscillating the distal end to move the distal end past the principal vasculature or nerve; and, of contacting the hard tissue and oscillating the distal end against the hard tissue to form an opening therein. This method can include using an elongate light guide for visualizing or imaging the disc, adjacent vertebras as well as any tissues, such as the annulus and/or nerves, associated therewith or adjacent thereto before, during, or after the oscillating step, displacement of nerve step, step of forming the opening, and inspection thereof. Also, this method can include the use of one or more light wavelengths or one or more dyes for coloring or contrasting of one or more tissues for visual differentiation.

In still a further embodiment of the invention, provided is an improved method for forming an opening in hard tissue. The method comprises the steps of providing an instrument with a distal end shaped and dimensioned to penetrate, when oscillated in and out, soft tissue and hard tissue; of oscillating the distal end to pass through the soft tissue to contact the hard tissue; and, of oscillating the distal end against the hard tissue to form an opening therein. This method can include using an elongate light guide for visualizing or imaging the disc, adjacent vertebras as well as any tissues, such as the annulus and/or nerves, associated therewith or adjacent thereto before, during, or after the one or more of the oscillating steps and inspection thereof. Also, this method can include the use of one or more light wavelengths or one or more dyes for coloring or contrasting of one or more tissues for visual differentiation.

In yet another embodiment of the invention, provided is an improved method for detecting principal vasculature and nerves. The improved method comprises the steps of providing an instrument with a distal end. The distal end is shaped and dimensioned to penetrate, when oscillated in and out, soft tissue; and, when contacting a principal circulatory/neural vessel, to prevent the distal end from cutting or piercing the principle circulatory/neural vessel. When the distal end contacts and is impeded by a principal vasculature or nerve, a resistance is generated that indicates that the distal end has contacted a principal circulatory/neural vessel. The method also comprises the step of oscillating the distal end to pass through the soft tissue until the resistance indicates that the distal end is contacting a principle circulatory/neural vessel. This method can include using an elongate light guide for visualizing or imaging the disc, adjacent vertebras as well as any tissues, such as the annulus and/or nerves, associated therewith or adjacent thereto before, during, or after the oscillating step and inspection thereof. Also, this method can include the use of one or more light wavelengths or one or more dyes for coloring or contrasting of one or more tissues for visual differentiation.

In yet a further embodiment of the invention, provided is an improved apparatus for forming an opening in hard tissue. The apparatus comprises an instrument with a tissue contacting rounded distal end shaped and dimensioned to penetrate, when oscillated, hard tissue. The distal end can be shaped and dimensioned, when contacting a principal vasculature or nerve, to prevent the distal end from cutting or piercing the principal vasculature or nerve, and to enable the distal end to move past the principal vasculature or nerve.

In yet still another embodiment of the invention, provided is an improved method of passing an implant through tissue to an intervertebral disc location. The method comprises the steps of providing an elongate guide unit; providing an implant structure shaped and dimensioned to pass through tissue and move along the guide unit; and, moving the implant structure through tissue along the guide unit to the intervertebral disc location. This method can include using an elongate light guide for visualizing or imaging the disc, adjacent vertebras as well as any tissues, such as the annulus and/or nerves, associated therewith or adjacent thereto before, during, or after the moving step and inspection thereof. Additionally, the elongate light guide can be configured as the elongate guide unit. Also, this method can include the use of one or more light wavelengths or one or more dyes for coloring or contrasting of one or more tissues for visual differentiation.

In another embodiment of the invention, provided is an improved method to treat a misaligned spine. The method comprises the steps of providing an implant shaped and dimensioned to slide down a guide wire to a selected position intermediate a pair of vertebra to contact and alter the alignment of said vertebra; and, sliding the implant down a guide wire to the selected position. This method can include using an elongate light guide for visualizing or imaging the disc, adjacent vertebras as well as any tissues, such as the annulus and/or nerves, associated therewith or adjacent thereto before, during, or after the sliding step and inspection thereof. Additionally, the elongate light guide can be configured as the guide wire. Also, this method can include the use of one or more light wavelengths or one or more dyes for coloring or contrasting of one or more tissues for visual differentiation.

In a further embodiment of the invention, provided is an improved method to treat a misaligned spine. The method comprises the steps of providing a guide member; providing an articulated implant shaped and dimensioned to slide down and off the guide member in a first orientation to a first selected position intermediate a pair of vertebra, to articulate to a second orientation and be pushed along a path of travel to a second selected position intermediate the pair of vertebra; sliding the implant down the guide member to the first selected position; and, pushing the implant in the second orientation along the path of travel to the second selected position. This method can include using an elongate light guide for visualizing or imaging the disc, adjacent vertebras as well as any tissues, such as the annulus and/or nerves, associated therewith or adjacent thereto before, during, or after the sliding step, pushing step and inspection thereof. Additionally, the elongate light guide can be configured as the guide member. Also, this method can include the use of one or more light wavelengths or one or more dyes for coloring or contrasting of one or more tissues for visual differentiation.

In still another embodiment of the invention, provided is an improved method to insert an implant intermediate a pair of vertebra. The method comprises the steps of providing an articulated implant shaped and dimensioned to be pushed along an arcuate path of travel to a selected position intermediate the pair of vertebra; inserting the implant intermediate the pair of vertebra; and, pushing the implant along the arcuate path of travel to the second selected position. This method can include using an elongate light guide for visualizing or imaging the disc, adjacent vertebras as well as any tissues, such as the annulus and/or nerves, associated therewith or adjacent thereto before, during, or after the inserting step, pushing step, and inspection thereof. The elongate light guide can be used to provide the arcuate path, and can function as a guide member for the insertion and pushing of the implant. Also, this method can include the use of one or more light wavelengths or one or more dyes for coloring or contrasting of one or more tissues for visual differentiation.

In still a further embodiment of the invention, provided is an improved method to insert an implant intermediate a pair of vertebra. The method comprises the steps of providing a guide wire having a distal end; providing a spinal implant shaped and dimensioned to slide along said guide wire to a selected position intermediate the pair of vertebra; inserting the guide wire to position the distal end adjacent the pair of vertebra; sliding the spinal implant along the guide wire to the selected position; and, removing the guide wire. This method can include using an elongate light guide for visualizing or imaging the disc, adjacent vertebras as well as any tissues, such as the annulus and/or nerves, associated therewith or adjacent thereto before, during, or after the inserting step, sliding step, removing step, and inspection thereof. The elongate light guide can be configured as the guide wire, and can even have a distal tip configured as a needle for initial insertion. Also, this method can include the use of one or more light wavelengths or one or more dyes for coloring or contrasting of one or more tissues for visual differentiation.

In yet still another embodiment of the invention, provided is an improved method to treat a misaligned spine. The method comprises the steps of determining the apex of the misaligned spine; selecting an adjacent pair of vertebra, at least one of the pair of vertebra being located at the apex; determining at least one direction in which to move at least one of the pair of vertebra to correct at least partially the misalignment of the spine; determining a spinal implant shape and dimension to achieve movement of the at least one of the pair of vertebra to correct at least partially misalignment of the spine; providing a selected spinal implant having the shape and dimension; determining a location intermediate the adjacent pair of vertebra at which to position the selected spinal implant to achieve the movement of the at least one of the pair of vertebra; and, inserting the selected spinal implant at the location. This method can include using an elongate light guide for visualizing or imaging the disc, adjacent vertebras as well as any tissues, such as the annulus and/or nerves, associated therewith or adjacent thereto before, during, or after one or more the determining, selecting, and inserting steps and inspection thereof. Also, this method can include the use of one or more light wavelengths or one or more dyes for coloring or contrasting of one or more tissues for visual differentiation.

In yet still a further embodiment of the invention, provided is an improved method to alter the alignment of a vertebra. The improved method comprises the steps of identifying a disc space location adjacent the vertebra; identifying a spinal implant shape and dimension to generate a force acting from the disc space to alter alignment of the vertebra; providing a selected spinal implant having the shape and dimension; and, inserting the selected spinal implant in the disc space. This method can include using an elongate light guide for visualizing or imaging the disc, adjacent vertebras as well as any tissues, such as the annulus and/or nerves, associated therewith or adjacent thereto before, during, or after the identifying and inserting steps and inspection thereof. Also, this method can include the use of one or more light wavelengths or one or more dyes for coloring or contrasting of one or more tissues for visual differentiation.

In another embodiment of the invention, provided is an improved method for inserting an implant. The method comprises the steps of providing an implant; providing a guide member shaped and dimensioned to permit the implant to move along the guide member without rotating on the guide member; and, moving the implant along the guide member to a selected location in a patient's body. This method can include using an elongate light guide for visualizing or imaging the disc, adjacent vertebras as well as any tissues, such as the annulus and/or nerves, associated therewith or adjacent thereto before, during, or after the moving step and inspection thereof. The elongate light guide can be configured as the guide member. Also, this method can include the use of one or more light wavelengths or one or more dyes for coloring or contrasting of one or more tissues for visual differentiation.

In a further embodiment of the invention, provided is an improved method for fixing an implant adjacent tissue in the body of a patient. The method comprises the steps of forming an implant with an outer surface having at least one opening that expands in size as the distance from the outer surface into the opening increases; and, inserting the implant adjacent viscoelastic tissue in the body to permit the tissue to move into the opening and expand inside the opening.

In still another embodiment of the invention, provided is an improved method to align vertebrae. The method includes the steps of providing an implant that aligns a pair of adjacent vertebra and permits movement of the pair of adjacent vertebra while, to protect the facets of said vertebrae, minimizing rotation of one of the vertebra with respect to the other of the vertebra; and, inserting the implant between the pair of vertebra to engage each of the pair of vertebra, alter the alignment of the vertebrae, permit movement of the vertebrae, and minimize rotation of one of the vertebrae with respect to the other of the vertebrae. The rotation of one of the vertebra about the longitudinal axis of the spine with respect to the other of the vertebra is limited by the implant to fifteen degrees or less, preferably ten degrees or less, and most preferably five degrees or less. If desired, the implant can restrict rotation of one of the vertebra about the longitudinal axis of the spine with respect to the other of the vertebra to three degrees or less. This method can include using an elongate light guide for visualizing or imaging the disc, adjacent vertebras as well as any tissues, such as the annulus and/or nerves, associated therewith or adjacent thereto before, during, or after the inserting step and inspection thereof. The elongate light guide can be configured as the guide member. Also, this method can include the use of one or more light wavelengths or one or more dyes for coloring or contrasting of one or more tissues for visual differentiation.

In still a further embodiment of the invention, provided is an improved method to insert an implant having at least one moving component. The method comprises the steps of providing a guide member to engage and insert the implant while immobilizing the moving component, and once the implant is inserted, to disengage from the implant and permit the moving component to move; engaging the implant with the guide member to immobilize the moving component; inserting the implant with the guide member; and, disengaging the guide member from the implant to permit movement of the moving component. This method can include using an elongate light guide for visualizing or imaging the disc, adjacent vertebras as well as any tissues, such as the annulus and/or nerves, associated therewith or adjacent thereto before, during, or after the inserting and disengaging steps and inspection thereof. The elongate light guide can be configured as the guide member. The elongate light guide can be configured as the guide member. Also, this method can include the use of one or more light wavelengths or one or more dyes for coloring or contrasting of one or more tissues for visual differentiation.

In yet still another embodiment of the invention, provided is an improved method to alter the alignment of the spine. The method comprises the steps of providing an implant shaped and dimensioned to engage each one of an adjacent pair of vertebra and including at least one displaceable member to translate laterally at least one of the pair with respect to the other of the pair; inserting the implant intermediate the pair of vertebra to engage each of the pair; and, displacing the member to translate laterally at least one of the pair. This method can include using an elongate light guide for visualizing or imaging the disc, adjacent vertebras as well as any tissues, such as the annulus and/or nerves, associated therewith or adjacent thereto before, during, or after the inserting and displacing steps and inspection thereof. Also, this method can include the use of one or more light wavelengths or one or more dyes for coloring or contrasting of one or more tissues for visual differentiation.

In yet still a further embodiment of the invention, provided is a method to position a pair of opposing tissue surfaces. The method comprises the steps of providing an implant comprised of at least an upper and a lower arcuate concave surface, the surfaces each contacting a different one of said tissue surfaces to space apart the surfaces; and, inserting the implant intermediate the opposing tissue surfaces. This method can include using an elongate light guide for visualizing or imaging the disc, adjacent vertebras as well as any tissues, such as the annulus and/or nerves, associated therewith or adjacent thereto before, during, or after the inserting step and inspection thereof. Also, this method can include the use of one or more light wavelengths or one or more dyes for coloring or contrasting of one or more tissues for visual differentiation.

In another embodiment of the invention, provided is a method to form an opening within the body. The method comprises the steps of providing an instrument with a distal end shaped and dimensioned to be manipulated to pass through tissue to a selected location within the body, and, housing a deployable instrument to make an opening; manipulating the distal end to pass through tissue to the selected location; deploying the instrument; and making an opening. This method can include using an elongate light guide for visualizing or imaging the disc, adjacent vertebras as well as any tissues, such as the annulus and/or nerves, associated therewith or adjacent thereto before, during, or after the deploying and making of the opening steps and inspection thereof. Also, this method can include the use of one or more light wavelengths or one or more dyes for coloring or contrasting of one or more tissues for visual differentiation.

In a further embodiment of the invention, provided is a method to fix an implant to at least one tissue surface. The method comprises the steps of providing an implant having a surface and at least one opening formed in the surface and increasing in width as the distance from the surface increases; packing the opening with a composition; and, inserting the implant adjacent the tissue surface such that the composition contacts the tissue surface. This method can include using an elongate light guide for visualizing or imaging the disc, adjacent vertebras as well as any tissues, such as the annulus and/or nerves, associated therewith or adjacent thereto before, during, or after the inserting step and inspection thereof. Also, this method can include the use of one or more light wavelengths or one or more dyes for coloring or contrasting of one or more tissues for visual differentiation.

In still another embodiment of the invention, provided is an improved method to fix an implant to at least one tissue surface. The method comprises the steps of providing an implant having a surface and an arm extending outwardly from the surface and shaped and dimensioned to penetrate and interlock with the tissue surface; and, inserting the implant adjacent the tissue surface such that the arm penetrates and interlocks with the tissue surface. This method can include using an elongate light guide for visualizing or imaging the disc, adjacent vertebras as well as any tissues, such as the annulus and/or nerves, associated therewith or adjacent thereto before, during, or after the inserting step and inspection thereof. Also, this method can include the use of one or more light wavelengths or one or more dyes for coloring or contrasting of one or more tissues for visual differentiation.

In still a further embodiment of the invention, provided is an improved method of passing an implant through tissue to a location intermediate a pair of opposing joint members. The method comprises the steps of providing an elongate guide unit; providing an implant structure shaped and dimensioned to pass through tissue and move along the guide unit; and, moving the implant structure through tissue along the guide unit to the location intermediate the joint members. The guide unit and implant can be shaped and dimensioned such that the guide unit can prevents rotation of the implant about the longitudinal axis of the guide unit. This method can include using an elongate light guide for visualizing or imaging the disc, adjacent vertebras as well as any tissues, such as the annulus and/or nerves, associated therewith or adjacent thereto before, during, or after the moving step and inspection thereof. The elongate light guide can be configured as the guide unit. Also, this method can include the use of one or more light wavelengths or one or more dyes for coloring or contrasting of one or more tissues for visual differentiation.

In yet still another embodiment of the invention, provided is a method to position a pair of opposing tissue surfaces. The method includes the steps of providing an implant having at least one pivot and a guide unit; and, inserting the implant with the pivot along the guide unit intermediate the opposing tissue surfaces. This method can include using an elongate light guide for visualizing or imaging the disc, adjacent vertebras as well as any tissues, such as the annulus and/or nerves, associated therewith or adjacent thereto before, during, or after the inserting step and inspection thereof. The elongate light guide can be configured as the guide unit. Also, this method can include the use of one or more light wavelengths or one or more dyes for coloring or contrasting of one or more tissues for visual differentiation.

In yet still a further embodiment of the invention, provided is an improved method to form a passageway within the body. The method comprises the steps of providing a guide wire; providing an instrument adapted to move along the guide wire and including a distal end shaped and dimensioned to pass through tissue to a selected location between two vertebrae; moving the instrument along the guide wire and manipulating the instrument to pass through tissue to the selected location; and, oscillating the instrument to form a passageway. This method can include using an elongate light guide for visualizing or imaging the disc, adjacent vertebras as well as any tissues, such as the annulus and/or nerves, associated therewith or adjacent thereto before, during, or after one or more of the moving and manipulating and oscillating steps and inspection thereof. The elongate light guide can be configured as the guide wire. Also, this method can include the use of one or more light wavelengths or one or more dyes for coloring or contrasting of one or more tissues for visual differentiation.

In another embodiment of the invention, provided is an improved method to alter the orientation of a vertebra. The method comprises the steps of providing a guide wire; providing an instrument adapted to move along the guide wire and including a distal end shaped and dimensioned to pass through tissue to a selected location between two vertebrae; moving the instrument along the guide wire and manipulating the instrument to pass through tissue to the selected location; and, manipulating the instrument to alter the orientation of one of the vertebrae with respect to the other of the vertebrae. This method can include using an elongate light guide for visualizing or imaging the disc, adjacent vertebras as well as any tissues, such as the annulus and/or nerves, associated therewith or adjacent thereto before, during, or after the moving and/or manipulating steps and inspection thereof. The elongate light guide can be configured as the guide wire. Also, this method can include the use of one or more light wavelengths or one or more dyes for coloring or contrasting of one or more tissues for visual differentiation.

In a further embodiment of the invention, provided is an improved method of fixing an implant intermediate an adjacent pair of vertebra. The method comprises the steps of inserting a first implant within an intervertebral disc between the pair of vertebra; inserting a second implant exterior of the intervertebral disc and between the pair of vertebra such that at least one of the vertebra pivots about at least one of the first and second implants to apply a force to the one of the implants between the vertebra. This method can include using an elongate light guide for visualizing or imaging the disc, adjacent vertebras as well as any tissues, such as the annulus and/or nerves, associated therewith or adjacent thereto before, during, or after one or more of the inserting, pivoting, and force-applying steps and inspection thereof. Also, this method can include the use of one or more light wavelengths or one or more dyes for coloring or contrasting of one or more tissues for visual differentiation.

In still another embodiment of the invention, provided is an improved method of fixing an implant intermediate an adjacent pair of vertebra. The method comprises the steps of inserting a first implant within an intervertebral disc between the pair of vertebra; and, inserting a second implant within an intervertebral disc between the pair of vertebra such that at least one of the vertebra pivots about at least one of the first and second implants to apply a force to the one of said implants between the vertebra.

In still a further embodiment of the invention, provided is a method of passing an implant through tissue to a location intermediate a pair of joint members. The method comprises the steps of providing an elongate guide unit having a longitudinal axis; providing an implant shaped and dimensioned to move along the guide unit; moving the implant structure along the guide unit to the location intermediate one of a pair comprising an opposing pair of spinous processes, and an opposing pair of facet joints. This method can include using an elongate light guide for visualizing or imaging the disc, adjacent vertebras as well as any tissues, such as the annulus and/or nerves, associated therewith or adjacent thereto before, during, or after one or more of the inserting steps and inspection thereof. The elongate light guide can be configured as the guide unit. Also, this method can include the use of one or more light wavelengths or one or more dyes for coloring or contrasting of one or more tissues for visual differentiation.

In yet still another embodiment of the invention, provided is an improved method of passing an implant through tissue to a location intermediate a pair of opposing vertebra. The method comprises the steps of providing an elongate guide unit having a longitudinal axis; providing an implant shaped and dimensioned to move along the guide unit; and, moving the implant structure along the guide unit to the location intermediate the opposing vertebra. The implant and the guide unit are shaped and dimensioned such that the guide unit prevents rotation of the implant about the longitudinal axis of the guide unit. This method can include using an elongate light guide for visualizing or imaging the disc, adjacent vertebras as well as any tissues, such as the annulus and/or nerves, associated therewith or adjacent thereto before, during, or after the moving step and inspection thereof. The elongate light guide can be configured as the guide unit. Also, this method can include the use of one or more light wavelengths or one or more dyes for coloring or contrasting of one or more tissues for visual differentiation.

In yet still a further embodiment of the invention, provided is an improved method to position a pair of opposing tissue surfaces. The method comprises the steps of providing a guide wire; providing an implant shaped and dimensioned to move along the guide wire and comprised of at least one tapered end to separate tissue, an upper surface and a lower surface, and an outwardly projecting lip intermediate said upper and lower surfaces; moving the implant along the guide wire to insert the implant intermediate the opposing tissue surfaces such that the upper surface and the lower surface each contact a different one of the tissue surfaces to space apart the tissue surfaces. This method can include using an elongate light guide for visualizing or imaging the disc, adjacent vertebras as well as any tissues, such as the annulus and/or nerves, associated therewith or adjacent thereto before, during, or after the moving and/or contacting steps and inspection thereof. The elongate light guide can be configured as the guide wire. Also, this method can include the use of one or more light wavelengths or one or more dyes for coloring or contrasting of one or more tissues for visual differentiation.

In another embodiment of the invention, provided is an improved method to position an implant between a pair of opposing tissue surfaces. The method comprises the steps of providing an elongate guide unit having a dispensing end; providing an implant comprised of at least one articulating joint, and shaped and dimensioned to move along the elongate guide unit, to exit the elongate guide unit from the dispensing end and articulate to travel along an arcuate path intermediate the pair of opposing tissue surfaces; moving the implant along the elongate guide unit; exiting the implant from the dispensing end of the guide unit intermediate the opposing tissue surfaces; and, articulating the implant to travel intermediate the pair of opposing tissue surfaces on exiting said elongate guide unit. This method can include using an elongate light guide for visualizing or imaging the disc, adjacent vertebras as well as any tissues, such as the annulus and/or nerves, associated therewith or adjacent thereto before, during, or after the moving and/or articulating steps and inspection thereof. The elongate light guide can be configured as the guide unit. Also, this method can include the use of one or more light wavelengths or one or more dyes for coloring or contrasting of one or more tissues for visual differentiation.

In a further embodiment of the invention, provided is an improved method to separate a pair of joint members. The method comprises the steps of inserting a first member intermediate the pair of joint members to fixedly engage one of the pair of joint members; and moving a second member between the first member and the other of the pair of joint members to separate the joint members. This method can include using an elongate light guide for visualizing or imaging the disc, adjacent vertebras as well as any tissues, such as the annulus and/or nerves, associated therewith or adjacent thereto before, during, or after the inserting, moving and/or separating steps and inspection thereof. Also, this method can include the use of one or more light wavelengths or one or more dyes for coloring or contrasting of one or more tissues for visual differentiation.

In still another embodiment of the invention, provided is an improved method for securing an implant between a pair of joint members. The method comprises the steps of providing a contoured implant with outer surfaces shaped and dimensioned to permit each of the joint members to seat on the implant; and, inserting the contoured implant intermediate the pair of joint members such that each of the joint members seats on the implant. This method can include using an elongate light guide for visualizing or imaging the disc, adjacent vertebras as well as any tissues, such as the annulus and/or nerves, associated therewith or adjacent thereto before, during, or after the inserting step and inspection thereof. Also, this method can include the use of one or more light wavelengths or one or more dyes for coloring or contrasting of one or more tissues for visual differentiation.

In still a further embodiment of the invention, provided is an improved method to restrict motion of one process with respect to another process of the spine about the longitudinal axis of the spine. The method comprises the steps of providing, for one of a pair consisting of two opposing spinous processes and two opposing transverse processes, a contoured implant with outer surfaces shaped and dimensioned to permit each one of the processes in the one of the pair to seat on the implant to restrict rotation or translation of one of the processes with respect to the other of the processes. The method also includes the step of inserting the contoured implant intermediate the opposing processes such that each of the processes seats on the implant to restrict at least one of a pair consisting of rotation and translation of one of the processes with respect to the other of the processes. This method can include using an elongate light guide for visualizing or imaging the disc, adjacent vertebras as well as any tissues, such as the annulus and/or nerves, associated therewith or adjacent thereto before, during, or after the inserting step and inspection thereof. Also, this method can include the use of one or more light wavelengths or one or more dyes for coloring or contrasting of one or more tissues for visual differentiation.

In yet another embodiment of the invention, provided is a method for securing an implant between an opposing pair of spinous processes of a spine. The method comprises the steps of inserting the implant intermediate the spinous processes; and securing the implant with at least one leg having a first end pivotally attached to the implant, and a second end attached to the spine. This method can include using an elongate light guide for visualizing or imaging the disc, adjacent vertebras as well as any tissues, such as the annulus and/or nerves, associated therewith or adjacent thereto before, during, or after the inserting and/or securing steps and inspection thereof. Also, this method can include the use of one or more light wavelengths or one or more dyes for coloring or contrasting of one or more tissues for visual differentiation.

In yet a further embodiment of the invention, provided is a method for securing an implant between an opposing pair of joint members. The method comprises the steps of providing a winged implant with at least one wing movable between a stowed position and a deployed position; providing the winged implant with the wing is the stowed position; inserting the winged implant between the opposing pair of joint members; and, moving the wing from the stowed position to the deployed position.

In yet still another embodiment of the invention, provided is an improved method to position a device at a selected location in a body to function as an implant. The method comprises the steps of providing a structure constructed to be utilized as an instrument and as an implant; utilizing the structure as an instrument to position the structure at the selected location in the body; and, leaving the structure at the selected location to function as an implant. This method can include using an elongate light guide for visualizing or imaging the disc, adjacent vertebras as well as any tissues, such as the annulus and/or nerves, associated therewith or adjacent thereto before, during, or after the utilizing and/or leaving steps and inspection thereof. The elongate light guide can be configured as the instrument. Also, this method can include the use of one or more light wavelengths or one or more dyes for coloring or contrasting of one or more tissues for visual differentiation.

In one embodiment of the invention, provided is an improved method of altering the tilt of one joint member with respect to another opposing joint member. The method comprises the steps of providing a resilient implant; providing a guide unit; inserting and manipulating the guide unit to tilt one of the opposing joint members; and, sliding the resilient implant along the guide unit intermediate the joint members. In one aspect, the method comprises the steps of providing a spring; providing a guide unit; and, sliding the spring along the guide unit to a selected position intermediate the opposing joint members. This method can include using an elongate light guide for visualizing or imaging the disc, adjacent vertebras as well as any tissues, such as the annulus and/or nerves, associated therewith or adjacent thereto before, during, or after the inserting, manipulating, and/or sliding step and inspection thereof. The elongate light guide can be configured as the guide unit. Also, this method can include the use of one or more light wavelengths or one or more dyes for coloring or contrasting of one or more tissues for visual differentiation.

In still another embodiment of the invention, provided is an improved method of dampening the load in a joint. The method comprises the steps of providing a resilient implant and an elongate guide unit; sliding the resilient implant along the guide unit; manipulating the guide unit adjacent the joint; and, dispensing the implant into the joint. This method can include using an elongate light guide for visualizing or imaging the disc, adjacent vertebras as well as any tissues, such as the annulus and/or nerves, associated therewith or adjacent thereto before, during, or after the sliding, manipulating, and/or dispensing steps and inspection thereof. The elongate light guide can be configured as the guide unit. Also, this method can include the use of one or more light wavelengths or one or more dyes for coloring or contrasting of one or more tissues for visual differentiation.

In yet another embodiment of the invention, provided is an improved method of dampening the load in a joint comprising the step of inserting an ovate coil spring in the joint, which can be performed with the elongate light guide.

In yet still another embodiment of the invention, provided is an improved method of dampening the load in a joint including a pair of opposing joint members. The method comprises the steps of providing a spring and an elongate guide unit; and, sliding the spring along the guide unit intermediate the joint members. This method can include using an elongate light guide for visualizing or imaging the disc, adjacent vertebras as well as any tissues, such as the annulus and/or nerves, associated therewith or adjacent thereto before, during, or after the sliding step and inspection thereof. The elongate light guide can be configured as the guide unit. Also, this method can include the use of one or more light wavelengths or one or more dyes for coloring or contrasting of one or more tissues for visual differentiation.

In a further embodiment of the invention, provided is an improved method of fixing an implant in a joint. The method comprises the steps of inserting an implant having an outer surface, and at least one opening having a portion in which the width diverges as the distance into the opening from the outer surface of the implant increases.

In still a further embodiment of the invention, provided is an improved method of inserting an implant in a joint having tissue with an initial color. The method comprises the steps of detecting a change in color; and, inserting the implant in the joint. This method can include using an elongate light guide for visualizing or imaging the disc, adjacent vertebras as well as any tissues, such as the annulus and/or nerves, associated therewith or adjacent thereto before, during, or after the detecting color change and inserting steps and inspection thereof. Also, this method can include the use of one or more light wavelengths or one or more dyes for coloring or contrasting of one or more tissues for visual differentiation.

In yet a further embodiment of the invention, provided is an improved method of inserting an implant in a joint having tissue with an initial contrast. The method comprises the steps of detecting a change in contrast; and, inserting the implant in the joint. This method can include using an elongate light guide for visualizing or imaging the disc, adjacent vertebras as well as any tissues, such as the annulus and/or nerves, associated therewith or adjacent thereto before, during, or after the detecting color change and inserting steps and inspection thereof. Also, this method can include the use of one or more light wavelengths or one or more dyes for coloring or contrasting of one or more tissues for visual differentiation.

In yet still a further embodiment of the invention, provided is an improved method of inserting an implant in a joint having tissue with an initial hardness. The method comprises the steps of detecting a change in hardness; and, inserting the implant in the joint.

In another embodiment of the invention, provided is an improved method of inserting an implant in a joint having tissue with an initial elasticity. The method comprises the steps of detecting a change in elasticity; and, inserting the implant in the joint.

In still another embodiment of the invention, provided is an improved method of inserting an implant in a joint having tissue with an initial texture. The method comprises the steps of detecting a change in texture; and, inserting the implant in the joint.

In yet another embodiment of the invention, provided is an improved method of inserting an implant in a joint having tissue with an initial color. The method comprises the steps of staining the tissue to change the color of the tissue from the initial color; detecting the change in color; and, inserting the implant. This method can include using an elongate light guide for visualizing or imaging the disc, adjacent vertebras as well as any tissues, such as the annulus and/or nerves, associated therewith or adjacent thereto before, during, or after the detecting color change and/or inserting step and inspection thereof. Also, this method can include the use of one or more light wavelengths or one or more dyes for coloring or contrasting of one or more tissues for visual differentiation.

In yet still another embodiment of the invention, provided is an improved method of inserting an implant in a joint having tissue having an initial color. The method comprises the steps of removing tissue to change the color of the tissue from the initial color; detecting the change in color; and, inserting the implant. This method can include using an elongate light guide for visualizing or imaging the disc, adjacent vertebras as well as any tissues, such as the annulus and/or nerves, associated therewith or adjacent thereto before, during, or after the detecting the color change and inserting steps and inspection thereof. Also, this method can include the use of one or more light wavelengths or one or more dyes for coloring or contrasting of one or more tissues for visual differentiation.

In an additional embodiment of the invention, provided is an improved method of inserting an implant in a joint having tissue having an initial texture. The method comprises the steps of changing the texture of the tissue; detecting the change in texture; and, inserting the implant. This method can include using an elongate light guide for visualizing or imaging the disc, adjacent vertebras as well as any tissues, such as the annulus and/or nerves, associated therewith or adjacent thereto before, during, or after the detecting change in texture and/or inserting steps and inspection thereof. Also, this method can include the use of one or more light wavelengths or one or more dyes for coloring or contrasting of one or more tissues for visual differentiation.

In still an additional embodiment of the invention, provided is an improved method of inserting an implant in a joint having tissue having an initial contrast. The method comprises the steps of changing the contrast of the tissue; detecting the change in contrast; and, inserting the implant. This method can include using an elongate light guide for visualizing or imaging the disc, adjacent vertebras as well as any tissues, such as the annulus and/or nerves, associated therewith or adjacent thereto before, during, or after the detecting change in contrast and/or inserting steps and inspection thereof. Also, this method can include the use of one or more light wavelengths or one or more dyes for coloring or contrasting of one or more tissues for visual differentiation.

In yet an additional embodiment of the invention, provided is an improved method of passing with an instrument by tissue comprising principal vasculature and nerves. The instrument has a portion with an offset axis of rotation such that a first section of the instrument to one side of the axis of rotation is wider than a second section of the instrument to the other side of the axis of rotation. The method comprising the steps of positioning the instrument with the second section of the instrument adjacent the tissue; and, rotating the instrument about the axis of rotation to contact and displace the tissue with the first section of the instrument. This method can include using an elongate light guide for visualizing or imaging the disc, adjacent vertebras as well as any tissues, such as the annulus and/or nerves, associated therewith or adjacent thereto before, during, or after the passing, positioning, and/or rotating steps and inspection thereof. The elongate light guide can be configured as the guide unit. Also, this method can include the use of one or more light wavelengths or one or more dyes for coloring or contrasting of one or more tissues for visual differentiation.

In yet still an additional embodiment of the invention, provided is an improved method of passing an instrument by tissue comprising principal vasculature and nerves. The instrument has a tapered portion with a width diverging from a smaller first section to a larger second section, the tapered portion having and circumscribing an elongate axis of displacement. The method comprises the steps of positioning the instrument with the smaller first section of the instrument adjacent the tissue; and, displacing the instrument in a direction parallel to the axis of displacement to contact and displace the tissue with the larger second section of the instrument. This method can include using an elongate light guide for visualizing or imaging the disc, adjacent vertebras as well as any tissues, such as the annulus and/or nerves, associated therewith or adjacent thereto before, during, or after the passing, positioning, and/or displacing steps and inspection thereof. The elongate light guide can be configured as the instrument. Also, this method can include the use of one or more light wavelengths or one or more dyes for coloring or contrasting of one or more tissues for visual differentiation.

In another embodiment of the invention, provided is an improved method of dissecting tissue with an instrument. The instrument has a cutting portion with an offset axis of rotation such that a first section of the cutting portion to one side of the axis of rotation is wider than a second section of the cutting portion to the other side of the axis of rotation. The method comprises the steps of positioning the instrument with the second section of the instrument adjacent tissue; and, rotating the instrument about the axis of rotation to contact and cut the tissue with the first section of the instrument. This method can include using an elongate light guide for visualizing or imaging the disc, adjacent vertebras as well as any tissues, such as the annulus and/or nerves, associated therewith or adjacent thereto before, during, or after the positioning, rotating, and cutting steps and inspection thereof. The elongate light guide can be configured as the instrument. Also, this method can include the use of one or more light wavelengths or one or more dyes for coloring or contrasting of one or more tissues for visual differentiation.

In still another embodiment of the invention, provided is an improved method of cutting tissue with an instrument. The instrument has an axis of rotation. The method comprises the steps of sliding the instrument along an elongate guide unit to a position adjacent the tissue; and, rotating the instrument about the axis of rotation and circumscribing an elongate axis of displacement to contact and cut the tissue. This method can include using an elongate light guide for visualizing or imaging the disc, adjacent vertebras as well as any tissues, such as the annulus and/or nerves, associated therewith or adjacent thereto before, during, or after the sliding, rotating, and cutting steps and inspection thereof. The elongate light guide can be configured as the instrument. Also, this method can include the use of one or more light wavelengths or one or more dyes for coloring or contrasting of one or more tissues for visual differentiation.

In yet still another embodiment of the invention, provided is an improved method of cutting tissue with an instrument. The instrument has a tapered portion with a width diverging from a smaller first section to a larger second cutting section, the tapered portion having and circumscribing an elongate axis of displacement. The method comprises the steps of positioning the instrument with the smaller first section of the tapered portion adjacent tissue; and, displacing the instrument in a direction parallel to the axis of displacement to contact and cut the tissue with the larger second cutting section of the tapered portion. This method can include using an elongate light guide for visualizing or imaging the disc, adjacent vertebras as well as any tissues, such as the annulus and/or nerves, associated therewith or adjacent thereto before, during, or after the positioning, displacing, and cutting steps and inspection thereof. The elongate light guide can be configured as the instrument. Also, this method can include the use of one or more light wavelengths or one or more dyes for coloring or contrasting of one or more tissues for visual differentiation.

In a further embodiment of the invention, provided is an improved method of delivering an implant to a selected location in the body. The method comprises the steps of providing an implant assembly consisting of a first component, and a second component removably interfit with the first component; providing a guide member slidably extending through the first and second components to maintain the components as a unitary implant in a selected registration; and, sliding the implant assembly along the guide member to the selected location in the body. This method can include using an elongate light guide for visualizing or imaging the disc, adjacent vertebras as well as any tissues, such as the annulus and/or nerves, associated therewith or adjacent thereto before, during, or after the sliding step and inspection thereof. The elongate light guide can be configured as the guide member Also, this method can include the use of one or more light wavelengths or one or more dyes for coloring or contrasting of one or more tissues for visual differentiation.

In still a further embodiment of the invention, provided is an improved method to deliver an implant to a selected location in the body. The method comprises the steps of providing an implant assembly consisting of a first component, and a second component housed within the first component; providing a guide member slidably extending through the first and second components to maintain the components as a unitary implant in a selected registration; and, sliding the implant assembly along the guide member to the selected location in the body. This method can include using an elongate light guide for visualizing or imaging the disc, adjacent vertebras as well as any tissues, such as the annulus and/or nerves, associated therewith or adjacent thereto before, during, or after the sliding step and inspection thereof. The elongate light guide can be configured as the guide member. Also, this method can include the use of one or more light wavelengths or one or more dyes for coloring or contrasting of one or more tissues for visual differentiation.

In yet a further embodiment of the invention, provided is an improved method of altering the orientation of at least one of a pair of vertebra. The method comprises the steps of providing a lever having a distal end and a proximate end; inserting the lever intermediate and contacting the pair of vertebra; and, displacing the lever to displace at least one of the pair of vertebra.

In yet still a further embodiment of the invention, provided is an improved method of separating tissue. The method comprises the steps of providing an instrument having a portion with an offset axis of rotation such that a first section of the instrument to one side of the axis of rotation is wider than a second section of the instrument to the other side of the axis of rotation; positioning the instrument with the second section of the instrument in the tissue; and, rotating the instrument about the axis of rotation to separate the tissue. This method can include using an elongate light guide for visualizing or imaging the disc, adjacent vertebras as well as any tissues, such as the annulus and/or nerves, associated therewith or adjacent thereto before, during, or after the positioning and rotating steps and inspection thereof. The elongate light guide can be configured as the instrument. Also, this method can include the use of one or more light wavelengths or one or more dyes for coloring or contrasting of one or more tissues for visual differentiation.

In an additional embodiment of the invention, provided is an improved method of inserting a device intermediate two adjacent vertebra. The method comprises the steps of providing an elongate guide unit; manipulating the guide unit to displace tissue; sliding a device along the guide unit to a position intermediate the vertebra and changing the shape of a disc intermediate the vertebra. This method can include using an elongate light guide for visualizing or imaging the disc, adjacent vertebras as well as any tissues, such as the annulus and/or nerves, associated therewith or adjacent thereto before, during, or after the manipulating, sliding, and shape changing steps and inspection thereof. The elongate light guide can be configured as the guide unit. Also, this method can include the use of one or more light wavelengths or one or more dyes for coloring or contrasting of one or more tissues for visual differentiation.

In still an additional embodiment of the invention, provided is an improved method of inserting a device intermediate two adjacent vertebra. The method comprises the steps of providing an elongate guide unit; manipulating the guide unit to displace tissue; and, sliding a device along the guide unit to a position intermediate and contacting the vertebra and changing the alignment of the vertebra. This method can include using an elongate light guide for visualizing or imaging the disc, adjacent vertebras as well as any tissues, such as the annulus and/or nerves, associated therewith or adjacent thereto before, during, or after the manipulating and sliding steps and inspection thereof. The elongate light guide can be configured as the guide unit. Also, this method can include the use of one or more light wavelengths or one or more dyes for coloring or contrasting of one or more tissues for visual differentiation.

In yet an additional embodiment of the invention, provided is an improved method of inserting a device intermediate two adjacent vertebra. The method comprises the steps of providing an articulating implant; inserting the implant intermediate the vertebra; articulating the implant; and, separating the implant into at least two portions. This method can include using an elongate light guide for visualizing or imaging the disc, adjacent vertebras as well as any tissues, such as the annulus and/or nerves, associated therewith or adjacent thereto before, during, or after the inserting, articulating, and/or separating steps and inspection thereof. Also, this method can include the use of one or more light wavelengths or one or more dyes for coloring or contrasting of one or more tissues for visual differentiation.

In yet still an additional embodiment of the invention, provided is an improved method to insert a device intermediate two adjacent vertebra. The method comprises the steps of providing an implant having at least two sides and an opening extending through the implant from one of the sides to the other of the sides; and, inserting the implant between the vertebras such that a different one of the sides contacts each of the vertebras independent of the device orientation. This method can include using an elongate light guide for visualizing or imaging the disc, adjacent vertebras as well as any tissues, such as the annulus and/or nerves, associated therewith or adjacent thereto before, during, or after the inserting step and inspection thereof. Also, this method can include the use of one or more light wavelengths or one or more dyes for coloring or contrasting of one or more tissues for visual differentiation.

In another embodiment of the invention, provided is an improved method of inserting an implant in a joint having tissue with an initial shape. The method comprises the steps of detecting a change in the shape of the joint; and, inserting the implant in the joint. This method can include using an elongate light guide for visualizing or imaging the disc, adjacent vertebras as well as any tissues, such as the annulus and/or nerves, associated therewith or adjacent thereto before, during, or after the detecting and inserting steps and inspection thereof. Also, this method can include the use of one or more light wavelengths or one or more dyes for coloring or contrasting of one or more tissues for visual differentiation.

In still another embodiment of the invention, provided is an improved method of inserting an implant in a joint having tissue having an initial shape. The method comprises the steps of changing the shape of the joint; detecting the change in shape; and, inserting the implant. This method can include using an elongate light guide for visualizing or imaging the disc, adjacent vertebras as well as any tissues, such as the annulus and/or nerves, associated therewith or adjacent thereto before, during, or after the changing, detecting and/or inserting steps and inspection thereof. Also, this method can include the use of one or more light wavelengths or one or more dyes for coloring or contrasting of one or more tissues for visual differentiation.

In yet another embodiment of the invention, provided is an improved method of inserting an implant in a joint. The method comprises the steps of providing an articulating implant unit having a hinge interconnecting at least a pair of body members; providing a guide unit; inserting the guide unit into the joint; sliding the implant unit along the guide unit and dispensing the implant unit from the guide unit to contact the joint, articulate, and position within the joint; and, detecting the location of one of a group of the body members and the hinge to determine the location of the implant unit in the joint. This method can include using an elongate light guide for visualizing or imaging the disc, adjacent vertebras as well as any tissues, such as the annulus and/or nerves, associated therewith or adjacent thereto before, during, or after the inserting, dispensing, articulating, positioning, and detecting steps and inspection thereof. The elongate light guide can be configured as the guide unit. Also, this method can include the use of one or more light wavelengths or one or more dyes for coloring or contrasting of one or more tissues for visual differentiation.

In yet still another embodiment of the invention, provided is an improved method of conforming an implant to the shape of a joint. The method comprises the steps of providing an articulating implant unit having a hinge interconnecting at least a pair of body members; providing a guide unit; inserting the guide unit into the joint; and, sliding the implant unit along the guide unit and dispensing the implant unit from the guide unit to contact the joint, articulate, and conform to the shape of the joint. This method can include using an elongate light guide for visualizing or imaging the disc, adjacent vertebras as well as any tissues, such as the annulus and/or nerves, associated therewith or adjacent thereto before, during, or after the inserting, sliding and dispensing steps and inspection thereof. The elongate light guide can be configured as the guide unit. Also, this method can include the use of one or more light wavelengths or one or more dyes for coloring or contrasting of one or more tissues for visual differentiation.

In a further embodiment of the invention, provided is an improved method of inserting an implant in a joint. The method comprises the steps of providing an elongate guide unit and implant configured to pass by an existing device adjacent a joint; inserting the guide unit and manipulating the guide unit by the existing device; and, inserting the implant into the joint. This method can include using an elongate light guide for visualizing or imaging the disc, adjacent vertebras as well as any tissues, such as the annulus and/or nerves, associated therewith or adjacent thereto before, during, or after the inserting steps and inspection thereof. The elongate light guide can be configured as the guide unit. Also, this method can include the use of one or more light wavelengths or one or more dyes for coloring or contrasting of one or more tissues for visual differentiation.

In still a further embodiment of the invention, provided is an improved method of inserting an implant into a disc intermediate two vertebra. The method comprises the steps of providing a guide unit and an implant configured to conform to the shape of said disc; inserting the guide unit adjacent the disc; manipulating the guide unit to conform to the shape of the disc; sliding said implant unit along the guide unit: and, inserting the implant into the disc. This method can include using an elongate light guide for visualizing or imaging the disc, adjacent vertebras as well as any tissues, such as the annulus and/or nerves, associated therewith or adjacent thereto before, during, or after the inserting and manipulating steps and inspection thereof. The elongate light guide can be configured as the guide unit. Also, this method can include the use of one or more light wavelengths or one or more dyes for coloring or contrasting of one or more tissues for visual differentiation.

In another embodiment of the invention, provided is a method and apparatus for inserting devices into joints or other body areas. Optical guide units are disclosed together with implants configured to slide, glide, or otherwise advance along a guide unit from a remote skin incision through tissue into a joint or other body area. Light, images, video signals, heat, and electrical current can be transmitted from or to the operator through the guide units and implants and recorded as required. This method can include using an elongate light guide for visualizing or imaging the disc, adjacent vertebras as well as any tissues, such as the annulus and/or nerves, associated therewith or adjacent thereto before, during, or after any medical procedure or implantation or inspection thereof. The elongate light guide can be configured as the optical guide unit. The elongate light guide can be used in a guide wire configuration or a guide conduit configuration. Also, this method can include the use of one or more light wavelengths or one or more dyes for coloring or contrasting of one or more tissues for visual differentiation.

In a further embodiment of the invention, provided is a method of inserting an implant into a joint comprising the steps of providing an optical guide unit; locating the joint by selecting a joint, inserting the guide unit, visualizing the joint with the guide unit; providing a perforated implant; inserting the guide unit at least partially within the implant perforation; and advancing the implant along the guide unit into the joint. The joint can be in the spine. This method can include using an elongate light guide for visualizing or imaging the disc, adjacent vertebras as well as any tissues, such as the annulus and/or nerves, associated therewith or adjacent thereto before, during, or after locating, inserting, visualizing and advancing steps or inspection thereof. The elongate light guide can be configured as the guide unit. The elongate light guide can be used in a guide wire configuration or a guide conduit configuration. Also, this method can include the use of one or more light wavelengths or one or more dyes for coloring or contrasting of one or more tissues for visual differentiation.

In still another embodiment of the invention, provided is an improved method of inserting an implant into a joint comprising the steps of providing an electrically conductive guide unit; locating the joint by selecting a joint, inserting the guide unit such that a portion of the guide unit is adjacent the joint, providing a current along the guide unit, recording a current along a nerve adjacent the joint; providing a perforated implant, inserting the guide unit at least partially within the implant perforation, and; advancing the implant along the guide unit into the joint. The joint can be in the spine.

In still a further embodiment of the invention, provided is an improved method of inserting an implant into a joint comprising the steps of inserting an optical guide unit into the joint; visualizing the joint with the guide unit; inserting a lever over the guide unit; manipulating the lever to make an opening in the joint; inserting a sleeve over the lever and removing the lever; and, inserting the implant along the sleeve into the joint. The joint can be in the spine. This method can include using an elongate light guide for visualizing or imaging the disc, adjacent vertebras as well as any tissues, such as the annulus and/or nerves, associated therewith or adjacent thereto before, during, or after inserting, visualizing, and manipulating steps or inspection thereof. The elongate light guide can be configured as the optical guide unit. The elongate light guide can be used in an optical guide unit configuration. Also, this method can include the use of one or more light wavelengths or one or more dyes for coloring or contrasting of one or more tissues for visual differentiation.

In yet another embodiment of the invention, provided is an improved method of visualizing a surgical site comprising the steps of providing a light source with a proximal and distal end, the distal end operable to illuminate the surgical site, the proximal end configured to at least partially insert within an implant perforation; providing a perforated implant; inserting the light source within a surgical site; illuminating the surgical site; and, inserting the implant into the surgical site along the light source. The implant can be inserted into the spine. This method can include using an elongate light guide for visualizing or imaging the disc, adjacent vertebras as well as any tissues, such as the annulus and/or nerves, associated therewith or adjacent thereto before, during, or after the providing, illuminating, and inserting steps or inspection thereof. The elongate light guide can be used as the light source in a guide wire configuration or a guide conduit configuration. Also, this method can include the use of one or more light wavelengths or one or more dyes for coloring or contrasting of one or more tissues for visual differentiation.

In yet a further embodiment of the invention, provided is an improved method of viewing the spine comprising the steps of providing an elongate optical unit, a camera, a light source, a monitor, and an implant configured for insertion into the spine; inserting the optical unit at least adjacent the spine; illuminating the spine with the light source; viewing the spine with the camera and the monitor; and, inserting an implant into the spine. The monitor can be hand held. The camera can detect temperature. Material can be removed from the spine. This method can include using an elongate light guide for visualizing or imaging the disc, adjacent vertebras as well as any tissues, such as the annulus and/or nerves, associated therewith or adjacent thereto before, during, or after the providing, illuminating, viewing, and inserting steps or inspection thereof. The elongate light guide can be configured as the elongate optical unit in a guide wire configuration or a guide conduit configuration. Also, this method can include the use of one or more light wavelengths or one or more dyes for coloring or contrasting of one or more tissues for visual differentiation.

In yet still another embodiment of the invention, provided is an improved apparatus for deposition intermediate two vertebra comprising an implant with at least one surface in contact with a vertebra of the two vertebra and at least one compressible slot, the slot having a variable shape and dimension about at least a portion of the circumference of the implant and operable in response to movement of the vertebra to variably compress and tilt. The apparatus can be configured to slide along an elongate guide unit intermediate two vertebra.

In an alternate embodiment of the invention, provided is a method of inserting a device into the spine comprising the steps of providing an implant having at least one slot of variable shape and dimension, and inserting the implant into the spine to expand differentially in response to loads applied to the implant. The implant can be inserted along an optical guide unit. This method can include using an elongate light guide for visualizing or imaging the disc, adjacent vertebras as well as any tissues, such as the annulus and/or nerves, associated therewith or adjacent thereto before, during, or after the inserting steps or inspection thereof. The elongate light guide can be configured as the optical guide unit, and can be used as the optical guide unit in a guide wire configuration or a guide conduit configuration. Also, this method can include the use of one or more light wavelengths or one or more dyes for coloring or contrasting of one or more tissues for visual differentiation.

In still another embodiment of the invention, provided is an improved implant for disposition in an intervertebral disc space intermediate a pair of opposing vertebra in a spine having a longitudinal axis, the vertebra initially spaced apart an original distance, $D_O$, prior to disposition of the implant. The disc space includes a height, a width, and an initial pressure, $P_O$, prior to disposition of the implant. The implant comprises a structure with a top; a bottom; an outer surface to contact at least one of the pair of vertebrae; at least one interlocking elongate slot including an opening at the outer surface. The slot diverges inwardly away from the outer surface; extends at least partially through the body; and, begins at the outer surface to diverge inwardly. The implant has a height sufficient when disposed in the disc space to increase the distance between the vertebra by a distance $\blacktriangle D$ sufficient to reduce while the vertebra are being separated the pressure by an amount $\blacktriangle P$ less than the initial pressure $P_O$. The implant has a first density. A tubular metallic marker is in the slot and has a second density greater than said first density. The marker can be porous. The implant can be substantially rigid and can include a rotatable wing. The area of the opening can be less than the area of the outer surface. The outer surface can be shaped and dimensioned to interlock at least one of the pair of vertebrae when the implant is inserted therebetween. The implant can be shaped and dimensioned such that when the implant is disposed intermediate said vertebra the wing is positioned outside the disc space. The implant can include fixation means to secure the wing to at least one of the vertebra. The implant can telescope. The can have at least two operative positions. The marker can have a smooth surface extending across said opening. The implant can include a plurality of unidirectional parallel interlocking elongate slots. When the marker is porous, the openings in the marker can be shaped and dimensioned to draw in portions of the pair of vertebrae by negative pressure; and, the openings can each have a width in the range of 100 microns to 500 microns.

In still a further embodiment of the invention, provided is an improved system to position an implant at a desired location in an intervertebral disc space intermediate a pair of opposing vertebra in a spine of an individual having a longitudinal axis, the vertebra initially spaced apart an original distance, $D_O$, prior to disposition of the implant. The disc spaces includes the disc space includes a height, a width, and pressure, $P_O$, prior to disposition of the implant in the disc space. The improved system includes a binary polymer implant structure having a top; a bottom; an outer surface, at least one interlocking aperture opening at the outer surface, diverging inwardly away from the outer surface, extending at least partially through the body, and beginning at the outer surface to diverge inwardly; a height sufficient when disposed in the disc space to increase the distance between the vertebra by a distance $\blacktriangle D$ sufficient to reduce while the vertebra are being separated the pressure by an amount $\blacktriangle P$ less than the initial pressure $P_O$; a first density; and, at least one metal marker at least partially filling the aperture of the binary implant and having a second density greater than the first density. The system also includes a support structure to secure the individual; and, detection apparatus positioned externally with respect to the spine to produce a display distinguishing the marker from the polymer implant and showing the location of the marker when the implant structure is disposed in the disc space with the marker in the aperture, and the individual is in the support structure. The marker can be porous. The aperture can comprise an elongate slot opening at and extending along the outer surface, and the marker can comprise a metallic rod laterally inserted in said slot.

In still a further embodiment of the invention, provided is an implant for disposition in an intervertebral disc intermediate a pair of opposing vertebra in a spine having a longitudinal axis, the vertebra initially spaced apart an original distance, $D_O$, prior to disposition of the implant. The disc includes an annulus, a height, a width, and a nucleus comprising nuclear material within the annulus, and having an initial intra nuclear pressure, $P_O$, prior to disposition of the implant. The implant comprises at least first and second articulating members movable between a first linear orientation and a second arcuate orientation. Each articulating member includes an outer surface at least including an upper surface to contact one of the pair of vertebra, and a bottom surface to contact the other of the pair of vertebra; a height sufficient when disposed in the nucleus of the disc space to increase the distance between the vertebra by a distance ▲D sufficient to reduce while the vertebra are being separated the intra nuclear pressure to a pressure less than the initial nuclear pressure $P_O$; and, a first density. The implant also includes at least one interlocking elongate slot formed in the outer surface of one of the articulating members and opening at and extending along said outer surface. The slot diverges inwardly away from the outer surface, extends at least partially through the body, and begins at the outer surface to diverge inwardly. The implant also includes a joint pivotally joining the articulating members, having an upper surface area, and shaped and dimensioned such that when the articulating members are in the second arcuate orientation a greater portion of the upper surface area is exposed than when the articulating members are in the first linear orientation. The implant also includes a tubular metallic marker in the slot, the marker having a second density greater than the first density.

In yet still another embodiment of the invention an implant is provided for indirect decompression of nerves adjacent a disc space by disposition into an intervertebral disc space intermediate a pair of opposing vertebra in a spine having a longitudinal axis. The vertebras are initially spaced apart an original distance prior to disposition of the implant. The disc space includes a height, a width, and an initial pressure prior to disposition of the implant. The implant comprises a structure with a top; a bottom; an outer surface to contact at least one of the pair of vertebrae; at least one interlocking opening at the outer surface, the opening diverging inwardly away from the outer surface, extending at least partially through the body, and beginning at the outer surface to diverge inwardly; a height sufficient when disposed in the disc space to increase the distance between the vertebra sufficient to reduce the pressure by an amount less than the initial pressure; and a first density. The implant also includes a marker having a second density different than said first density. The marker can be porous and/or substantially rigid. The implant can include a rotatable wing. The area of the opening can be less than the area of the outer surface. The outer surface can be shaped and dimensioned to interlock at least one of the pair of vertebrae when the implant is inserted there between. The implant can be shaped and dimensioned such that when the implant is disposed intermediate the vertebra the wing is positioned outside the disc space. The implant can include fixation means to secure the wing to at least one of the vertebra. The implant can open. The implant can have at least two operative positions. The marker can have a smooth surface extending across the opening. The implant can include a plurality of unidirectional parallel interlocking elongate slots. The openings in the porous marker can be shaped and dimensioned to draw in portions of the pair of vertebrae by negative pressure. The openings can have a width in the range of about 1 microns to 5000 microns, or 10 microns to 2000 microns, or 25 microns to 1000 micros, or 50 microns, to 500 microns, or 100 microns to 250 microns, or about 150 to 200 microns.

In a further embodiment of the invention, provided is a system for indirect decompression of nerves adjacent a disc space intermediate a pair of opposing vertebra in a spine of an individual having a longitudinal axis. The vertebra are initially spaced apart an original distance. The disc space includes a height, a width, and an initial pressure. The system comprises an implant structure. The implant structure has a top; a bottom; an outer surface; a height sufficient when disposed in the disc space to increase the distance between the vertebra by a distance sufficient to reduce the pressure by an amount less than the initial pressure; a first density; and, at least one marker at least partially filling the implant. The marker has a density different than the first density. The system also includes a detection apparatus positioned with respect to the spine to produce a display distinguishing the marker from the implant when the implant structure is disposed in the disc space with the marker. The marker can be porous. The outer surface can comprise an opening. The marker can be inserted in the opening.

In another embodiment of the invention, provided is an improved implant for indirect decompression of nerves adjacent a disc space by disposition in an intervertebral disc space intermediate a pair of opposing vertebra in a spine. The vertebras are initially spaced apart an original distance prior to disposition of the implant. The space has an initial pressure prior to disposition of the implant. The implant comprises at least first and second articulating members movable between a first orientation and a second orientation. Each member includes an outer surface at least including an upper surface to contact one of the pair of vertebra, and a bottom surface to contact the other of the pair of vertebra; a height sufficient when disposed in the nucleus of the disc space to increase the distance between the vertebra by a distance sufficient to reduce the pressure on nerves adjacent the disc space to a pressure less than the initial pressure; and, a first density. The implant also includes a marker pivotally joining the articulating members, having an upper surface area, and shaped and dimensioned such that when the articulating members are in the second orientation a greater portion of the upper surface area is exposed than when the articulating members are in the first orientation. The marker has a second density different than the first density. The area of the opening is greater than the area of the outer surface. The area of said opening can be equal to the area of the outer surface. The marker can be a pivot.

In a further embodiment of the invention, provided is an improved method of performing spine surgery. The method comprises the steps of forming an opening in tissue to access the spine; inserting a cannula having a non-round cross-section through tissue until the distal tip of the cannula is positioned adjacent a desired implant location; and, sliding an implant through the non-round cannula and out of the distal tip of the non-round cannula to position the implant in the desired implant location. The step of forming an opening in tissue can comprise inserting a wire through body tissue; and, sliding a dilator over the wire. The step of inserting a wire can comprise inserting a non-round wire. The step of sliding a dilator can comprise sliding a dilator having a non-round cross section over the wire. The step of inserting a cannula can comprise sliding the non-round cannula over the non-round dilator. The implant can be non-round and the step of sliding the implant through the non-round cannula can further comprise orienting the implant to the non-round cannula shape and sliding the implant through the non-round cannula to maintain the orientation of the implant relative to the cannula during insertion of the implant. The method can further comprise the step of orienting the non-round cannula relative to the desired implant location in order to orient the delivery orientation of the implant. The non-round cannula can have a substantially square cross-section and the step of inserting an implant can comprise inserting an implant having a substantially square cross section through the substantially square cannula. The step of inserting a non-round cannula can comprise sliding the non-round cannula over the dilator. The method can further comprise the step of removing the wire and dilator prior to sliding an implant through the non-round cannula. The method can further comprise the step of removing the dilator prior to sliding an implant through the non-round cannula. The step of sliding an implant can comprise providing a cannulated implant, mounting the cannulated implant over the wire, and sliding the implant over the wire through the non-round cannula. The step of inserting the wire can comprises a non-round wire. The step of sliding an implant can comprise providing an implant having a non-round cannulated opening, and sliding the implant over the non-round wire such that the implant cannot rotate relative to the wire. The step of sliding an implant can comprise providing a cannulated implant having an oval opening, mounting the cannulated implant over the wire, and sliding the implant over the wire through the non-round cannula. The step of sliding an implant can comprise providing an implant having a first body portion and a second body portion, the first body portion and the second body portion connected to each other so that the first and second body portions assume a first position substantially aligned with each other a second, articulated position with the first and second body portions angled relative to each other; and, sliding the implant through the non-round cannula with the first and second body portions in the first, substantially aligned position. The step of sliding the implant through the non-round cannula and out of the distal tip of the non-round cannula can further comprise pivoting the implant into the second, articulated position in the desired implant location. The step of sliding the implant can comprise sliding the implant through the non-round cannula into a position intermediate two vertebrae. This method can include using an elongate light guide for visualizing or imaging the disc, adjacent vertebras as well as any tissues, such as the annulus and/or nerves, associated therewith or adjacent thereto before, during, or after the providing, sliding, dilating, illuminating, inserting, and removing steps or any other step in such a medical procedure or inspection thereof. The elongate light guide can be configured as the optical guide unit in a guide wire configuration or a guide conduit configuration, such as an optical cannula. Also, this method can include the use of one or more light wavelengths or one or more dyes for coloring or contrasting of one or more tissues for visual differentiation.

In still another embodiment of the invention, provided is an improved spinal implant. The implant comprises a first body portion having a top surface configured and dimensioned to engage a first vertebra and a bottom surface configured and dimensioned to engage a second vertebrae and a first body portion central opening therethrough; and a second body portion having a top surface configured and dimensioned to engage the first vertebra and a bottom surface configured and dimensioned to engage the second vertebra and a second body portion central opening therethough, the first body portion and the second body portion connected together at an articulating junction such that the first body portion and the second body portion articulate bout an axis that is substantially perpendicular to at least one of the top and bottom surface of the first body portion. The first body portion and the second body portion assume a first position substantially aligned with each other and with the first body portion central opening and the second body portion central opening aligned, and a second position with the first body portion and second body portion disposed at an angel relative to each other wherein the first body portion central opening and the second body portion central opening are configured and dimensioned to receive a wire. The articulating junction can comprise a hinge. The hinge can be offset from the central axis of the first and second body portions. The first and second body portions can be transparent, semi-transparent, or opaque. The articulating junction can comprise a hinge disposed perpendicular to and off axis relative to the axis of the first body portion central opening.

Turning now to the drawings, which depict the presently preferred embodiments of the invention for the purpose of illustrating the practice thereof and not by way of limitation of the scope of the invention, and in which like reference characters refer to corresponding elements throughout the several views, FIGS. 1 to 5 illustrate a disc revitalization device constructed in accordance with the principles of the invention and generally indicated by reference character 100.

Disc revitalization device 100 includes a housing having an upper generally semi-oval member 42 and a lower generally semi-oval member 41. Shaft 59 is mounted on and inside the housing. The head 30 of shaft 59 includes an hex opening or indent 31A shaped to contour to and receive slidably the hexagonally shaped end of an elongate tool used to turn the head 30 of shaft 59. Unitary master cam 10 is fixedly secured to the center of shaft 59, along with externally threaded member 57 and externally threaded member 58. Member 57 is received by an internally threaded aperture in member 42A. Member 58 is received by an internally threaded aperture in member 43A. Conical members 42A and 43A each have a truncated conical exterior shape and have inner cylindrical openings that can slide along shaft 59 in the directions indicated by arrows B and C, respectively, when members 57, 58 rotate and displace members 42A, 43A along shaft 59. Members 57 and 58 are oppositely threaded such that when shaft 59 is turned in the direction of arrow A, member 57 turns inside conical member 42A and slidably displaces member 42A along shaft 59 in the direction of arrow B, and, member 58 turns inside conical member 43A and slidably displaces members 43A along shaft 59 in the direction of arrow C.

When members 42A and 43A are slidably displaced along shaft 59 in the direction of arrows B and C, respectively, the outer conical surfaces of members 42A and 43A slide over the arcuate inner surface 11B and 11C of arcuate shells 11 and 11A, respectively, and displace shell 11 upwardly away from shaft 59 in the direction of arrows D and E and shell 11A downwardly away from shaft 59 in directions X and Y opposite the directions indicated by arrows D and E.

Figure 1:
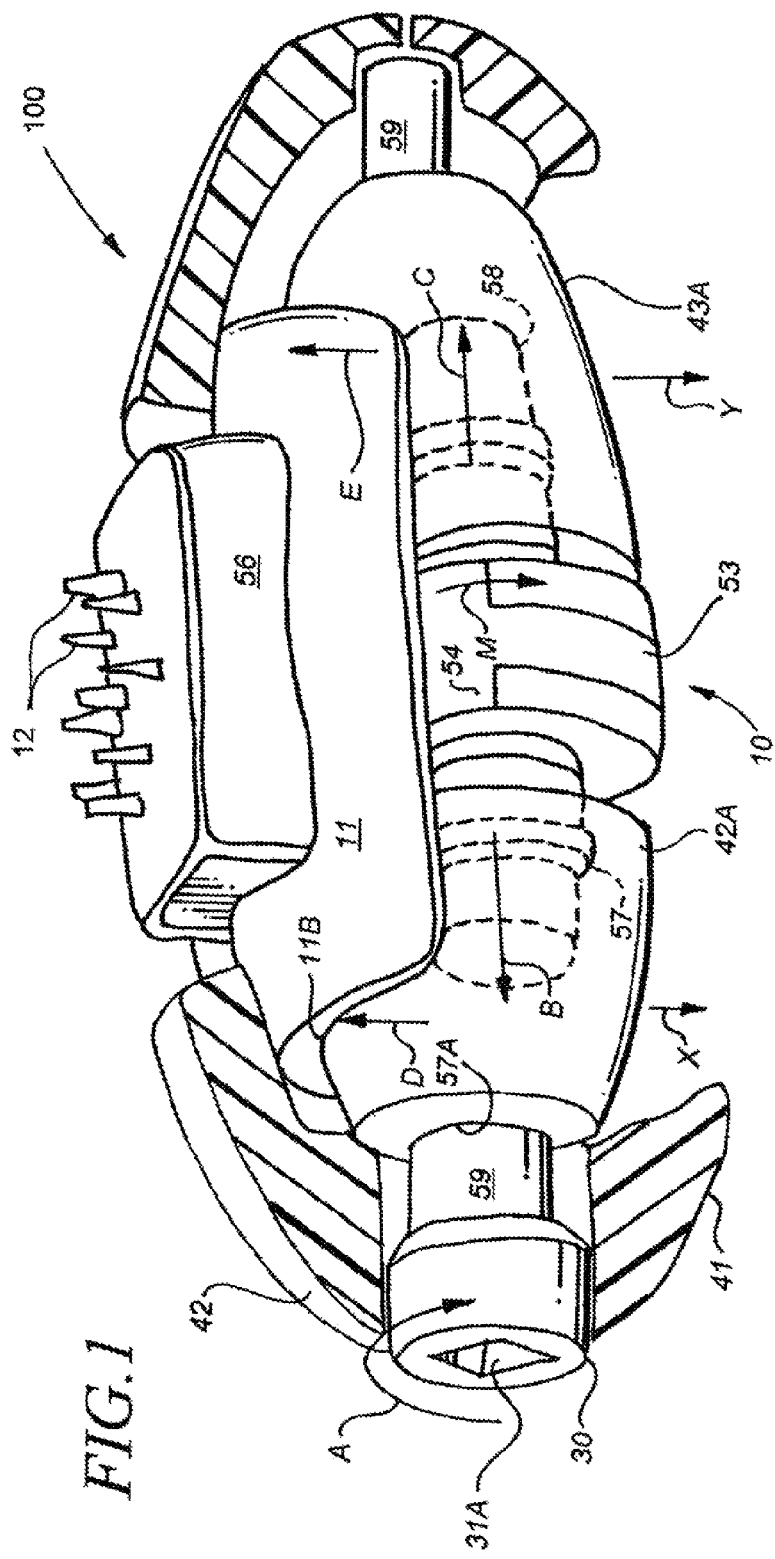
FIG. 1 is a perspective view illustrating an intervertebral device constructed in accordance with the principles of the invention.
Figure 2:
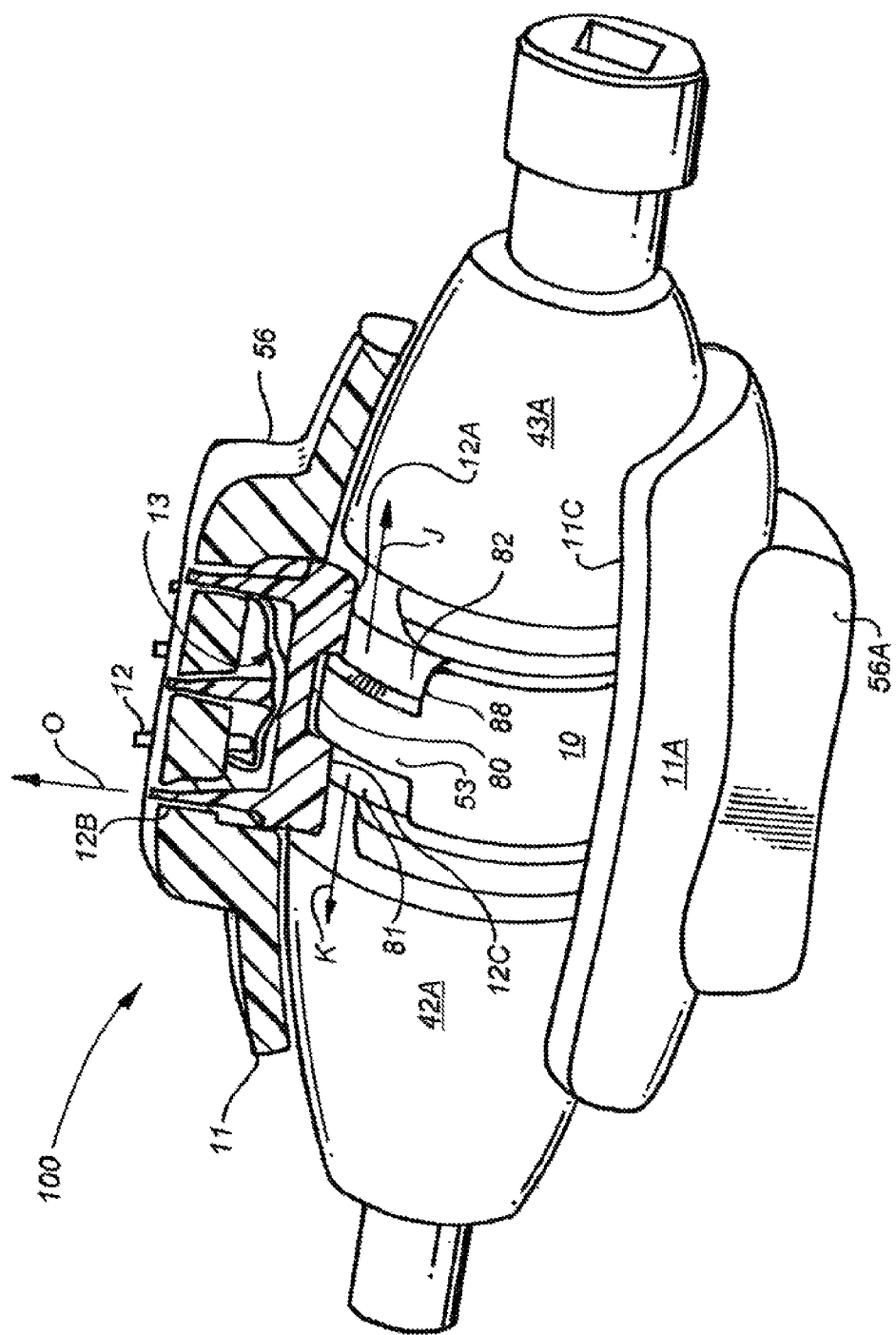
FIG. 2 is a perspective-partial section view of the device of FIG. 1 illustrating additional construction details thereof.
Figure 4:
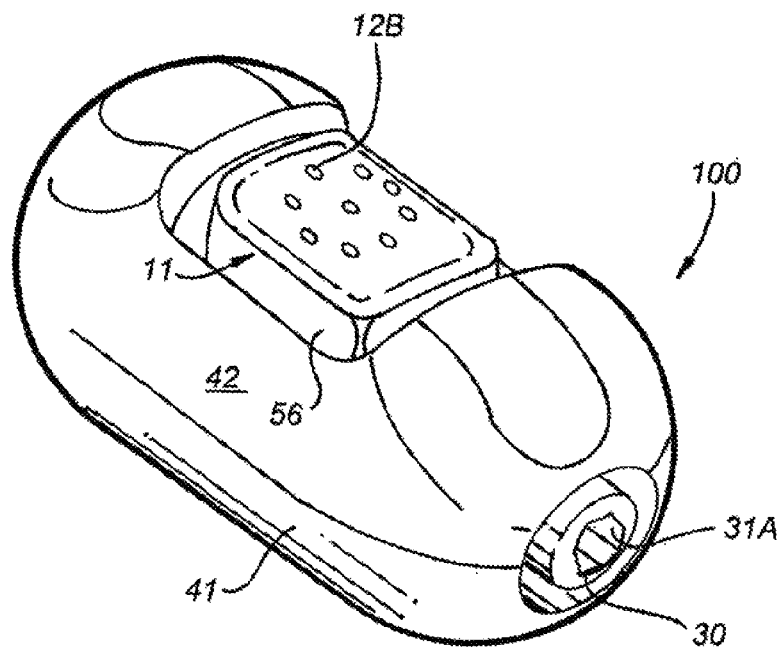
FIG. 4 is a perspective view further illustrating the device of FIG. 1.
Figure 5:
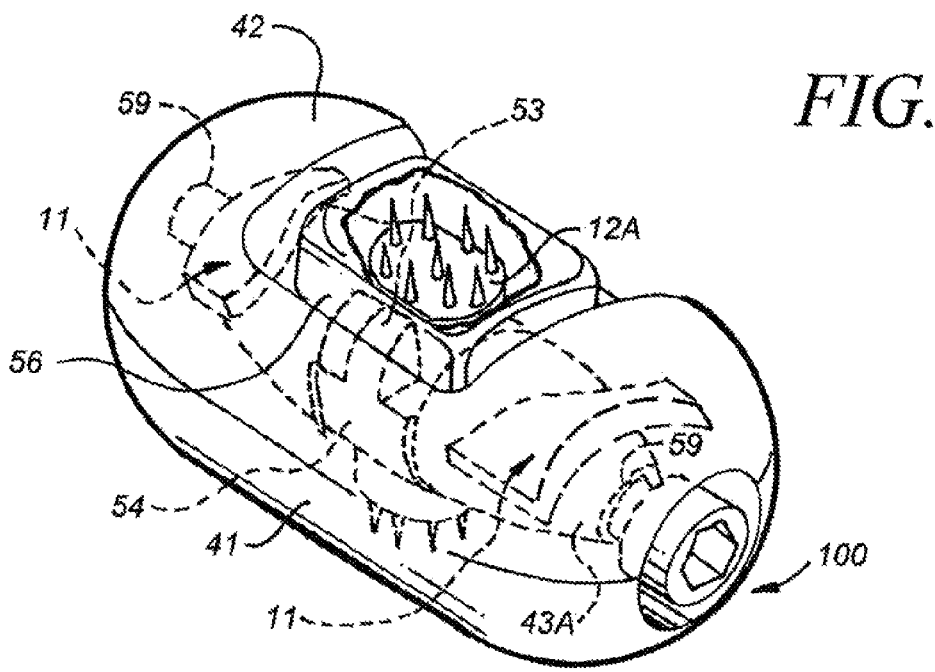
FIG. 5 is a perspective view of the device of FIG. 1 illustrating certain components in ghost outline.

Teeth or pins 12 depend outwardly from base 12A (FIG. 2) and are shown in the refracted position in FIGS. 2 and 4. Base 12A is mounted inside shell 11 beneath and within the head 56 of shell 11. Wave spring 13 contacts an undersurface of head 56 and downwardly displaces base 12A away from the head 56. Spring 13 therefore functions to maintain teeth 12 housed and retracted in openings 12B. Openings 12B extend through head 56. When teeth 12 are in the retracted position illustrated in FIG. 2, edge 88 of master cam 10 is in the position illustrated in FIG. 2 such that rib 53 engages slot 80 on the bottom of base 12A and prevents base 12A (and shell 11) from moving laterally in the directions indicated by arrows J and K in FIG. 2. When, however, a hex tool is used to rotate head 30 and shaft 59 in the direction of arrow A, master cam 10 rotates simultaneously with shaft 59 in the direction of arrow M (FIG. 1) until rib 53 turns completely out of slot 80 and smooth cam surface 54 engages and slidably contours to the arcuate bottom 12C of base 12A. When surface 54 engages bottom 12C, surface 54 is flush with adjacent portions of the conical outer surfaces of members 42A and 43A such that bottom 12C of base 12A and bottom 11B of shell 11 are free to slide laterally in the directions of arrows B and C over surface 54 and the outer conical surfaces of members 42A and 43A, and such that bottom 12C of base 12A and bottom 11B of shell 11 are free to rotate or slide in the direction of arrow M (FIG. 1) and in a direction opposite that of arrow M over surface 54 and the outer conical surfaces of members 42A and 43A. This ability of shell 11 and base 12A to move bidirectionally or multidirectionally (i.e., to move polyaxially) by sliding laterally (in the direction of arrows J and K), by sliding forwardly or rotationally (in the direction of arrow M), and by sliding in direction intermediate said lateral and forward directions facilitates the ability of device 100 to adapt to movement of a vertebra. In addition, as rib 53 is turned out of and exits slot 80, cam surfaces 81 and 82 contact and slidably displace base 12A upwardly in the direction of arrow O (FIG. 2) to compress and flatten wave spring 13 and to displace teeth 12 outwardly through openings 12B such that teeth 12 are in the deployed position illustrated in FIG. 1.

Figure 3:
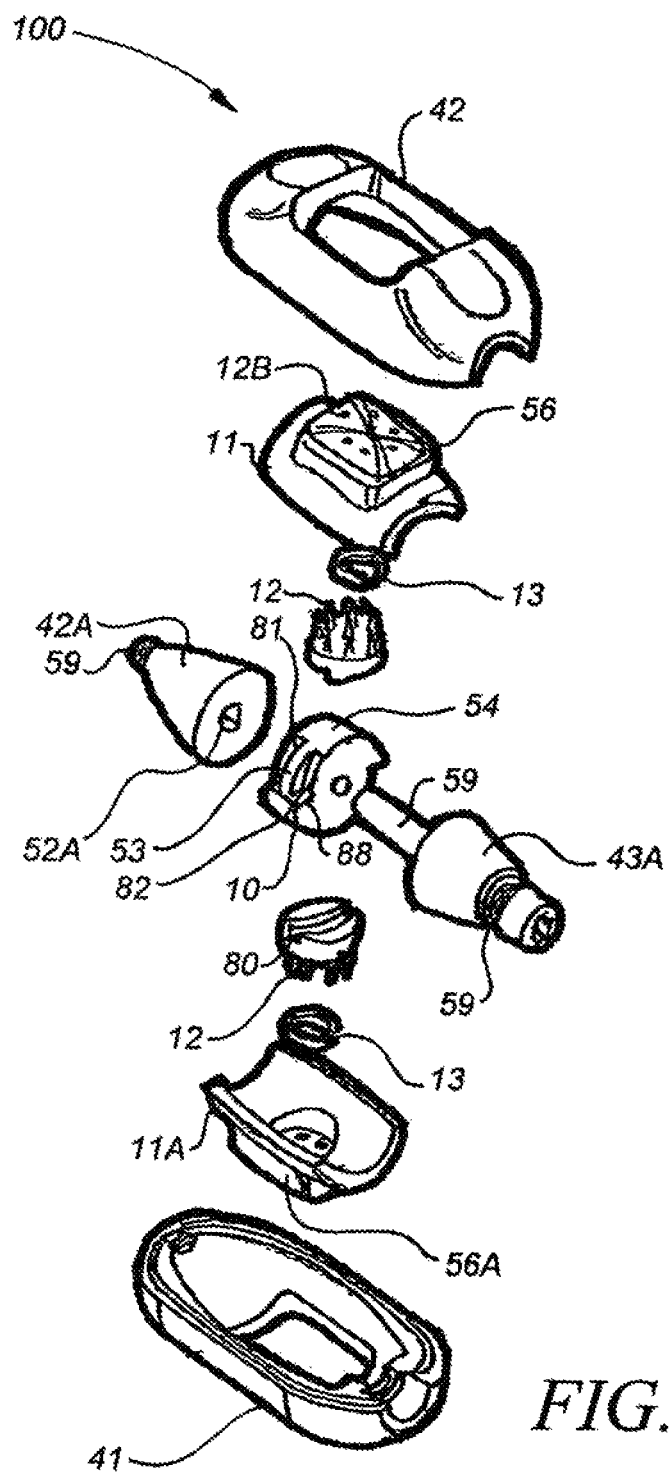
FIG. 3 is an exploded view of certain components of the device of FIG. 1.

As can be seen in FIG. 3, the construction of shell 11A and the base, head 56A, and teeth in shell 11A is equivalent to that of shell 11, base 12A, and teeth 12.

In FIG. 3, the end of shaft 59 is slidably received by aperture 52A formed in member 42A and interlocks with another portion of shaft 59 (not visible) inside member 42A. Members 57 and 58 are not, for sake of clarity, illustrated on shaft 59 in FIG. 3.

Figure 1A:
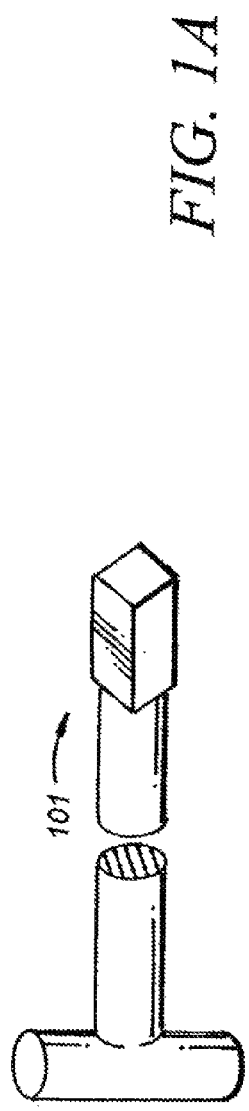
FIG. 1A is a perspective view of a tool that can be utilized in the practice of the invention.
Figure 6:
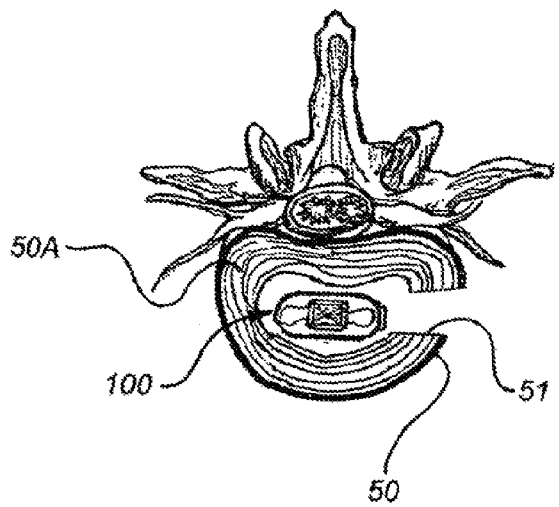
FIG. 6 is a top view illustrating the insertion of the device of FIG. 1 in an intervertebral disc adjacent the spinal column.

FIG. 6 illustrates the insertion of device 100 in a disc 50. An opening 51 is formed through the annulus 50A and device 100 is inserted inside the annulus. In FIG. 6, the size of the opening 51 is greater than normal and is exaggerated for purposes of illustration. When device 100 is inserted in disc 50, teeth 12 are retracted (FIG. 4). After device 100 is inserted, the hex end of a tool (FIG. 1A) is inserted in and engages opening or indent 31A and the tool is used to turn shaft in the direction of arrow A to outwardly displace shells 11 and 11A and to deploy teeth 12 (FIG. 1).

Another particular advantage of the invention is that in many cases it is not necessary to make an opening in disc 50 in order to insert device 100. Device 100 preferably has a shape and dimension that permit insertion through a pre-existing rupture in the annulus of a disc 50. The device can be inserted through the rupture "as is" (i.e., as the rupture exists), or the rupture can, if necessary, be widened sufficiently to permit insertion of device 100 through the rupture and annulus into the nucleus area circumscribed by the annulus. When a device 100 is inserted through a pre-existing rupture—either by inserting device 100 through the rupture as is or by widening and increasing the size of the rupture—it is not necessary to form another opening in the disc annulus.

Figure 7:
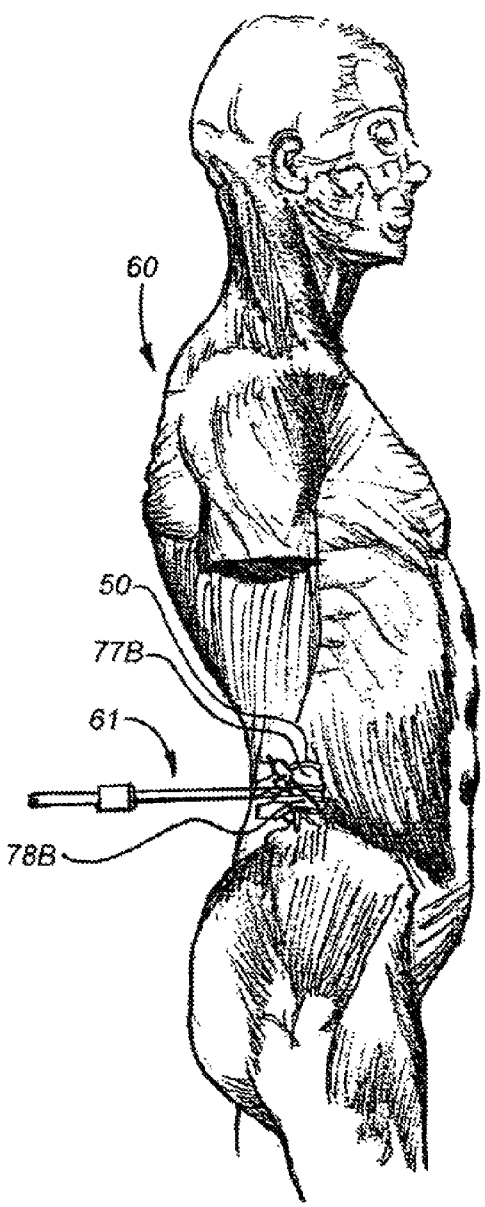
FIG. 7 is a side elevation view further illustrating the insertion of the device of FIG. 1 in the spinal column.

FIG. 7 illustrates a surgical instrument 61 being utilized to insert disc revitalization device 100 in an intervertebral disc 50 that is adjacent and intermediate an upper vertebra 77B and a lower vertebra 78B in the spinal column of an individual 60. As would be appreciated by those of skill in the art, individual 60 is normally in a prone position when a device 100 is inserted in a disc 50.

One particular advantage of the invention is that in many cases it is not necessary to force apart the vertebra 77B and 78B bounding a disc 50 in order to insert device 100. Device 100 preferably has a shape and dimension that permits an incision to be made in disc 50 (preferably without cutting out a portion of disc 50) and the incision to be widened sufficiently to insert device 100 inside the disc 50. Any desired method can be utilized to insert device 100 in disc 50.

One method for inserting device 100 in the interior of disc 50 is utilized to insert device 100 in the front, back, or one of the sides of a disc 50 without separating the pair of vertebra between which disc 50 is sandwiched. This method may include the step of using a needle to palpate and penetrate the annulus to the center of the disc. The stylette is removed from the needle and a guide wire is inserted until the tip of the wire is in the disc. The needle is removed from the guide wire. A dilator is placed on the guide wire and is used to enlarge the opening in the annulus. The wire is removed. A tube is inserted over the dilator. The dilator is removed. The device 100 is inserted through the tube into disc 50. The tube is removed. Before the tube is removed, an appropriately shaped and dimensioned tool 101 (FIG. 1A) can be inserted through the tube to engage and turn head 30 to outwardly displace shells 11 and 11A and deploy teeth 12.

Figure 8:
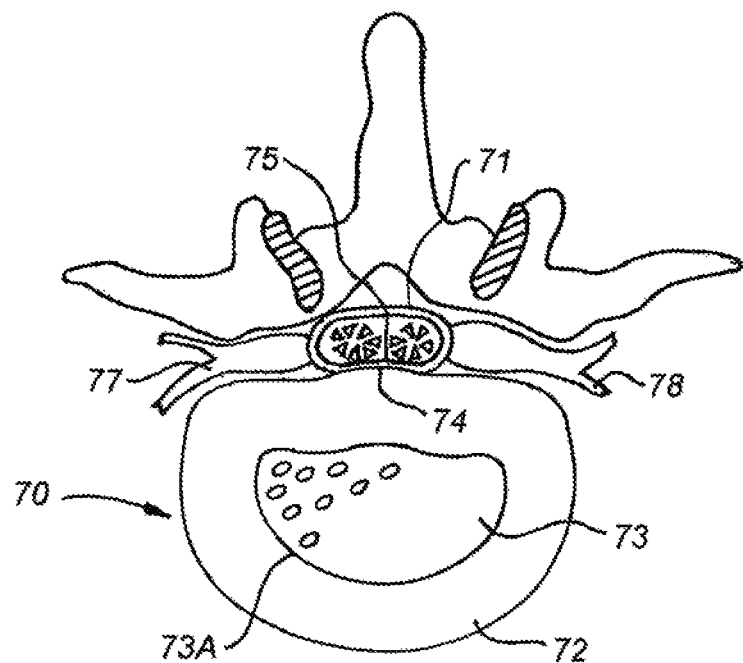
FIG. 8 is a top view illustrating a damaged intervertebral disc with a portion thereof bulging and pressing against the spinal column.

FIG. 8 illustrates a damaged disk 70 that has developed a convex bulge in portion 74 of the annulus 72. The bulge generates pressure against the inner portion 75 of the spinal column 71. The pressure compresses nerves in the spinal column 71, causing pain. Similar pressure against nerve roots 77 and 78 can be generated when the annulus bulges and/or ruptures and material from the nucleus 73 herniates through the rupture and produces pressure against spinal column 71 or nerve roots 77 and 78.

Figure 9:
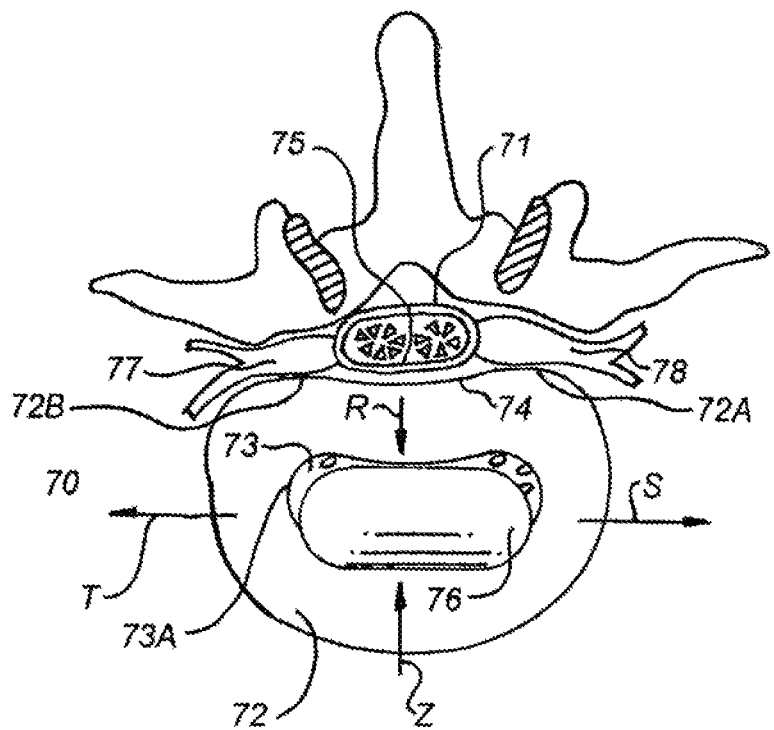
FIG. 9 is a top view illustrating the disc of FIG. 8 manipulated with a device constructed in accordance with the invention to alter the shape and dimension of the disc to revitalize the disc and take pressure off the spinal column.

FIG. 9 illustrates one procedure to relieve the pressure caused by bulge 74. A disc revitalization device 76 is inserted inside the annulus 72 and generates pressure against the annulus 72 in the direction of arrows S and T that causes the annulus to lengthen in those directions. When the annulus lengthens, the middle portions of the annulus tend to be drawn in the direction of arrows R and Z, narrowing the annulus and displacing the convex bulge away from the portion 75 of the spinal column 71. The shape and dimension of device 76 can be varied as desired to alter the shape of annulus 72, nucleus 73, and disc 70 in any desired manner when device 76 is inserted in disc 70. While portions of the nucleus 73 and annulus 72 can be removed to insert device 76, it is preferred that little, if any, of the nucleus 73 and annulus 72 be removed during installation of device 76. The principal object of the invention is, as much as possible, to revitalize a disc 70 so that the functioning of disc 70 resembles as closely as possible the functioning of a normal healthy disc, or resembles as closely as possible the functioning of disc 70 before it was compressed, widened, bulged, herniated, ruptured, or otherwise damaged. To achieve this object, it normally is desirable to leave in place as much as possible of the original disc material.

In FIG. 9, portion 74 has taken on a concave orientation. The disc 70 in FIG. 9 has a so-called "C-shape" generally associated with a normal healthy disc. The C-shape of disc 70 is produced in part because of the concave orientation of portion 74, which represents the center portion of the C-shape. One drawback of the C-shape of disc 70 is that portions 72A and 72B of disc 70 are, as can be seen in FIG. 9, adjacent nerve roots 78 and 77, respectively, which makes it more likely that portions 72A and 72B can, by bulging, by herniation of the nucleus through a rupture, by adding materials to the annulus, by inserting devices that widen when compressed, or otherwise, exert undesirable pressure on nerve roots 78 and 77. The embodiment of the invention illustrated in FIG. 11 minimizes the likelihood of such an occurrence.

Figure 11:
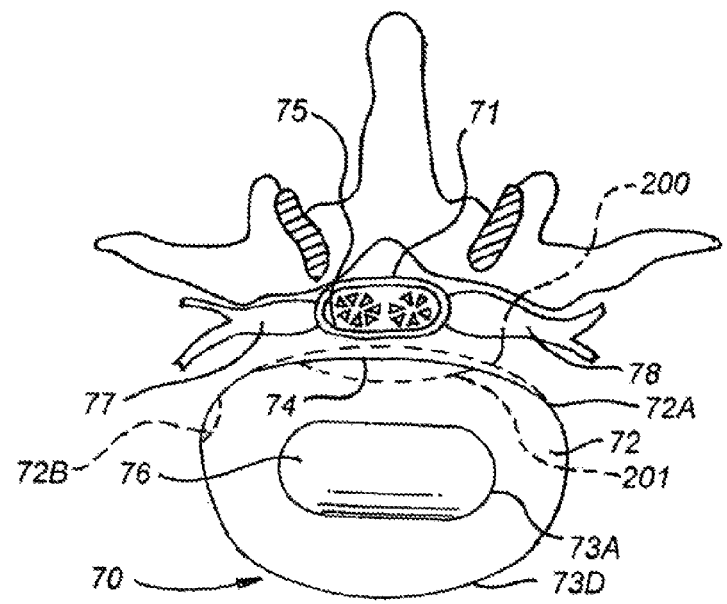
FIG. 11 is a top view illustrating the disc of FIG. 8 manipulated in accordance with the invention to alter the shape of the disc from a normal "C-shape" to an oval shape.

In FIG. 11, the disk revitalization device 76 is shaped and dimensioned such that when device 76 is inserted in disc 70, the inner wall 73A of annulus 72 contacts and conforms to device 76 such that disc 70 no longer has a C-shape, but has an oval shape.

The outer arcuate wall 73D of disc 70 becomes convex along its entire length. The oval shape of disc 70 spaces portions 72A and 72B further away from nerve roots 78 and 77 and reduces the likelihood that a bulge or hernia will contact and produce undue pressure on roots 78 and 77. In the practice of the various embodiments of the invention described herein, it is not required that disc 70 be manipulated by a device 76 or other means to take on an oval shape, and it is not required that the normal C-shape of a disc 70 be dispensed with. It is, however, preferred that disc revitalization device 76 manipulate a disc 70 such that the shape of disc 70 tends to change from the normal C-shape and become more oval, or that at least the section of disc 70 that is adjacent spinal column 71 and nerve roots 78 and 77 and that is comprised of portions 72A, 74, and 72B tend to become more convex and adopt a curvature more comparable to a portion of an oval.

Figure 10:
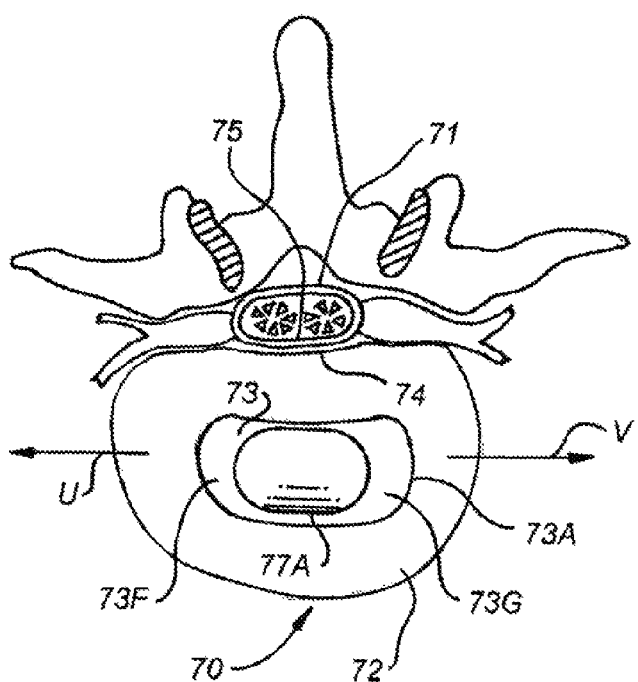
FIG. 10 is a top view illustrating the disc of FIG. 8 manipulated with an alternate device constructed in accordance with the invention to alter the shape and dimension of the disc to revitalize the disc and take pressure off the spinal column.

It is not believed necessary for a disc revitalization device to contact the inner wall 73A of the annulus 72 of a disc 70 in order for the device to cause the shape of a disc to change. For example, FIG. 10 illustrates a disc revitalization device 77A that is inserted in the nucleus 73 of a disc 70 and that does not contact the inner wall 73A of the annulus 72. Device 77A is shaped such that it tends to force material comprising the nucleus 73 to gather and be compressed in areas 73F and 73G. Such a compression of nuclear material can generate forces that act in the direction of arrows U and V and that tend to cause disc 70 to elongate in the directions of arrows U and V. Regardless of whether a device 76, 77A, 100 contacts the inner wall 73A of the annulus 72 of a disc 70, it is preferred that all, or substantially all, of the outer surface of the portion of the housing 41, 42 that will contact the nucleus 73 or the annulus 72 have a smooth, preferably arcuate, shape about at least one axis. By way of example, and not limitation, the surface of a cylindrical is arcuate about one axis. The surfaces of a sphere or egg are each arcuate about more than one axis.

Use of a disc revitalization device 100 is further described with reference to FIGS. 12 and 13. In FIG. 12, damaged disc 95 has been compressed between vertebra 90 and 91 and is bulging outwardly through and from the bottom 92 of disc 90 and the top 93 of disc 91. The disc 95 has ruptured at two locations and herniated material 96, 97 from the nucleus extends outwardly through the ruptures. In FIG. 12, the bulging of disc 95 outside of vertebra 90 and 91 is, for sake of simplicity, pictured as being uniform around the perimeter of the vertebrae. This is not normally the case. The amount that the disc 95 bulges typically varies with the location on the periphery of the bottom 92 of vertebra 90 and top 93 of vertebra 91. Similarly, the herniation of nucleus material 96, 97 is, for sake of simplicity, pictured in a generally uniform spherical shape. This is not normally the case. The shape of a herniation of nucleus material need not be uniform or have the shape and dimension of any recognizable symmetric geometric figure.

After device 100 is inserted internally into the nucleus of disc 95, a tool with a hex end is inserted in opening 31A and the tool is utilized to turn head 30 in the direction of arrow A (FIG. 1) to displace and expand shell 11 outwardly in the direction of arrows D and E, to displace and expand shell 11A of FIG. 2 outwardly in the direction of arrows X and Y and away from shell 11 (FIG. 1), to deploy teeth 12 to engage a portion of the bottom 92 of vertebra 90 (FIG. 12), to deploy teeth associated with shell 11A to engage a portion of the top 93 of vertebra 91, and to subject disc 95 to internal traction by displacing vertebra 90 and/or 91 vertically along axis G in a direction generally normal to the bottom 92 of vertebra 90 and to the top 93 of vertebra 91 to increase the separation distance between vertebra 90 and 91, to increase the height H of disc 95, and to decrease the width W of disc 95. Since a spine is generally curved along its length, vertebra in the spine are not stacked one directly on top of the other along a straight vertical axis. One vertebra usually is slightly canted with respect to its adjacent vertebra. Nonetheless, the axis G can be said to be generally normal (with plus or minus 45 degrees) to the bottom 92 of one vertebra and to the top 93 of an adjacent vertebra.

When disc 95 is subjected to internal traction, the disc 95 often tends to undergo a transformation from the short, squat, bulged configuration of FIG. 12 to the tall, retracted configuration illustrated in FIG. 13. The bulged part of the disc 95 retracts inwardly to a position between vertebrae 90 and 91 in the same general manner that the bulge 105 in rubber band or string 102 (FIG. 14) retracts inwardly when the ends of the string 102 are pulled in the directions indicated by arrows 103, 104 to produce the "taller" (i.e., longer) string 102 illustrated in FIG. 15. When bulge 105 retracts inwardly, the width W of the disc 95 is reduced.

Further, when disc 95 takes on the tall refracted configuration of FIG. 13, the volume of the space inside and circumscribed by the inner edge 73A (FIG. 10) of the annulus (i.e., the space in which material comprising the nucleus 73 is found) increases because the increase in the height of the space concomitant with the increase in the height of disk 95 usually offsets and is greater than the decrease in the diameter or width of the space concomitant with the retraction of the disk 95. The increase in the volume of the space in which the nucleus is found generates negative pressure or generates forces that tend to pull or permit the herniated nucleus material 96, 97—that prior to internal traction extended outwardly through ruptures in the annulus 94 in the manner illustrated in FIG. 12—to move through the associated disc ruptures and back into the inner annular space in which nucleus material is ordinarily found. Increasing the height of and retracting disc 95 also tends to close or partially close ruptures 98 formed in the annulus 94 (FIG. 13) so that the ruptures often will heal completely closed of their own accord. Similarly, if an opening has been made through the annulus 94 to facilitate insertion of a disc revitalization device 100, the internal traction of disc 95 tends to close the opening to facilitate healing of the opening. Such an incision normally, but not necessarily, would be vertically oriented in the same manner that annulus rupture 98 is vertically oriented in FIG. 13.

The device 100 can be oversized and shaped such that during internal traction the device 100 prevents the internal opening (which opening would be bounded by the internal wall 73A of the annulus) in the annulus of disc 95 from completely retracting or reducing in size to a particular width when a disc moves from the bulging configuration of FIG. 12 to the retracted, taller configuration of FIG. 13. When device 100 prevents the internal opening in the annulus from fully inwardly refracting or constricting along axes that lie in a horizontally oriented plane that is generally normal to axis G in FIG. 13, the annulus and/or nucleus generate and maintain for at least a while compressive forces against the device 100. This "tensioning" of the annulus and/or nucleus tends to anchor the device 100 in position in disc 95, to prevent migration of device 100, and therefore to produce a unitary, stronger structure comprised of the disc 95 and the "captured" or a "squeezed" device 100.

The shape and dimension and constructions of the disc revitalization device 100 can vary as desired provided that device 100, when inserted in a disc 95, can be utilized to separate a pair of adjacent vertebrae 90, 91 the distance necessary during internal traction to obtain the desired retraction and height increase of a disc 95 intermediate the pair of vertebrae. It is desirable that device 100 functions to contact the nucleus and/or annulus of the disc 95 to produce the desired shape of disc 95, and/or that the device 100 functions to contact the nucleus and/or annulus of the disc 95 to produce tension in the annulus and/or nucleus because the device 100 prevents disc 95 from fully retracting and causes the nucleus and/or annulus to squeeze or compress device 100.

In FIG. 11, one acceptable contour of the portion of a disc 70 that is closest to nerves 77, 78 and spinal column 71 is the oval convex shape indicated by dashed line 200. A more preferred contour (than the contour indicated by dashed line 200) is the relatively flat contour depicted by the flat line representing portion 74 of disc 70. The most preferred contour is the concave contour represented by dashed line 201. The contour represented by dashed line 201 is most preferred because it is less likely that any bulge or herniation of disc 70 will press against nerves 77, 78 or against spinal column 71. It is, of course, preferred that each of the contours 200, 74, 201 of disc 70 be spaced apart from nerves 77, 78 and spinal column 71 to minimize the likelihood that a portion of disc 70 will contact nerves 77, 78 and spinal column 71. As used herein in connection with the invention and the claims, a disc includes at least fifty percent (50%) of its original annulus and may or may not include all or a portion of its original nucleus.

Figures 16, 17:
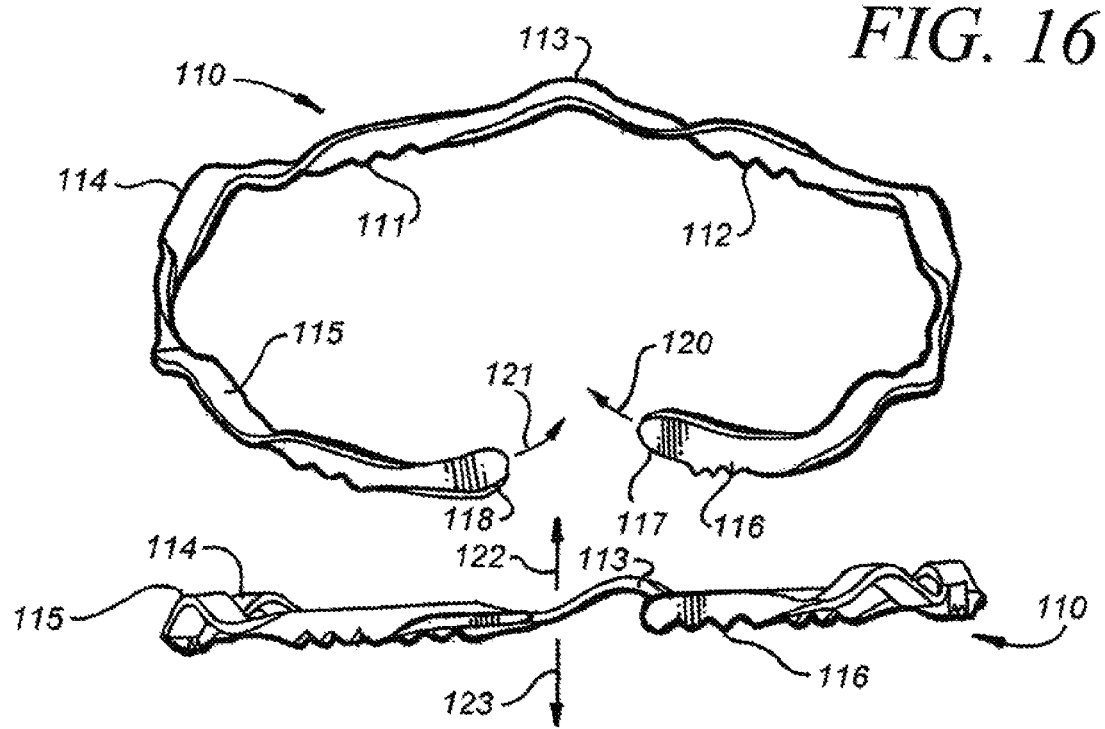
FIG. 16 is a perspective view illustrating a spring apparatus in accordance with an alternate embodiment of the invention.
FIG. 17 is a front elevation view illustrating the embodiment of the invention of FIG. 16.

FIGS. 16 and 17 illustrate a unitary ribbon spring apparatus constructed in accordance with the invention and generally indicated by reference character 110. Apparatus 110 includes ends 117 and 118, raised portions or peaks 113 to 115, and teeth 111, 112, 116.

In use, apparatus 110 is placed in an intervertebral disc between an opposing pair of vertebrae. Apparatus 110 can circumscribe material in the nucleus of the disc, can circumscribe material in the annulus of the disc, can circumscribe material in the annulus and the nucleus of the disc, or, when the nucleus or a portion of the nucleus has been removed, can circumscribe only a small amount of disc material or circumscribe no disc material at all. When the vertebrae are in their normal relatively uncompressed state (as when an individual is walking slowly, is in a relaxed standing position, or is reclining) apparatus 110 may contact each of the vertebrae pair, may contact only one vertebra, or may "float" in the disc without contacting either of the adjacent vertebrae. When the vertebrae are compressed, the top vertebra presses against and flattens elastic peaks 113 to 115, on the first surface of apparatus 110, in a direction toward the bottom vertebra. Flattening peaks 113 to 115 causes apparatus 110 to lengthen inwardly in the manner indicated by arrows 120 and 121. Apparatus 110 may also roll and slide inwardly over the adjacent vertebrae. If, however, peaks 113 to 115 are sufficiently compressed, teeth 111, 112, 116, on the second surface of apparatus 110 fixedly engage the bottom vertebra (or the top vertebra if teeth are provided along the first surface of apparatus 110) and prevent further movement of apparatus 110 until the opposing vertebrae separate and the compressive force acting on peaks 113 to 115 is released. When the compressive force is released, apparatus 110 elastically partially or completely returns to the configuration of FIG. 16. Teeth 11, 112 can completely disengage from the lower (or upper) vertebra. If teeth 111, 112, 116 remain engaged or partially engaged with the lower (or upper) vertebra, then apparatus 110 may only partially return to its configuration of FIG. 16.

As noted, flattening peaks 113 to 115 causes ends 117 and 118 to move inwardly in the direction of arrows 120 and 121, respectively. A section of the disc nucleus or other disc material typically is circumscribed by apparatus 110. When ends 117 and 118 move inwardly (away from the outer peripheral edge 72A (FIG. 21) of annulus 72) in the direction of arrows 120 and 121 (FIG. 16), ends 117 and 118 tend to gather disc material (nucleus and/or annular material) by compressing a portion of the section of the disc nucleus that is circumscribed by apparatus 110. In addition, when ends 117 and 118 move inwardly, they tend to gather disc material by drawing inwardly portions of the disc that are not circumscribed by apparatus 110 but that are contacting or near ends 117 and 118. Gathering disc material and displacing inwardly portions of the disc reduces the horizontal expansion forces 150 to 153 (FIG. 21) acting on the disc. Compressing apparatus 110 acts to horizontally narrow, inwardly contract, or un-bulge the disc in the direction of arrows 140-142 to counteract horizontal expansion forces 150 to 153. When portions of the disc are drawn inwardly, vertical "anti-compression" forces each acting against a vertebra in the direction of arrows 122 and 123 (FIG. 17) are also generated which tend to offset a portion of the compressive forces generated against the disc by the adjacent vertebrae. Vertical anti-compression forces 122 and 123 are generated by apparatus 110 when the disc is compressed between and by its neighboring pair of vertebrae. Vertical anti-compression forces 122, 123 tend to increase the height of the disc and further horizontally narrow, inwardly contract or un-bulge, the disc. Vertical anti-compression forces 122, 123 are each generally normal to the bottom surface 92 of vertebrae 90 or top surface 93 of vertebra 91 in FIG. 12, 13. Horizontal inward forces 140-143 acting opposite horizontal outward forces 150-153 in FIG. 21 are generally parallel to the bottom surface 92 of vertebra 90 or top surface 93 of vertebra 91 in FIG. 12, 13.

Figure 18:
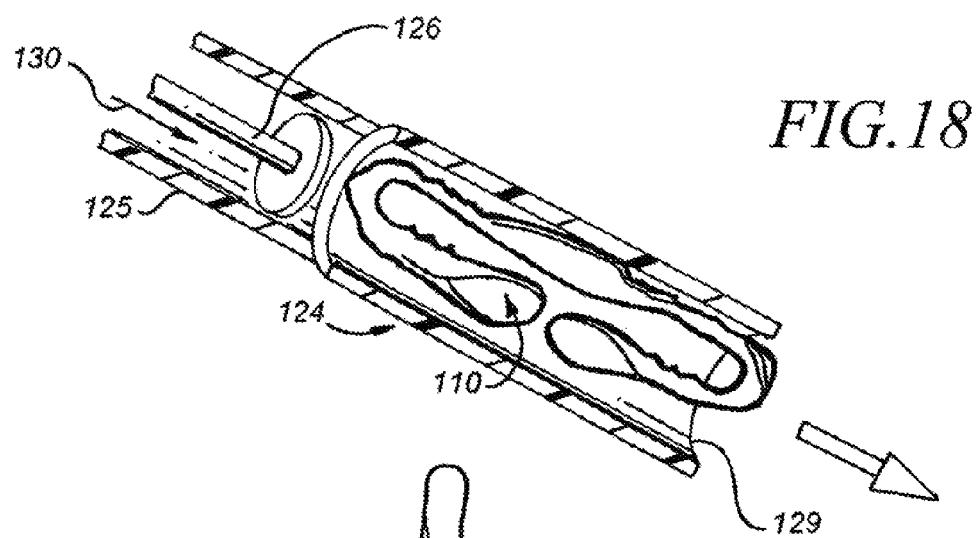
FIG. 18 is a perspective view illustrating an insertion member utilized to implant the spring apparatus of FIG. 16 in a spinal disc.
Figure 19:
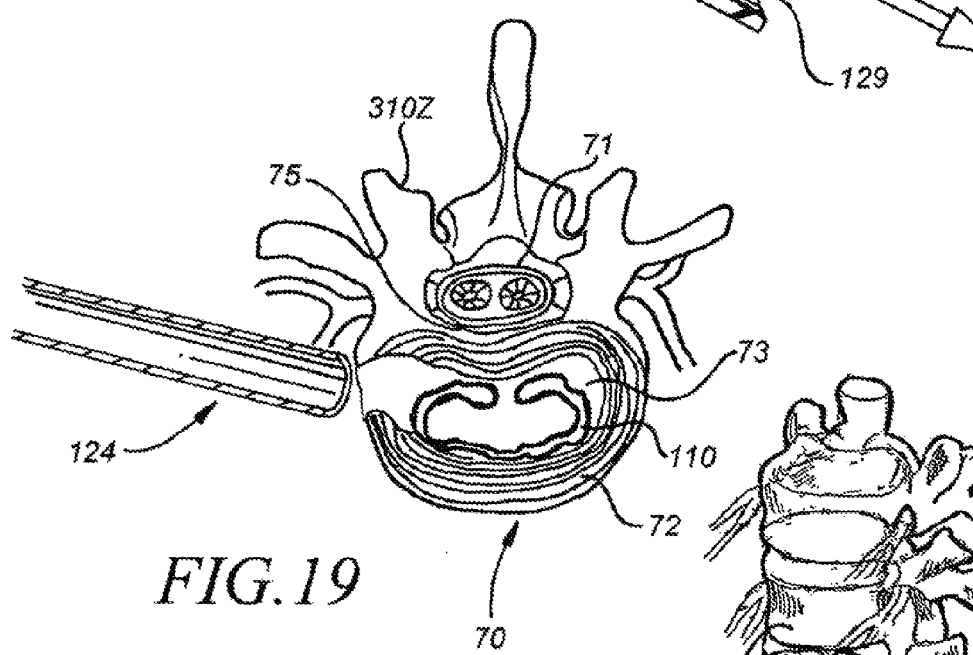
FIG. 19 is a top view illustrating the insertion member of FIG. 18 after the spring apparatus is implanted in a spinal disc.

FIG. 18 illustrates insertion apparatus 124 that can be utilized to implant spring apparatus 110 in a disc. Insertion apparatus 124 includes hollow channel 125. Apparatus 110 is housed in the end of channel 125. After the distal end 129 of channel 125 is positioned adjacent or in an opening in the annulus 72 in FIG. 19, plunger 126 is displaced in the direction of arrow 130 to eject apparatus 110 out of distal end 129 and into the disc to the position illustrated in FIG. 19. When apparatus 110 is inserted in a disc 70, apparatus 110 draws disc material away from the inner part 75 of the spinal column 71 to reduce the pressure generated on nerves in the spinal column 71. When apparatus 110 is compressed between a pair of vertebrae, ends 117 and 118 in FIG. 16 or other portions of apparatus 110 draw nuclear material or other disc material away from the inner part 75 of the spinal column 71 to reduce the pressure generated on nerves in the spinal column 71. (FIG. 19).

Figure 20:
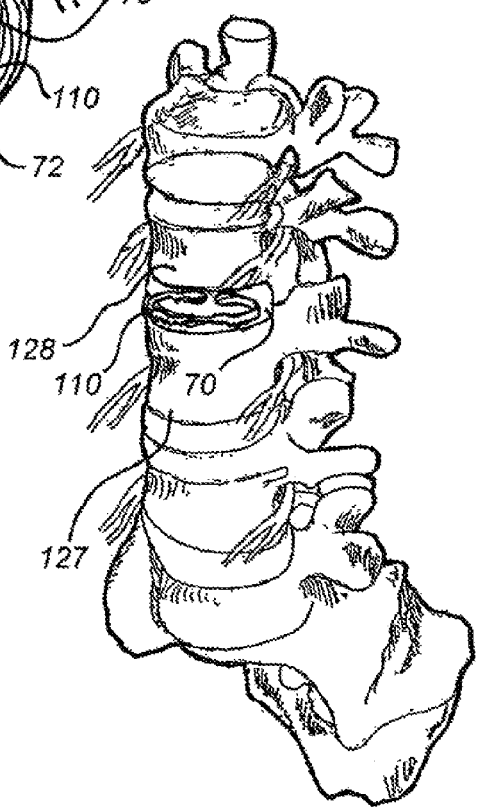
FIG. 20 is a top view of a portion of a spinal column illustrating the spring of FIG. 16 inserted in a disc.

FIG. 20 illustrates apparatus 110 inserted inside a disc 70 and intermediate vertebrae 127, 128.

Figure 21:
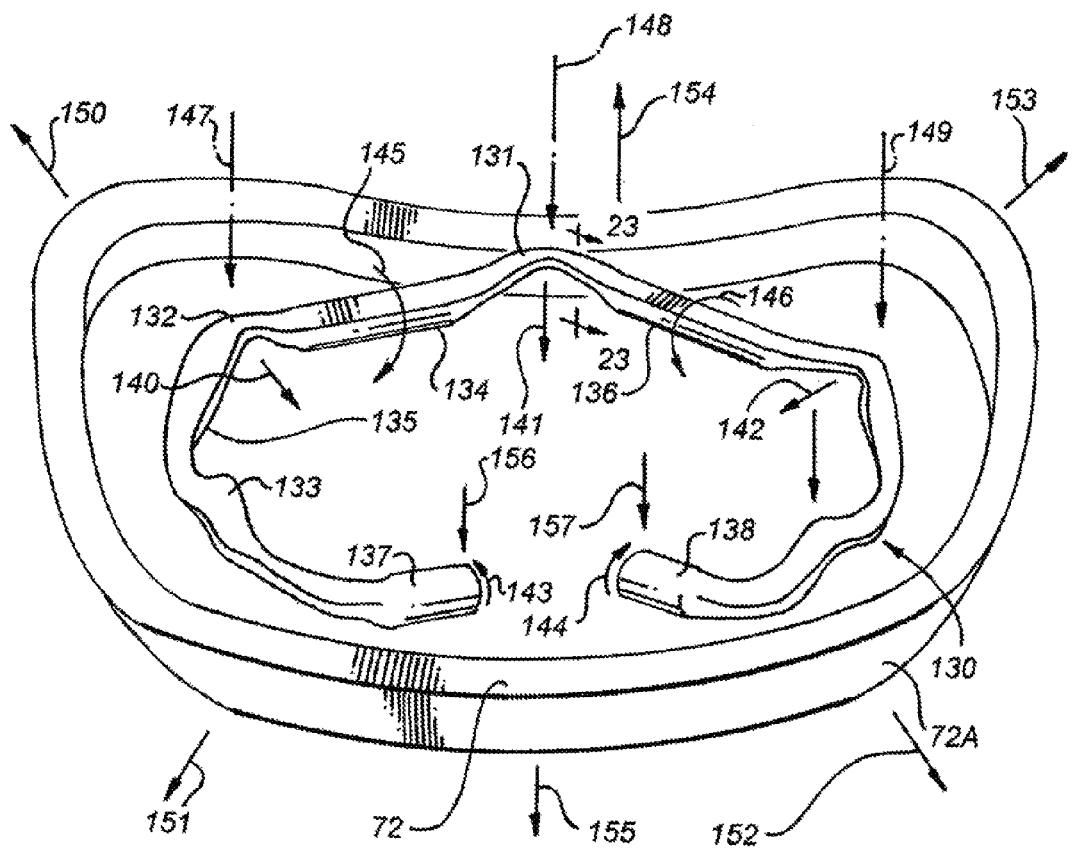
FIG. 21 is a perspective view illustrating a spring apparatus constructed in accordance with a further embodiment of the invention.
Figure 23:
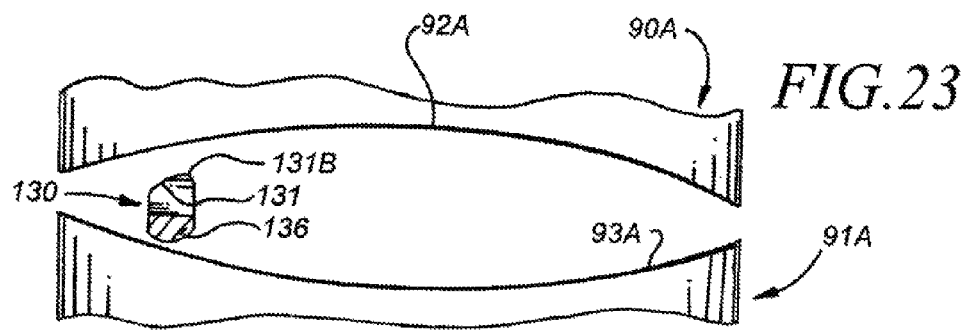
FIG. 23 is a side section view illustrating the mode of operation of the spring apparatus of FIG. 21 when interposed between an opposing pair of vertebra in a spinal column.
Figure 24:
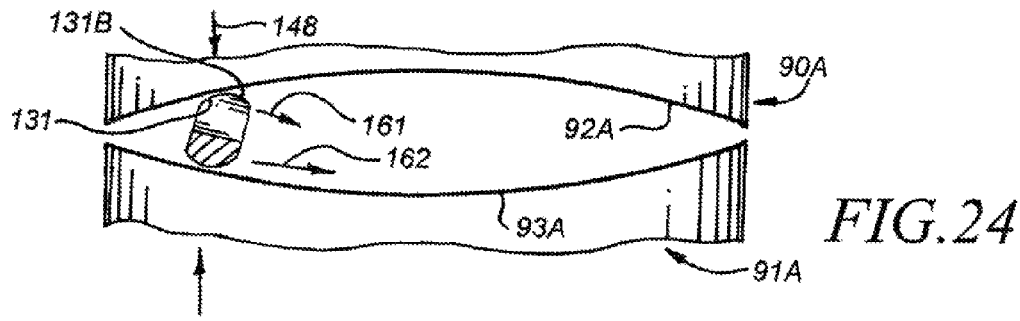
FIG. 24 is a side view further illustrating the mode of operation of the spring apparatus of FIG. 21 when compressed between an opposing pair of vertebra in a spinal column.

FIG. 21 illustrates an alternate unitary spring apparatus 130 constructed in accordance with the invention. Apparatus 130, like apparatus 110, includes a first surface with peaks 131 to 133. Peaks 131 to 133 are, as illustrated in FIGS. 23 and 24, higher toward the inside of apparatus 130 than toward the outside of apparatus 130. As will be discussed below, this height or elevation differential causes each peak 131 to 133 to function like a cam when apparatus 130 is compressed between a pair of vertebra (FIG. 24). Apparatus 130 also includes cylindrical, paddle shaped, spaced apart ends 137 and 138 and includes members 134 to 136. Each member 134 to 136 includes a semi-cylindrical bottom second surface that rolls and slides over the vertebra contacted by the semi-cylindrical bottom surface.

When apparatus 130 is compressed by vertical forces 147 to 149 generated by a vertebra contacting peaks 131 to 133, peaks 131 to 133 cant inwardly away from the outer circumference or peripheral edge of the annulus 72A in the directions indicated by arrows 140 to 142. This inward canting causes the semi-cylindrical bottom surfaces of members 134 to 136 to roll, and/or slide, inwardly in the manner indicated by arrows 145 and 146. Ends 137 and 138 are also caused to roll, and/or slide, inwardly in the manner indicated by arrows 143 and 144. When a vertebra contacts peaks 131 to 133, the vertebra, in addition to causing the peaks to roll inwardly, also flattens the peaks 131 to 133 to cause a lengthening of apparatus 130 akin to the lengthening produced in apparatus 110 in FIG. 16 when the peaks of apparatus 110 are flattened; and, to cause an inward displacement of ends 137, 138 (FIG. 21) akin to the inward displacement of ends 117 and 118 in the direction of arrows 120 and 121 (FIG. 17). When apparatus 110 is utilized, teeth 111, 112 on the apparatus dig into a vertebra each time the apparatus 110 is compressed. Consequently, the teeth may damage the vertebra. Apparatus 130 does not have such teeth. Apparatus 130 only slides or rolls over the surface of a vertebra. In this respect, apparatus 130 is sometimes preferred over apparatus 110. The inward displacement of ends 137, 138 gathers and compresses some of the disc material (i.e., nuclear and/or annular material) that is circumscribed and enclosed by apparatus 130 and/or that is adjacent ends 137, 138. Such gathering of disc material produces two additional results.

First, vertical anti-compression forces 154 and 155 (FIG. 21) are generated which offset to some extent the compression forces generated against the annulus 72 and nucleus of the disc. Forces 154 and 155 are generally perpendicular to the top 93 and bottom 92 of the vertebrae adjacent the disc. (FIG. 12).

Second, the portion of disc material gathered and compressed by apparatus 130 is elastic. The gathered up disc material produces its own outwardly acting return forces 156, 157 that act on ends 143 and 144 and other portions of apparatus 130 and assist in returning spring apparatus 130 to its original configuration when the vertebrae adjacent the disc separate toward their normal relatively uncompressed configuration and release the compressive forces acting on apparatus 130. Similar return forces are generated by compressed elastic disc material and act on apparatus 110 when apparatus 110 is compressed and gathers elastic disc material. (FIG. 16,17).

Figure 22:
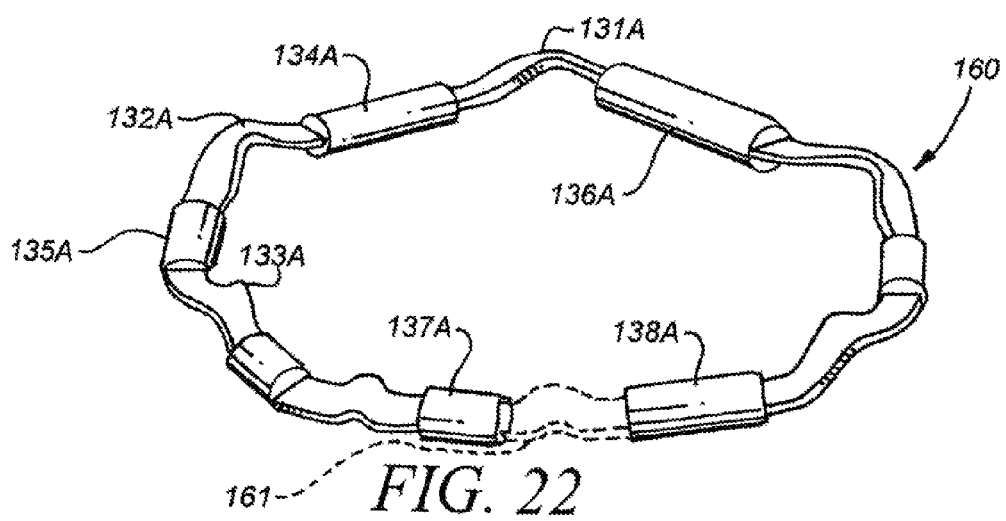
FIG. 22 is a perspective view illustrating a spring apparatus constructed in accordance with another embodiment of the invention.

The spring apparatus 160 illustrated in FIG. 22 is similar to apparatus 130 (FIG. 21), except that semi-cylindrical members 134 to 136 of apparatus 130 comprise—in apparatus 160—cylindrically shaped members 134A to 136A. Peaks 131A to 133A are equivalent to peaks 131 to 133 of apparatus 130. Ends 137A and 138A of apparatus 160 are equivalent to ends 137 and 138 of apparatus 130. Ends 137A and 138A can, if desired, be interconnected by a member 161. The shape and dimension and construction of a spring apparatus utilized in the practice of the invention can vary as desired.

The functioning of spring apparatus 130 is further illustrated in FIGS. 23 and 24. In FIGS. 23 and 24, the disc that is normally between vertebrae 90A and 91A is omitted for sake of clarity. Apparatus 130 would ordinarily preferably be implanted inside the disc between vertebrae 90A and 91A. FIG. 23 illustrates a portion of apparatus 130 prior to the vertebrae being compressed together. In FIG. 24, the vertebrae 90A and 91A have been compressed together and force 148 is acting on the various peaks of apparatus 130, including the specific peak 131 shown in FIG. 23. Tip 131B of peak 131 is higher than the remainder of the peak and functions as a cam. When bottom of vertebra 92A presses downwardly in the direction of force 148 against tip 131B (FIG. 24), peak 131 is displaced and cants inwardly in the direction indicated by arrow 161, causing the semi-cylindrical bottom surface of member 130 to tilt and/or slid on the top 93A of vertebra 91A in the direction of arrow 162. The inward canting and rolling or sliding of portions of spring apparatus 130 functions to gather in and compress nuclear and/or annular disc material that is circumscribed by apparatus 130. After the vertebra 90A and 91A separate and the compressive force 148 is released, apparatus 130 elastically returns to its normal orientation illustrated in FIG. 23 and peak 131 and member 136 return to the orientation illustrated in FIG. 23.

Figures 25, 26, 27:
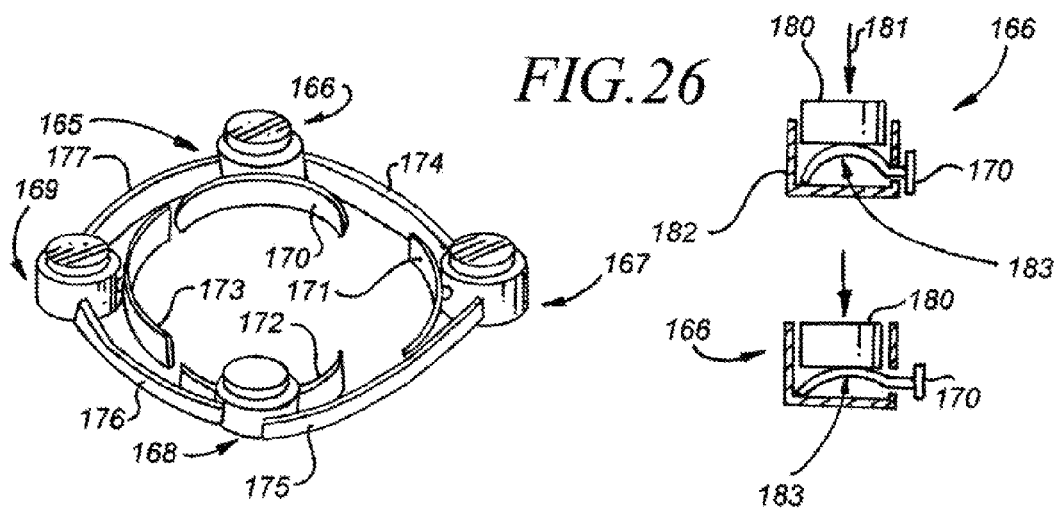
FIG. 25 is a perspective view illustrating still another spring apparatus constructed in accordance with the invention.
FIG. 26 is a side section view of a portion of the spring apparatus of FIG. 25 illustrating the mode of operation thereof.
FIG. 27 is a side section view of a portion of the spring apparatus of FIG. 25 further illustrating the mode of operation thereof.

Another spring apparatus 165 of the invention is illustrated in FIGS. 25 to 27 and includes four mini-towers 166 to 169. The towers 166 to 169 are interconnected by flexible strips 174 to 177. The construction of each tower 166 to 169 is identical. Tower 166 is illustrated in FIGS. 26 and 27. Tower 166 include cylindrical plunger 180 slidably received by hollow cylindrical base 182. Plunger 180 rests on spring 183 mounted in base 182. When a compressive force 181 is applied to plunger 180, spring 183 is downwardly deflected and flattened, pushing cupped member 170 away from base 182 and inwardly away from the outer peripheral edge 72A (FIG. 21) of the disc in which apparatus 165 (FIG. 25) is implanted. Consequently, when the apparatus 165 is implanted in an intervertebral disc and bottom 92A of a vertebrae (FIG. 24) compresses plunger 180 (FIG. 27), members 170 to 173 (FIG. 25) are inwardly moved and function to gather up and compress disc material that is within and circumscribed by apparatus 165.

Figure 28:
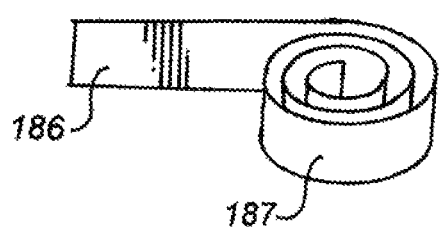
FIG. 28 is a perspective view illustrating a constant force coil leaf spring used in still a further embodiment of the invention.

A constant tension coil—ribbon spring 185 is illustrated in FIG. 28 and includes end 186 and coil 187.

Figure 29:
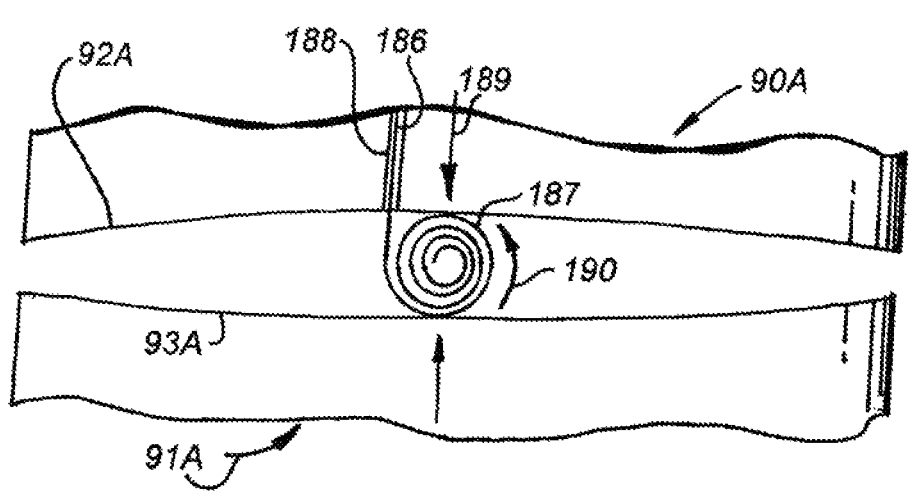
FIG. 29 is a side view illustrating the mode of operation of a constant force spring inserted between an opposing pair of vertebra.

The intervertebral disc is, for sake of clarity, omitted from FIG. 29. End 186 of spring 185 is fixedly secured in an opening 188 formed in vertebra 90A. Coil 187 is positioned intermediate vertebrae 90A and 91A. When vertebrae 90A and 91A move toward one another a compressive force 189 is generated. Force 189 compresses the disc intermediate the vertebrae, and compress coil 187 that winds or coils more tightly in direction 190 and tends to draw inwardly into coil 187 adjacent disc material. When the compressive force 189 is released, coil 187 elastically unwinds to return to its normal uncompressed state.

Figure 30I:
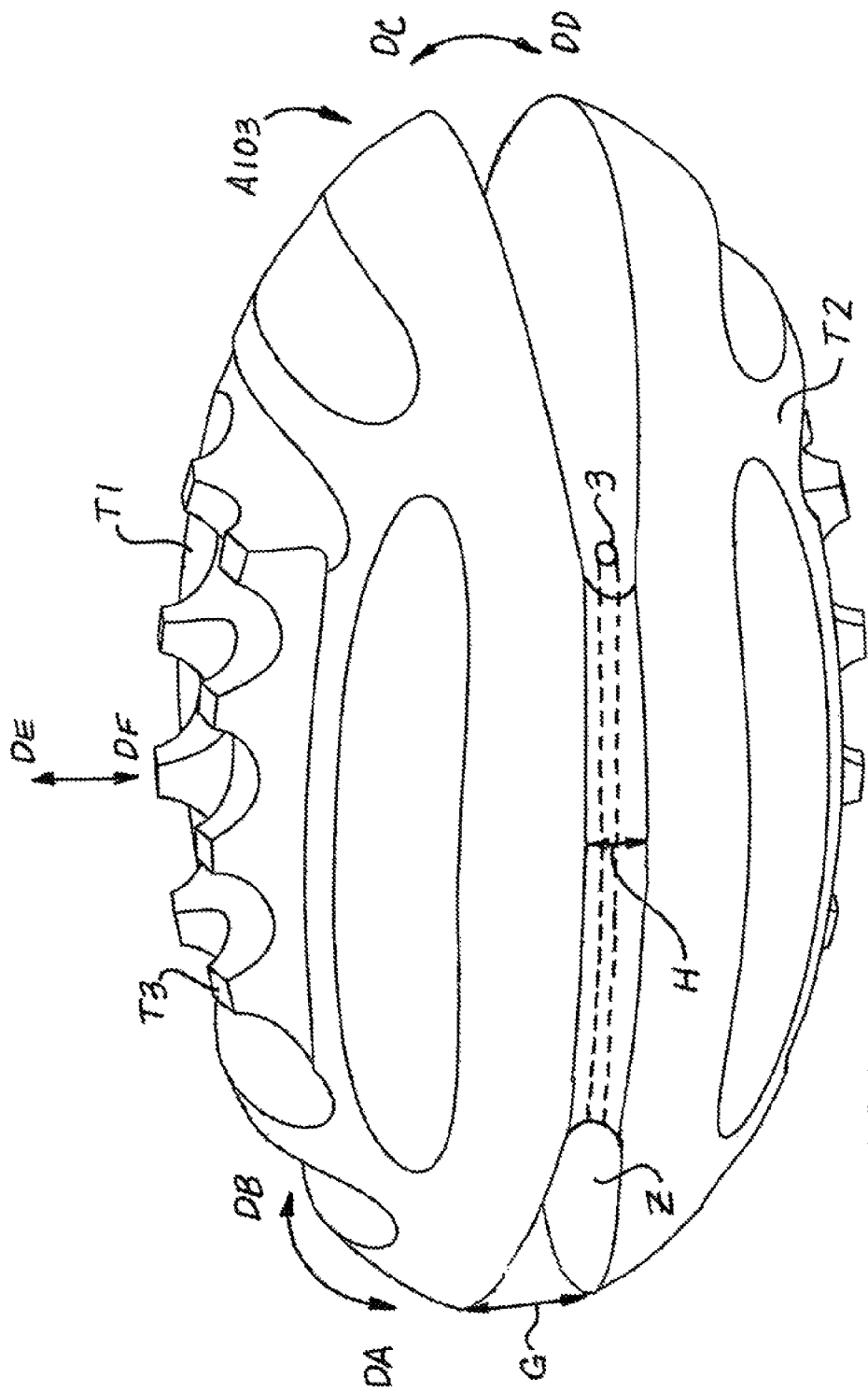
FIG. 30 is a side section view illustrating still another embodiment of the spring apparatus of the invention.
FIG. 30A is a front perspective view of the spring apparatus of FIG. 30.

FIGS. 30, 31, 30A, and 31A illustrate another embodiment of the invention in which a spring apparatus 191 (FIG. 30A) is provided that has the same general shape and dimension as apparatus 110 (FIG. 16), except that the peak portions 113, 114, 115 are replaced by portions 192 that bow inwardly when the apparatus 191 (FIG. 30A) is compressed in the direction of 194 (FIG. 30, 31). FIGS. 30 and 30A illustrate apparatus 191 in its normal "at rest" state. FIGS. 31 and 31A illustrate apparatus 191 when it is under compression and portions 192 have elastically bowed portion 193 inwardly to gather in and compress disc material circumscribed by apparatus 191.

An apparatus 100 (FIG. 1), 76 (FIG. 9), 77A (FIG. 10), 110 (FIG. 16), 130 (FIG. 21), 160 (FIG. 22), 165 (FIG. 25), 185 (FIG. 28), and 191 (FIG. 30A) can be inserted in a disc in one, two, or more separate pieces that are not interconnected and may independently function in the disc. The spring apparatus and other apparatus described herein may be utilized in other body in joints and locations other than within intervertebral discs and between vertebrae in the spine. The intervertebral disc is an example of a soft tissue compartment adjoining first and second bones (vertebra) having an initial height and an initial width. Other joints consisting of a soft tissue compartment adjoining at least first and second bones having an initial (vertical) height and an initial (horizontal) width may include the joints of the hand, wrist, elbow, shoulder, foot, ankle, knee, and hip.

The materials utilized to construct an apparatus 100 (FIG. 1), 76 (FIG. 9), 77A (FIG. 10), 110 (FIG. 16), 130 (FIG. 21),

160 (FIG. 22), 165 (FIG. 25), 185 (FIG. 28), and 191 (FIG. 30A) can vary as desired. Metals and metal alloys are presently preferred.

Figures 32, 33:
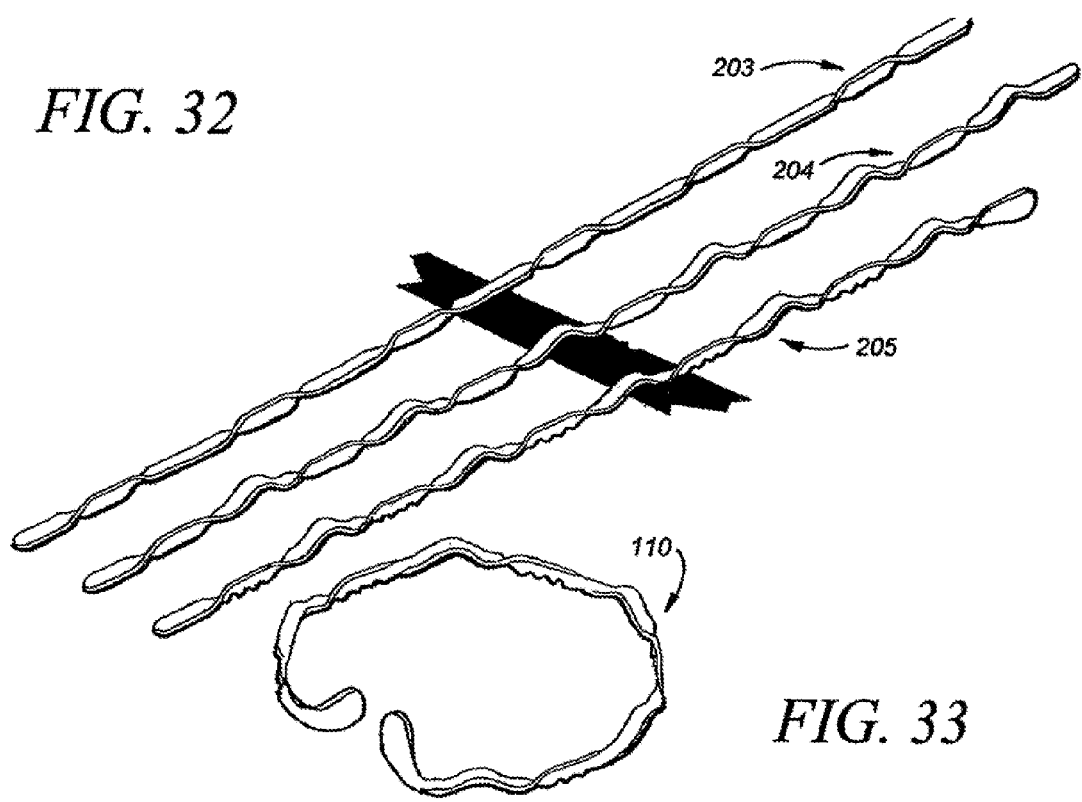
FIG. 32 is a perspective view illustrating the manufacture of the spring apparatus of FIG. 16.
FIG. 33 is a perspective view illustrating a spring apparatus producing in accordance with the manufacturing process illustrating in FIG. 32.

One method for constructing a spring apparatus 110 is illustrated in FIGS. 32 and 33. The first step of the process is to feed a metal ribbon through stepper collet jaws to articulate twists incrementally at a 90 degree orientation with respect to each other to produce the articulated ribbon 200. In the second step, the articulated ribbon 200 is formed in matching dies to produce vertical bends or peaks in horizontal flat portions of the ribbon. This result is the articulated "peaked" ribbon 201 shown in FIG. 32. The third step of the process is to grind or otherwise form teeth in the vertically oriented sections of the ribbon to produce the articulated "peaked" toothed ribbon 202 shown in FIG. 32. The fourth and final step of the process is to roll the ribbon 202 to produce the annular ring shape of apparatus 110 (FIG. 33).

Anatomical planes are drawn through an upright body. These planes include the coronal plane, the sagittal plane, and the axial plane. FIG. 34 illustrates the general relationship of anatomical planes with vertebrae 90B, 91B and disc 70A in the spinal column. The coronal, or frontal, plane 210 is a vertically oriented plane that is generally parallel to the front of an individual's body. The sagittal plane 211 is a vertically oriented plane that is normal to the coronal plane and that is parallel to the sides of an individual's body. The transverse, or axial, plane 212 is a horizontally oriented plane that passes through the waist of an individual's body and that is normal to the coronal and sagittal planes.

The spine has normal curvatures which are either kyphotic or lordotic. Scoliosis is a deformity of the spinal column in which the spinal column is curved from its normal upright orientation laterally in the coronal plane in the direction of arrow 218 or of arrow 217. Lordosis is a deformity of the spinal column in which the spinal column is curved from its normal upright orientation rearwardly in the sagittal plane in the direction of arrow 216. In contrast to the normal curvatures of the spine, lordosis produces an excessive inward curvature of the spine. Kyphosis is a deformity of the spinal column in which the spinal column is curved from its normal upright orientation forwardly in the sagittal plane in the direction of arrow 215. Scoliosis, lordosis, and kyphosis can be accompanied by a rotation 214 of the spine about a vertically oriented axis 213, and can also be accompanied by undesirable movement of the ribs and or pelvis. For example, scoliosis often is characterized by both lateral curvature and vertebral rotation. As scoliosis advances, vertebrae spinous processes in the region of the major curve rotate toward the concavity of the curve. The ribs move close together towards the pelvis on the concave side of the curve. The ribs are widely spaced apart on the convex side of the curve. Continued rotation of the vertebral bodies is accompanied by increases deviation of the spinous processes to the concave side. The ribs follow the rotation of the vertebrae. On the convex side, the ribs move posteriorly and produce a rib hump commonly associated with thoracic scoliosis. On the concave side, the ribs are pushed anteriorly and deform the chest. Lordosis can occur simultaneously with scoliosis, as can kyphosis. Any of the apparatus previously described herein can, when appropriate and desirable, be utilized in the processes described below in conjunction with FIGS. 35 to 40 to treat deformities of the spinal column.

In FIG. 35, cylindrical apparatus 230 is inserted between a pair 228, 229 of canted, spaced apart panel members. When a downward displacement force 231A is applied to panel 228, panel member 228 pivots about apparatus 230 in the same manner that a door rotates about its hinge. Panel member 228 moves about apparatus 230 in a single rotational direction indicated by arrow 232 such that the outer edge 246 of panel member 228 moves toward panel member 229. Likewise, a displacement force 231B acting against panel member 229 can cause panel member 229 to pivot about apparatus 230 in a single rotational direction indicate by arrow 233. Arrows 232 and 233 each lie in a common plane.

As is illustrated in FIG. 36, cylindrical apparatus 230 can be utilized to treat adjacent vertebrae that are misaligned or misrotated due to scoliosis, lordosis, kyphosis, or other causes. In FIG. 36 vertebra 90B is canted from its normal orientation with respect to vertebra 91B. In its normal orientation, the bottom 90C of vertebra 90B would be generally parallel to the top 90D of vertebra 91B. Elongate cylindrical apparatus 230 is positioned intermediate vertebrae 90B, 91B adjacent opposing edge portions 220, 221 of vertebrae 90B, 91B, respectively, on the "concave" side of the misalignment. Edge portions 222, 223 of vertebrae 90B, 91B, respectively, are on the "convex" side of the misalignment of the vertebrae. Apparatus 230 may be (1) constructed in any desired manner, and (2) positioned between vertebrae 90B, 91B in any desired manner and at any desired location therebetween as long as apparatus 230 functions to improve the alignment of vertebrae 90B, 91B such that bottom 90C is more nearly parallel to top 90D and/or such that at least one of vertebrae 90B, 91B is rotated about a vertical axis 213 in FIG. 34, to more closely approach its natural position or to more closely approach another desired position and orientation. By way of example, and not limitation, when apparatus 230 is inserted it may (1) only contact top 90D and may or may not be secured to top 90D, (2) be secured to and only contact bottom 90C, (3) be positioned further away from edge portions 220, 221 and nearer the center of bottom 90C and top 90D, (4) comprise a spring that is "loaded" and generates a force 224 that (like force 231 in FIG. 35) acts upwardly against bottom 90C until edge portions 220 and 221 are a selected distance apart, or (5) comprise, in contrast to the spring just mentioned, a solid non-elastic member that functions only as a pivot point like the hinge of a door.

Figure 37:
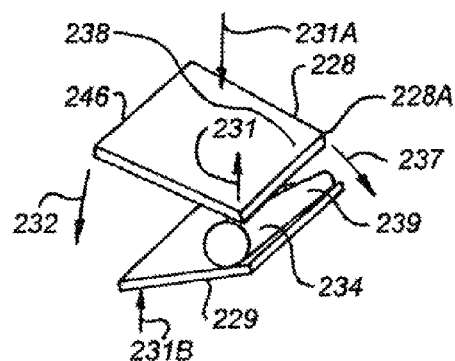
FIG. 37 is a perspective view illustrating the use of an apparatus to pivot in at least two rotational directions one member with respect to another adjacent.

In FIG. 37, conical apparatus 234 is inserted between a pair 228, 229 of canted, spaced apart panel members. When a downward displacement force 231A is applied to panel member 228, panel member 228 pivots about apparatus 234 in the same manner that a door rotates about its hinge. Since, however, there is a space between panel member 228 and the tapered end 239 of apparatus 234, panel member 228 also pivots about the larger end of member 234 such that end 228A moves downwardly toward end 239 in the manner indicated by arrow 237. Consequently, when apparatus 234 is inserted and force 231A is applied to panel member 228, panel member 228 moves about apparatus 234 in at least a pair of rotational directions indicated by arrows 232 and 237. Likewise, a displacement force 231B acting against panel member 229 can cause panel member 229 to pivot about apparatus 230 in at least a pair of rotational directions.

Figure 38:
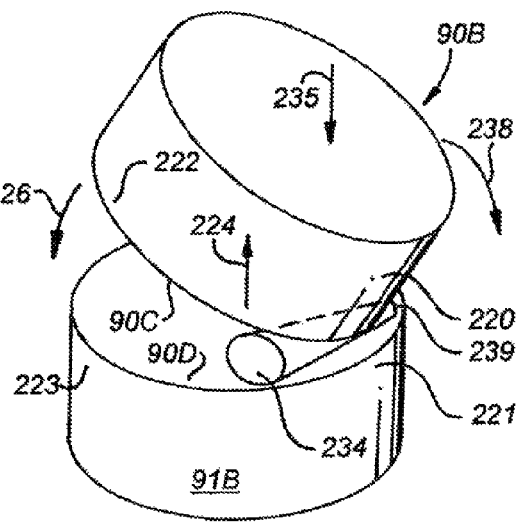
FIG. 38 is a perspective view illustrating the use of the apparatus of FIG. 37 to pivot in at least two rotational directions one vertebra with respect to an adjacent vertebra.

As is illustrated in FIG. 38, conical apparatus 234 can be utilized to treat adjacent vertebrae that are misaligned or misrotated due to scoliosis, lordosis, kyphosis, or other causes. In FIG. 38 vertebra 90B is canted from its normal orientation with respect to vertebra 91B. In its normal orientation, the bottom 90C of vertebra 90B would be generally parallel to the top 90D of vertebra 91B. Elongate conical apparatus 234 is positioned intermediate vertebrae 90B, 91B adjacent opposing edge portions 220, 221 of vertebrae 90B, 91B, respectively, on the "concave" side of the misalignment. Edge portions 222, 223 of vertebrae 90B, 91B, respectively, are on the "convex" side of the misalignment of the vertebrae.

Apparatus 234 may be (1) constructed in any desired manner, and (2) positioned between vertebrae 90B, 91B in any desired manner and at any desired location therebetween as long as apparatus 234 functions to improve the alignment of vertebrae 90B, 91B such that bottom 90C is more nearly parallel to top 90D and/or such that at least one of vertebrae 90B, 91B is rotated about a vertical axis 213 in FIG. 34, to more closely approach its natural position or to more closely approach another desired position and orientation. By way of example, and not limitation, when apparatus 234 is inserted it may (1) only contact top 90D and may or may not be secured to top 90D, (2) be secured to and only contact bottom 90C, (3) be positioned further away from edge portions 220, 221 and nearer the center of bottom 90C and top 90D, (4) comprise a spring that is "loaded" and generates a force 224 that acts upwardly against bottom 90C until edge portions 220 and 221 are a selected distance apart, or (5) comprise, in contrast to the spring just mentioned, a solid non-elastic member that functions only as a pivot point like the hinge of a door.

Figure 39:
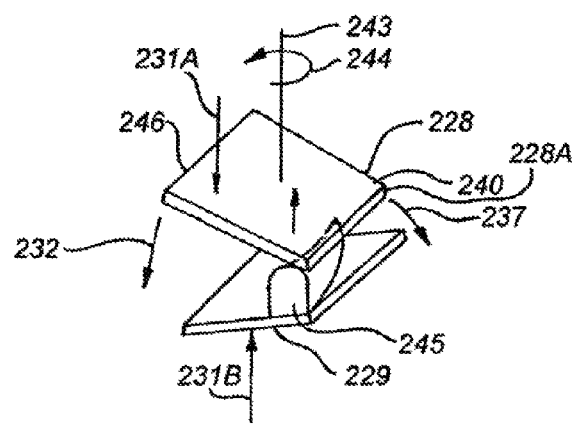
FIG. 39 is a perspective view illustrating the use of apparatus to pivot in at least two rotational directions and to rotate one member with respect to another adjacent member.

In FIG. 39, tapered arcuate apparatus 245 is inserted between a pair 228, 229 of canted, spaced apart panel members. When a downward displacement force 231A is applied to panel member 228, panel member 228 pivots about apparatus 245 in the same manner that a door rotates about its hinge. Since, however, there is a space between panel member 228 and the tapered end 240 of apparatus 245, panel member 228 also pivots about the larger end of member 245 such that end 228A moves downwardly toward panel member 229 in the manner indicated by arrow 237. Further, arcuate apparatus 245 is shaped to cause panel member 228 to rotate in the direction indicated by arrow 244 about a vertical axis 243. Consequently, when apparatus 245 is inserted and force 231A is applied to panel member 228, panel member 228 moves about apparatus 245 in at least a pair of rotational directions indicated by arrows 232 and 237, as well as in a rotational direction indicated by arrow 244.

Figure 40:
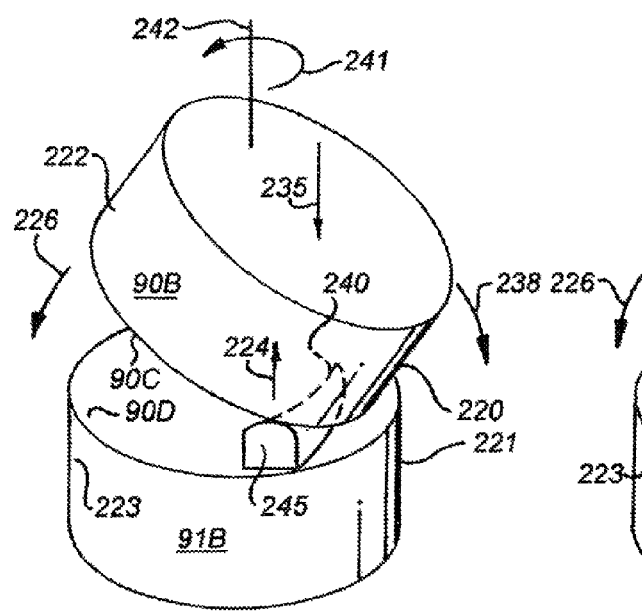
FIG. 40 is a perspective view illustrating the use of the apparatus of FIG. 39 to pivot in at least two rotational directions and to rotate one vertebra with respect to an adjacent vertebra.

As is illustrated in FIG. 40, tapered arcuate apparatus 245 can be utilized to treat adjacent vertebrae that are misaligned or misrotated due to scoliosis, lordosis, kyphosis, or other causes. In FIG. 40 vertebra 90B is canted from its normal orientation with respect to vertebra 91B. In its normal orientation, the bottom 90C of vertebra 90B would be generally parallel to the top 90D of vertebra 91B. Tapered arcuate apparatus 245 is positioned intermediate vertebrae 90B, 91B adjacent opposing edge portions 220, 221 of vertebrae 90B, 91B, respectively, on the "concave" side of the misalignment. Edge portions 222, 223 of vertebrae 90B, 91B, respectively, are on the "convex" side of the misalignment of the vertebrae. Apparatus 245 may be (1) constructed in any desired manner, and (2) positioned between vertebrae 90B, 91B in any desired manner and at any desired location therebetween as long as apparatus 245 functions to improve the alignment of vertebrae 90B, 91B such that bottom 90C is more nearly parallel to top 90D and/or such that at least one of vertebrae 90B, 91B is rotated about a vertical axis 213 in FIG. 34, to more closely approach its natural position or to more closely approach another desired position and orientation. By way of example, and not limitation, when apparatus 245 is inserted it may (1) only contact top 90D and may or may not be secured to top 90D, (2) be secured to and only contact bottom 90C, (3) be positioned further away from edge portions 220, 221 and nearer the center of bottom 90C and top 90D, (4) comprise a spring that is "loaded" and generates a force 224 that acts upwardly against bottom 90C until edge portions 220 and 221 are a selected distance apart, or (5) comprise, in contrast to the spring just mentioned, a solid non-elastic member that functions only as a pivot point like the hinge of a door.

An apparatus 230, 234, 245 typically generates a force 224 acting on a vertebra 90B in at least one of two ways. If the apparatus 230, 234, 245 is elastic or non-elastic and is forced between portions 220 and 221, the apparatus 230, 234, 245 at the time it is inserted produces an upwardly directed force 224 that acts to move portion 220 upwardly and therefore tends to cause portion 222 to pivot in the direction of arrow 226. Or, if the apparatus 230, 234, 245 is elastic or non-elastic and is not forced between portions 220 and 221, then when an individual's spine is compressed, either artificially or during normal movement of the individual, and a downward compressive force 235 is generated on vertebra 90B to press vertebra 90B against apparatus 230, 234, 245, then when portion 220 is pressed against apparatus 230, 234, 245, apparatus 230, 234, 245 produces a counteracting upwardly acting force 224 that, along with force 235, functions to cause vertebra 90B to pivot and/or rotate about apparatus 230, 234, 245 such that portion 222 pivots in the direction of arrow 226, or such that vertebra 90B rotates in a direction 241 about a vertical axis 242 (FIG. 40).

In FIGS. 36, 38, 40, the intervertebral disc has been omitted for sake of clarity. Although apparatus 230, 234, 245 can be utilized when the intervertebral disc is not present, it is presently preferred in the spirit of the invention that most or all of intervertebral disc be present and that apparatus 230, 234, 245 be inserted within the annulus of the disc and between vertebrae 90B, 91B. Consequently, while apparatus 230, 234, 245 functions to correct deformities in the spine, apparatus 230, 234, 235 also functions to improve the functioning and shape of discs intermediate spinal vertebrae.

In one embodiment, an intervertebral implant can include: a tapered arcuate shape as shown in FIGS. 39-40. The implant can be a unitary member, or prepared from two or more members linked together. When two or more members, the individual members can be coupled together through a hinge as described herein (see FIGS. 95-99, 110-112, and 268-287. In fact, any of the implants described and/or illustrated herein can be modified to be formed to have the general tapered arcuate implant shape of FIGS. 39-40.

The tapered arcuate implant can include a solid non-elastic portion. The implant can include an implant-suitable material, such as a biocompatible metal or polymer or ceramic or composite or combination thereof. The implant can be at least partially porous. For example, the porous portion can be a vertebra-facing portion, such as the rounded surface or substantially flat surface. In one aspect, the pores can be filed with a biodegradable material that can include one or more active agents, such as growth factors. Also, the implant can be formed from a hybrid of at least two implant-suitable materials. For example, the implant can include a metal with a cavity or pores filed with a biodegradable polymer. The biodegradable polymer can include the growth factors, such as bone growth factors, which are known or later developed. The growth factor can help the bone grow into the cavity or pores on a surface mounted to the vertebra to enhance the therapy.

In one embodiment, the tapered arcuate implant can include a body having a rounded surface and a substantially flat surface as shown in FIGS. 39-40. Optionally, the substantially flat surface can be opposite of the rounded surface. The rounded surface and substantially flat surface can extend from a base to a tip of the tapered arcuate shape. The base may also be substantially flat, where the tip can be rounded. The tapered arcuate shape can extend from a substantially flat base and curve to a tip of the arc. The tapered arcuate shape may also be conical from a base to a tip, the conical body providing the taper.

In one embodiment, the tapered arcuate implant can be configured in accordance with one or more of the following: the substantially flat surface can be configured to be mounted on a surface of a vertebra of two adjacent vertebras; the rounded surface can be configured to contact a surface of a vertebra of two adjacent vertebras; the implant can be configured to be secured to and only contact the surface of the vertebra; the substantially flat surface can be configured to be secured to a surface of a vertebra of two adjacent vertebras such that the other vertebra is capable of pivoting and rotating about the rounded surface; or a body having the tapered arcuate shape extending from a substantially flat base to a tip, the body having a rounded surface and a substantially flat surface opposite of the rounded surface, the surfaces extending between the base and tip of a body having the tapered arcuate shape extending from a substantially flat base to a tip, the body having a rounded surface and a substantially flat surface opposite of the rounded surface, the surfaces extending between the base and tip. The implantation and mounting can be performed as described herein or known in the art. For example, the implant can include a surface adapted for mounting to a bone, such as a surface having the recesses, divots, cut-outs, or other features that allow bone growth therein. This can facilitate securing the implant to the vertebra. Also, a rounded surface can facilitate contact to a vertebra to allow rotation of the vertebra around the implant without securing the rotatable vertebra to the rounded surface.

In one embodiment, a tapered arcuate implant can include a spring that is configured to generate force between two adjacent vertebras when the spring is loaded. The spring can be a conventional spring or any spring described herein. The spring can be integrated or coupled to the body of the tapered arcuate implant.

In one embodiment, the tapered arcuate implant can be configured for implantation between two adjacent vertebras. That is, the implant can be configured to be implanted between the facing surfaces of two adjacent vertebras. This can include the implant being completely within a peripheral edge of one of the facing surfaces of the adjacent vertebras. Also, the implant can be dimensioned to be implanted between and edge portion (e.g., periphery) and center of the two adjacent vertebras. Implantation and positioning can be performed with any method or device or system as described herein. For example, the tapered arcuate implant can include a lumen or channel that receives the elongate light guide, which can be used to implant the tapered arcuate implant. A cannula can also be used, such as the cannula described herein. In one aspect, the cannula having the implant can be moved around a nerve, by rotating the cannula to move the nerve, as described and illustrated in connection to FIGS. 235F-235I.

In one embodiment, the tapered arcuate shape can be configured to align two adjacent vertebras. For example, the tapered arcuate implant can align the vertebras as described in connection to FIGS. 39-40. Also, the tapered arcuate implant can be used to induce internal traction and separation of the vertebras, which can cause the disc to be drawn in. This can include any herniation of the disc to be drawn into the disc due to the tapered arcuate implant. Also, the alignment can be performed by the implant rotating the two adjacent vertebras around the tapered arcuate shaped implant in one or more of three axes of rotation. At least two axes of rotation can be relative to the sagittal and coronal planes and one of the axes is the vertical axis of rotation. In one aspect, the tapered arcuate shape is configured to align two adjacent vertebras by: rotating surfaces of the two adjacent vertebras around the tapered arcuate implant in at least one axis of rotation; and/or rotating the surfaces of the two adjacent vertebras around a vertical axis of rotation. In one aspect, the tapered arcuate shape can be configured to provide rotation about a vertical axis of rotation from a wide portion to a tip of the tapered arcuate shape in the direction of its arc. In one aspect, the tapered arcuate shape can include a surface configured to be secured to a surface of a vertebra between two adjacent vertebras. In one aspect, the tapered arcuate shape can include a surface configured to pivotally contact a surface of a vertebra between two adjacent vertebras. In one aspect, the tapered arcuate shape includes a surface configured to pivotally and rotatably contact a surface of a vertebra between two adjacent vertebras. The tapered arcuate implant can be positioned as desired to get a desired rotation in one, two, or all three axis of rotation. Often, the rotation will be on the vertical axis. Also, the rotation can be on an axis that bisects the vertical axis. An axis that bisects the vertical axis can be related to or between the sagittal and coronal planes.

In one embodiment, mechanically aligned adjacent vertebras can include the tapered arcuate implant located between the adjacent vertebras as shown in FIGS. 39-40. The tapered arcuate implant can be configured as described herein and may include features and configurations of any of the implants, which implants can be modified to have the tapered arcuate shape. The tapered arcuate implant can be in the disc between the two adjacent vertebras. The implant can align the two adjacent vertebras by imparting a mechanical action. The mechanically aligned adjacent vertebras that contain the implant can be from a spine having scoliosis, lordosis, and/or kyphosis without the implanted tapered arcuate implant between the adjacent vertebras. The tapered arcuate implant can provide a therapy for these ailments. The tapered arcuate implant can be in any position between the adjacent vertebras so that an artificial mechanical system modulates the alignment of the adjacent vertebras.

In one embodiment, a method of treating adjacent vertebras can include: providing the tapered arcuate implant as described herein; and inserting the implant between two adjacent and misaligned vertebras so as to align the two adjacent vertebras. The two adjacent vertebras can include a vertical axis of rotation, a first vertebra having a bottom surface, and a second vertebra having a top surface. Optionally, the adjacent vertebras can include a vertical axis of rotation, a first vertebra having a bottom surface that faces a top surface of a second vertebra. The adjacent vertebras can be treated to be better aligned compared to before the adjacent vertebras receive the tapered arcuate implant.

In one embodiment, the method can include at least one or only one of the following: contacting the tapered arcuate implant with the top surface of the second vertebra, and securing the implant to the top surface of the second vertebra; contacting the implant with the top surface of the second vertebra without contacting the bottom surface of the first vertebra, and securing the implant to the top surface of the second vertebra; or contacting the implant with the top surface of the second vertebra without contacting the bottom surface of the first vertebra or securing the implant to the top surface of the second vertebra; or contacting the implant with the top surface of the second vertebra without securing the implant to the top surface of the second vertebra; or contacting the implant with the bottom surface of the first vertebra, and securing the implant to the bottom surface of the first vertebra; or contacting the implant with the bottom surface of the first vertebra without contacting the top surface of the second vertebra, and securing the implant to the bottom surface of the first vertebra; or contacting the implant with the bottom surface of the first vertebra without contacting the top surface of the second vertebra or securing the implant to the bottom surface of the first vertebra; or contacting the implant with the bottom surface of the first vertebra without securing the implant to the bottom surface of the first vertebra; or contacting the implant with the bottom surface of the first vertebra and top surface of the second vertebra. The surfaces for contact without securing can be smoother or more rounded compared to the surfaces for contact and securing. The surfaces for securing can include recesses, teeth, pores, or other features that promote securing of an implant to a bone, which can include any of the properties described herein.

In one embodiment, a method of treating adjacent vertebras can include: selecting the tapered arcuate implant as described herein; identifying two adjacent vertebras having a vertical axis of rotation and adjacent surfaces being nonparallel; and inserting the tapered arcuate implant between the vertebras at a location between the vertical axis of rotation and edge portions of the two adjacent vertebras; and rotating the two adjacent vertebras around the tapered arcuate implant in at least one axis of rotation. The axis of rotation can be vertical with respect to the spine or any axis that intersects the spine, such as a substantially horizontal or diagonal axis. The method can also include rotating the two adjacent vertebras so as to be about parallel or more parallel than before receiving the tapered arcuate implant. In one aspect, the method can include rotating the two adjacent vertebras around the implant in at least two axes of rotation, wherein the at least two axes of rotation are relative to at least one of the sagittal, coronal planes, and vertical axis of rotation. In one aspect, the method can include rotating the two adjacent vertebras around the implant in at least three axes of rotation.

In one embodiment, the method of treating adjacent vertebras can include locating the tapered arcuate implant to be closer to the edge portions of the two adjacent vertebras than the vertical axis of rotation. Alternatively, the method of treating adjacent vertebras can include locating the tapered arcuate implant to be closer to the vertical axis of rotation than the edge portions. The taper can be positioned to have a tip that points to any location so that the desired rotation, such as vertical rotation, is achieved. The taper can also be configured to have a steepness that facilitates the rotation. Thus, the dimensions of the tapered arcuate implant and amount of curvature of the arc can be modulated as desired. However, the tapered arcuate implant can be dimensioned to be retained within an edge or within a periphery of the adjacent vertebras.

As noted, an intervertebral disc interconnects vertebra bones in a spinal column. The disc includes an annulus and a nucleus. As used herein, the annulus is a hard tissue compartment that houses soft tissue comprising the nucleus. Other hard tissue found in the body includes bone, cartilage, and the capsules located at the end of bones at the joints of the hand, wrist, elbow, shoulder, foot, ankle, knee, and hip. Soft tissue in the body includes epithelium, fascia, muscle, fat, vasculature, and nerves.

Vasculature and nerves of differing width, or diameter, exist throughout the body. The larger vasculature and nerves are deemed principal vasculature and nerves. The lesser vasculature and nerves are deemed minor vasculature and nerves. As used herein, principal vasculature and nerves have a width of at least one millimeter (mm).

An object of many surgical procedures is to produce an opening in an intervertebral disc or other hard tissue including cartilage, bone, and the capsules around joints. During these surgical procedures, the distal end of an instrument often is passed through soft tissue in order to reach the hard tissue in which the opening is to be formed. Since the distal end of the instrument often has a sharp tip or cutting edge that is used to form an opening in the hard tissue, there is a significant risk that the distal end will cut or pierce principal vasculature or nerves and produce a serious injury, possibly a life threatening injury.

Figure 41:
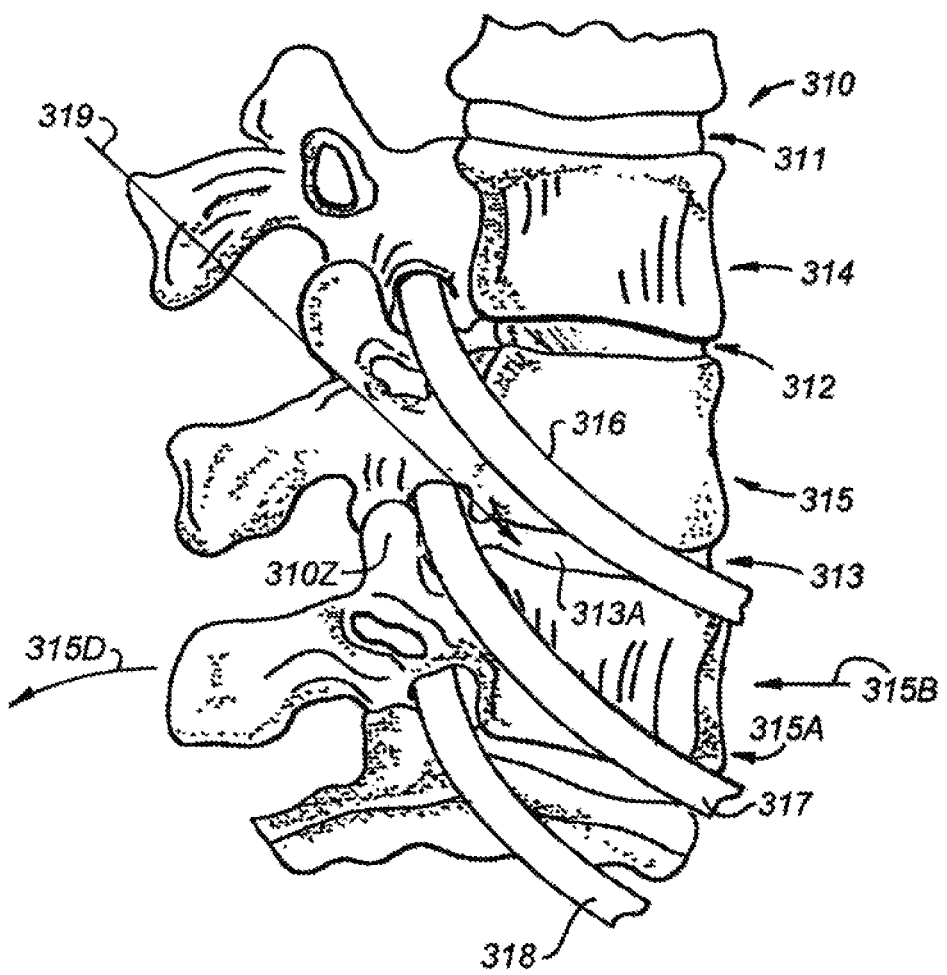
FIG. 41 is a side elevation view of a portion of a spine illustrating principal nerves that exit the spine.

FIG. 41 illustrates a portion 310 of a spinal column, including vertebrae 314, 315, 315A, and intervertebral discs 311, 312, 313. Principal nerves 316, 317, 318 emerge from the spinal column. Arrow 319 illustrates a preferred path for an instrument to travel in order to avoid nerves 316 and 317 and to impinge on the annulus 313A of disc 313. Path 319 may not, however, avoid impingement on a nerve 316, 317 in the event a nerve 316 happens to be in an unusual position, in the event disc 313 is squeezed into a bulging configuration that causes vertebrae 315 and 315A and nerves 316 and 317 to move closer together, etc.

Figure 42:
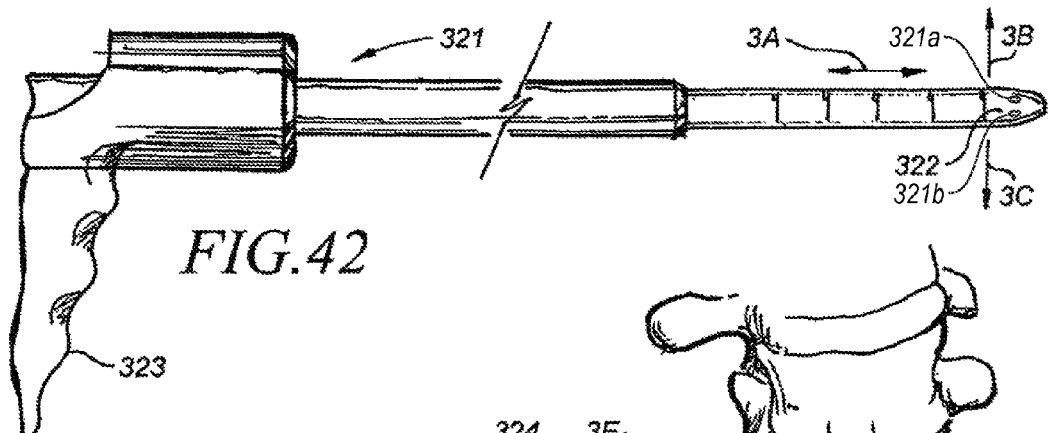
FIG. 42 is a side view illustrating an instrument constructed in accordance with the principles of the invention to minimize the risk of injury to soft tissue and hard tissue while producing an opening in the tissue.
Figure 43:
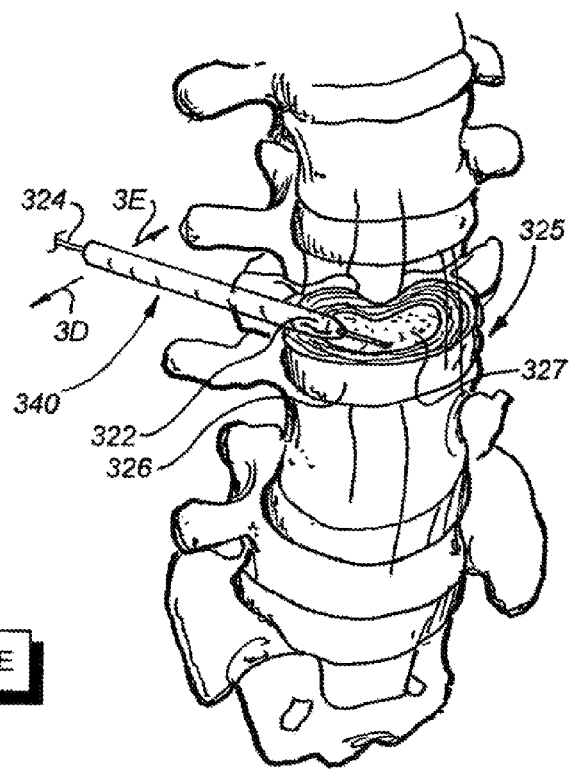
FIG. 43 is a front view of a portion of a spine illustrating the insertion along a wire of an instrument constructed in accordance with the invention.
Figure 44:
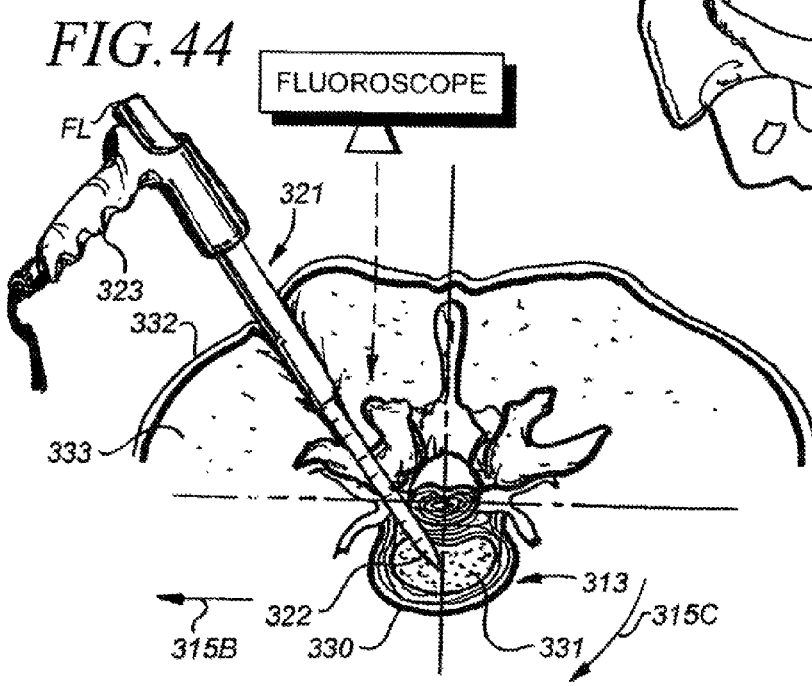
FIG. 44 is a top view illustrating the mode of operation of the instrument of FIG. 42.
Figure 45:
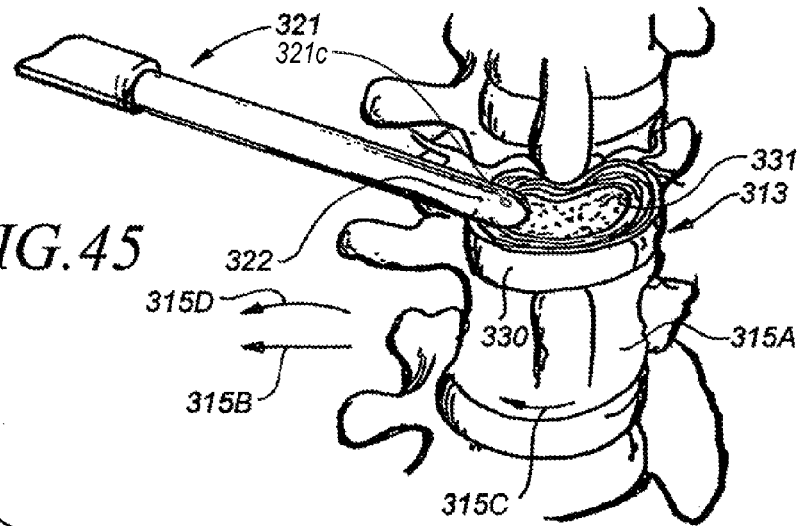
FIG. 45 is a front view further illustrating the mode of operation of the instrument of FIG. 42.

FIGS. 42, 44, 45 illustrate apparatus 321 constructed in accordance with the invention and including a distal end 322 and handle 323. The apparatus 321 can be configured as an elongate light guide as described herein such as in a conduit or cannula configuration with an internal lumen, or it may include an internal lumen to receive an elongated light guide in a guide wire 324 configuration as shown FIG. 43. As shown in FIG. 42, the apparatus 321 can include one or more optical elements 321a, 321b that include components of a light guide or light conduit, where optical element 321a includes optical components to transmit light and optical element 321b includes optical components to receive light so as to be capable of visualization during the medical procedure. In FIG. 42, the apparatus 340 can include an internal conduit with a distal opening 340 that allows the optical guide wire 324 to pass therethrough. FIG. 45 shows a single optical element 321c, which can be a bidirectional optical element that allows for both light transmission and reception so as to both shine light and receive light for viewing. The optical elements 321a,b,c can be located at any position on the distal end, and may be in the center, off-center, or on a curved surface.

During insertion in the body of a patient, apparatus 321 is manually or mechanically oscillated back and forth in the direction of arrows 3A, oscillated up and down in the direction of arrows 3B and 3C, oscillated laterally in the direction of arrows 3E and 3D (FIG. 43), oscillated in a manner that combines movement in two or more of said directions 3A to 3E, i.e., the distal end 322 can be moved along an elliptical or circular path, oscillated radially in and out in the manner of fingers 365, 366, 368, and 369 in FIG. 47D, and/or oscillated rotationally about the longitudinal axis of the apparatus in the manner indicated by arrows 3P in FIG. 47C. Since the purpose of moving end 322 is to produce an opening in and through tissue, the in-and-out oscillating movement indicated by arrows 3A (FIG. 42) is preferred and typically is required even if oscillating movement of end 322 in the direction of arrows 3B and 3C, in the direction of arrows 3E and 3D (FIG. 43), along a circular path, radially, or rotationally is also employed. The frequency and amplitude of oscillation can vary as desired, as can the force or pressure applied to handle 323 to press end 322 into tissue 332, 333 toward selected hard tissue 330 (FIG. 44). When passing end 322 through soft tissue, particularly soft tissue where there is no principal vasculature or nerves. A longer amplitude and smaller frequency is typically employed. When passing end 322 through hard tissue, a higher frequency and smaller amplitude typically is preferred. By way of example, and not limitation, the frequency of radial, linear, or rotational oscillation through soft tissue or hard tissue is greater than or equal to 0.1 cycles per minute. The amplitude of oscillation can vary as desired, but the amplitude of oscillation typically is greater in soft tissue than it is in hard tissue.

Apart from forward movement of a distal end 322, 322B to 322E (FIGS. 47, 48, 49, 47B, 47C) caused by oscillation, forward movement of a distal end 322 through soft tissue in a direction L (FIG. 47) can vary as desired, but typically is greater in soft tissue than it is in hard tissue.

The pressure required for a rounded distal end 322, 322B to 322E to tear or pierce or otherwise injure a principal nerve or vasculature varies depending on the shape of the tip of the end 322, 322B to 322E and on the size and makeup of the nerve or vasculature, but is readily determined by experimentation so that a surgeon can avoid applying pressure in the direction of travel L (FIG. 47), having a magnitude sufficient to injure a principal nerve or vasculature.

FIG. 44 illustrates the location of instrument 321 and distal end 322 after end 322 has been oscillated to pass through epithelium 332, through other soft tissue including fat, facia, muscle, minor vasculature and nerves, and principal vasculature and nerves, and through the annulus 330 of disc 313 into the nucleus 331. Since the epithelium 332 can be difficult to penetrate initially, a small incision can be made in epithelium 332 to facilitate the passage of end 322 therethrough.

The shape of end 322 is important. Various shapes of end 322 are illustrated in FIGS. 46 to 49, and in FIGS. 47B, 47C, 47D and 47E.

Figure 46:
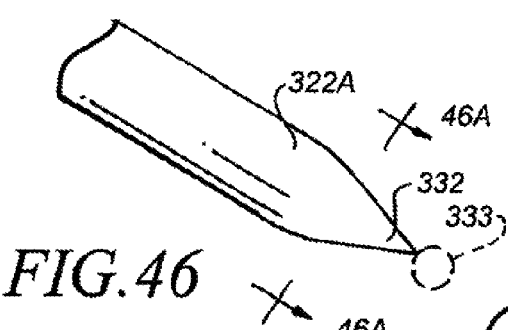
FIG. 46 is a top view illustrating an instrument construction that is to be avoided in the practice of the invention.

The distal end 322A in FIG. 46 has a sharp tip, or point, 332. Distal end 322A is not utilized in the practice of the invention because tip 332 can readily puncture or cut a principal nerve 33 or vasculature. Similarly, a distal end that includes a cutting edge is not preferred in the practice of the invention.

Figure 47:
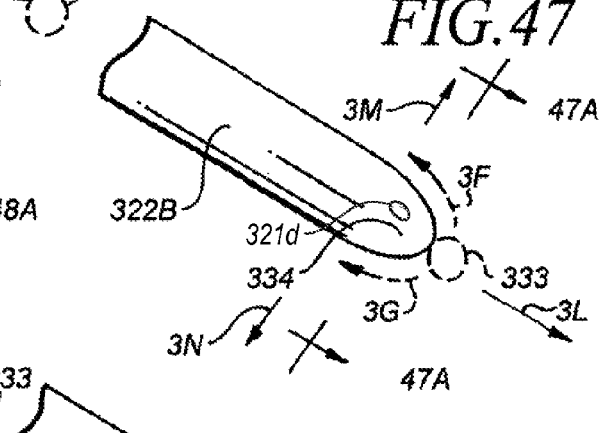
FIG. 47 is a top view illustrating an instrument construction that can be utilized in the practice of the invention.

The distal end 322B illustrated in FIG. 47 has a rounded tip 334 and is a preferred construct in the practice of the invention. Also, FIG. 47 shows a single optical component 321*d*, which can represent one or more optical components that are coupled to optical fibers for transmission and/or receiving light for viewing the medical procedure. If tip 334 contacts a principal nerve 333 while moving and/or oscillating in the direction of arrow 3L, it is likely that nerve 333 will slide off to one of the sides indicated by arrows 3F and 3G. If, on the other hand, tip 334 contacts nerve 333 "dead on" and nerve 333 impedes the progress of tip 334 in the direction of arrow 3L, the surgeon that is manually oscillating instrument 321 will feel the resistance (or a sensor on a machine that is oscillating instrument 321 will detect the resistance) and can laterally displace tip 334 in the direction of arrow N or M to facilitate the movement of nerve 333 in the direction of arrow 3G or F over end 334 so that tip 334 can continue moving in the direction of arrow 3L. The surgeon increases the certainty that tip 334 has contacted principal nerve 333 or principal vasculature by determining the location of tip 34 with a fluoroscope, with an endoscope, by direct visualization, by patient feedback, by an electrical recording of a nerve, by an alteration of blood pressure or pulse rate caused by contacting a blood vessel, or any other desired means.

Figure 48:
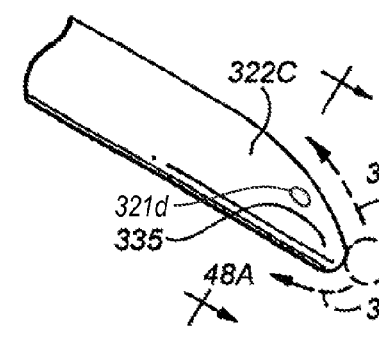
FIG. 48 is a top view illustrating another instrument construction that can be utilized in accordance with the invention.

The distal end 322C illustrated in FIG. 48 has a rounded tip 335 and is also a preferred construct in the practice of the invention. If tip 335 contacts a principal nerve 333 or vasculature while moving and/or oscillating in a direction toward nerve 33, it is likely that nerve 333 will slide off to one of the sides of end 322C indicated by arrows H and I. If, on the other hand, tip 335 contacts nerve 333 "dead on" and nerve 333 impedes the progress of tip 35, the surgeon that is manually oscillating instrument 321 (or a sensor on a machine that is oscillating instrument 321) will detect the resistance and can manipulate the handle 323 of instrument 321 (FIG. 44) to laterally displace tip 335 to facilitate the movement of nerve 333 in the direction of arrow 3H or 3I over end 335 so that tip 335 can continue moving past nerve 333. The surgeon increases the certainty that tip 335 has contacted principal nerve 333 or principal vasculature by determining the location in the patient's body of tip 335 with a fluoroscope, with an endoscope, by direct visualization, by patient feedback, by an electrical recording of a nerve, by an alteration of blood pressure or pulse rate caused by contacting a blood vessel, or any other desired means. Once the surgeon determines the location of tip 335, the surgeon's knowledge of the normal anatomy of an individual and/or knowledge of the patient's particular anatomy assists the surgeon in determining if a principal nerve or vasculature has been contacted by tip 335.

Figure 49:
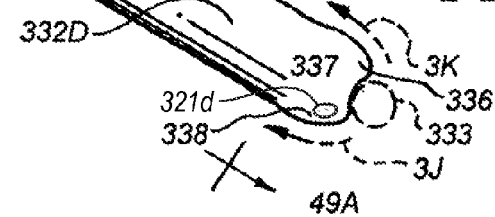
FIG. 49 is a top view illustrating a further instrument construction that can be utilized in the invention.

The distal end 322D illustrated in FIG. 49 has a rounded tips 336, 338 and detent 337 and is also a preferred construct in the practice of the invention. If tip 336 or 338 contacts a principal nerve 333 while moving and/or oscillating in a direction toward nerve 333, it is likely that nerve 333 will slide off to one of the sides of end 322D in a direction indicated by arrow 3K or 3J. If, on the other hand, detent 337 contacts nerve 333 "dead on" and nerve 333 seats in detent 337 and impedes the progress of end 322D, the surgeon that is manually oscillating instrument 321 will feel the resistance (or a sensor on a machine that is oscillating instrument 321 will detect the resistance) and can manipulate the handle 323 of instrument 321 (FIG. 44) to laterally displace distal end 322D to facilitate the movement of nerve 333 in the direction of arrow 3J or 3K over end 322D so that end 322D can continue moving past nerve 333. The surgeon increases the certainty that end 322D has contacted principal nerve 333 or principal vasculature by determining the location in the patient's body of tips 336, 338 with a fluoroscope, with an endoscope, by direct or indirect visualization such as with the elongate light guide described herein, by patient feedback, by an electrical recording of a nerve, by an alteration of blood pressure or pulse rate caused by contacting a blood vessel, or any other desired means. Once the surgeon determines the location of tips 336, 338, the surgeon's knowledge of the normal anatomy of a the body of a human being or animal and/or knowledge of the patient's particular anatomy, assists the surgeon in determining if a principal nerve or vasculature has been contacted by end 322D.

The spoon-shaped distal end 322E illustrated in FIG. 47B has a curved paddle surface 356 and a rounded edge 357 and is also a preferred construct in the practice of the invention. If rounded edge 357 contacts a principal nerve 333 while moving and/or oscillating in a direction toward nerve 333, it is likely that nerve 333 will slide off to one of the sides of end 322E. It is preferred that edge 357 contact nerve 333 (or principal vasculature) in the manner illustrated in FIG. 47B with surface 356 generally parallel to the longitudinal axis 333A of the nerve. If, on the other hand, edge 357 contacts nerve 333 in an orientation in which the spoon surface 356 of FIG. 47B is rotated ninety degrees such that surface 536 is generally normal to axis 333A, there is a greater risk of injury to nerve 333. If edge 357 contacts nerve 333 "dead on" such that nerve 333 impedes the progress of end 322E in the direction of arrow 3X, the surgeon that is manually oscillating instrument 321 (FIG. 44) will feel the resistance (or a sensor on a machine that is oscillating instrument 321 will detect the resistance) and can manipulate the handle 323 of instrument 321 (FIG. 44) to laterally displace distal end 322E (FIG. 47B) to facilitate the movement of nerve 333 laterally from edge 357 so that end 322E can continue moving past nerve 333. The surgeon increases his certainty that edge 357 has contacted principal nerve 333 or principal vasculature by determining the location in the patient's body of edge 357 with a fluoroscope, with an endoscope, by direct visualization, by patient feedback, by an electrical recording of a nerve, by an alteration of blood pressure or pulse rate caused by contacting a blood vessel, or any other desired means. Once the surgeon determines the location of edge 357, the surgeon's knowledge of the normal anatomy of a the body of a human being or animal and/or knowledge of the patient's particular anatomy assists the surgeon in determining if a principal nerve or vasculature has been contacted by end 22E.

Figure 47E:
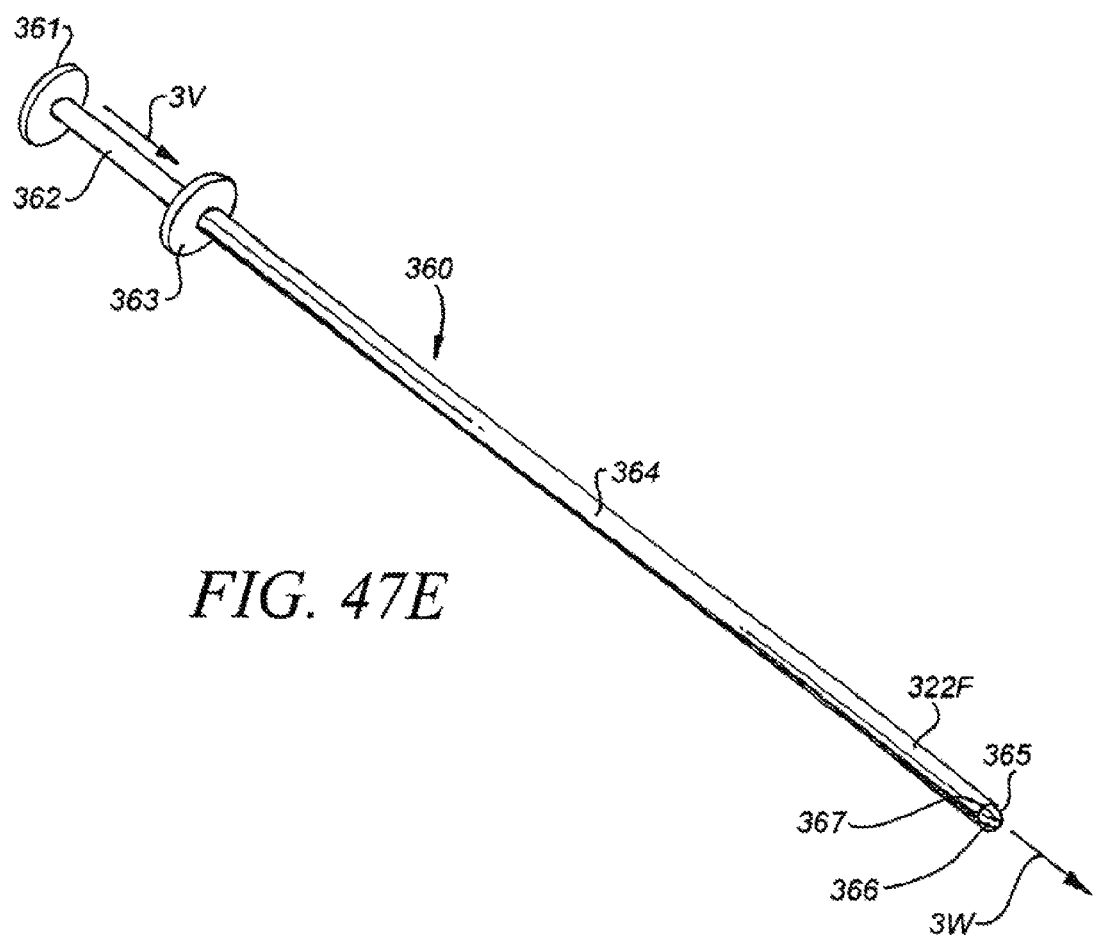
FIG. 47E is a perspective view illustrating the mode of operation of the instrument of FIG. 47D.

The distal end 322F illustrated in FIG. 47D includes a plurality of curved fingers 365, 366, 368, and 369 depicted in their deployed, open position. The fingers are shown in FIG. 47E in their normal stowed position adjacent and in opening 367 formed in distal end 322F of instrument 360. The opening 367 can host an elongate light guide configured as a guide wire as described herein. In the stowed position, a substantial portion of fingers 365, 366, 368, and 369 is drawn through opening 367 to a position inside hollow cylindrical body 364. In the stowed position, however, the curved distal ends of fingers 365, 366, 368, and 369 extend outwardly from opening 367 in the manner illustrated in FIG. 47D and generally collectively form an arcuate surface similar to the surface on the end of an egg. Moving end 361 in the direction of arrow 3V (FIG. 47E) causes neck 362 to slide into hollow cylindrical body 364 to displace fingers 365, 366, 368, and 369 outwardly in the direction of arrow 3W. When fingers 365, 366, 368, and 369 are outwardly displaced in the direction of arrow 3W, they open radially in the directions indicated by arrows 3S, 3Q, 3R, and 3T, respectively, to the expanded deployed position illustrated in FIG. 47D When end 361 is released, it moves in a direction opposite that of arrow 3V and returns to the position illustrated in FIG. 47E, and, similarly, fingers 365, 366, 368, and 369 move back to the stowed position illustrated in FIG. 47E. Consequently, repeatedly manually (or mechanically) pressing end 361 in the direction of arrow 3V and then releasing end 361 causes fingers 365, 366, 368, and 369 to oscillate radially in and out in the directions indicated by arrows 3Q to 3T, and causes fingers 365, 366, 368, and 369 to oscillate back and forth in the direction of arrow 3W and in a direction opposite that of arrow 3W. Rotating distal end 322E in FIG. 47C back and forth in the directions indicated by arrows 3P causes end 322E to oscillate back and forth. Continuously rotating end 322E. Also, practically speaking, causes end 322E to oscillate because of the flat spoon shape of end 322E.

FIG. 50 further illustrates the insertion of instrument 340 along wire 324, such as an elongate optical light guide configured as a guide wire, through epithelium 332 and other soft tissue 333 toward the annulus 326 of disc 325. FIG. 51 also illustrates instrument 340 slidably mounted on the wire 324. The configuration of the wire 324 as an elongate light guide allows for visualization and observation of the medical procedure during implantation of the implant 380. FIG. 52 illustrates an instrument 350 that is utilized to insert an implant 352 in the nucleus 327 of an intervertebral disc 326 (FIG. 43) or to insert the implant 352 in another location in a body. The implant 350 can be modified with an internal conduit that can receive elongate light guide (e.g., configured as a guide wire) thereghrough to assist with locating the implant to the proper location as well as implantation and inspection thereof. The rounded tip of the implant 352 functions in a manner equivalent to the rounded tips of distal ends 322B (FIG. 47), 322C (FIG. 48), 322D (FIG. 49), 322E (FIGS. 47B and 47C), and 322F (FIG. 47D) to facilitate the passage through tissue of the tip of implant 352. An implant 380 (FIG. 51) can have a rounded tip like implant 352, can function in a manner equivalent to the rounded tips of distal ends 322B, 322C, etc., and can also have an opening formed therethrough that permits implant 380 to slide or otherwise move along a wire 324 or other elongate member such as the elongate light guide in a guide wire configuration. The shape and dimension of the opening formed through implant 380 can vary as desired, as can the shape and dimension of the elongate member. If an opening of sufficient size exists in tissue and if wire 324 is appropriately oriented, implant 380 may slide along wire 324 of its own accord under the force of gravity to a desired location in a patient's body. Or, a surgeon's hand or hands or an auxiliary instrument 350 (FIG. 52) can be utilized to contact and move implant 380 along wire 324 (FIG. 51) to a desired location. As utilized herein, a distal end 322B, 322C, 322D, etc. can comprise an instrument that oscillates or otherwise moves through tissue, as can an implant 380. The combination of an auxiliary instrument 350 (FIG. 52) with a distal end 322B, 322C, 322D, etc. or implant 380 can also comprise an instrument as long as the combination functions in accordance with at least one of the principles of the invention and separates tissue, forms an opening in tissue, passes through tissue, and/or delivers an implant to a selected location in a patient's body. Grasping handle 351 and depressing member 353 releases implant 352 from instrument 350. While not illustrated, the features of the elongate light guide can be also be utilized with the instruments 340 or 350 to facilitate visualization during the medical procedure and implantation of the implant 380.

Forming an opening in tissue with a distal end 322 (FIG. 44) shaped and dimensioned in accordance with the invention requires the end 322 to produce radial forces that work to form an opening in tissue. The tapered configuration of the tips of distal ends 322, 322B to 322F facilitate the generation of such outwardly acting radial forces. The outward movement of fingers 365, 366, 368, 369 when moving from their stowed to their deployed position generates such radial forces. Rotating or oscillating distal end 322E (FIG. 47C) in the manner indicated by arrows 3P also generates such "opening widening" radial forces. An opening is formed either by widening an existing opening or by forming an opening in tissue at a location at which no opening previously existed. The elongate light guide as described can be used for visualizing the medical procedure that uses an existing opening or for forming the opening.

Figures 53, 54:
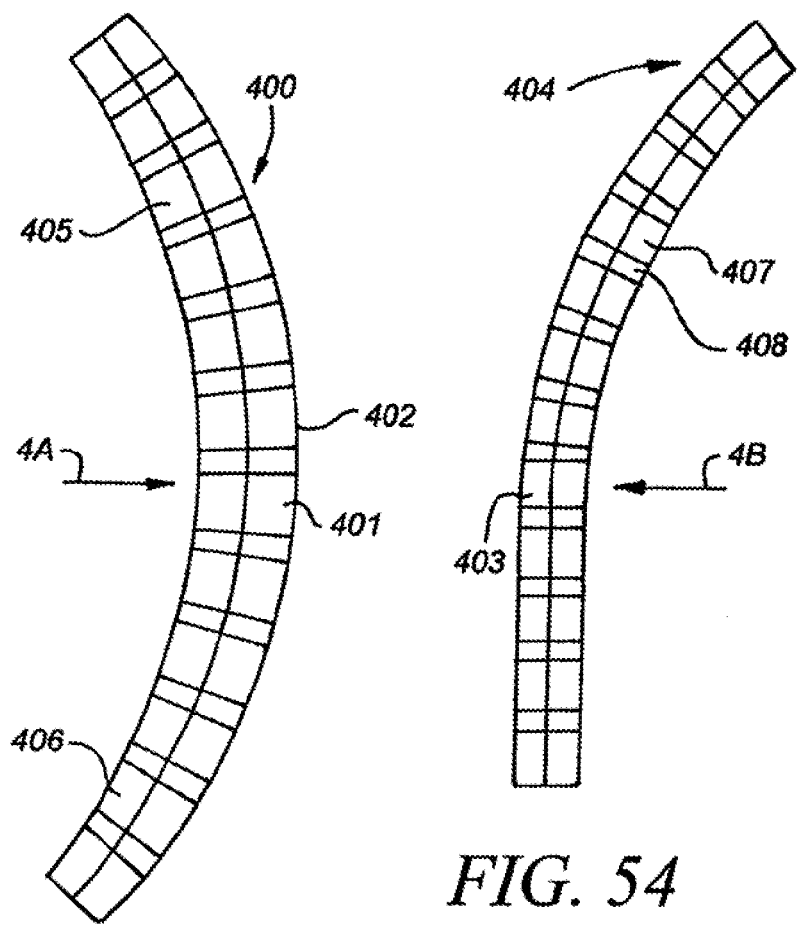
FIG. 53 is a side view illustrating the apex of a misaligned spine.
FIG. 54 is a side view illustrating the apex of another misaligned spine.

In one method utilized in the practice of the invention, an implant is utilized to alter the alignment of one or more vertebra, typically to adjust for misalignment of the spine. The first step in this method is to determine how a patient's spine is misaligned. This is done by taking one or more X-ray pictures of the spine to determine if the spine or a portion of the spine is abnormally tilted or bent toward the front of the patient, is abnormally tilted or bent toward the back of the patient, is abnormally tilted or bent toward one side of the patient, is rotated from its normal position about the vertical axis of the spine, and/or is laterally (horizontally) displaced from its normal position. When the spine is misaligned, the apex constitutes the vertebra(s) or disc that is rotated and/or laterally displaced, but that is least tilted from its normal position. In FIG. 53, vertebrae 401, 402 of spine 400 comprise the apex because both vertebrae generally are not tilted even though they have been laterally displaced in the direction of arrow 4A. In FIG. 54, vertebra 403 of spine 404 comprises the apex because vertebra generally is not tilted even though it has been laterally displaced in the direction of arrow 4B.

Lateral displacement of a disc 313 or vertebra 315A is indicated by arrow 315B in FIGS. 41, 44 and 45. Rotations of a disc 313 or vertebra about the longitudinal axis of a spine is indicated by arrow 315C in FIG. 44. Tilting of a disc 313 or vertebra 315A in one particular direction is indicated in FIGS. 41 and 45 by arrow 315D. A disc or vertebra can, of course, tilt in a variety of directions away from its normal desired orientation in the spine of a patient. In FIG. 53, vertebrae 405 and 406 are tilted away from their normal desired orientation, as is vertebra 407 and disc 408 in FIG. 54.

The vertebra at the apex or immediately adjacent an intervertebral disc comprising the apex is identified. While an implant can be inserted at any desired location along a patient's spine, in the embodiment of the invention currently under discussion, an implant is inserted in the spine in a location that is adjacent the end of the vertebra that is at or closest to the apex. It is preferred, although not require, that the implant be inserted within an intervertebral disc or portion of an intervertebral disc that is adjacent the end of the vertebra that is at or closest to the apex.

The shape of the implant and the particular location on the end of the vertebra is determined after the particular misalignment of the spine is determined. For example, if the vertebrae between which the implant is to be positioned are tilted with respect to one another such that the disc is compressed in one area and is taller in another area (i.e., the disc is compressed into a wedge shape), it often is desirable to position the implant between the adjacent pair of vertebra near the point of compression of the vertebrae such that the vertebrae will tend to rotate about the implant so that the distance between the vertebrae increases at the point of closest approach of the vertebrae and such that the distance between the vertebrae decreases at the point at which the vertebrae are spaced furthest apart. If the desired rotation of the vertebrae about the implant is similar to the movement of a door about its hinges, then the implant may have a substantially cylindrical shape. If, on the other hand, the adjacent vertebrae are not tilted with respect to one another, but are rotated (about the longitudinal axis of the spine), then the implant may have a tapered or other shape that will produce rotation of one vertebrae with respect to another. It is possible that an implant can be shaped and dimensioned to produce multiple movements of a pair of adjacent vertebrae; for example, to produce simultaneously both rotation of one or more vertebra (i.e., rotation about the longitudinal axis of the spine) and hinge-like pivoting (i.e., pivoting about a horizontally oriented axis that is normal to the longitudinal axis of the spine). In some cases, it may be desirable to utilize first an implant that produces only lateral displacement (or rotation or hinge-like pivoting) and, after the necessary movement of a vertebra(s) has occurred, to remove the implant and insert another implant that will produce hinge-like pivoting (or lateral displacement or rotation). This permits spines that are misaligned in two or more ways to be correct one step at a time.

One preferred method of inserting an implant is, as earlier noted, to slide the implant along a guide wire, which can be an elongate light guide, to a desired location in an intervertebral disc and between a selected pair of vertebrae. The guide wire can be inserted utilizing a needle or any other desired apparatus or procedure such that the distal end of the wire is at the desired location in a patient's body. Typically, the distal end of the guide wire will be located inside an intervertebral disc at the location at which it is desired to deliver an implant.

Figure 55:
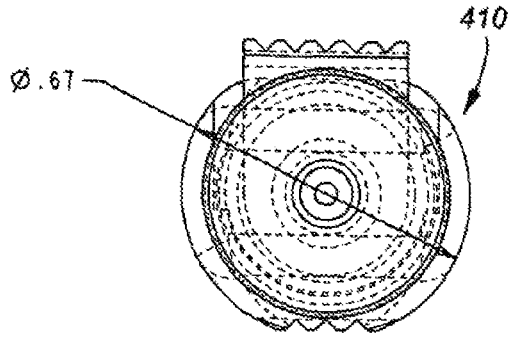
FIG. 55 is an end view illustrating an intervertebral implant.
Figure 56:
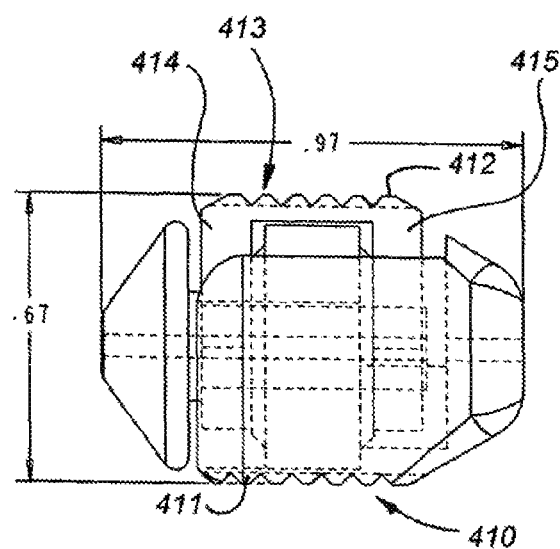
FIG. 56 is a side view illustrating the implant of FIG. 55.
Figure 73:
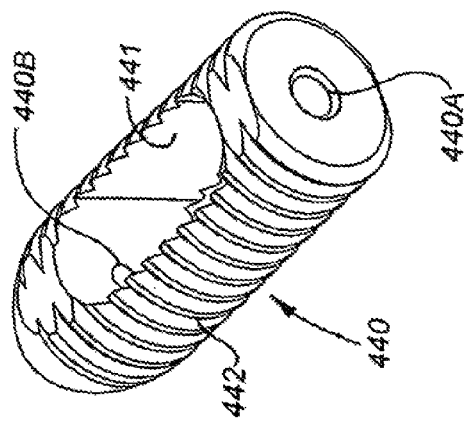
FIG. 73 is a perspective view illustrating an intervertebral implant having an aperture formed therethrough to receive slidably a guide wire.
Figure 74:
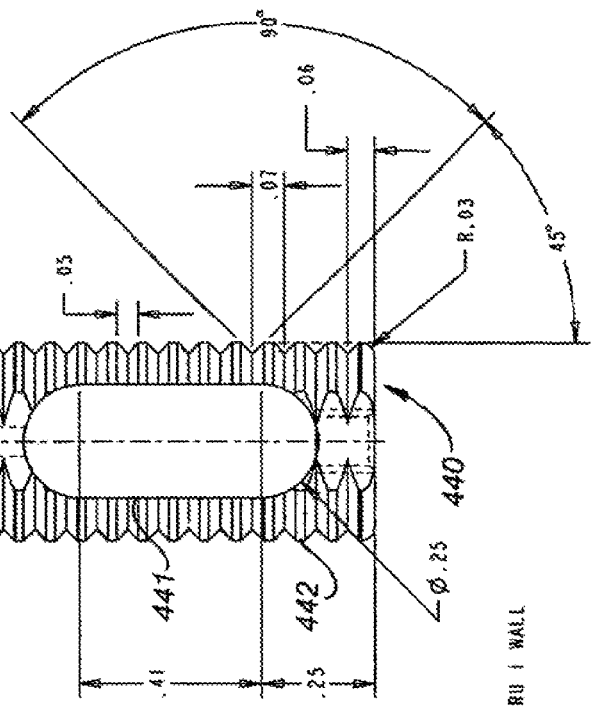
FIG. 74 is a top view illustrating the implant of FIG. 73.
Figure 75:
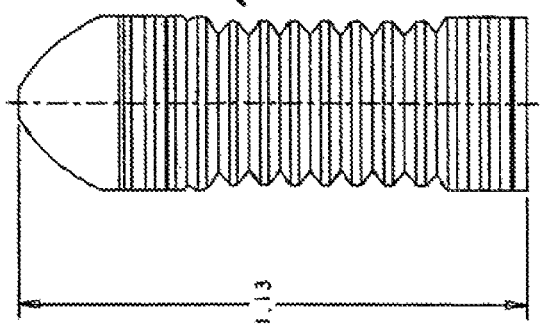
FIG. 75 is a side view illustrating the implant of FIG. 73.
Figure 76:
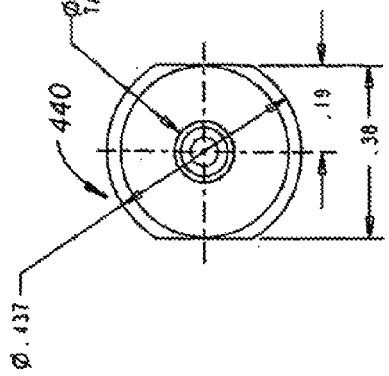
FIG. 76 is an end view illustrating the implant of FIG. 73.

FIGS. 55 and 56 illustrate an intervertebral implant 410 constructed in accordance with the invention and including vertebrae engaging teeth 411 and 412. U-shaped member 413 includes legs 414 and 415. As will be appreciated by those of skill in the art, the intervertebral implants illustrated herein may, if desired, be utilized at other locations in a patient's body.

FIGS. 57 to 61 illustrate an intervertebral implant 415 including upper portion 416 and lower portion 417. Pin 422 of portion 416 pivots in portion 417 and permits portion 416 to rock back and forth in the manner indicated by arrows 4C and 4D in FIG. 58. Portion 416 includes tissue engaging teeth 418. Portion 417 includes tissue engaging teeth 419.

FIGS. 62 to 68 illustrate an intervertebral implant 425 including upper portion 426 and lower portion 427. Portion 426 includes spaced—apart tissue engaging circular ridges 428. Portion 427 includes tissue engaging teeth 429.

FIGS. 69 to 72 illustrate a unitary implant 435 including inset channels 436, 437 formed to increase in width beneath outer surface 438 such that channels 436, 437 interlock bone or other material that is placed, packed or grows into channels 436, 437 and solidifies. The intervertebral implants illustrated herein can be formed from any desired material, but presently preferably comprise stainless steel, titanium alloys, polymers, composites, ceramics, bone, or another material.

FIGS. 73 to 76 illustrate a unitary cylindrically shaped implant 440 with an aperture 441 formed therethrough and with tissue engaging circular ridges 442. The aperture 441, as well as any aperture, perforation, or other conduit through an implant, can be configured to slide along an elongate light guide configured as a guide wire. When desired, implant 440 can be utilized as a fusion device by packing aperture 441 with bone or other material that will fixedly engage and fix in place an opposing pair of vertebrae. The cylindrical shape of implant 440 facilitates implant 440 being utilized as a hinge between a pair of opposing vertebrae to cause the vertebrae to pivot about implant 440 to an alignment in which the spacing between the vertebrae is more uniform at all points. Apertures 440A and 440B permit a guide wire to be slidably inserted longitudinally through implant 440.

FIGS. 77 to 80 illustrate a unitary implant 450 with an aperture 451 formed therethrough and with tissue engaging circular ridges 452. When desired, implant 450 can be utilized as a fusion device by packing aperture 451 with bone or other material that will fixedly engage and fix in place an opposing pair of vertebrae. Apertures 450A and 450B permit a guide wire, such as the elongate light guide in the guide wire configuration, to be slidably inserted longitudinally through implant 440. Apertures 460A and 460B can be internally threaded to permit a tool to be removably turned into the apertures to facilitate insertion of implant 450.

Implant 440 (FIGS. 72 to 76) and implant 450 (FIGS. 77 to 80) can have tissue engaging ridges along their entire length.

FIGS. 81 to 85 illustrate a unitary implant 460 with tissue engaging teeth 461 and 462.

FIGS. 86 and 87 illustrate a unitary implant 470 similar to implant 460, but with a reduced height.

FIGS. 88 and 89 illustrate a unitary implant 471 similar to implant 460, but with a further reduced height.

Figure 90:
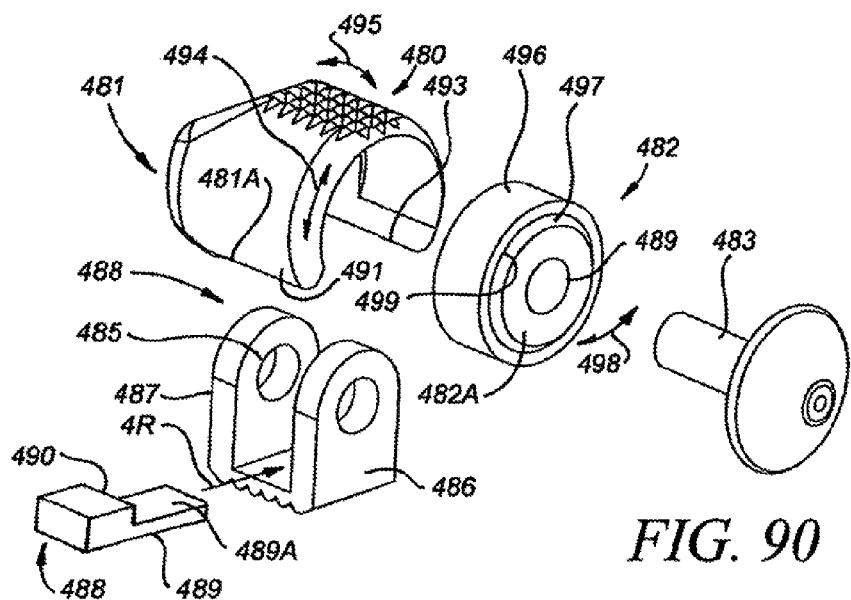
FIG. 90 is an exploded perspective view illustrating an intervertebral implant.

FIG. 90 is an exploded view of an implant 480 similar to implant 410 (FIGS. 55, 56) including members 481 and 482 that pivot about cylindrical pin 483 when member 482 is inserted intermediate upstanding arms 486 and 487, when pin 483 is inserted through apertures 484, 489, and 485, and, when member 481 is fixedly attached to member 482. Member 482A is a bearing with a spherically shaped convex outer surface or edge 497. Hollow cylindrical sleeve 496 includes an inner concave surface that glides over surface 497 such that sleeve 496 can tilt forwardly, rearwardly, and, as indicated by arrows 498, laterally on bearing 482A. Sleeve 496 can also rotate over surface 497 and around pin 483. Member 481 is fixedly mounted to sleeve 496 and moves about bearing 482A simultaneously with sleeve 496. When implant 480 is being inserted between a pair of vertebrae with a tool 488, the end 489 of tool 488 is preferably shaped to slide intermediate arms 486 and 487 in the direction of arrow 4R such that lower edge 481A bears against upper surface 489A and prevents member 481, and therefore sleeve 496 from moving. Edge 490 bearing against the lower outer surface 491 contributes to stabilizing implant 480. After implant 480 is inserted between a pair of vertebra, tool 488 is removed in a direction opposite that of arrow 4R. Tool 488 can take on any shape and dimension as long as tool 488 prevents, at least in part, implant 480 (or any desired component(s) of an implant) from moving while the implant is being inserted at a desired location in a patient's body.

Figure 91:
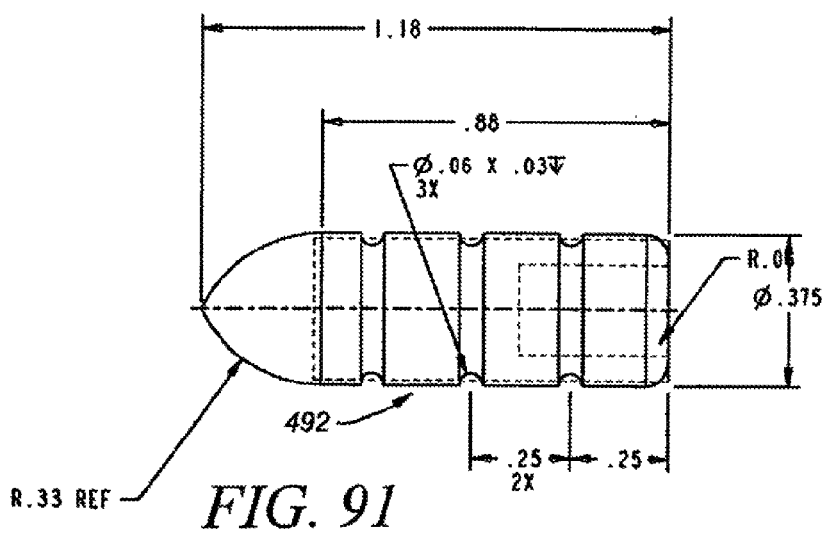
FIG. 91 is a side view illustrating a unitary intervertebral implant.
Figure 92:
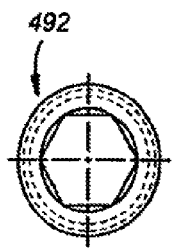
FIG. 92 is an end view illustrating the implant of FIG. 91.

FIGS. 91 and 92 illustrate a unitary implant 492.

Figure 93:
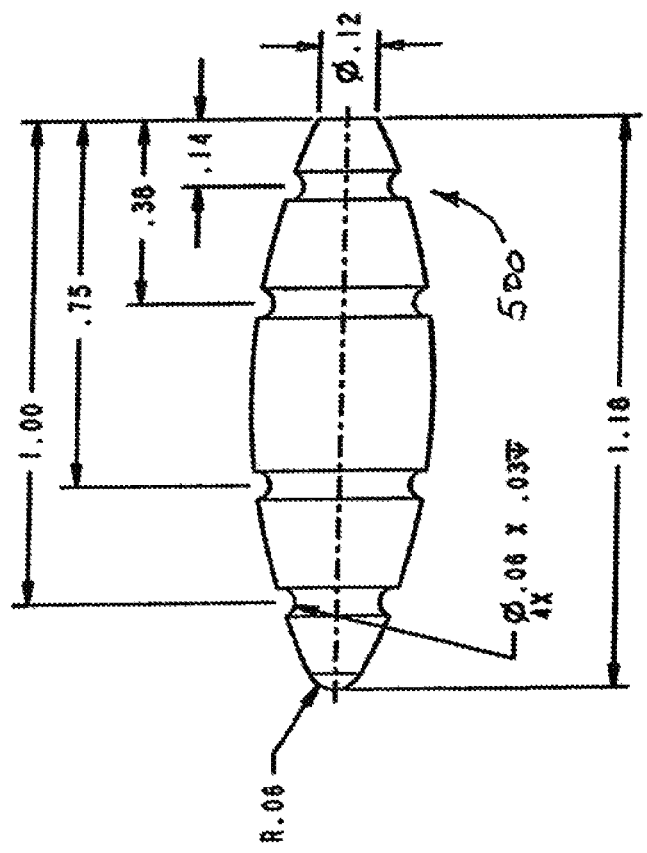
FIG. 93 is a side view illustrating a unitary intervertebral implant.
Figure 94:
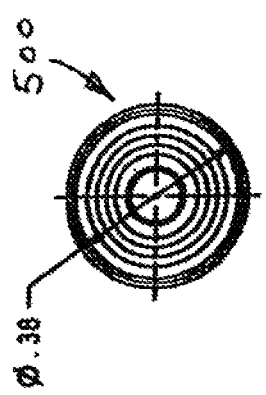
FIG. 94 is a left hand end view illustrating the implant of FIG. 93.
Figure 95:
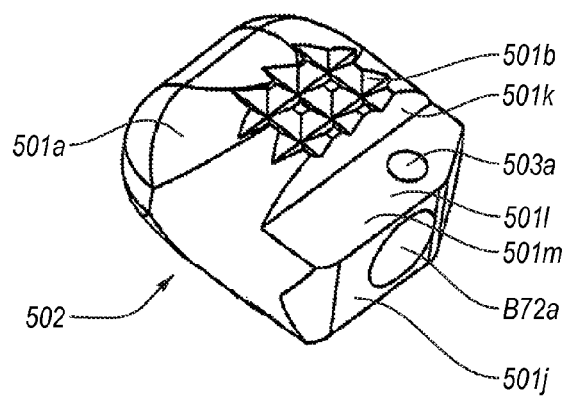
FIG. 95 is a perspective view illustrating a portion of an articulating intervertebral implant.
Figure 96:
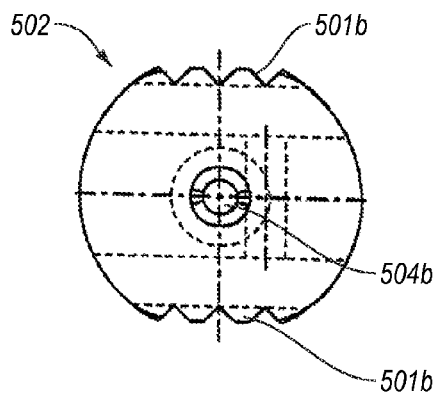
FIG. 96 is a back view illustrating the implant portion of FIG. 95.
Figure 97:
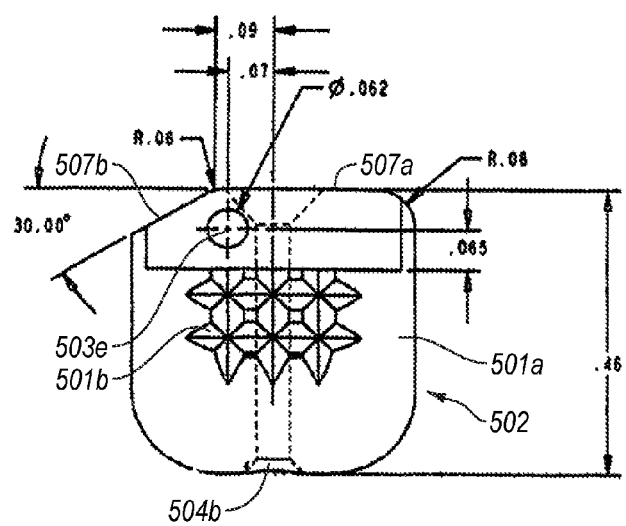
FIG. 97 is a top view illustrating the implant portion of FIG. 95.
Figure 98:
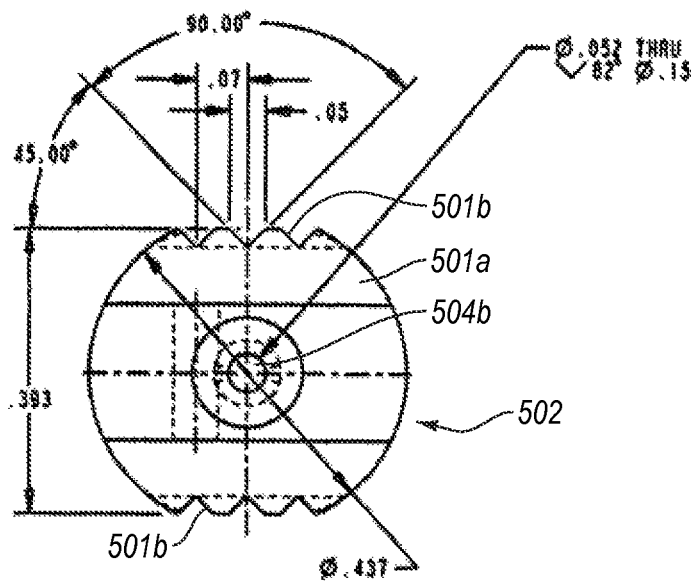
FIG. 98 is an end view illustrating the implant portion of FIG. 95.
Figure 99:
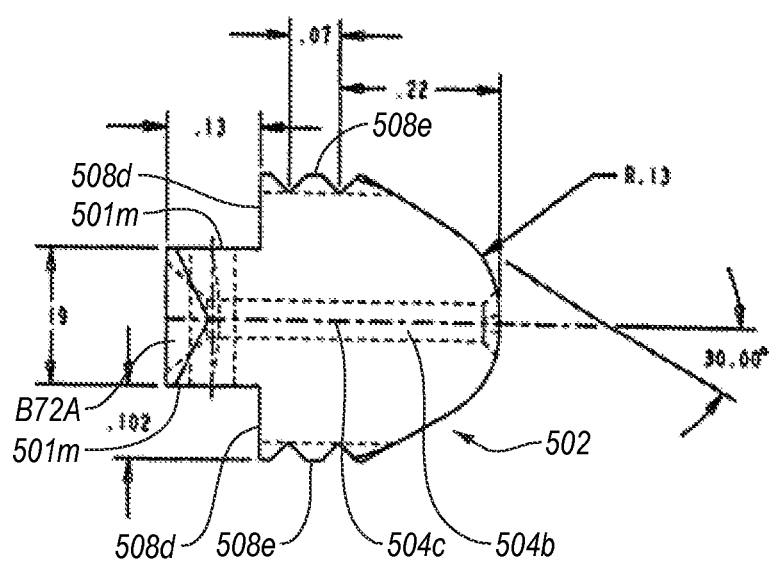
FIG. 99 is a side view illustrating the implant portion of FIG. 95.

FIGS. 93 and 94 illustrate a unitary implant 500.

FIGS. 95 to 99 illustrate a portion 501 of an articulated implant.

FIGS. 100 to 102 illustrate a unitary cylindrical, ridged, implant 510 which can have tissue engaging ridges along the entire length of implant 510 and can be rotated or screwed into position as can implants 440 and 450 (FIGS. 73 to 80).

Figure 103:
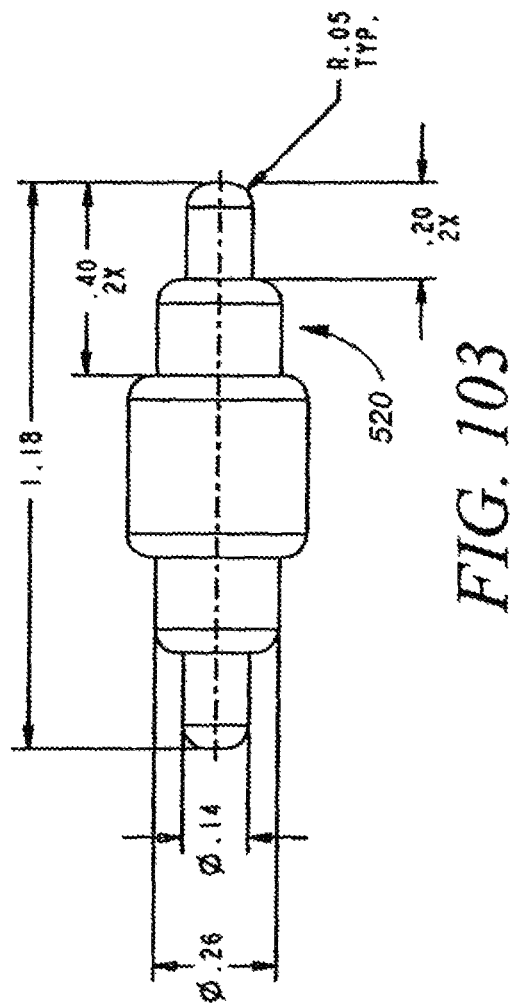
FIG. 103 is a side view illustrating an intervertebral implant.
Figure 104:
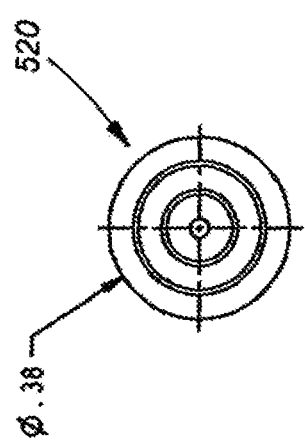
FIG. 104 is an end view illustrating the implant of FIG. 103.
Figure 105:
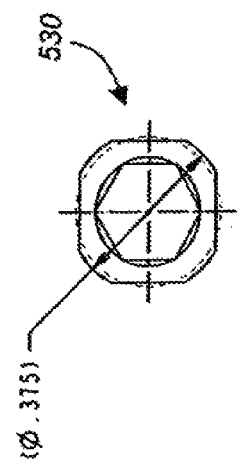
FIG. 105 is a perspective view illustrating an intervertebral implant.
Figure 108:
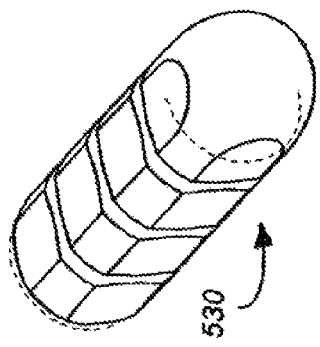
Figure 106:
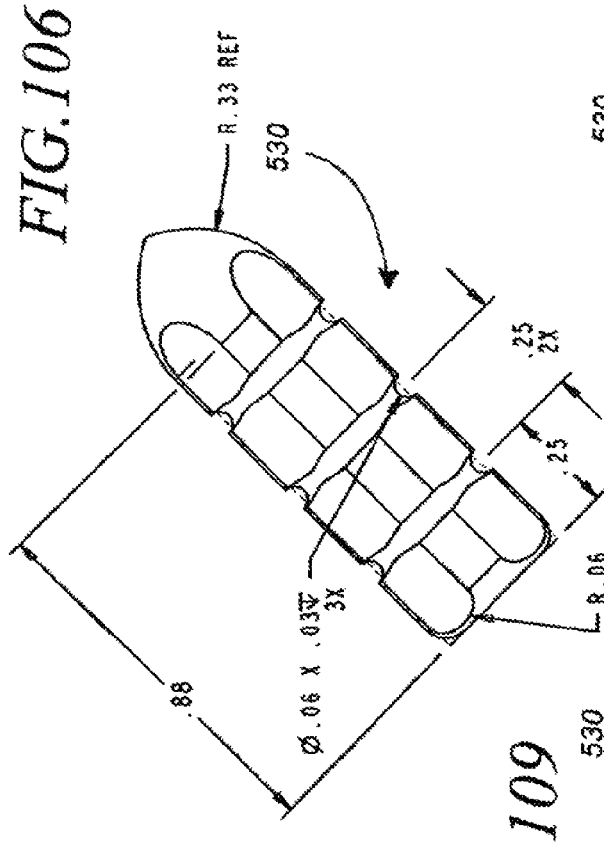
FIG. 106 is a side view illustrating the implant of FIG. 105.
Figure 107:
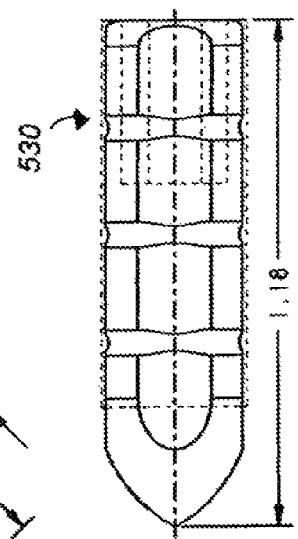
FIG. 107 is a top view illustrating the implant of FIG. 105.
Figure 109:
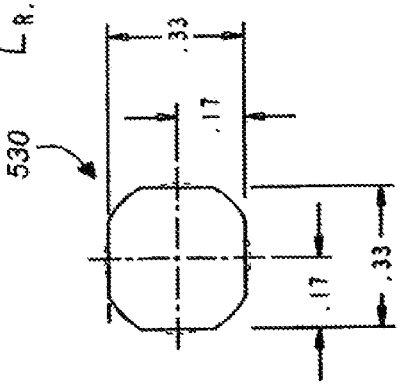

FIGS. 103 and 104 illustrate a unitary stepped implant 520.

FIGS. 105 to 109 illustrate a unitary implant 530.

Figure 111:
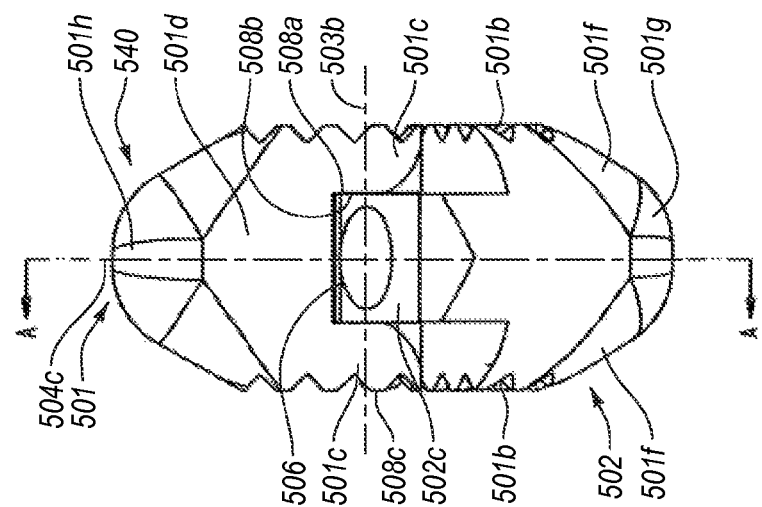
Figure 110:
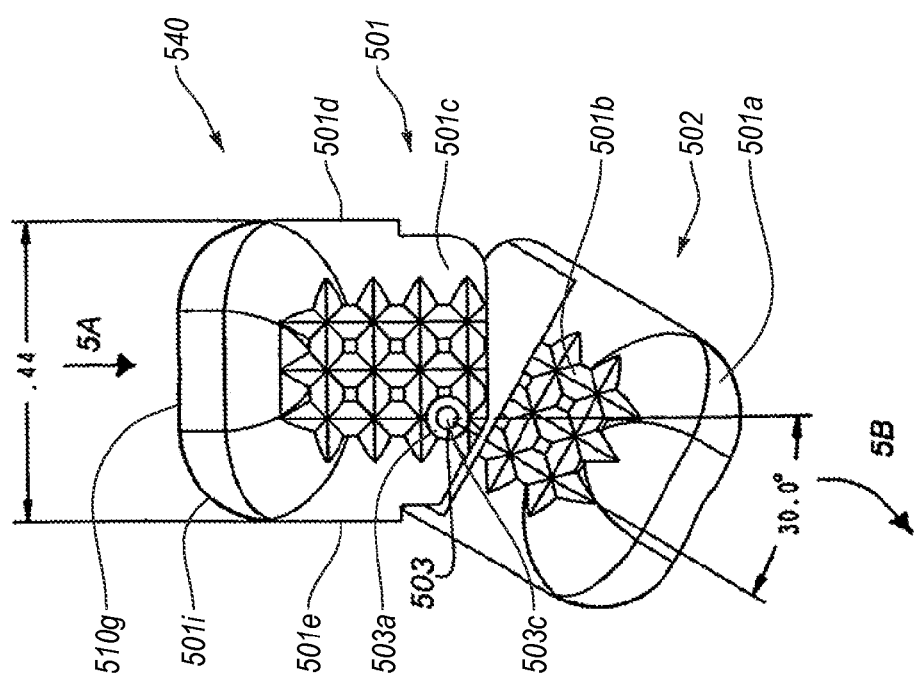
Figure 112:
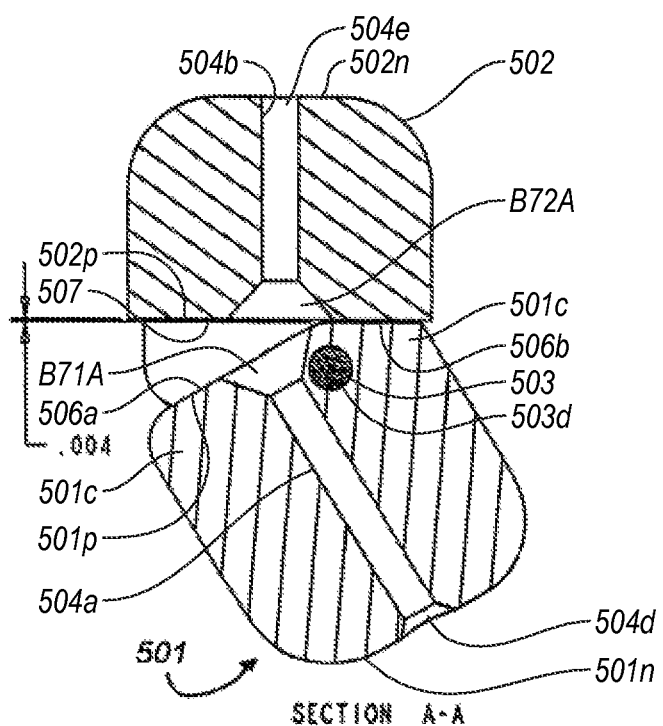
Figure 113:
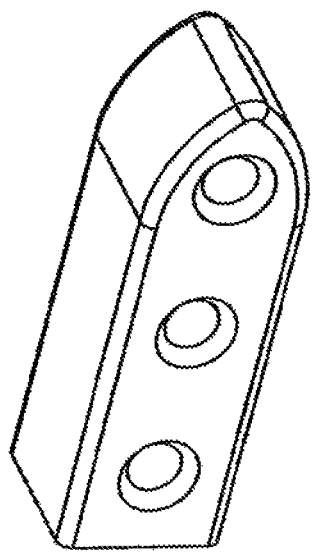
Figure 116:
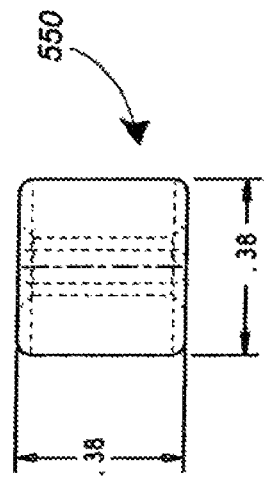
Figure 114:
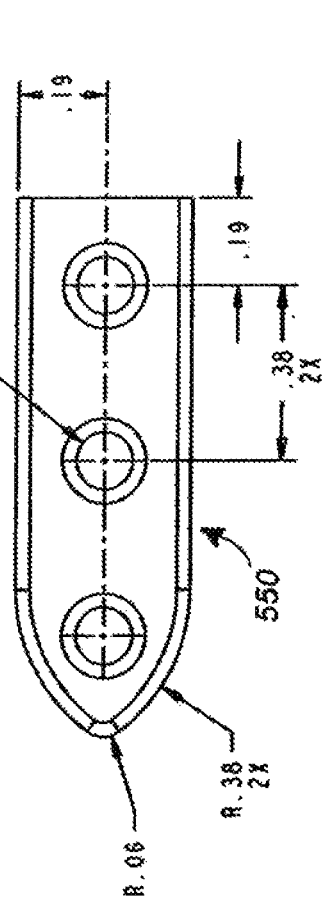
Figure 115:
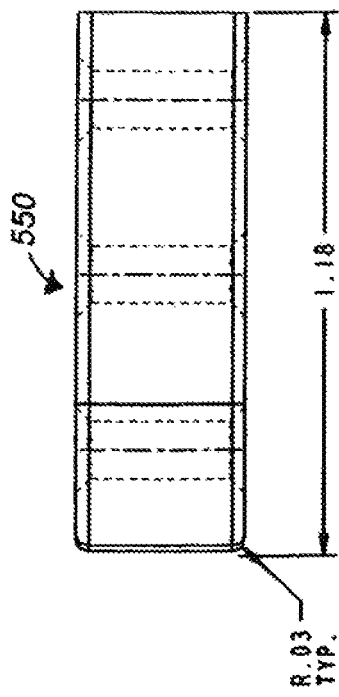

FIGS. 110 to 112 illustrate an articulated implant 540 including portions 501 (FIGS. 95-99) and 502 hinged together by pin 503. Pin 503 is offset, or positioned, such when implant 540 is in the aligned orientation illustrated in FIG. 111 and is pushed in the direction indicated by arrow 5A in FIG. 110, portion 501 pivots about pin 503 in the direction indicated by arrow 5B. This enables implant 540 to follow a curved path of travel. When implant 540 is inserted to a desired location intermediate a pair of vertebrae, it presently preferably travels along a guide wire, such as an elongate light guide configured as a guide wire, to said desired location. Cylindrical apertures 503 and 504 formed through portions 502 and 501, respectively, slidably receive and slide along the guide wire. Apertures 503 and 504 also function to maintain implant 540 in the general alignment illustrated in FIG. 111 while implant 540 slides along the guide wire. Once, however, implant 540 exits the distal end of the guide wire, utilizing any method or instrument to push implant 540 in the direction indicated by arrow 5A causes portion 501 to pivot in the direction of arrow 5B such that implant 540 can move a curved path of travel. This often is desirable when it is desired to move implant 540 along a curved path of travel intermediate a pair of adjacent and opposing vertebrae.

As shown in FIGS. 110-112, an intervertebral spacer implant assembly 540 can include a plurality of links 501, 502. Each link 501, 502 of said plurality of links can include a longitudinal hole 504*a*, 504*b* bored through a longitudinal axis 504*c* of said link 501, 502. The longitudinal hole 504*a*, 504*b* of each link 501, 502 of said plurality of links can align to form a continuously-alignable longitudinal hole 504*a*, 504*b* bored through said plurality of links 501, 502. The first link 501 of said plurality of links 501, 502 is pivotally engaged to a second link 502 of said plurality of links 501, 502. An elongated member (e.g., guide wire) adapted to retain said plurality of links 501, 502. The elongated member (e.g., guide wire) is configured to mate with each said longitudinal hole 504*a*, 504*b* of each link 501, 502, of said plurality of links 501, 502. In one aspect, the elongated member is a guide wire.

In one embodiment, the plurality of links 501, 502 can include a body 501*a* having one or more serrated sides 501*b*. The elongate member (e.g., guide wire) can be positioned transverse to the one or more serrated sides 501*b*.

In one embodiment, at least one link 501 includes a body 501*a* at least one hole 503*a* transverse to said longitudinal hole 504*a*, 504*b*.

In one embodiment, the elongated member (e.g., guide wire) can be adapted to allow said plurality of links 501, 502 to rotatably articulate with respect to one another. As such, the links 501, 502 can be rotatably articulated with respect to one another by a hinge 503. Also, the links 501, 502 are rotatably articulated with respect to one another by the longitudinal holes 504*a*, 504*b* having conical openings B71A, B72A that prevent the elongate member (e.g., guide wire) from binding by forming a smooth arcuate path between longitudinal holes 504*a*, 504*b*. Additionally, the longitudinal holes 504*a*, 504*b* and elongate member (e.g., guide wire) are shaped and dimensioned so that the implant 540 slides down the elongate member under force of gravity. Moreover, the longitudinal holes 504*a*, 504*b* and elongated member (e.g., guide wire) are configured so that the implant 540 can move along the elongated member.

FIGS. 110-112 also show an intervertebral spacer implant assembly 540 including a plurality of links 501, 502. Each link 501, 502 of said plurality of links can include a longitudinal hole 504*a*, 504*b* bored through a longitudinal axis 504*c* of said link 501, 502. The longitudinal hole 504*a*, 504*b* of each link 501, 502 of said plurality of links can be configured to align to form a continuously-alignable longitudinal hole 504*a*, 504*b* bored through said plurality of links 501, 502. The first link 501 of said plurality of links 501, 502 is pivotally engaged to a second link 502 of said plurality of links 501, 502. An elongated connector mechanism (e.g., guide wire) can be adapted to retain said plurality of links 501, 502 and allow said plurality of links 501, 502 to rotatably articulate with respect to one another. The elongated connector mechanism can be configured to mate with each said longitudinal hole 504*a*, 504*b* of each link 501, 502, of said plurality of links 501, 502. In one aspect, the elongated connector mechanism includes a guide wire. The link 501 includes a body 501*a* at least one hole 503*a* transverse to said longitudinal hole 504*a*, 504*b*.

In one embodiment, at least one link 501 of the plurality of links 501, 502 includes a body 501*l* having one or more serrated sides 501*b*. The elongate connector mechanism (e.g., guide wire) can be positioned transverse to the one or more serrated sides 501*b*.

The elongated connector mechanism (e.g., guide wire) can be adapted to allow said plurality of links 501, 502 to rotatably articulate with respect to one another by rotation of the said plurality of links 501, 502 around a plurality of hinges 503 that pivotally engage the plurality of links 501, 502 with each other. Accordingly, the links 501, 502 are rotatably articulated with respect to one another by a hinge 503. Also, wherein the links 501, 502 are rotatably articulated with respect to one another by the longitudinal holes 504*a*, 504*b* having conical openings B71A, B72A that prevent the elongate connector mechanism (e.g., guide wire) from binding by forming a smooth arcuate path between longitudinal holes 504*a*, 504*b*. The longitudinal holes 504*a*, 504*b* and elongate connector mechanism (e.g., guide wire) are shaped and dimensioned so that the implant 540 slides down the elongate member under force of gravity. The longitudinal holes 504*a*, 504*b* and elongated connector mechanism (e.g., guide wire) are configured so that the implant 540 can move along the elongated connector mechanism.

FIGS. 110-112 also show an intervertebral spacer implant assembly 540 that can include: a plurality of links 501, 502, wherein each link 501, 502 of said plurality of links comprises a longitudinal hole 504a, 504b bored through a longitudinal axis 504c of said link 501, 502, and said longitudinal hole 504a, 504b of each link 501, 502 of said plurality of links aligns to form a continuously-alignable longitudinal hole 504a, 504b bored through said plurality of links 501, 502; and an elongated connector mechanism (e.g., guide wire) adapted to retain said plurality of links 501, 502, wherein said elongated connector mechanism is configured to mate with each said longitudinal hole 504a, 504b of each link 501, 502, of said plurality of links 501, 502, wherein one of said plurality of links comprises a body portion 501a comprising: partially serrated sides 501b; at least one first hole 503a configured through a top of said body portion 501a; and a connector mechanism positioned transverse to said partial serrated sides 501b. The allows for the plurality of links 501, 502 to rotate with respect to each other FIGS. 110-112 also show an intervertebral spacer implant assembly 540 that can include: a plurality of links 501, 502, wherein each link 501, 502 of said plurality of links comprises a longitudinal hole 504a, 504b bored through a longitudinal axis 504c of said link 501, 502, and said longitudinal hole 504a, 504b of each link 501, 502 of said plurality of links aligns to form a continuously-alignable longitudinal hole 504a, 504b bored through said plurality of links 501, 502; and an elongated connector mechanism (e.g., guide wire) adapted to retain said plurality of links 501, 502, wherein said elongated connector mechanism is configured to mate with each said longitudinal hole 504a, 504b of each link 501, 502, of said plurality of links 501, 502, wherein one of said plurality of links comprises a body portion 501a comprising: partially serrated sides 501b; a hole 503a configured through a top of said body portion 501a; a pair of connector flanges 501c positioned transverse to said serrated side 501b; a hole 503 configured through each of said pair of connector flanges 501c; and a connector mechanism (e.g., guide wire) positioned transverse to said partial serrated sides 501b.

FIGS. 110-112 also show an intervertebral spacer implant assembly 540 that can include: a plurality of links 501, 502, wherein each link 501, 502 of said plurality of links comprises a longitudinal hole 504a, 504b bored through a longitudinal axis 504c of said link 501, 502, and said longitudinal hole 504a, 504b of each link 501, 502 of said plurality of links aligns to form a continuously-alignable longitudinal hole 504a, 504b bored through said plurality of links 501, 502; and an elongated connector mechanism (e.g., guide wire) adapted to retain said plurality of links 501, 502, wherein said elongated connector mechanism is configured to mate with each said longitudinal hole 504a, 504b of each link 501, 502, of said plurality of links 501, 502, wherein one of said plurality of links comprises a body portion 501a comprising: partially serrated sides 501b; a hole 503a configured through a top of said body portion 501a; a pair of connector flanges 501c positioned transverse to said serrated side 501b; and a hole 503 configured through each of said pair of connector flanges 501c.

FIGS. 110-112 also show an intervertebral spacer implant assembly 540 that can include: a plurality of links 501, 502, wherein each link 501, 502 of said plurality of links comprises a longitudinal hole 504a, 504b bored through a longitudinal axis 504c of said link 501, 502, and said longitudinal hole 504a, 504b of each link 501, 502 of said plurality of links aligns to form a continuously-alignable longitudinal hole 504a, 504b bored through said plurality of links 501, 502; an elongated connector mechanism (e.g., guide wire) adapted to retain said plurality of links 501, 502, wherein said elongated connector mechanism is configured to mate with each said longitudinal hole 504a, 504b of each link 501, 502, of said plurality of links 501, 502; and a hinge pin 503 adapted to connect a first link 501 of said plurality of links 501, 502 to a second link 502 of said plurality of links.

FIGS. 110-112 also show an intervertebral spacer implant assembly 540 that can include: a plurality of hinged (e.g., hinge 503) links 501, 502, wherein each link of said plurality of links comprises: a longitudinal hole 504a, 504b bored through a longitudinal axis 504c of said link 501, 502; and a hinge 503 positioned long an axis 503b perpendicular to said longitudinal hole 504a, 504b; an elongated connector mechanism (e.g., guide wire) adapted to retain said plurality of links 501, 502; and wherein said elongated connector mechanism is configured to mate with each said longitudinal hole 504a, 504b of each link 501, 502, of said plurality of links 501, 502. In one aspect, said hinge 503 includes a hinge pin 503c. In another aspect, a first link 501 of said plurality of links 501, 502 is pivotally connected to a second link 502 of said plurality of links via said hinge 503.

FIG. 110-112 also show schematic diagrams of the first link 501 of the articulating interbody spacer apparatus 540 according to an embodiment herein. The first link 501 comprises a body portion 501a having a top end 501d and a bottom end 501e. The body portion 501a of the first link 501 also comprises a pair of opposed partially serrated sides 501b each terminating with unserrated tapered walls 501f towards a front end 501g of the body portion 501a. The top end 501d terminates with a downwardly sloping wall 501h towards the front end 501g. Moreover, the bottom end 501e terminates with an upwardly sloping wall 501i towards the front end 501g. The back end 501j of the body portion 501a comprises a generally sloping wall 501k having a connector mechanism 501l extending therefrom. The connector mechanism 501l has generally flat side surfaces 501m and a throughhole 503a configured transversely with respect to the longitudinal axis 504c of the body portion 501a. The link 502 is shown to have a pair of connector flanges 501c. Each connector flange 501c comprises a throughhole 503a aligned with one another. When the elongate member or elongate connector mechanism is a single cable or guide wire (not shown, see FIGS. 43, 50-52) that is allowed to flex or bend where the plurality of hinged links 501, 502 respectively articulate.

Also shown is an intervertebral spacer implant assembly having a plurality of links 502, 502 including at least a first link 501 pivotally engaged to a second link 502 of said plurality of links. The plurality of links 501, 502 can have a linear orientation when aligned and an arcuate orientation when pivoted with respect to each other. When aligned, a continuous internal channel is formed through the implant 540. When pivoted, the conical shaped openings of the internal channels 504 are connected and form an angle so that a guide wire can be bent therein.

The first link 501 can include a first body having a first guide hole 504a extending from a first opening 504d in a first end 501n to a first conical opening B71A in a first hinged end 501p and adapted to receive an elongate member (e.g., guide wire) therethrough. The first hinged end 501p having at least one first connector flange 501c with an off-centered first hinge pin hole 503d extending therethrough such that the first hinge pin hole 503d is traverse to the first guide hole 504a. The second link 502 includes a second body having a second guide hole 504b extending from a conical second opening B72A in a second hinged end 502p to a second opening 504e in a second end 502n and adapted to receive an elongate member (e.g., guide wire) therethrough. The second hinged end 502p having at least one second connector flange 502c with an off-centered second hinge pin hole 503e extending therethrough such that the second hinge pin hole 503e is traverse to the second guide hole 504b and such that the second hinge pin hole 503e aligns with the first hinge pin hole 503d. A hinge pin 503 located in and extending through and between the first hinge pin hole 503a and second hinge pin hole 503e.

The implant 540 can have the first hinged end 501p of the first link 501 with at least a pair of first connector flanges 501c with a gap therebetween with an off-centered first hinge pin hole 503a extending from the gap through each of the pair of first connector flanges 501c such that the first hinge pin hole 503a is traverse to the guide hole 504a. The second connector flange 502c is located in gap between the pair of first connector flanges 501c.

The implant 540 can include at least one first connector flange 501c of the first link 501 with the off-centered first hinge pin hole 503a having a first traverse abutting surface 506a that abuts with the second link 502 when in the linear orientation, and a first angled stop-pivot surface 506b that abuts the second link 502 when in the arcuate orientation. Also, at least one second connector flange 502c of the second link 502 with the off-centered second pin hole 503e can include a second traverse abutting surface 507a that abuts with first link 501 when in the linear orientation and a second angled stop-pivot surface 507b that abuts the first link 501 when in the arcuate orientation.

The at least one first connector flange 501c of the first link 501 with the off-centered first hinge pin hole 501 includes a first traverse abutting surface 506a that abuts with a second traverse pivot-stop surface 507 that is orthogonal and connected to the second connector flange 502c of the second link 502 when in the linear orientation and a first angled stop-pivot surface 506b that abuts with the second traverse pivot-stop surface 507 of second link 502 when in the arcuate orientation. At least one second connector flange 502c of the second link 502 with the off-centered second pin hole 502e includes a second traverse abutting surface 507a that abuts with a first traverse pivot-stop surface 506 that is orthogonal and between the one or more first connector flanges 501c of the first link 501 when in the linear orientation and a second angled stop-pivot surface 507b that abuts the first traverse pivot-stop surface 506 of the first link 501 when in the arcuate orientation.

The implant 540 can include the first link 501 having the first traverse abutting surface 506a connected to the first angled stop-pivot surface 506b so as to form a first angle adjacent to the first hinge pin hole 503a. Similarly, the second link 502 can include the second traverse abutting surface 507a connected to the second angled stop-pivot surface 507b so as to form a second angle adjacent to the second hinge pin hole 503e. The implant 540 can include the first link 501 having the first traverse abutting surface 506a and first angled stop-pivot surface 506b forming the first angle adjacent to and longitudinally aligned with the first hinge pin hole 503a, wherein the first guide hole 504a is longitudinal. Similarly, the second link 502 can include the second traverse abutting surface 507a and second angled stop-pivot surface 507b forming the second angle adjacent to and longitudinally aligned with the second hinge pin hole 503e, wherein the second guide hole 504b is longitudinal.

The implant 540 can include the first guide hole 504a being along a centered axis 504c of the first body 501, and the first hinge hole 504a does not intersect the first guide hole 504a. Also, the second guide hole 504b can be along a centered axis 504c of the second body 502 and the second hinge hole 503e does not intersect the second guide hole 504b.

When the implant 540 is in the arcuate orientation, the conical first opening B71A of the first guide hole 504a of the first link 501 can have a wall that aligns with the second guide hole 504b of the second link 502. When the implant 540 is in linear orientation, the conical first opening B71A of the first guide hole 504a of the first link 501 is defined by a conical first opening surface that abuts a conical second opening surface of the second conical opening B72A of the second guide hole 504b of the second link 502.

The implant 540 can include one or more first connector flanges 501C of the first link 501 having a textured outer surface 501b and a smooth inner surface 508a that is slidable with respect to a surface 508b of the one or more second connector flanges 502c. In one aspect, the one or more second connector flanges 502c of the second link 502 are devoid of a textured surface, or only have smooth surfaces 508b.

The implant 540 can include the first end 501n of the first link 501 being a terminus of the implant 540 and the second end 502n of the second link 502 is an opposite terminus of the implant 502. However, one or more links can be located between the first link 501 and second link 502 with similar linear and arcuate orientations and similar configurations.

The implant 540 can include a surface 508c of the one or more first connector flanges 501c being an outer surface of the first link 501. A surface 501m of the one or more second connector flanges 502c connects to an orthogonal surface 508d that extends to and is orthogonal with an outer surface 508e of the second link 502.

The implant 540 can include a surface 508c of each of two first connector flanges that is an outer surface of the first link 501, and two surfaces 501m of the one or more second connector flanges connects to different orthogonal surfaces 508d that each extend to and is orthogonal with opposite outer surfaces 508e of the second link 502.

When in the linear orientation the first guide hole 504a and second guide hole 504b form a linear continuous channel. When in the arcuate orientation the first conical opening B71A of the first guide hole 504a and second conical opening B72A of the second guide hole 504b form an arcuate channel.

FIGS. 113 to 116 illustrate a unitary implant 550.
FIGS. 117 to 120 illustrate a unitary implant 560.
FIGS. 121 to 124 illustrate a unitary implant 570.
FIGS. 125 to 129 illustrate a unitary implant 580 with an aperture 581 formed therethrough to slidably receive a guide wire
FIG. 130 is an exploded perspective view of the implant of FIGS. 57 to 61.
FIGS. 131 to 136 further illustrate a component 416 of the implant of FIG. 130, including a cylindrical aperture 416A formed therethrough. The aperture can, as indicated by aperture 416B in FIG. 136, be oval shaped (along with pin 422 in FIG. 148) to prevent component 416 from rotating on pin 422.
FIGS. 137 to 140 further illustrate a component 421 of the implant of FIG. 130, including apertures 420 and 421A formed therein. Aperture 420 slidably receives the distal end 420A of a tool 420B (FIG. 149). End 420A bears against or otherwise engages pin 422 to stabilize the implant and prevent the components from tilting or otherwise moving while the implant is inserted. Once the implant is inserted, end 420A is removed and the implant components and pin are free to cant, tilt, or move as designed.
FIGS. 142 to 145 further illustrate a component 417 of the implant of FIG. 130 and of the implant 415 (FIGS. 57, 60, 61), including aperture 417A formed therethrough and including socket 417C (FIG. 141) shaped to receive foot 424 of pin 422 (FIG. 130).
FIGS. 146 to 148 further illustrate the pin 422 and foot 424 utilized in the implant of FIG. 130.

FIG. 149 further illustrates the implant of FIG. 130 assembled. Member 421 rocks back and forth in the manner indicated by arrows 4E on the peaked surface 417S of member 417. Member 416 rocks back and forth in the manner indicated by arrows 4C and 4D on the peaked surface 421S of member 421. Member 416 rocks in directions transverse the directions in which member 421 rocks. Members 416 and 421 can also rock in directions intermediate arrows 4C, 4D, and 4E. Pin 422 can be sized to be slightly smaller in diameter than the apertures 417A, 421A, and 416A (FIG. 130) so that there is slack or "play" and pin 422 can tilt short distances in apertures 417A, 421A, and 416A in directions 4F, 4G, 4H, and 4I (FIG. 149), allowing member 421 to slide over peaked surface 417S and allowing member 416 to slide over peaked surface 421S. One advantage of the implant of FIG. 149 is that it can be constructed to minimize or prevent rotation in the directions indicated by arrows 4T and 4U about pin 422 by utilizing peaked surfaces 417S and 421S. Another way this can be accomplished is by utilizing, as earlier noted, an oval pin 422 and aperture 416B (FIG. 136) that is shaped to receive the oval pin (or oval portion of the pin 422). Any other desired construction can be utilized to achieve such a limitation of rotation while still permitting members 416 and 421 and pin 422 to tilt or slide in any various desired directions 4C, 4D, 4E, 4F to 4I, etc. Limiting rotation of an implant helps minimize wear of and facilitates protection of the spine, especially the facet joints 310Z (FIG. 41).

FIGS. 150 to 160 illustrate an alternate implant 600 including a base 601 with apertures 605 to 608 (FIGS. 157, 159), including a rocker member 602 with aperture 604 (FIG. 153), and including a pin 603 that extends through apertures 605, 604, and 606 to permit member 602 to pivot on pin 603 in the manner indicated by arrows 6A (FIG. 150). Pin 603 can be sized slightly smaller in diameter than aperture 604 so that there is slack or "play" and rocker member 602 can move in the direction of arrows 6B, 6C or in any desired direction (FIG. 151). Pin 603 can also be attached to a bearing 482A (FIG. 90) fixed within rocker member 602 to allow motion in the direction of and intermediate to the directions indicated by arrows 6A, 6B, and 6B. Opening 607 in base 601 (FIG. 157) is constructed to minimize or prevent rotation of rocker member 602 in the directions indicated by arrows 6C (FIG. 151). Any other desired construction can be utilized to achieve such a limitation of rotation while still permitting member 602 and pin 603 to tilt or slide in any various desired direction. Limiting rotation of an implant helps minimize wear of and facilitates protection of the spine.

FIGS. 161 to 163 illustrate an implant 620 similar to implant 600. Implant 620 includes a base 601A and a rocker member 602A pivotally mounted in based 601A on a pin 621.

FIG. 164 illustrates an implant 630 includes an upper shell that can tilt or cant in directions indicated by arrows 7B, 7C, 7D, or in directions intermediate arrows 7B, 7C and 7D. The "football" shape is desirable for insertion into an intervertebral disc because, among other things, it can help minimize invasive surgical procedures.

When an implant is inserted by sliding or moving the implant through a hollow guide member, the guide member can be shaped and dimensioned (for example, the guide member can be shaped to have a triangle, square, rectangle, pentagon, or other polygon inner opening and the outer surface of the implant can have a corresponding shape) to engage the implant to prevent the implant from rotating in the guide member while the implant in inserted through the guide member. A guide member can detachably engage an implant by turning or threading into an opening formed in the implant, or by any other desired means or construct. The guide member can be hollow with an internal conduit through which the implant slides. Also, a push member can be operably coupled with the implant in order to push the implant through the internal chamber of the guide member. The elongate light guide can be used to inspect the implant after implantation and the structures adjacent to the implant and detachment for the guide member.

Forming openings on implants that expand in size as the opening moves away from the outer surface of the implant is preferred because such openings are believed to tend to draw viscoelastic cartilage, bone, disc nucleus, disc annulus tissue and other material into such openings and to permit the tissue or other material to expand, creep, or otherwise move into the openings such that the material tends to interlock with the openings. Tissue ordinarily moves into openings 655A, 655 (FIG. 168) because the tissue is continuously or intermittently compressed against an implant and is caused to creep or flow into the openings. Tissue can also be scraped into an opening 655A, 655 when an implant moves transversely over tissue and a tooth edge or other portion of the implant moves transversely over tissue surface and causes tissue from the surface to move into the opening. Such "scraping" can sometimes occur simultaneously with the implant being compressed against the tissue, which facilitates the ability of a tooth edge or other portion of an implant to scrape tissue into an opening.

FIGS. 165 to 170 illustrate an intervertebral implant 650 utilized to translate laterally a vertebra, or possibly an intervertebral disc, with respect to an adjacent vertebra. The individual components of implant 650 are most readily apparent in FIG. 170, and include a base 652, a translation member 651 shaped to slide over base 652, and a rotatable screw member 653 for laterally displacing member 651 in the direction of arrow 6R (FIG. 171). Internally threaded nut 661 is mounted orthogonal opening 658 formed in base 652. Hexagonal opening 654 is formed in the head of member 653. Leg 662 extends through opening 660, through opening 658, through opening 657 in foot 656, and into aperture 659. Openings 659, 657, and 660 are not internally threaded. A metal ring (not shown) extends around leg 662 inside opening 658 and adjacent opening 660 to secure leg 662 and maintain leg 662 inside opening 658 when member 653 is turned in the direction of arrow 6N (FIG. 170). A portion of leg 662 is externally threaded such that turning the head of member 653 in the direction of arrow 6N with an Allen wrench inserted in opening 654 (or by any other desired means) causes internally threaded nut 661 to move along externally threaded member 662 in the direction of arrow 6T such that nut 661 bears against foot 656 and displaces foot 656 and translation member 651 in the direction of arrow 6R (FIG. 171). The presently preferred "starting position" of member 651 is illustrated in FIG. 171, although, as would be appreciate by those of skill in the art, the "starting position" of member 651 can correspond to the position illustrated in FIG. 165 and member 651 can be moved from the position of FIG. 165 to the position shown in FIG. 171. When, however, member 651 is displaced from the beginning position illustrated in FIG. 171 in the direction of arrow 6R, member 651 functions to displace simultaneously in the direction of arrow 6R a vertebra V1 that is contacted and engaged by member 651. While vertebra V1 is transversely or laterally displaced in the direction of arrow 6R, the adjacent vertebra V2 contacted and engaged by base 652 can remain substantially fixed, or, vertebra V2 can be transversely displaced in the direction of arrow 6M while vertebra V1 moves in the direction of arrow 6R, or, vertebra V1 can remain substantially stationary and not move in the direction of arrow 6R while vertebra V2 moves and is transversely displaced in the direction of arrow 6M.

Implant 650, as do various other implants illustrated in the drawings herein, includes teeth which function to engage vertebra surfaces contacted by the implant. These teeth are typically illustrated herein with interlocking openings 655A (FIG. 168) formed therebetween that have an arcuate cross-section profile. The width of these interlocking openings increases in at least one direction or dimension as the distance from the outer surface(s) of the implant 650 increases. The shape and dimension of such interlocking openings can vary as desired and can, for example, have a trapezoidal 655 cross-sectional profile instead of an arcuate profile. The width of openings 655A, 655 need not increase in one or more dimensions as the distance traveled into the openings increases. The width can actually instead remain constant or can actually decrease. It is, as noted, preferred that the width increase so that the openings tend to interlock with tissue that enters and expands into the openings. While not specifically shown or illustrated, the implant 650 can have a longitudinal opening 655A that can extend across the length of the implant 650, either only on one side, both sides, or a plurality of sides relative to a longitudinal axis. The longitudinal opening 655A can be used for engaging the adjacent vertebras as described. The one or more longitudinal openings 655A (and or grooves that can function to steer or direct the implant) can also serve as a conduit for the elongate light guide configured as a guide wire. The internal conduit of the guide member may also include rails or other features that provide guides the one or more longitudinal openings, which can provide for the implant 650 to rotate with the guide member. A push member can be used to push the one or more longitudinal openings 655A along the guides.

FIGS. 172 to 177 illustrate an intervertebral implant 670 utilized to translate laterally a vertebra, or possibly an intervertebral disc, with respect to an adjacent vertebra. The individual components of implant 670 are most readily apparent in FIG. 172, and include a base 672, a translation member 671 shaped to move pivotally and transversely with respect to base 672, and a rotatable screw member 677 for actuating member 671 to move in the direction of arrow 6U (FIG. 177) when member 677 is turned in the direction of arrow 6V (FIG. 177) by an Allen wrench inserted in hexagonally shaped socket 678 (FIG. 174). Member 671 includes platform 673 with a plurality of tissue engaging teeth formed thereon. The upper end of leg member 674 is pivotally connected to platform 673 by pin 675 (FIGS. 172, 177). The lower end of leg member 674 is pivotally connected to base 672 by pin 679 (FIGS. 172, 177). Member 677 includes an externally threaded leg similar to leg 662 of implant 650 (FIG. 170). The externally threaded leg of member 677 extends into an opening formed in T-shaped member 676 such that turning member 677 in the direction of 6V when implant 670 is in the starting orientation illustrated in FIG. 177 displaces member 676 laterally in the direction of arrow 6P (FIG. 177). When member 676 moves laterally or transversely in the direction of arrow 6P, member 676 bears against and displaces leg 674 in the direction of arrow 6P such that leg 674 and platform 673 upwardly pivot in the direction of arrow 6U (FIG. 177).

When platform 673 is displaced from the beginning position illustrated in FIG. 177 in the upward arcuate direction of travel indicated by arrow 6U (FIG. 177), platform 673 functions to displace upwardly and laterally in the direction of arrow 6U a vertebra V3 that is contacted and engaged by member platform 673. While vertebra V3 is upwardly and laterally displaced in the direction of arrow 6U, the adjacent vertebra V4 contacted and engaged by base 672 can remain substantially fixed, or, vertebra V4 can be transversely displaced in the direction of arrow 6W while vertebra V3 moves in the direction of arrow 6U, or, vertebra V3 can remain substantially stationary and not move in the direction of arrow 6U while vertebra V4 moves and is transversely displaced in the direction of arrow 6W. How implant 670 transversely moves vertebrae V3 and V4—and how implant 650 transversely moves vertebrae V1 and V2—depends on a number of factors including the configuration of the patient's spine, the position of the patient, the position of the implant intermediate the adjacent pair of vertebrae, etc.

When member 676 displaces arms 674 in the direction of arrow 6P, arms 674 continue to pivot about pin 679 until arms 674 nest in and are stopped by U-shaped opening 680 formed in base 672 (FIGS. 172, 173, 177). Platform 673 or vertebra V3 can, if desired, pivot in the directions indicated by arrows 7R (FIG. 172) on pin 675 when platform 673 is in the fully displaced position illustrated in FIG. 172.

FIGS. 178 and 179 illustrate an instrument constructed in accordance with the invention and generally indicated by reference character 760, which can include an one or more optical components 321d that are each configured to include features of the elongate light guide described herein. The distal end 722F includes a rounded tip 765 shaped to be oscillated in and out in directions parallel to the longitudinal axis of instrument 760 in order to facilitate the passage of tip 765 through tissue. Tip 765 includes slot 767 formed therein. Hollow tubular member 764 houses cylindrical member 762 such that member 762 can slide back and forth in member 764. The distal end (not visible) of cylindrical member 762 is provided with a blade 768 (FIG. 179). Blade 768 includes cutting edge 769. In FIG. 178, blade 768 is in a stowed position inside the distal end 722F of member 764 and is not visible. In FIG. 179, member 762 and blade 768 have been displaced in the direction of arrow 7W and blade 768 has slid through opening 767 to a deployed position shown in FIG. 179. The shape and dimension of blade 768 and tip 765 can vary as desired. Blade 768 and member 762 are moved between the stowed position of FIG. 178 and the deployed position of FIG. 179 by displacing end 761 in the direction of arrow 7V (to move blade 768 from the stowed to the deployed position) and in a direction opposite that of arrow 7V (to move blade 768 from the deployed to the stowed position). In one mode of operation of instrument 760, tip 765 is, with blade 768 stowed, oscillated back and forth in directions parallel to arrow 7V in order to pass tip 765 through tissue to a desired location in an individual's body. Once tip 765 is at the desired location, end 761 is displaced to form an incision in tissue adjacent tip 765. To form an incision, blade 768 can be displaced in the direction of arrow 7W into tissue while member 764 is held in fixed position. Or, after blade 768 is deployed, member 764 and blade 768 can be moved simultaneously to form an incision in tissue. Instrument 760 can be used to make an incision in any tissue in the body such as skin, blood vessels, nerves, organs, joints, etc. One advantage of instrument 760 is that blade 768 can be safely passed among people when blade 768 is in the stowed position and also when not in use.

In the event hollow member 764 is intended to house an implant that slides through member 764 to a desired location in an individual's body, the inner channel in member 764 and opening 767 through which the implant slides can have an orthogonal or other shape or configuration (as can the implant) that engages the implant and prevents the implant from rotating inside member 764 about the longitudinal axis of member 764. The inner channel can also include on optical fiber and/or other optical components 321d of an elongate light guide for visualization of the medical procedure. In this fashion, the physician utilizing member 764 can more readily determine the orientation of the implant once the implant exits the distal end of member 764 into a patient's body. If the member 764 is not rotated (about the longitudinal axis of member 764) while the implant is being inserted in a patient's body, then the orientation of the implant therein remains the same (i.e., the implant does not rotate inside member 764 about the longitudinal axis of member 764) while the implant slides therethrough.

Similarly, if an implant has an opening formed therethrough that permits the implant to slide down the outside of member 764, of a wire, etc., the opening formed through the implant and/or the shape and dimension of the outside of member 764 or the wire prevent the implant from rotating about the longitudinal axis of member 764 or of the wire while the implant slides therealong. This enables a surgeon to more readily ascertain the orientation of the implant once the implant passes into a patient's body. If either member 764 or the wire is not rotated while the implant is being inserted into a patient's body, then the orientation of the implant thereon remains the same while the implant slides therealong.

The position of member 764 or of an implant may also be verified by direct visualization, arthroscope, endoscope, an elongate light guide either combined or separate from member 764, any illuminated light source, fluoroscope, x-ray, camera, video recording, patient feedback, electrical stimulation, ultrasound, or any other desired means.

FIGS. 69 to 72 illustrate an implant 435 provided with openings 436, 437 having a width that initially expands as the distance from the outer surface of the implant increases. As is illustrated in FIG. 71, these openings can be packed or filled with a composition that forms a tooth 700 that engages or penetrates tissue. The composition of tooth 700 can vary as desired. Tooth 700 need not be, but is preferably substantially rigid. Tooth 700 can be porous to facilitate the ingrowth of tissue from a patient's body and/or resorb over time. In one application, tooth 700 is formed from bone, in which case tooth 700 may fuse with similar tissue in a patient's body.

Another tooth 701 illustrated in FIG. 71 and includes an outwardly extending tip that functions to penetrate and interlock with tissue in a patient's body. If tissue in a patient's body is pressed against the tip of tooth 701, or vice-versa, the tissue may flow or move around and envelop the tip of tooth 701. Tooth 700, 701 can comprise an integral part of an implant and need not consist of a separate composition that is added to the implant. For example, implant 435 can be cut from a block of stainless steel or any other desired material and include the outwardly extending part of tooth 701, in which case opening 437 would not exist. The shape and dimension of teeth 700 and 701 can vary as desired. In one embodiment of the invention, an implant includes one or more teeth 700, 701 shaped like the keel of a boat.

To facilitate inserting implant 435, openings 436, 437 can be filled with a composition that remains flush, extends outward from, or is partially recessed from the outer surface of implant 435. At least partially filling openings 436, 437 may prevent implant 435 from "hooking" or catching on tissue when implant 435 is inserted. Openings 436, 437 can be filled with cement or other bonding materials that are press fit or injected from within or around implant 435.

As would be appreciated by those of skill in the art, the various implants described herein can be inserted in any desired joint in a patient's body or at any other desired location in a patient's body, including but not limited to a patient's jaw in connection with the insertion of dental implants or other dental work. Other such joints, by way of example and not limitation, include facet joints, intervertebral discs, and interspinous process joints in the spine.

The floating implant 770 of FIG. 180 includes a flat, football-shaped platform 771 that tends to float on tissue and to ameliorate subsidence of the implant in the tissue. Teeth 772 extend outwardly from platform 771. Openings 773 are formed intermediate adjacent teeth 772. The width of an opening 773 initially increases as the distance into the opening 773 increases and the distance away from outer surface(s) 774 increases. For example, opening 773 initially expands as the distance into opening 773 and away from surface 774 increases. Platform 771 can have any shape or dimension and may be "bean" or "C" shaped to contour to vertebral bones. Platform 771 may be configured to resist subsidence in tissue after removal of a prior implant and/or tissue. Floating implant 770 can be used in revision surgery or to fill substantial defects within the spine. Teeth 772 can be configured as an arcuate concave surface above and below platform 771 to conform to adjacent vertebra. Teeth 772 can have any shape or dimension.

FIG. 184 illustrates an orthogonal implant system in which a wire 780, such as an elongate light guide configured as a guide wire, is first inserted in a direction indicated by arrow 7P into a body to position end 780A at a selected location in or at a joint or at another location in the body. After end 780A is positioned at the selected location, dilator 781 is slid over wire 780 in the manner indicated by arrow 7Q. Elongate, longitudinal, cylindrical channel 782 formed through dilator 781 slides over wire 780. Tip 781A of dilator 781 is used to form or expand the size of an opening in the body. Tip 780A, 781A can be orthogonal, round or any shape or dimension. Wire 780 or dilator 781 can be used to manipulate and position tissue such as a displaced intervertebral disc and/or misaligned vertebra. Cannula 783 is slid over dilator 781 in the manner indicated by arrow 7R until edge 785 is at a desired location adjacent or in the opening formed by dilator 781. In one aspect, cannula 783 can be configured as an elongate light guide that includes an internal lumen or internal conduit for operating as described, and also allowing for transmitting and receiving light for visualization of the medical procedure. Here, an implant with an internal conduit running from one end to another can be slide along an elongate light guide configured as a guide wire 780 and/or through a cannula 783, optionally configured as a hollow elongate light guide. Hollow, orthogonal channel 784 in cannula 783 is concentric to and slides over the orthogonal outer surface of dilator 781. Driver 786 is slide over dilator 781 until end 788 contacts end 789 of cannula 783. Hollow, orthogonal channel 787 in driver 786 is concentric to and slides over the orthogonal outer surface of dilator 781. A hammer or other instrument is used to strike cap 790 in the direction of arrow 7T to drive cannula 783 to a desired location. Driver 786 is removed from dilator 781. Dilator 781 is removed. Wire 780 can also, if desired, be removed or can remain in cannula 783. An implant is inserted in end 789 and slid through channel 784 and out the lower end of channel 784 into the body. If wire 780 is left in cannula 783, the implant can, as previously shown, include an opening formed therethrough that permits the implant to slide down wire 780. Alternatively, the cannula 783 is removed, and the implant is slide down wire 780. When an implant is slid through channel 784, the implant is preferably shaped and dimensioned such that is cannot rotate about the longitudinal axis of cannula 783 (or rotate about a wire 780) while sliding through channel 784. In FIG. 184, the longitudinal axis of cannula 783 is parallel to and coincident with arrow 7S. The combined lengths of driver 786 and cannula 783 exceed the length of wire 780 or dilator 781 so that striking cap 790 does not function to contact end 780B or end of dilator 781 and drive wire 780 into the body.

The orientation of an implant inserted into the body using the implant system in FIG. 184 need not be restricted to prevent rotation. For example, a threaded cylindrical implant may be rotated within the implant system in FIG. 184 to facilitate insertion within the body. The instruments and implant described herein—including but not limited to instrument 760 (FIG. 178), the implant system in FIG. 184, implant 435 in FIGS. 69-72, and/or implant 770 in FIGS. 180 to 183—can be transparent, semi-transparent, or opaque to control the amount of light, x-ray, ultrasound, current, etc. used to determine the position of the instrument and/or implant.

An alternate construction of dispensing end 322F of instrument 360 (FIG. 47E) is illustrated in FIG. 185 and includes fingers 369A and 365A. Each finger 365A, 369A includes a flat surface 369B that engages a flat surface 352B, 352C on an implant 352A to prevent the implant 352A from rotating about the longitudinal axis of body 364 (FIG. 47E). The shape and dimension of body 364 can vary as desired and can, by way of example and not limitation, take on the orthogonal shape of drive 786 in FIG. 184. Fingers 369A, 365A (FIG. 185) deploy and release implant 352A in a manner similar to fingers 365, 366, 368, 369 in FIG. 47D.

Implant 650A illustrated in FIG. 186 is an alternate configuration of the implant 650 illustrated in FIGS. 165 to 170. Implant 650A is generally used to separate a pair of vertebra V3, V4. In contrast, implant 650 is intended to laterally translate a pair of adjacent vertebra. Implant 650A is similar in construction and operation to implant 650 except that translation member 651A can include a smooth, and not serrated, upper surface 651B. Upper surface 651B can also be shaped or formed to permit surface 651B to slide smoothly inwardly over vertebra V3 in the direction of arrow X8, and to cause surface 651B to engage vertebra V3 and resist movement of surface 651B over vertebra V3 if surface 651B is, after being inserted intermediate vertebrae V3 and V4, displaced in a direction opposite that of arrow X8.

In use, base 652 is placed atop vertebra V4 in the manner illustrated in FIG. 186 such that nose 651C of member 651A is positioned outside vertebra V3. Member 653 is turned with an Allen wrench to displace member 651A in the direction of arrow X8 to force nose 651C intermediate vertebra V3 and base 652 such that vertebra V3 and V4 are separated and the distance X7 intermediate the vertebra V3 and V4 increases. The shape and dimension of the various components of implant 650A, and any other implants described herein, can vary as desired as long as the function heretofore described is achieved.

Instrument 800 illustrated in FIGS. 187 and 188 include handle 801 and distal end 802. End 802 is preferably, but not necessarily rounded. End 802 can be orthogonal as is end 781A in FIG. 184. End 802 can also include one or more optical components 321*d* that are each coupled to an optical light guide for visualization of the medical procedure as described herein such that instrument 800 is configured as or includes an elongate light guide. In use, any desired method can be utilized to position end 802 anywhere intermediate two vertebrae, adjacent or in a disc 70 or other joint, or between two spinous processes or transverse processes. One presently preferred method consists of oscillating handle 801 in the directions indicated by arrows E8 to pass end 802 through tissue to a desired location at or in a joint. Once distal end 802 is positioned between a pair of adjacent vertebra in the manner indicated in FIG. 188, handle 801 can be laterally displaced in any direction—including the directions indicated by arrows C8, D8, A8, and B8—in order to manipulate end 802 like the end of a lever to separate, rotate, or laterally displace vertebra 127, 128. Similarly, when end 802 is in a disc 70, is intermediate a pair of vertebra 127 and 128, or is between two spinous processes or transverse processes, then handle 801 can be displaced to separate, rotate, and/or laterally displace vertebra. An opening (not shown) can be formed generally parallel to the longitudinal axis of handle 801 and end 802 to permit instrument 800 to slide along a wire or other elongate guide unit to facilitate insertion of instrument 800 at a desired location in a patient's body. End 802 can also function as an implant reversibly threaded or otherwise attached to handle 801. End 802 can be detached from handle 801 intermediate two vertebrae (inside a disc 70, anywhere intermediate a pair of vertebra 127 and 128, between two spinous processes, between two transverse processes, etc.) after vertebrae 127, 128 are manipulated.

FIG. 189 illustrates the use of two or more implants in a joint to pivotally displace a joint member. A number of possible scenarios are illustrated in FIG. 189 and described below; to position, separate (space apart) opposing tissue surface; reshape an intervertebral disc, and/or to alter the orientation of the vertebra.

In a first scenario, only implants 803 and 805 are utilized, and implant 804 is not utilized. Implant 803 is inserted between vertebra 315 and vertebra 315A at the location shown in FIG. 189, after which implant 805 is inserted between spinous processes 806 and 807 at the location shown in FIG. 189. Implant 805 is sized to increase the distance D9 between spinous processes 806 and 807, and to upwardly displace spinous process 806 in the direction of arrow C9. This causes vertebra 315 to pivot about implant 803 and to generate compressive forces acting on implant 803 in the direction of arrow A9 that tend to maintain implant 803 intermediate vertebra 315 and 315A.

In a second scenario, only implants 804 and 805 are utilized, and implant 803 is not utilized. Implant 804 is inserted between vertebra 315 and vertebra 315A at the location shown in FIG. 189, after which implant 805 is inserted between spinous processes 806 and 807 at the location shown in FIG. 189. Implant 805 is sized to upwardly displace spinous process 806 in the direction of arrow C9. This causes vertebra 315 to pivot about implant 804 and to generate compressive forces on implant 804 that tend to maintain implant 804 intermediate vertebra 315 and 315A.

In a third scenario, only implants 803 and 804 are utilized, and implant 805 is not utilized. Implant 803 is inserted between vertebra 315 and vertebra 315A at the location shown in FIG. 189, after which implant 804 is inserted between vertebra 315 and 315A at the location shown in FIG. 189. Implant 804 is sized to upwardly displace spinous process 806 and vertebra 315 in the direction of arrows B9 and C9. This causes vertebra 315 to pivot about implant 803 and to generate compressive forces on implant 803 that tend to maintain implant 803 intermediate vertebra 315 and 315A.

In a fourth scenario, only implants 803 and 805 are utilized, and implant 804 is not utilized. Implant 805 is inserted between spinous processes 806 and 807 at the location shown in FIG. 189, after which implant 803 is inserted between vertebra 315 and 315A at the location shown in FIG. 189. Implant 803 is sized to upwardly displace vertebra 315 in the direction of arrow A10 to pivot spinous process 806 about implant 805 and to compress implant 805 intermediate spinous processes 806 and 807.

In a fifth scenario, implants 803, 804, 805 are utilized. Implant 805 is inserted between spinous processes 806 and 807 at the location shown in FIG. 189, after which implants 803 and 804 are inserted between vertebra 315 and 315A at the locations shown in FIG. 189. Implants 804 and 803 are sized to upwardly displace vertebra 315 in the directions indicated by arrows B10 and A10, respectively. This causes vertebra 315 and spinous process 806 to pivot about implant 805 and to generate compressive forces on implant 805.

Any desired combination of implants, as well as any desired sizes and shapes of implant, can be utilized to pivot a vertebra in the manners illustrated in FIG. 189. Implants 803, 804 and 805 can exert a force anywhere within or adjacent the spinous processes, transverse processes, facet joints, intervertebral disc, etc. Implants 803, 804 and 805 can likewise function to alter the orientation of a vertebra 315, 315A; to reshape a disc; and, to separate and lengthen tissues to decompress nerves or vessels (i.e., internal traction). Implants can be placed in any desired location and be constructed from any desired material. Implants can also be inserted into multiple intervertebral discs in a spine, including implants in intervertebral discs on each "side" or at each end of a vertebra in the spine. Implants in one intervertebral disc in a spine may work in tandem with implants in another intervertebral disc to achieve a desired result is spacing or positioning one or more vertebrae or discs.

The diagrammatic illustration of FIG. 190 depicts an egg-shaped implant 805 interposed between an opposing pair of spinous processes 806 and 807. Implant 805 does not prevent spinous processes 806 and 807 from laterally, slidably moving over implant 805 in the directions indicated by arrows R8. The shape and dimension and construction (i.e., one or more pieces, different materials, resiliency, flexibility, etc.) of implant 805 can vary as desired.

The diagrammatic illustration of FIG. 191 depicts an egg-shaped implant 805A including depressions 808 and 809 in which an opposing pair of spinous processes 806 and 807, respectively, seat. Depressions 808 and 809 function to at least partially restrict the lateral movement of processes 806 and 807 in the directions indicated by arrows R8 in FIG. 190. The shape and dimension and construction of implant 805A can vary as desired.

The diagrammatic illustration of FIG. 192 depicts an egg-shaped implant 805B including depressions 808A and 809A in which an opposing pair of spinous processes 806 and 807, respectively, seat. Depressions 808A and 809A more closely conform to spinous processes 806 and 807 than do depressions 808 and 809 (FIG. 191) and, consequently, tend to restrict to a greater degree lateral movement of spinous processes 806 and 807 in the directions indicated by arrows R8 in FIG. 190. The shape and dimension and construction of implant 805B and depressions 808A and 809A can vary as desired (FIG. 192). By way of example, and not limitation, a depression 809A can take on the flared shape indicated for depression 809C. Such a flared shape can be advantageous because a spinous process tends to flare (i.e., its width tends to increase) at the edge of the process that is closest to the opposing spinous process.

Implants 805, 805A and 805B can be fabricated in part or in whole from a resilient material which, when placed between and contacted by a pair of spinous or transverse processes, is resiliently compressed by the processes to form indents 808, 809, 808A, and/or 809A (FIGS. 190 to 192).

An implant, particularly a unitary implant, that restricts lateral movement of one spinous process in the direction of arrows R8 (and therefore restricts rotation movement of the spinous process about the longitudinal axis of the spine) with respect to another opposing spinous process is one particularly desirable embodiment of the invention because such an implant causes an opposing pair of spinous processes to function in part like a facet joint. An implant 805, 805A, 805B can also be shaped and dimensioned and constructed to be positioned intermediate a pair of opposing transverse processes to limit, or prevent, the lateral rotation of the spinous processes about the longitudinal axis of the spine. In addition to allowing normal movement or rotation or restricting normal movement or rotation in the manner described above, an implant 805, 805A, 805B can be constructed to fuse together a pair of opposing spinous or transverse processes.

An implant 805, 805A, 805B (FIGS. 190-192) and/or implant 816 (FIG. 196) can also be constructed or positioned to restrict, in the manner of a facet joint, the transverse or shear movement of opposing processes and vertebra in the direction indicated by arrows R9 (FIGS. 189, 196). For example, in FIG. 196, positioning implant 816 in the location illustrated restricts transverse (i.e., shear) movement of processes 806 and 807 in the directions indicated by arrows R9. Alternatively, implant 805C (FIG. 193-196) can be shaped and contoured to permit the rounded tips 806A, 807A (or other portions) of an opposing pair of processes to seat in implant 805C so that transverse movement of the processes in the direction of arrows R9 is restricted or prevented.

As is illustrated in FIGS. 192 to 196, one or more leg units 812 can be utilized to secure an implant 805B, 805C in position intermediate a pair of opposing spinous processes or transverse processes. The construction of a leg unit 812 can vary as desired. It is, however, presently preferred that a leg unit 812 include ball 811 and socket 814, a leg 810 securing the ball 811 to the implant, and a leg 813, 815 securing the socket 814 to a vertebra, a transverse process, a spinous process, or other portion of the spine (FIGS. 193 to 196). FIGS. 193 to 196 are diagrammatic illustrations illustrating leg units in conjunction with an implant 805C. Legs 813 and 815 in FIG. 194 do not utilize a ball and socket connection with implant 805C. Instead, each leg 813 includes an elbow 814A that secures the leg to implant 805C. The ball and socket is an example but not a limitation of a poly axial or other joint pivotally attaching an implant to the spine.

If desired, an implant 816 (FIG. 196) can be placed between opposing arcuate surfaces 817 and 818 of a pair of spinous processes 806 and 807.

FIG. 197 illustrates another implant 820 that can be utilized within an intervertebral disc, intermediate a pair of spinous processes or transverse processes, or at another desired location at or in a joint. Implant 820 includes a hollow cylindrical housing 820A with aperture 820B formed at one end and a slot 820C formed in the other end. Externally threaded end 827 of a screw 828A is located inside housing 820A. Head 828 is fixedly mounted on the other end of the screw 828A, and slot 829 is formed therein. The screw 828A is moved in the direction of arrow T8 by pressing head 828 in the direction of arrow T8 such that screw 828A slides through aperture 820B. Moving end 827 in the direction of arrow T8 downwardly pivots and displaces blade 825 in the direction of arrow T6. Blade 825 is fixedly mounted on a cylindrical axle or pin. One end 823 of the pin is slidably received by slot 821. The other end 824 of the pin is slidably received by slot 822. A cylindrical hub is also fixedly mounted on the pin and includes internally threaded aperture 823A. When the screw 828A is moved in the direction of arrow T8, end 827 pivots blade 825 in the direction of arrow T6, displaces blade 825 in the direction of arrow T8, and causes ends 823 and 824 to slide along slots 821 and 822 in the direction of arrow T5. Continuing to move screw 828A in the direction of arrow T8, and continuing to move blade 825 and ends 823 and 824 in the direction of arrow T5, eventually causes ends 823 and 824 to reach the end of their travel in slots 821 and 822, and causes blade 825 to pivot about the pin and through slot 820C to the deployed position indicated by dashed lines 825A. At the time blade 825 reaches said deployed position, internally threaded aperture 823A has rotated ninety degrees from the position illustrated in FIG. 197 and is in alignment with externally threaded end 827, and head 828 is near or contacts the end 820E of housing 820A. Turning head 828 in the direction of arrow T7 turns end 827 into aperture 823A and draws deployed blade 825A toward end 820E such that ends 823 and 824 slide along slots 821 and 822, respectively, in a direction opposite that of arrow T5. This decreases the distance between head 828 and deployed blade 825A such that blade 825A and head 828 contact and compress therebetween side portions of tissue such as the spinous processes 806 and 807 (FIGS. 189 to 196) when implant housing 820A is positioned intermediate a pair of opposed spinous processes 806 and 807 in the manner of implant 805 in FIGS. 189 and 190, implant 805A in FIG. 191, implant 805B in FIG. 192, 805C in FIGS. 193 to 196, and implant 816 in FIG. 196. Alternatively, the distance between head 828 and blade 825A can be decreased an amount that still permits some lateral or other movement of the opposing pair of spinous processes (or transverse processes if implant 820 is inserted therebetween). The mechanism utilized to deploy a blade 825A and to draw together a head 828 and blade 825 can be constructed in any desired manner. Implant 820 can be inserted between a pair of opposing vertebra, and can be inserted in an intervertebral disc to compress tissue between head 828 and blade 825A.

FIG. 198 illustrates an implant 830 including a deployable wing 833 stored in hollow cylindrical housing 830A provided with a rounded semi-spherical nose 830B. Wing 833 includes upstanding lip 834 sized such that lip 834 will not fit through slot 832. Turning screw 831 in the direction indicated by arrow T9 through internally threaded opening 830C and against the canted edge of wing 833 displaces wing 833 through slot 832 in the direction of arrow T10 until lip 834 bears against the inside of housing 830A adjacent slot 832 and until wing 833 is in the deployed position indicated by dashed lines 833A. When deployed, wing 833A produces a greater surface area bearing within or against a vertebra, tissue surface, or other joint member and reduces subsidence of the implant 830 or attaches the implant 830 into the tissue. As can be seen in FIG. 204, wing 833 can have a downward arcuate shape 833B. Wing 833B tends to gather and displace vertebral material or other tissue toward housing 830A. Wing 833C in FIG. 205 has a "T" shape. The shape and dimension of implant 830 and one or more wings 833, 833A, 833B, 833C provided by the implant 830 can vary as desired. Implants 820, blade 825A (FIG. 197), implant 830 (FIGS. 198, 204, 205), and wings 833, 833A, 833B, 833C (FIGS. 198, 204, 205) can act to gather and displace tissue to create a passageway when the implants are oscillated.

A multi-part implant 835 is illustrated in FIGS. 199 to 203. Implant 825 includes base 836, platform 838, tab 838A, socket 838B, locking member 837, and bolts 841, 842 that extend in part through base 836 and into member 837 to secure member 837 in the position depicted in FIGS. 200 to 203. Locking member 837 secures ball 839 of platform member 838 in socket 840 of base 836. When the bottom of one vertebra is canted with respect to the top of an opposing vertebra, platform 838 pivots to better position implant 835 intermediate the vertebrae to engage said bottom and top surfaces. Platform 838 engages one of the vertebrae surfaces (for example, the bottom of the upper vertebra); base 836 engages the other (for example, the top of the lower vertebrae). Tab 838A is fixed to member 838. Tab 838A functions to restrict movement of member 838 when tab 838A resides with socket 838B of base 836. The controlled movement of member 838 on base 836 functions to restrict rotation of the vertebra and can protect the facet joint, intervertebral disc, or other structures of the spine.

Any implant disclosed herein—including but not limited to implant 352A (FIG. 185), implant 650A (FIG. 186), tip 802 of instrument 800 (FIGS. 187, 188), tip 781A (FIG. 184), implants 803 to 805, 805A, 805B, 805C, 820, 830, 835 (FIGS. 189 to 205)—can be cannulated and inserted using any method, including but not limited to using an elongate guide unit such as instrument 360 (FIG. 47E), instrument 340 (FIG. 51), instrument 350 (FIG. 52), instrument 760 (FIG. 178), wire 780 (FIG. 184), and implant system (FIG. 184) to position a pair of opposing tissue surfaces and separate, lengthen and/or shape hard or soft tissue. Hard or soft tissue can include bone, cartilage, ligaments, tendons, joint capsules, intervertebral discs, etc.

As used herein, an instrument (i.e., a medical instrument) is an article that is utilized to perform an operation or other medical procedure performed on the body of the patient (human or animal) and that is, after the medical procedure is completed, not left in the body. Examples of instruments are scalpels, retractors, scissors, drills, etc.

As used herein, an implant is an article that is inserted in the body during an operation or other medical procedure performed on the body and that is, at the conclusion of the medical procedure, left in the body to perform a selected function. A catheter inserted in a patient's bladder to collect urine is therefore, until it is removed, an implant. Suture inserted in patient's body is an implant. Examples of implants disclosed herein include, without limitation, implants 352A (FIG. 185), implant 650A (FIG. 186), tip 802 of instrument 800 (FIGS. 187, 188), tip 781A (FIG. 184) of instrument 781, and implants 803 to 805, 805A, 805B, 805C, 820, 830, 835 (FIGS. 189 to 205), implant 380 of instrument 340 (FIG. 51), and, implant 352 of instrument 350 (FIG. 52).

In general, a medical procedure is concluded at the point implants are inserted and the medical instruments are no longer required to complete the procedure, and the patient leaves the operating room or is sent, "post-op", to a recovery room in a hospital, home, or other facility. It is, of course, possible for a patient (human or animal) to require a further medical procedure and the use of instruments while in recovery (particularly while in intensive care) or after being removed from recovery, but once such a further medical procedure is completed and the patient is, "post-op", out of the operating room or sent to or remains in recovery, that particular medical procedure is deemed completed.

It is possible for an article to function (1) only as an implant, (2) only as an instrument, and (3) both as an instrument and an implant. In what is a novel aspect of the invention, articles are provided that function both as an instrument and as an implant. This is demonstrated by the use of an implant to oscillate or otherwise pass through tissue to a location in a body where the implant is to be deposited.

The concave resilient spring A10 of FIG. 206 is inserted between a pair of adjacent vertebra, i.e. joint, to space the vertebra apart and to permit a desired tilt of one vertebra with respect to the other. If spring A10 is stiff, spring A10 limits the tilting of one vertebra with respect to another. If spring A10 is not stiff, and is readily compressed, then spring A10 permits more tilting of one vertebra with respect to another. When spring A10 is inserted, upper end A101 bears against one vertebra while lower end A102 bears against the other vertebra.

The convex resilient spring A11 of FIG. 207 is inserted between a pair of adjacent vertebra, i.e. joint, to space the vertebra apart and to permit a desired tilt of one vertebra with respect to the other. If spring A11 is stiff, spring A11 limits the tilting of one vertebra with respect to another. If spring A11 is not stiff, and is readily compressed, then spring A11 permits more tilting of one vertebra with respect to another. When spring A11 is inserted, upper end A111 bears against one vertebra while lower end A112 bears against the other vertebra. If the height of springs A10 and A11 is the same, and the resistance of each spring to compression (i.e., joint dampening by pressing ends A101 and A102, or, ends A111 and A112 toward each other) is the same, spring A10 ordinarily allows more tilt than spring A11. As the cant, or tilt, of one vertebra with respect to another increases, the resistance of spring A10 or A11 increases and tends to prevent or slow further tilting. In FIG. 208, dashed lines A120 indicate the tilting of vertebra A12 in the direction of arrow 121 with respect to vertebra A13. The tilting of vertebra A12 is exaggerated for purposes of illustration.

FIG. 208 illustrates a cylindrical resilient spring A14 inserted between a pair of adjacent vertebra A12, A13 to space apart the vertebra and to permit a desired tilt, or canting, of one vertebra with respect to another. The upper end of spring A14 contacts the bottom of vertebra A12. The lower end of spring A14 contacts the top of vertebra A13.

The ovate implant A15 illustrated in FIG. 209 is fabricated from bone, metal, polymer, gel, or some other resilient material. If desired, an aperture can be formed through implant A15 to permit the implant to slide along a guide wire to a desired location in a patient's body. Alternatively, implant A15 can be slide through a hollow guide member to a desired location in a patient's body. One use of implant A15 is to serve as a resilient spacer when inserted between a pair of vertebra. Another use is to permit one vertebra to tilt with respect to another when implant A15 is inserted between a pair of vertebra. The implant can be slotted so the implant A15 functions in a manner similar to a coil spring and has a structure similar to a coil spring. Slot A15A functions to absorb or dampen compressive loads applied to implant A15 within a joint.

Another implant A16 is illustrated in FIG. 210. Implant A16, as can implant A15 (FIG. 209) and A18 (FIG. 211) and A20 (FIG. 212) and A21A (FIG. 212A), be fabricated from any desired material. Implant A16 is, however, presently preferably fabricated from a resilient material and includes upper concave surface A11 with edge, or tooth, A171.

Implant A18 illustrated in FIG. 211 is presently, although not necessarily, fabricated from resilient material and includes groove A19 that initially increases in width as the distance into groove from surface A191 increases.

Implant A20 illustrated in FIG. 212 is presently, although not necessarily, fabricated from resilient material and includes upstanding tooth A21 depending from surface A212. Implant A21A illustrated in FIG. 212A is presently, although not necessarily, fabricated from resilient material and is inserted into a joint and can function to dampen compressive loads and includes groove A21B that has an initial inverted pyramid opening A21D that inwardly tapers and decreases in width and then expands as the distance into the groove from the outer surface A21C increases to form a cylindrical opening A21E adjacent the inverted pyramid opening A21D.

Instrument A32 in FIG. 213 includes a tapered distal end or tip A24, proximate end or elongate handle A22, and outwardly projecting cam member A25. Cam member A25 can be rounded or shaped and dimensioned to not cut tissue, or, if desired, can include an outer cutting edge. When member A25 is not shaped to cut tissue, instrument A32 can be utilized in various ways.

A first application of instrument A32 is to insert instrument A32 in tissue such that cam A25 is adjacent a principal vasculature or principal nerve. The instrument is then rotated a sufficient distance in a direction indicated by arrows A23 about the longitudinal axis of elongate handle to permit cam A25 to contact and laterally displace the principal vasculature or principal nerve away from the longitudinal axis of handle A22. Instrument A32 is pushed further into tissue in a direction parallel to the axis of displacement. In this manner, cam A25 assists in displacing principal vasculature or principal nerves to permit the safe passage of instrument A32 and of an implant or other article carried by or mounted on instrument A32.

A second application of instrument A32 is to insert instrument A32 in tissue and then to rotate instrument A32 in a direction indicated by arrows A23 to separate the tissue to either form an opening in the tissue or to produce a portion of tissue (separate tissue) that is no longer connected to the adjacent portion of tissue.

When cam A25 is provided with a cutting edge, then inserting tapered tip A24 and cam A25 into tissue and turning instrument A32 in a direction indicated by arrows A23 enables cam A25 to cut tissue. A guide wire can be provided and cam A25 can be housed within tip A24. Moving a guide wire along the interior of instrument A22 can deploy recessed cam A25 similar to deployable wing 833A in FIG. 198.

Additionally, instrument A32 can include one or more optical elements 321d as described herein. The optical elements 321d can be coupled to an optical or other imaging system to allow for visualization of the tissues during the procedure described to be implemented by instrument A32, and can allow for visualization before, during and after inserting the instrument, displacing tissue such as nerves or vasculature, or cutting tissue, such as the annulus or other disc tissue.

The implant illustrated in FIG. 214 includes a pair A30, A26 of members that can be removably interlocked one with the other by sliding member A30 into member A26 such that U-shaped grooves interfit. The shape and dimension of members A30 and A26 can vary widely as long as members A30 and A26 can be interlocked or interfit one with the other. Apertures A34 and A35 are formed through members A30 and A26, respectively, such that a wire can inserted through apertures A34 and A35 and the implant can be inserted by sliding the implant along a wire. Members A30 and A26 can function as an implant assembly of two components removably interfit as a unitary implant. Members A30 and A26 can slide along a guide member (not shown) through apertures A34 and A35. A guide wire, (or hollow guide unit), can maintain the assembly as a unitary implant until dispensed at a selected location within the body, and the members A30 and A26 can remain unitary or separate into two portions.

Cutting instrument A40 is illustrated in FIGS. 215 to 217 and includes opening A48 extending therethrough and bounded by cutting edges A41 and A45. Aperture A42 is formed through the front end A46 of instrument A40. Aperture A43 is formed through back end of handle A44. Apertures A42 and A43 permit a wire to pass therethrough and also through opening A48 such that instrument A40 can be slid along a guide wire such as an elongate light guide configured as a guide wire, or through a hollow guide unit such as en elongate light guide configured as a cannula with an internal lumen, to a desired location in a patient's body. Once instrument is at a desired location in the patient's body, it is rotated in the manner indicated by arrows A47 (FIG. 216) about the longitudinal axis of handle A44 and instrument A40 such that edges A41 and A45 contact and cut tissue.

Another cutting instrument A50 is illustrated in FIGS. 218 to 221 and includes opening A58 extending therethrough and bounded by cutting edge A55. Aperture A52 is formed through the front end of instrument A50. Aperture A53 is formed through handle A54. Apertures A52 and A53 permit a wire, such as optical guide wire to pass therethrough and through opening A58 such that instrument A50 can be slid along a guide wire or along a hollow guide unit to a desired location in a patient's body. Once instrument A50 is at a desired location in the patient's body, it is rotated in the manner indicated by arrows A56 (FIG. 218) about the longitudinal axis of handle A54 and instrument A50 such that edge A55 contacts and cuts tissue.

Still a further cutting instrument A60, similar to instruments A40 and A50, is illustrated in FIGS. 222 to 227 and includes opening A68 extending therethrough and bounded by cutting edge A61. Aperture A62 is formed through the front end of instrument A60. Aperture A63 is formed through handle A64. Apertures A62 and A63 permit a guide wire, such as the elongate light guide, to pass therethrough and through opening A68 such that instrument A60 can be slid along a guide wire, or through a hollow guide unit, to a desired location in a patient's body. Once instrument A60 is at a desired location in the patient's body, it is rotated in the manner indicated by arrows A66 (FIG. 226) about the longitudinal axis of handle A64 and instrument A60 such that edge A61 contacts and cuts tissue.

FIGS. 227A and 227B illustrate an alternate embodiment A60A of the instrument

A60. Instrument A60A includes aperture A63A extending completely through instrument A60A along the longitudinal centerline thereof. The apertures A62A and/or A63A can be configured as a conduit for an elongate light guide or having an elongate light guide. The elongate light guide can also pass through the opening A68 from the aperture A63 to aperture A62. Handle A64 is connected to elongate cylindrical neck A65. Handle A64 facilitates insertion of edge A61 in a patient's body and facilitates rotation A69 of neck A65 about the longitudinal axis of instrument A60A.

Cam A25 in FIG. 213, instrument edges A41 and A45 in FIG. 215, edge A55 in FIG. 219, and edge A61 in FIG. 227A can be serrated, toothed, textured, etc., and can be configured as desired.

Implant insertion tool A73 is illustrated in FIGS. 228 to 231 and includes insertion end A70 attached to one end of hollow handle A75 and handle A74 attached to the other end of handle A75. Tool A73 is slidably mounted on a guide wire (not shown, but which can be en elongate light guide) that extends through aperture A76 in handle A 74 (FIG. 231), through hollow handle A75 (FIG. 230), and through aperture A78 formed in insertion end A70 (FIG. 228). Tool A73 could be slidably mounted in a hollow guide unit along with or without a guide wire. If an implant is mounted at end A70, the guide wire, such as an elongate light guide, may also slidably pass through the implant. In use, tool A73 is slid along the wire, or through a hollow guide unit, until end A70 is at a desired location in a patient's body. An implant comparable to implant B66 in FIG. 230, 231D is mounted on pin A72 (FIG. 230) or is otherwise mounted on end A70. Once the implant reaches a desired location, handle A74 and/or handle A75 is utilized to withdraw instrument A73 from the patient's body. Pin A72 slides out of the implant, leaving the implant intermediate a pair of vertebra, in a joint, or at another desired location in the patient's body. Pin A72 is fixedly secured in aperture A71 (FIG. 228). Alternatively, pin A72 is fixedly secured to the implant and slides out of aperture A71 and remains in an implant when tool A73 is extracted from a patient's body. Pin A72 can also control rotation or the orientation of an implant turned onto threaded insertion end B64 of instrument B60 in FIG. 231A. For example, when instrument B60 is unthreaded from the implant (for example implant B66 in FIG. 231D) and is removed from instrument A73 pin A72 prevents the implant from rotating. Accordingly, the implantation tool A73 and insertion end A70 can be used with the elongate light guide configured as a guide wire for visualization of any aspect of the implantation procedure.

FIGS. 231A, 231B illustrate an elongate instrument B60 includes head or handle B61 connected to one end of elongate neck B62. The other end B64 of neck B62 can, if desired, be internally or externally threaded to removably connected to a pin or aperture on an implant. Aperture B63 extends completely along the length of instrument B60 and along the longitudinal centerline of neck B62 and permits a wire, such as an elongate light guide, or other elongate guide member to be slidably inserted in aperture B62 such that instrument B60 can slide along the guide member to a desired location in a patient's body. Accordingly, the elongate instrument B60 can be used with the elongate light guide configured as a guide wire for visualization of any aspect of the implantation procedure, where the elongate guide member can extend from the handle B61 and other end (e.g., distal end B64).

FIGS. 231C, 231D, and 231E illustrate how instruments B60 and A73 can be utilized cooperatively by sliding the neck B62 into hollow instrument A73 in the manner indicated by arrow B65 in FIG. 231C. FIG. 231D illustrates instruments B60 and A73 assembled with an implant B66 mounted and turned on externally threaded end B64. Pin A72 (FIG. 230) is slidably inserted in implant B66 to prevent implant B66 from rotating about the longitudinal axis of necks B62 and A75 (FIGS. 231C and 230). The instrument assembly illustrated in FIG. 231D can slidably move along an elongate guide wire (not shown, which can be an elongate light guide), through a hollow guide unit, or other guide member until implant B66 is at a desired location in a patient's body. Handle B61 is rotated in the direction indicated by arrow B67 (FIG. 231D) to unthread end B64 from implant B66. After end B64 is unthreaded, instruments A73 and B60 are pulled along the guide wire in the direction of arrow B68 in FIG. 231D. Pin A72 slides out of implant B66, leaving B66 in place in the patient's body. The elongate light guide can also be used with this configuration.

FIGS. 232 to 235 illustrate another instrument A80 that can be utilized to penetrate, separate, or cut tissue, and be used as a guide for an elongate guide member. The pointed distal end of instrument A80 includes conical surface A82. Handle A87 is relatively short as pictured in FIG. 232, and normally is significantly longer so handle A87 can, practically speaking, extend from a point exterior a patient's body to a location in the patient's body and can be manipulated as a lever. The instrument A80 and handle A87 can be any length that is suitable for insertion adjacent to or into a disc between adjacent vertebras. Although the length of the handle of an instrument can vary as desired, other handles that are shown in the drawings herein and that are relatively short typically are, in practice, longer. Aperture A81 is formed through handle A87 and the distal end of instrument A80 such that a guide wire, such as en elongate light guide, can be inserted through aperture A81 and instrument A80 can be slid—to a desired location in a patient's body—along the guide wire in a direction generally parallel to, but offset from, the longitudinal axis of instrument A80. Once the distal end of instrument A80 is at a desired location in a patient's body, instrument A80 can be rotated about a wire in aperture A81 in the manner indicated by arrows A83. Instrument A80 can be manipulated as a lever when inserted into a joint. Instrument A80 can displace vertebra, altering the orientation, alignment, etc. of the vertebra, and/or shape of the disc when inserted intermediate two adjacent vertebra. Since aperture A81 is offset from the longitudinal axis of instrument A80, instrument A80 functions along its length like a cam, or lever, much like instrument A32 illustrated in FIG. 213. Consequently, instrument A80, like instrument A32, can be utilized to pass by principal vasculature or principal nerves, can be used to separate tissue, and can, if provided with a cutting edge at its distal end, be used to cut or resect tissue. Handle A87 includes end A84. Instrument A80 can be hollow and used in a cam-like manner and/or as a lever, to separate, move, or displace tissue and principal blood vessels and nerves to safely deliver an implant to a desired location in a patient's body, as is described below in conjunction with FIGS. 235E, 235F, 235G, 235H, 235I. After instrument A80 is slid over a guide wire, either instrument A80 or the guide wire can function as an elongate guide unit. Another hollow instrument (not shown) or an implant can slide along the guide wire or instrument A80.

FIGS. 235A to 235D illustrate another instrument C60 that can be utilized to penetrate, separate, or cut tissue. The pointed distal end of instrument C60 includes conical surface C66. Handle C67 is relatively short as pictured in FIG. 235A, and normally is significantly longer so handle C67 can, practically speaking, extend from a point exterior a patient's body to a location in the patient's body and can be manipulated as a lever. Although the length of the handle of an instrument can vary as desired, other handles that are shown in the drawings herein and that are relatively short typically are, in practice, longer. Apertures C61, C62, and C63 are formed through handle C67 and the distal end of instrument C60 such that one or more guide wires, such as an elongate light guide, can be inserted through apertures C61, C62, or C63 and instrument C60 can be slid—to a desired location in a patient's body—along the guide wire in a direction generally parallel to, but offset from, the longitudinal axis of instrument C60. Once the distal end of instrument C60 is at a desired location in a patient's body, instrument C60 can be rotated about a wire in aperture C61, C62, or C63 in the manner indicated by arrows C69. A wider circumferential tissue separation occurs when instrument C60 is rotated about axis C61 or C63 when compared to moving tissue by rotating instrument C60 about central axis C62. Conical surface portion C65 with offset axes C61 and C63 provide instrument sections of at least two different widths. Instruments C60 can function with variable axes of rotations. Since aperture C61 (and C63) is offset from the longitudinal axis of instrument C60, instrument C60 functions along its length like a cam, much like instrument A32 illustrated in FIG. 213 and instrument A80 illustrated in FIGS. 232 to 235. Consequently, instrument C60, like instruments A32 and A80, can be utilized to pass by principal vasculature or principal nerves, can be used to separate tissue, and can, if provided with a cutting edge C65 at its distal end, be used to resect tissue. Handle C67 includes end C68. If a guide wire is inserted through central aperture C62 or offset axis C61, C63, instrument C60 can be utilized in a cam-like fashion in the manner described below with respect to hollow instrument A80B in FIGS. 235E-I. Instrument C60 can also function as an elongate guide unit after sliding over a guide wire and another hollow instrument (not shown) can slide over instrument C60 or an implant can slide through instrument C60. The elongate light guide configured as the guide wire can also allow for visualization for enhanced performance of the medical procedure.

FIGS. 235E to 235H illustrate a hollow embodiment A80B of instrument A80. Instrument A80B can, if desired, include a plunger or syringe B72 that can function either to push an implant B74 out end B81 or, when syringe B72 slidably seals against inner cylindrical surface B73 of instrument A80B, can function to generate suction when syringe B72 is displaced in the direction of arrow B 81 (FIG. 235E). The instrument A80B can also include an elongate light guide for visualization of the medical procedure, where the elongate light guide can be inserted through inner cylindrical surface B73, when configured as an internal conduit. Implant B74 can fit around the elongate light guide. When syringe B72 is utilized to generate suction, it can draw tissue or an implant up into end B81.

The use of instrument A80B in a cam-like fashion is illustrated more precisely in FIGS. 235F to 235H. FIGS. 235F and 235G illustrate instrument A80B inserted such that pointed, canted, end B81 is adjacent a nerve B76. The oval mouth B86 at end B81 "opens up" in FIGS. 235F and 235G. When instrument A80B is rotated in the direction of arrow B78, the peripheral oval-shaped edge of mouth B86 contacts nerve B76, and, as instrument A80B continues to rotate, pushes nerve B76 laterally in the direction of arrow B77 and permits instrument A80B to move past nerve B76 in the direction of arrow B79 (FIG. 235G). After instrument A80B is rotated about a quarter-turn (the amount by which instrument A80B is rotated can, of course, vary as desired) or is laterally displaced, and is forwardly advanced, it is in the position illustrated in FIGS. 235H and 235F (as dashed lines A80BR), with mouth B86 adjacent and generally conforming to the peripheral surface B83 of disc B75. An alternate position A80B2 of instrument A80B is also shown in FIG. 235F prior to instrument A80B2 being rotated, laterally displaced, or forwardly advanced. The new position A80B3 of instrument A80B after being laterally displaced is further illustrated in FIG. 235I. Consequently, instrument A80B can, as desired, be rotated, laterally displaced, and/or forwardly advanced after instrument A80B is place in a desired position adjacent principal vasculature or nerves. Visualization with an elongate light guide can also enhance positioning without damaging nerves.

For example, the elongate light guide can be used for visualizing vertebral separation, implant expansion or articulation, and implant effects on adjacent tissues during internal traction. Visualization can be used to identify problematic areas in order to prevent subsidence of the implant from vertebral endplate fracture.

FIG. 235I illustrates instrument A80B being inserted on a side of the spine opposite that illustrated in FIG. 235F. Instrument A80B can be inserted in any desired direction as indicated by positioning end B81 of instrument A80B in FIG. 235F and FIG. 235I. Instrument A80B can be laterally displaced in the manner indicated by dashed lines A80B3 in FIG. 235I.

FIGS. 236 to 241 illustrate an implant A90, with apertures A91 (FIG. 237) and A92 (FIGS. 239, 241) that receive a guide wire and permit implant A90 to slide therealong to a desired location in a patient's body. Aperture A91 is formed in tip A93. Opening A94 (FIG. 237) extends through implant A90 and can removably house in aperture A94 a second component (not shown) such as bone, polymer, spring, etc. such that a guide wire or other guide member slidably extends through implant A90 and through the second component such that the guide wire maintains the second component in a selected position in implant A90. Opening A94 can extend to or from one or more sides of an implant. In FIG. 237, opening A94 extends to four different sides of the implant A90. This provides ease of insertion between a pair of vertebra and implant A90 can function between the vertebra regardless of the orientation of implant A90 during, before, and after implant A90 is inserted between the vertebra. When the implant A90 is inserted, each one of an opposing pair of the sides ordinarily will always contact a pair of opposed adjacent vertebra, and, each of the sides will open on a portion of a second component housed in implant A90.

FIGS. 242 to 248 illustrate an implant B10, with apertures B11 (FIG. 243) and B12 (FIG. 248) that receive a guide wire and permit implant B10 to slide therealong. Opening B15 (FIG. 242) extends through implant B10. Circular openings B13 (FIG. 247) may or may not be formed through wall of implant B10. Toothed openings B14 are formed in implant B10 and initially widen as the distance into the openings B14 from the outer surface of implant B10 increases (FIG. 246). Toothed openings B14 can be configured in any desired manner and can, for example, be configured with only a portion of the toothed opening diverging into the implant like opening A21B in FIG. 212A. As shown, a longitudinal toothed opening B14A can be configured to slide along an elongate light guide or other guide feature of an internal conduit of a cannula guide member. Such a longitudinal toothed opening, or a plurality thereof either centered or off-axis, can be included on any of the implants described herein.

FIGS. 249 to 252 illustrate a "boat" implant B20 that includes outwardly extending flat surfaces B21 (FIGS. 249 to 252) that are intended to help prevent subsidence of implant B20 into a vertebra or other tissue. Beveled flat surfaces B24, B25 can also function to align implant B20 diagonally within an elongate guide unit such as orthogonal implant cannula 783 (FIG. 184). Surfaces B24, B25 can conform to and slide along an interior portion of cannula 783. Aperture B24 formed in tip B22 (FIG. 250) and aperture B23 receive a guide wire 780 (FIG. 184) that also extends through opening B25 such that implant B20 can slide along the guide wire, such as elongate light guide, to a desired location in a patient's body, after which the guide wire is removed, leaving the implant. Opening B25 (FIG. 251) extends through implant B20 and can house a second component (not shown) such as bone, polymer, spring, etc. such that a guide wire or other guide member slidably extends through implant B20 and through the second component such that the guide wire maintains the second component in a selected position in implant B20. Opening B25 can extend to or from one or more sides of an implant.

FIGS. 253 to 259 illustrate an implant B30 that includes opening B35 (FIGS. 258, 253) formed therethrough and includes apertures B42 (FIG. 261) and B31 (FIG. 258) that receive a guide wire extending through implant B30 so that implant B30 can slide along the guide wire to a desired location in a patient's body, after which the guide wire is, as is usually the case when implants are inserted in a patient's body, removed. Openings B33 (FIGS. 257, 258) may or may not be formed through a wall of implant B30. Toothed openings B34 (FIGS. 257, 258, 259) are formed on implant B30. Toothed openings B34 can also be configured in any desired manner and can, for example, be configured like opening A21B in FIG. 212A.

FIGS. 260 to 267 illustrate an implant B40 that includes opening B47 (FIG. 265) formed therethrough and includes apertures B42 (FIG. 261) and B44 (FIG. 267), each of which receive a guide wire that extends through implant B40 such that implant B40 can slide along the guide wire to a desired location in a patient's body. Aperture B42 extends through nose B46. Toothed openings B41 (FIG. 261) are formed in implant B40.

FIGS. 268 to 272 illustrate a two piece implant B50 that includes body members nose B51 pivotally attached to tail B52 by hinge pin B53. Implant B50 functions in a manner similar to implant 502 in FIGS. 110-112. Apertures are formed through implant B50 such that it can received and slide along a guide wire to a desired location in a patient's body. Nose B51 can either remain attached to tail B52 by pin B53 or can detach from tail B52 after being dispensed from a guide wire (not shown) or hollow guide unit. Implant B50 can function as one or two implants, one implant when the nose and tail remain attached, and two implants when the nose and tail separate. Body members nose B51 and tail B52 can articulate on hinge pin B53 after implant B50 is dispensed from an elongate guide unit. The elongate guide unit can comprise, for example, a guide wire or hollow guide tube or member. The degree or amount that implant B50 and implant 502 (FIGS. 110-112) articulate while moving in or along a joint (or disc) depends on the resistance, shape, elasticity, hardness, etc. of the joint (or disc). Implant B50 can consist of a string of two or more pivotally connected, articulating body members.

Problems associated with inserting an implant in a joint, including by way of example and not limitation, an intervertebral disc, include identifying the general location of the subject disc, identifying the location of an instrument with respect to the subject disc, and identifying the specific desired or damaged location in the disc or intermediate a pair of vertebra.

One method of facilitating locating a subject disc comprises first identifying, by fluoroscopy the general location of the disc, then by light source, camera, arthroscopy, endoscopy, laparoscopy, open direct visualization, or other means, observing the disc.

One specific method of locating a diseased, injured, degenerated, or otherwise damaged portion in the disc is by observing the color, texture, contrast, shape, elasticity, hardness, and the like relative to the color, texture, contrast, shape, elasticity, hardness, etc. of a normal, healthy, undamaged portion of the disc.

Another method of locating a diseased, injured, degenerated, or otherwise damaged portion in the disc is by observing the color, texture, contrast, shape, elasticity, hardness, etc. relative to the color, texture, contrast, shape, elasticity, hardness, or the like of a normal, healthy, undamaged portion of the disc after staining, injecting contrast, removing tissue or manipulation.

Another specific method of locating a damaged portion in the disc is by observing the color, texture, contrast, shape, or the like of tissue adjacent the disc after contrast or colored dye is inject inside the nucleus of the disc, and leaks out from the disc through a tear staining or highlight the preexisting rupture or openings made in the disc, identifying the disc portion to be treated and or location for an implant to be inserted.

Diseased, injured degenerated, or otherwise damaged tissue appears torn, ruptured, frayed, rough, discolored, deformed, etc., compared to normal smooth, healthy tissue. Likewise, damaged tissue accepts stain, contrast, light, or the like differently from normal undamaged tissue. Variation in tissue color, shade, contrast, texture, shape, or the like can reveal the degree to which the tissue is damaged.

The operator palpating tissue with an instrument can locate a damaged portion. A surgeon pushing a needle or guide wire, such as elongate light guide, in a disc can determine the elasticity or hardness of the annulus and locate a tear.

The surgeon clinically determines superficial (skin) landmarks corresponding to a disc (joint) location and inserts a needle into the skin. The needle is advanced towards the disc using fluoroscopy, x-ray, ultrasound, computer tomography, or other means. The disc is palpated and penetrated with the needle. A guide wire is inserted along the needle further palpating the disc. The needle can be removed. A dilator can be inserted along the guide wire. Optionally, the elongate light guide can have an end configured as a needle, such as being sharp, and thereby the elongate light guide can be operated as both the needle and guide wire. A hollow guide unit can be inserted along the dilator. The dilator can be removed. A light source, camera, arthroscope, combination thereof or the like can be inserted along the guide wire, with or without using the dilator, and/or along the hollow guide unit. The disc is visualized. The disc can be treated and/or implant inserted. Positioned instruments, treated disc and/or the inserted implant can be visualized with a fluoroscope, light source, camera, arthroscope, or any desired means. However, the guide wire can be an elongate light guide as described herein.

Another specific method of identifying the desired area of the disc is by changing the color, texture, contrast, or shape of a portion of the disc. One way of changing the color, contrast, texture, shape, etc., of a particular area of a disc is by resecting a portion of the disc. This causes blood vessels within tissues, vertebra, etc., adjacent the disc to bleed, which changes the color of the disc. One way of changing the color of a particular area of a disc is by using a syringe or other means to inject a dye (e.g., a colored dye or contrast dye) into a particular area of the disc to change the color and/or contrast of the disc. When the color and/or contrast of a disc or portion of a disc (or vertebra) is altered, the location of an instrument in a patient's body can be determined with a fluoroscope, elongate light guide, or other means and correlated with the location of the portion of the disc that has changed color and/or contrast. Similarly, removing damaged tissue by smoothing or roughening the disc can prepare the disc for an implant. Manipulating a disc or vertebra with any of the instruments discussed herein can change the shape of the disc or joint. A colored dye can sometimes function as a contrast dye when viewed radiographically, viewed with a camera, or viewed by any other desired means.

Other physical or chemical or electrical properties of a disc (or vertebra or joint or nerve or blood vessel) can be monitored to facilitate locating the disc and locating the position of an instrument or implant with respect to the disc. For example, the initial contrast, hardness, elasticity, texture, conductivity, or other property of the disc or adjacent tissues can be determined, followed by monitoring the disc, or an area of the disc, or area adjacent the disc, to determine when and if a change in the property occurs in order to safely insert an instrument, treat tissue, and/or insert an implant.

In an alternate embodiment of the invention, a hinged implant (for example, implant B50 (FIG. 270) is provided with a pin B53 or other hinge made of metal. The hinge interconnects the nose B51 and tail B52. The nose B51 and tail B52 are made from a polymer. The metal pin B53 facilitates location of the implant B50 in an individual's body or joint because the pin B53 is fabricated from metal and can be more readily located radiographically or by other desired methods.

In a further embodiment of the invention instruments and/or implants are adapted (configured) to pass by flexible devices previously inserted, which flexible devices can, for example, comprise a flexible wire, flexible light guide, or cannula or any combination thereof. A rod or other support member that is secured along and inside or outside the spine or another joint can have an access portion that includes an opening that permits a desired instrument to access a particular selected area of the spine. The access portion can, by way of example and not limitation, be hollow, be C-shaped, be bent, be curved, be straight, or extend laterally to one side of a desired area of the spine. Consequently, a rod secured along the spine can have a C-shaped portion connected to and intermediate straight portions of the rod. When the rod is installed, the C-shaped portions extends around a selected area of the spine and permits ready access to the selected area of the spine by a particular instrument or instruments or implants. The implants and instruments described herein can be constructed of rigid, semi-rigid, or resilient (flexible, elastic, etc.) material to conform around implants or instruments or joints or discs, through openings in implants or instruments or joints or discs, or adjacent to existing implants or instruments or joints or discs.

Use of Spring and Hinge in Implants

In one embodiment of the invention, an implant comprises a spring. See FIGS. 16, 17, 28, 29, 206, 207, and 209.

In another embodiment of the invention, an implant includes a spring that functions to space apart and separate portions of an implant. See FIG. 208.

In a further embodiment of the invention, an implant functions as a hinge. See, for example, FIGS. 34 to 40.

In still another embodiment of the invention, an implant includes a hinge. The hinge can be generally horizontally oriented in the manner illustrated in FIGS. 90 (pin 483), 150 to 152 (pin 603), 161 to 163 (pin 621), 172 to 175 (pins 675, 679), 192 (leg 810), or, the hinge can be generally vertically oriented in the manner indicated in FIGS. 110 to 112 (pin 503), 149 (pin 422), 199 to 201 (ball and socket), and 268 to 271 pin B53). Other pivots or hinges are illustrated in FIG. 1 as shaft 59, members 42A and 43A, and cam 10, in FIG. 9 as device 76, in FIGS. 35 and 36 as apparatus 230, in FIGS. 37 and 38 as apparatus 234, in FIGS. 39 and 40 as apparatus 245, and the like.

FIG. 273 illustrate a spring B67 and hinge B64 utilized in combination to open an implant by causing portions B61, B62 of implant B60 to pivot about hinge pin B64 extending through each of said portions. Portions B61, B62 presently are fabricated from rigid metal, but can be constructed from elastic material, from bendable material, or from any desired material. When implant B60 is being inserted at a desired location in the body of a patient, in particular at a desired location in the spine of the patient, implant B60 slides along a guide wire extending through elongate apertures B71 and B72 (shown in FIG. 275). The wire is sized such that apertures B71 and B72 are, in contrast to the misalignment of apertures B71 and B72 in FIG. 275, co-linear and in alignment. When apertures B71 and B72 are in alignment, portions B61 and B62 are in alignment in a linear configuration; stop surfaces B65 and B66 are, in contrast to FIG. 273, spaced apart from and do not contact each other; and, spring B67 is compressed between and extends from opening B73 in portion B61 to opening B74 in portion B62 (FIG. 275). If desired, in addition to or in place of the guide wire, such as elongate light guide, implant B60 can be inserted in the body of a patient by sliding implant B60 down an elongate guide tube, sleeve, or other guide unit or member that functions to maintain implant B60 in alignment and to prevent portions B61 and B62 from pivoting about hinge pin B64. As soon as implant B60 leaves an end of the guide wire, or leaves the end of the elongate guide tube, portions B61 and B62 are free to pivot about hinge pin B64; and, compressed spring B67 expands and causes portion B62 to pivot about hinge pin B64 in the manner indicated by arrows B68 and B69 so that portions B61 and B62 assume the open arcuate orientation illustrated in FIGS. 273 to 275. When implant B60 is in the open orientation illustrated in FIGS. 273 to 275, stop surfaces B65 and B66 contact each other in the manner illustrated in FIG. 273 and prevent further pivoting of portions B61 and B62 about hinge pin B64 in the direction of arrow B68. The size and shape of apertures B71 and B72 can vary as desired. Conically shaped openings B71A, B72A function to prevent a guide wire from binding by producing a smooth arcuate path between apertures B71 and B72 when these apertures are canted with respect to one another. This is important because when spring B67 expands and causes portion B61 to pivot and cant with respect to portion B62, portions of the sides of apertures B71 and B72 are forced against a wire extending through said apertures and, accordingly, generate frictional forces acting on the wire. Consequently, openings B71A and B72A facilitate implant B60 smoothly sliding along a wire extending from portion B61 to portion B62 of implant B60.

If desired, in another embodiment of the invention, instead of utilizing a tensioned spring B67 that functions to push apart portions B61 and B62 in the manner illustrated in FIGS. 273 to 275, a tensioned spring, indicated by dashed line B78 in FIG. 273, can be utilized that functions to pull portions B61 and B62 from a linear orientation to the open orientation that is illustrated in FIGS. 273 to 275. When such a tensioned "pulling" spring is utilized in place of the "pushing" spring B67, the portions B61 and B62 of implant B60 are still maintained in a linear orientation while the implant B60 slides down a guide wire or along a guide tube, which guide wire or guide tube can be configured as an elongate light guide. Once the implant B60 exits the guide wire or guide tube, spring B78 (FIG. 273) pulls portions B61 and B62 from the linear orientation to the open arcuate orientation illustrated in FIGS. 273 to 275.

The spring utilized to push or pull portions B61 and B62 into an open orientation (or from an open orientation into a linear orientation) can be mounted on the exterior of and extend between portions B61 and B62 in the manner indicated by dashed lines B77 in FIG. 273. If desired, implant B60 can reform or articulate from a first linear configuration to a second arcuate configuration simply by contacting a resistance within a joint after the implant B60 is released from a guide unit. As utilized herein, reform means to change shape. Conform means to chance shape in response to forces generated by an adjacent joint or other tissue.

Multiple Articulations

The implant B60 has a single articulation, i.e., has a single articulating joint. As is illustrated in FIGS. 276 to 281, an implant B80 can have two or more articulations. Implant B80 has three articulations. Implant B80 includes portions B81, B82, B83, and B84. Hinge pin B85 pivotally interconnects portions B81 and B82. Hinge pin B86 pivotally interconnects portions B82 and B83. Hinge pin B87 pivotally interconnects portions B83 and B84. FIGS. 276 to 278 illustrate implant B80 in a linear orientation. FIGS. 279 to 281 illustrate implant B80 in an open, arcuate orientation. When implant B80 is in a linear orientation, it extends over an area of an adjacent joint or other tissue that is generally circumscribed and indicated by dashed lines B88 in FIG. 276. When implant B80 is in an open, arcuate orientation, it extends over an area of an adjacent joint or other tissue that is generally circumscribed and indicated by dashed lines B89 in FIG. 279. The area indicated by dashed lines B89 is greater than the area indicated by dashed lines B88 because hinge pins B85, B86, B87 are spaced apart from the elongate centerline BX of implant B80 (FIG. 276) and permit implant B80 to articulate into an open arcuate orientation. When implant B80 is in the linear orientation of FIG. 276, opposing surfaces C22, C23 are adjacent (and surface C20 and C21 are each adjacent to their opposing surface), and stop surfaces C24 and C25 are spaced apart. After portions B81 to B84 each pivot about their respective hinge pins B85 to B87, surfaces C22 and C23 are spaced apart (i.e., have "opened") and stop surfaces C24 and C25 are adjacent one another. In FIG. 279, implant B80 is in an "open" arcuate orientation, and the pie-shaped opening or space extending between the opposing pair of surfaces C22 and C23 is larger than the pie-shaped opening extending between the opposing pair of surfaces C24 and C25 in FIG. 276. In FIG. 276, implant B80 is in a "closed", linear orientation. Since the pie-shaped opening between opposing surface pair C22 and C23 (and other comparable surface pairs in articulating implant B80) in FIG. 279 is larger than the opening between opposing surface pair C24 and C25 (and other comparable surface pairs in implant B80) in FIG. 276, when implant B80 is in the non-linear arcuate orientation of FIG. 279, it extends over a greater surface area of a joint than when implant B80 is in the linear orientation of FIG. 276. This result is achieved in implant B80 because pivot pins B85 to B87 are laterally spaced away from centerline BX (FIG. 276).

If, after an implant is inserted in a joint, the implant alters shape and the joint surface area over which the implant extends is increased, such an increase tends to minimize migration of the implant and to reduce the amount of subsidence of the implant into adjacent joint tissue.

The hinge pin B64 (FIG. 275) for implant B60 is also, like hinge pins B85 to B87, spaced apart from the center line that passes through implant B60 when implant B60 is in a linear orientation. This offsetting of pin B64 facilitates the articulation of implant B60 from a linear orientation to an open, arcuate orientation. The size of the area covered by implant B60 can, however, also be increased if pin B64 is, instead of being offset from the centerline BX of implant B60, positioned on the centerline. This is accomplished by placing pin B64 in a slot B70 that permits pin B64 to slide along the slot so that portion B62 is pushed away from portion B61 by a compressed spring that extends between portions B61 and B62, or, is pushed away from portion B61 by forces generated and acting on portion(s) B61 and/or B62. If desired, the spring can, like pin B64, be positioned along the centerline of implant B60 that exists when implant B60 is in a linear orientation. This could permit portion B62 to be pushed directly away from portion B61 such that portion B62 does not cant away from a linear orientation in the manner that portion B62 cants away from a linear orientation in FIG. 275.

Hinge Pins

In FIGS. 273 to 281, the hinge pins B64, B85 to B87 are each positioned between the centerline and periphery of implants B60 and B80, respectively. If desired, a hinge pin B96 can be positioned at the convex periphery of an elliptical implant B95 in the manner illustrated in FIG. 282. When portions B97 and B98 of implant B95 pivot about pin B96 in the direction of arrow B99 from the linear orientation of FIG. 282 to the arcuate open orientation of FIG. 283, pin B96 is said to reside at a concavity of implant B95 because the inner side of implant B95 on which pin B96 resides in FIG. 283 has taken on a concave shape. In contrast, in FIG. 282, pin B96 is said to be located at a convexity of implant B95 because the side of the implant at which pin B96 is located has a convex shape.

In FIG. 284, hinge pin C11 is located at a concavity of implant C10. In FIG. 285, after portions C12 and C13 have pivoted about pin C11 in the direction of arrow C14 to the linear orientation of FIG. 285, hinge pin C11 is located at a convexity of implant C10.

In FIG. 286, hinge pin C16 is located at a concavity of implant C15. Implant C15 is in a closed linear orientation. In FIG. 287, after portions C17 and C18 have pivotally moved about hinge pin C16 in the direction of arrow C19 to the open orientation illustrated in FIG. 287, hinge pin C16 is still located at a concavity of implant C15.

Fixation with Hinge

In one embodiment of the invention, a hinge pin or other hinge is provided with a tooth B75, B76 or other fixation structure that extends outwardly from an implant B60 (FIG. 274). This fixation structure engages, and may penetrate, bone, cartilage, a disc, vertebra, or any other tissue that is adjacent the implant and functions to help secure or fix the implant in position adjacent the tissue. One virtue of this structure is that even though the top and/or bottom of the hinge can engage and be in a relatively fixed position, this normally does not prevent operation of the hinge and does not prevent one portion B61 of an implant from rotating with respect to another portion B62 of the implant, particularly just after the implant has been inserted at a desired location in the body of a patient. Other examples of implant structures that are associated with hinges and that help with teeth to fix an implant in position can be seen in FIGS. 172 and 201.

Positioning Implant in Joint

In one embodiment of the invention, implant B60 is moved along a guide wire to a selected location in a joint or other tissue and only leading portion B61 or B62 is dispensed from the end of the guide wire at a selected location. As soon as portion B62 is dispensed, spring B67 causes leading portion B61 or B62 to pivot about hinge pin B64 such that implant B60 takes on the orientation shown in FIG. 275. The implant B60 is then pushed completely off the guide wire so that the implant B60 moves from the selected location in the joint to another, second, location in the joint. When the implant is moved to the second location in the joint, the implant can encounter resistance which makes leading portion B61 or B62 move in a direction opposite that of arrow B68 so that portion B62 overcomes resistance offered by spring B67 and compresses spring B67, so that leading portion B61 or B62 pivots about pin B64, and so that openings B73 and B74 move somewhat closer together without implant B60 returning to its original linear orientation. When openings B73 and B74 move closer together, implant B60 take on another, third, configuration that is intermediate its original linear configuration and the open configuration illustrated in FIGS. 273 to 275. Likewise, if an implant has two or more articulations, the implant will have the ability to sequentially articulate as it is dispensed and freed from the confines of a guide unit. When the hinge pin of the implant moves free from the guide unit, it is, even though it is linked to an implant portion that is still on and under the constraints of the guide unit, free to articulate to some extent about a hinge or pivot point shared with the portion that is still on and under the constraints of the guide unit. The remaining portion(s) of the implant that are still in or on the guide unit are restricted by the guide unit and normally can only slide up or down the guide unit, such as the elongate light guide. When each of the remaining portions is dispensed from the end of the guide unit, these units too are free to articulate or move. Implant B60 can be at least partially inserted into a joint in a first linear configuration, articulate to a second intermediate configuration, be fixed to the joint by toothed hinge pin B75, B76, and further articulate to at least a third arcuate configuration. Implant B60 can also assume an expanded arcuate configuration by lengthening when a pin on a portion of implant B60 slides along slot B70 in FIG. 275.

The configuration of an implant can, if desired, also vary (i.e., expand or contract) along its length to conform to the shape of a joint. Examples of implants that function to dampen the movement of a joint are seen in FIG. 1, where movement of portions of the implant 100 absorb energy, and are seen in the slotted spring-like implant A15 in FIG. 209. An implant that functions to fuse together opposing joint surfaces can be achieved by filling opening B81A in FIG. 279 with bone or other osteogenic material that fuses to a joint.

In another embodiment of the invention, an implant functions to seal an opening in a disc (or other tissue) because when the implant is dispensed through an opening in the disc to occupy at least a portion of the interior of the disc, the implant changes shape by enlarging, by articulating to a curved orientation from a linear orientation, etc. This change in shape makes it more difficult for the implant to escape from the disc through the opening that was originally used to insert the implant in the disc. When the implant changes shape it can also function to block the opening in the disc, making it difficult to insert other instruments or material in the disc.

If desired, hinge pin B86 in FIG. 276 can be positioned opposite hinge pins B85 and B87 (on the other side of centerline BX of implant B80). When hinge pin B86 is positioned on the other side of centerline BX and hinge pins B85 and B86, then when implant B80 is articulated, implant B80 assume a zig-zag shape wherein hinge pin B86 remains in the concavity of portions B82 and B83, and wherein hinge pin B87 remains in the concavity of portions B83 and 84, and wherein hinge pin B85 remains in the concavity of portions B81 and B82.

In another embodiment of the invention, provided is an improved method to treat an intervertebral disc including an annulus having a height and a width and a periphery, a nucleus circumscribed by the annulus, and nuclear material in the nucleus. The method begins by determining if a rupture is formed in and extends from the nucleus completely through the annulus. If a rupture exists that extends from the nucleus completely through the annulus, an incision is made to expose peripheral white tissue at the periphery of the intervertebral disc. Since nerve tissue and disc tissue are each white to the eye in normal ambient light, a procedure is utilized to visually determine if the peripheral white tissue being viewed is nerve tissue or disc tissue. A first procedure which is utilized comprises directing light, normal light other than normal ambient light (i.e., other than sunlight or indoor lighting utilized in operating rooms, such as infrared light or ultraviolet light or other wavelength that can be observed and/or measured with an instrument coupled with an elongate light guide) at the peripheral white tissue, which light will generate a first color of reflected light for nerve tissue and a second color of reflected light different from said first color for disc tissue. Infrared light, ultraviolet light, or other wavelengths of electromagnetic radiation can be utilized as desired. While this aspect of the invention refers to a first color and a second color, the first and second colors could also be shades or other visually differentiated appearance, whether the first and second color are truly different wavelengths, different intensities, or other differentiations such that the first color is visually or measurable different from the second color. That is, the first and second colors can be other than truly different wavelengths unless specified. However, in some instances, the use of a dye or contrast agent can cause the colors of different tissues to be different such that they look like two different colors.

For example, when performing a medical procedure the medical practitioner may encounter two different tissues where one is damaged. The damaged tissue may be frayed or torn so as to expose more material of the tissue that absorbs color or stains more intensely or differently than undamaged tissue. Similarly, damaged and undamaged portions of the same tissue can be distinguished similarly to as describe for different tissues. Accordingly, a dye or contrast agent can be used so that there is a difference in color between different tissues or difference between damaged and healthy portions of the same tissue. For example, the disc tissue absorbs dye differently than nerve tissue. As such, the same dye will appear to be different colors, shades, or intensity when in different tissues or when in healthy and damaged tissues. Smooth disk where dye doesn't stick, then if torn or frayed, surface area increases and dye sticks and shows. nerve and disk have inherently different absorption of dyes and shows differently when viewed.

Accordingly, the use of a coloring agent can be employed in any of the methods described herein, such as those that use the elongate light guide as described herein. Additionally, the elongate light guide as described herein can be adapted for a coloring agent conduit that allows for the injection of the coloring agent through the elongate light guide so that the coloring agent can facilitate observation or other visual or wavelength analysis of a medical procedure. While an elongate light guide or other elongate guide member is not specifically shown to have a separate conduit for the coloring agent, such a modification is well within the skill of one or ordinary skill in the art. In one example, the optical components 231d as illustrated herein can represent a coloring agent conduit, and a simple plunger mechanism can be used to inject the coloring agent before, during, or after the medical procedure, or injected before or during visualization of the medical procedure, such as in confirming success of the medical procedure.

Some examples of dyes to color tissues can include methylene blue and trypan blue. However, many other dyes may be suitable. For example, it may be possible to use dyes of other colors, such as known or later developed. Also, fluorescent dyes may be suitable, especially when using UV light. In a specific example, methylene blue is a coloring agent that stains the nucleus of the intervertebral disc to distinguish the nucleus from the annulus.

Some examples of contrast agents can include fluorophores such as steryl pyridinium, indocyanine green, or the like. Fluorophores such as steryl pyridinium are contrast agents specific for different spinal structures to distinguish the intervertebral disc from nerve roots, ligaments, bone, and the like. While procedures are described herein with either dyes or contrast agents, either can be used in place of the other in most instances. The term "coloring agent" can be used for both dyes and contrast agents.

A second procedure which is utilized comprises injecting a dye into contact with the white tissue, which dye generating a first color of reflected light for nerve tissue and a second color of reflected light different from said first color of disc tissue. Any desired dye or coloring agent can be utilized. Once it is determined whether the white tissue is nerve tissue and/or disc tissue, an opening can be made in the disc without damaging nerve tissue. After the opening is made, an implant is inserted to treat the rupture. When at the beginning of the foregoing method a determination is made whether there is a rupture in the disc, a determination can also, if desired, be made whether a nuclear herniation extends into and through said rupture and outwardly from the annulus. A first procedure which is utilized comprises directing light, normally light other than normal ambient light (i.e., other than sunlight or indoor lighting utilized in operating rooms) at peripheral disc tissue, which light will generate a first color of reflected light for the nuclear herniation and a second color of reflected light different from said first color for annular tissue, nerve tissue, or other tissue adjacent the disc and nuclear herniation. Infrared light, ultraviolet light, or other wavelengths of electromagnetic radiation can be utilized as desired. A second procedure which is utilized comprises injecting a dye into the disc, which dye will pass outwardly through the rupture and reveal the herniation. The dye can, if desired, generating a first color of reflected light for herniation tissue and a second color of reflected light different from said first color for annular tissue, nerve tissue, or other tissue adjacent the disc. Any desired dye can be utilized.

If such a nuclear herniation exists, it can be treated by making an opening and inserting an implant to generate negative pressure within the disc sufficient to draw inwardly said nuclear herniation through the rupture and back into the nucleus. An implant can be inserted in the disc and extend through the opening made in the disc, through the disc, and through the rupture. Alternatively, after the herniation is treated, the implant may be inserted through the rupture, without making another opening in the disc. The implant will extend into the disc and outwardly through the rupture to seal the rupture. FIGS. 288 to 291 illustrate such an implant, generally indicated by reference character D10. Implant D10 is, as are each of the other implants herein, currently preferably made out of stainless steel or another metal. The material used to make implant D10 and the other implant illustrated herein can vary as desired, and include elastic or resilient or other materials. There are, for example, polymers available that produce a rigid, hard implant generally comparable to that produced by stainless steel. The presently preferred implant components are, however, metallic and substantially rigid, as well as being relatively hard, in the manner of stainless steel. Of course, the implant can include an aperture or slot to be delivered via an elongate light guide member as described herein.

Implant D10 includes a rigid stainless steel body D16 with large apertures D18 formed therethrough and with smaller openings D17. Each opening D17 diverges inwardly beginning at and extending inwardly from the outer surface D19. Openings D17 do not pass completely through implant D10, although such is possible. If an opening passing completely through implant D10, the tissue can be pressed through the top (or bottom) of the implant to the bottom (or top) and press against and meld or attach to the opposing vertebrae, which is presently not preferred. As is evident from various other implants illustrated herein, each opening D17 preferably, although not necessarily, includes an edge D20. Edges 20 function like teeth and tend to grip intervertebral and/or discal tissue that is pressed into diverging openings D17 when an implant D10 is inserted in an annulus (or between a pair of vertebrae if the disc is removed) and is compressed between a pair of vertebrae.

Rotatable wings D11, D12 are each pivotally attached to a different one of the ends of body D16. Each wing D11, D12 normally is in a stowed position in which the wing is aligned and in registration with body D16 in the manner illustrated in FIG. 289. Winds D11, D12 are in this aligned orientation when implant D10 is inserted through an opening made in a disc and through a rupture in the disc such that wing D11 is positioned outside and adjacent the rupture and wing D12 is positioned outside and adjacent the opening. Consequently, implant D10 extends completely through the disc and the end of body D16 extend outwardly through the annulus via said opening or said rupture. After implant D10 is so positioned, wing D11 is rotated ninety degrees in the direction of arrow D24 to the deployed position illustrated in FIG. 288 and wing D12 is rotated ninety degrees in the direction of arrow D25 to the deployed position illustrated in FIG. 288. When wings D11 and D12 are in the deployed position of FIGS. 288, 290, and 291, they seal, partially or completely, the rupture and opening, respectively, in the disc annulus. If desired, screws, bone, adhesive, or other fasteners or fastening material can be inserted through apertures D26 and D27 in wing D12 to secure wing D12 in position. Screws inserted through apertures D26 and D27 would turn into vertebrae D14 and D15, respectively. One or more apertures comparable to apertures D26 and D27 can, if desired, be formed in wing D11 to secure wing D11 to vertebrae D14, and D15. The disc positioned between vertebrae D14 and D15 is omitted from FIGS. 288 to 291 for sake of clarity.

In another embodiment of the invention, provided is an improved method to treat an intervertebral disc including an annulus having a height and a width and a periphery, a nucleus circumscribed by the annulus, and nuclear material in the nucleus. The method begins by determining if a rupture is formed in and extends from the nucleus completely through the annulus. If a rupture exists that extends from the nucleus completely through the annulus, an incision is made to expose peripheral white tissue at the periphery of the intervertebral disc. Since nerve tissue and disc tissue are each white to the eye in normal ambient light, a procedure is utilized to visually determine if the peripheral white tissue being viewed is nerve tissue or disc tissue. A first procedure which is utilized comprises directing light, normal light other than normal ambient light (i.e., other than sunlight or unfiltered indoor lighting utilized in operating rooms) at the peripheral white tissue, which light will generate a first color of reflected light for nerve tissue and a second color of reflected light different from said first color for disc tissue. Infrared light, ultraviolet light, or other wavelengths of electromagnetic radiation can be utilized as desired. A second procedure which is utilized comprises injecting a dye or other coloring agent into contact with the white tissue, which dye generating a first color of reflected light for nerve tissue and a second color of reflected light different from said first color of disc tissue. Any desired dye can be utilized. Once it is determined whether the white tissue is nerve tissue and/or disc tissue, an opening can be made in the disc without damaging nerve tissue. After the opening is made, an implant is inserted to treat the rupture. When at the beginning of the foregoing method a determination is made whether there is a rupture in the disc, a determination can also, if desired, be made whether a nuclear herniation extends into and through said rupture and outwardly from the annulus. A first procedure which is utilized comprises directing light, normally light other than normal ambient light (i.e., other than sunlight or unfiltered indoor lighting utilized in operating rooms) at peripheral disc tissue, which light will generate a first color of reflected light for the nuclear herniation and a second color of reflected light different from said first color for annular tissue, nerve tissue, or other tissue adjacent the disc and a nuclear herniation. Infrared light, ultraviolet light, or other wavelengths of electromagnetic radiation can be utilized as desired. A second procedure which is utilized comprises injecting a dye into the disc, which dye will pass outwardly through the rupture and reveal the herniation. The dye can, if desired, generate a first color of reflected light for herniation tissue and a second color of reflected light different from said first color for annular tissue, nerve tissue, or other tissue adjacent the disc. Any desired dye can be utilized. If such a nuclear herniation exists, it can be treated by making an opening and inserting an implant to generate negative pressure within the disc sufficient to draw inwardly said nuclear herniation through the rupture and back into the nucleus. An implant can be inserted in the disc and extend through the opening made in the disc, through the disc, and through the rupture. Alternatively, after the herniation is treated, the implant may be inserted through the rupture, without making another opening in the disc. The implant will extend into the disc and outwardly through the rupture to seal the rupture. FIGS. 288 to 291 illustrate such an implant, generally indicated by reference character D10. Implant D10 is, as are each of the other implants herein, currently preferably made out of polymer, carbon fiber, or metalor any other suitable or reasonable material. The material used to make implant D10 and the other implant illustrated herein can vary as desired, and include elastic, resilient, porous or other materials. There are, for example, polymers available that produce a rigid, hard implant generally comparable to that produced by porous metal. The presently preferred implant components are, however, solid and substantially rigid, as well as being relatively hard, in the manner of metal. The implant can be grooved, channeled, recessed, or otherwise shaped and dimensioned to allow flexability of rigid materials (FIG. 301)

Implant D10 includes a rigid body D16 with large apertures D18 formed therethrough and with smaller openings D17. Each opening D17 diverges inwardly beginning at and extending inwardly from the outer surface D19. Openings D17 do not pass completely through implant D10, although such is possible. If an opening passing completely through implant D10, the tissue can be pressed through the top (or bottom) of the implant to the bottom (or top) and press against and meld or attach to the opposing vertebrae. As is evident from various other implants illustrated herein, each opening D17 preferably, although not necessarily, includes an edge D20. Edges D20 function like teeth and tend to grip intervertebral and/or disc tissue that is pressed into diverging openings D17 when an implant D10 is inserted in an annulus (or between a pair of vertebrae if the disc is removed) and is compressed between a pair of vertebrae.

Rotatable wings D11, D12 are each pivotally attached to a different one of the ends of body D16. Each wing D11, D12 normally is in a stowed position in which the wing is aligned and in registration with body D16 in the manner illustrated in FIG. 289. Wings D11, D12 are in this aligned orientation when implant D10 is inserted through an opening made in a disc and through a rupture in the disc such that wing D11 is positioned outside, within, and/or adjacent the rupture and wing D12 is positioned outside, within, and/or adjacent the opening. Consequently, implant D10 extends completely through the disc and the end of body D16 extend outwardly through the annulus via said opening or said rupture. Alternatively, implant D10 can reside at least partially, or even completely intermediate two verterbra and when wing D11 or D12 are rotated (by turning a recess (not shown) in wing D11 or D12 with an instrument, wing D11 or D12 functions as a cam to either fix implant D10 to bone or disc by pressing into a vertebra or function as a cam to separate two vertebra. Wings D11, D12 can be toothed, at least partially porous, etched, or coated to facilitate bone to bond, ingrow, or attach into wing D11 or D12 (or any portion or recess of implant D10). Rotating wing D11, D12 expands implant D10 vertically separating adjacent vertebra, and can reshape the disc, reduce pressure, and perform indirect decompression of nerves adjacent the disc with internal fraction. After implant D10 is so positioned, wing D11 is rotated ninety degrees in the direction of arrow D24 to the deployed position illustrated in FIG. 288 and wing D12 is rotated ninety degrees in the direction of arrow D25 to the deployed position illustrated in FIG. 288. When wings D11 and D12 are in the deployed position of FIGS. 288, 290, and 291, they seal, partially or completely, the rupture and opening, respectively, in the disc annulus and can assist in the reduction of a disc hernia. If implant D10 is constructed to permit the wings D11 and D12 to be drawn and move toward one another, such movement of wings D11 and D12 can also assist in reducing a disc hernia and forcing herniated nuclear material back through the annulus and into the disc nucleus. If desired, screws, bone, adhesive, or other fasteners or fastening material can be inserted through apertures D26 and D27 in wing D12 to secure wing D12 in position. Screws inserted through apertures D26 and D27 would turn into vertebrae D14 and D15, respectively. One or more apertures comparable to apertures D26 and D27 can, if desired, be formed in wing D11 to secure wing D11 to vertebrae D14, and D15. The disc positioned between vertebrae D14 and D15 is omitted from FIGS. 288 to 291 for sake of clarity.

If the adjacent vertebra are translated, canted, or rotated with respect to each other, wings can be used to draw together (or separate) the adjacent vertebra into a new orientation. Such realignment forces can be generated with a reversibly threaded member similar to member 827 in FIG. 197.

In a further embodiment of the invention, provided is a method to treat an intervertebral disc including an annulus having a height and a width and a periphery, a nucleus circumscribed by the annulus, and nuclear material in the nucleus. The method includes determining if a rupture is formed in the annulus and a nuclear herniation extends from the nucleus completely through the rupture to the exterior of the annulus. This determination being made by employing one of a pair consisting of (1) directing light at the periphery of the disc, the light generating a first color of reflected light for said nuclear herniation and a second color of reflected light different from said first color for tissue other than said nuclear herniation tissue, and (2) injecting a dye or other colorant into the nucleus of the disc and examining to determine if dye has passed through a rupture in the annulus to a nuclear herniation extending outside the annulus. If a nuclear herniation exists that extends from the nucleus completely through the annulus, an incision is made to expose peripheral white tissue at the periphery of the intervertebral disc. It is then visually determined by the surgeon whether the peripheral white tissue is nerve tissue or disc tissue by employing one of a pair consisting of directing light at the peripheral white tissue, the light generating a first color of reflected light for nerve tissue and a second color of reflected light different from said first color for disc tissue, and of injecting a dye into contact with the white tissue, the dye generating a first color of reflected light for nerve tissue and a second color of reflected light different from said first color of disc tissue. Since in normal unfiltered, ambient light nerve tissue and disc tissue both look white, a surgeon cannot readily visually distinguish nerve tissue and disc tissue. If, however, in accordance with the invention, the surgeon illuminates the tissue with a ultraviolet light, infrared light, or another desired wavelength of electromagnetic wave or radiation, the nerve tissue will have a different color or appearance than the disc tissue, and the surgeon will be able with his eyes (understanding that the surgeon may be looking through a microscope, endoscope, or other instrument) to visually differentiate and distinguish the nerve tissue from the disc tissue.

A meter or sensor can measure the wavelengths of light emitted from the tissues and quantify their amount, above at and/or below a certain threshold, for distinguishing the tissues. Wavelengths of light can be converted to electrical signals using any available means including but not limited to, CMOS or CCD sensors. Such signals can be measured and be converted into auditory signals or sound waves alerting the operator with music, tones, or special sounds such as a roaring lion, etc. Images can also be manipulated using any desired computer software to further distinguish the tissues so that healthy tissue portions and damaged tissue portions can be distinguished, or that different tissues such as nerves and annulus can be distinguished. Modifying the images with software may eliminate the need to inject dye or other materials into or adjacent the disc providing for a less-invasive treatment.

After the surgeon distinguishes the nerve tissue from the disc tissue, he or she is able to make carefully an opening in the disc and is much more likely to accomplish such without damaging nerve tissue. Of course, in some instances, the surgeon may use an existing rupture in a disc and not be required to make an additional opening in the disc. The surgeon then inserts into the disc through the opening at least one implant to treat said nuclear herniation by generating negative pressure within the disc sufficient to draw inwardly said nuclear herniation through the rupture and back into the nucleus. The implant can also extend through the opening, through the disc, and out through the rupture to seal rupture and opening.

Before a disc is treated, an original pressure, $P_O$, exists in the nucleus of the disc. The disc is located in the space between a pair of vertebra. If there is a nuclear herniation in the disc, the original pressure, $P_O$, promotes the herniation and acts against any attempt for the herniation to pass through the annulus back in the disc. When an implant is inserted in the nucleus of a disc, the implant occupies a volume in the nucleus that further displaces nuclear material, and produces an increased new pressure, $P_P$, in the disc. The amount, $\Delta P$, that the implant initially increases the pressure in the disc is indicated by the new pressure $P_P$ less the original pressure $P_O$. If there is a rupture or nuclear herniation in the disc, the pressure increase, $\Delta P$, may increase the severity of the rupture or herniation by forcing additional nuclear material out through the herniation. Consequently, in the prior art, increasing intradiscal pressure is a problem and, as a result, disc material often is at least partially removed before inserting an implant, or the disc must be intact with an "uncompromised annulus with no significant tears and with the original nucleus intact" (Trieu US 2004/0186471, para. 0003, 0015, 0028). And, installing an implant, simply because the implant increases intra-nuclear pressure, produces forces which act to widen a disc. Consequently, even if an implant is profiled and tends to produce negative pressure which reduces somewhat intra-discal forces by spreading the vertebrae—or even by deflating, or removing at least a portion of the implant—such a pressure reduction typically is not enough to reduce the intra-disc pressure back to the original pressure, $P_O$, much less reduce intra-discal pressure below the original intra-discal pressure (less than $P_O$) sufficiently to draw a herniation back into a disc. One ideal implant for, in accordance with various of the embodiments disclosed herein, producing a quantity of negative pressure sufficient to draw a nuclear herniation back into the nucleus of a disc utilizes an implant with an outer surface (438) configured with tissue interlocking openings (463) (see FIG. 69) that diverge away from the outer surface, and minimize the pressure increase when inserted in the nucleus of a disc. The implant must spread the vertebrae sufficiently to produce the needed negative pressure. The implant preferably occupies a relatively constant volume in a disc, i.e., if the implant expands in the manner of the implant of FIGS. 172 to 176. Since the components of this implant are solid and rigid (which is presently—without foreclosing the possibility of other constructs—preferred in all implant disclosed herein) the volume occupied by the implant generally does not increase as the implant expands. This is especially the case if the implant is hollow or includes openings which are exposed when the implant expands and which permit disc tissue to flow into the openings and, if appropriate, into contact with therapeutic materials provided within the implant. In contrast, an implant consisting of an inflatable balloon typically continues to expand and occupy more volume as it inflates. Such an inflatable balloon implant is not preferred when it is desired to produce sufficient negative pressure to draw a herniation back into the nucleus of a disc. As would be obvious to those skilled in the art, inflating a balloon implant could separate vertebra and change the shape of a disc without generating sufficient, if any, negative pressure to draw disc hernias back into the disc.

Another aspect of the invention employs gathering material inside the implant to offset the volume of the implant. Drawing nuclear material inside the implant can at least partially offset expansive forces acting on the disc during implant insertion. The pressure required for herniated disc material to move through a small opening is greater than the pressure required for herniated disc material to move through a large opening. The high insertion pressure is used to force disc, vertebral or other material into the implant through smaller surface openings into larger spaces within the implant. Once inside the implant the tissue may expand (due to lower pressure in a larger space) to assist in locking the implant in place.

Converting implant insertion pressure into forces used to treat disc hernias is neither obvious nor anticipated in the prior art. Likewise safely visualizing the effects of the converted insertion pressure to reduce disc hernias is a unique event.

Elongate Optical Guide Member

Turning to FIG. 292, elongate shaft A101 extends from proximal end A106 to distal tip T101. Light post A107 reversible attaches to shaft A101 at proximal portion A105 and at end A106. The light post A107 can be any optical element or handle component that is configured to receive the elongate shaft A101 as described herein. The shaft A101 is hollow and stuffed with one or more optical fibers (not shown). Optical fiber can be constructed of plastic, glass, or any desired material as long as light is transmitted from light post A107 to end A106 through shaft A101 and tip T101, and any number of optical fibers can be used and arranged as needed in order to implement the methods described herein. Tip T101 is usually inserted through a needle into a surgical site. However, the tip 101 can be configured as a needle. Perforated implant A103 has a channel A103A through which shaft A101 resides. End A106 is detachable from post A107 and shaft A101 has a uniform diameter along the entire length of shaft A101. For example, end A106 can be configured to facilitate dethatching the shaft A101 from the post A107 by post A107 and end A106 being cooperatively threaded, snap-fit, friction-fit, or the like. Tip T101 can be inserted into implant A103 or implant A103 can be inserted over end A106. Implant A103 can be advanced, with any suitable instrument, such as those described herein and particularly as shown in FIGS. 228-231D, along shaft A101 and inserted into a joint or other location within the body of a patient or animal.

For example, the shaft A101 can be received through the aperture B63 of device B60 so that the device B60 can facilitate implantation of an implant by the implant and device B60 passing over the shaft A101. While these instruments and devices are not shown together, it is reasonable from the descriptions herein to indicate that the shaft A101 and aperture B62 can be cooperatively dimensioned such that the aperture B62 receives the shaft A101 therethrough. Similarly, any aperture, conduit, or perforation described herein or even a longitudinal recess can be adapted to slide over the shaft A101. Also, any aperture, conduit, perforation or longitudinal recess may be configured as a "C" shape so as to still be capable of sliding over the shaft A101.

In one embodiment, the shaft A101 can be configured as an elongate light guide as described herein. In one example, the shaft A101 can be configure to function as a light guide wire to allow for transmitting and receiving light therethrough for implementing a medical procedure as described herein. In another example, the shaft A101 can be configure to function as an elongate light guide that is a cannula as described herein.

In one embodiment, the light post A107 can be a handle, and may be ergonomically shaped and include the features of the handle H1 shown in FIGS. 298 and 299. However, the light post A107 can be an optically coupling member or other optical component (e.g., including a lens, collimator, etc.) that can coupled to a handle, such as handle H1. Alternatively, the light post A107 can couple to an optical coupling element that transmit the optical data to a computing system.

As shown in FIG. 293, the shaft A101 can be bendable. While only a section of the shaft A101 is shown to be bendable, the entire length can be bendable. The shaft A101 can be as bendable as an optical fiber. Exceptionally small optical fibers with very narrow diameters can be extremely bendable, such as to be capable of being bent up to 90 degrees, or even up to 120 degrees or more. These small optical fibers an also be wound in a tight coil, and thereby can be negotiated through the back in relation to the spine and adjacent vertebras and into and around the intervertebral disc. The bending of the bendable shaft A101 can be accomplished in any manner shown for bending optical fibers as well as catheters or the like. That is, the shaft A101 can bend merely be being pushed through a natural or surgical tunnel in the body and bend be being deflected. Also, the bending can be accomplished by including one or more mechanical features that when actuated cause the shaft A101 to bend in one direction or more than one direction. In some instance the tip can be manually bent and the rest of the shaft A101 can bend accordingly or by deflection once the tip T101 is passed around a bend.

FIG. 293 also shows that the shaft A101 can be telescoping and can be inserted into the light post A107 at variable depths between the dimension D3. Also, the shaft A106 and/or the post A107 can be extended through a handle (not shown) such that the effective length can change between distance D1 and D2. The bending of the bendable configuration of the shaft A106 may also change the effective length.

FIG. 294 illustrates a lighting system 100L, such as an optical fiber and optical elements, that can be included in the elongate shaft A101 (FIG. 293) or be coupled to the shaft A101. The lighting system 100L can include optical cable L1 extending from coupler B1 to couple B2. Optical couplers B1 and B2 can include various optically components that can functionally couple an optical cable L1 so that light can pass therethrough to be observed, recorded, or the like. That is, the optical couplers, can include one or more lenses, collimators, and housing and adjustable means for focusing light passing therethrough. For example, optical coupler B1 can be adapted as the distal end that is inserted into a surgical site and optical coupler B2 can be adapted to be coupled to a handle or other imaging device. For example, coupler B1 can include optical components o1 and o2, which can be any optical component for receiving light and optical images. Also, coupler B1 can be adjusted between distance D4, such as by telescoping, which may be for focusing the light. Additionally, coupler B2 can include adjustment mechanism B3 that can be used to focus the light, and can include receptacle B4 for being plugged into an imaging device. Receptacle B4 can have a depth of D6, which can be varied as needed for being coupled to an optical device. In one option, coupler B1 is configured to attach the proximal end A106 of the shaft A101. In one option, coupler B2 is configured to attached to the tip T101 of the shaft.

Also, shaft A101 can be flexible and can be manipulated in the body. Shaft A101 can operate at an initial length, and tip T101 can be positioned at length D2 or positioned at length D1 relative to post A107. The ability of shaft A101 to configure within the body to multiple lengths allows for a larger field of illumination when shaft A101 is positioned at length D2, D3 and allows for a smaller skin opening when shaft A101 is inserted straight. The ability of shaft A101 to configure within the body to multiple lengths also allows for precision placement of implant A103. Implant A103 in FIG. 292 is shown in one configuration. Implant A103 in FIG. 293 is shown in a second configuration. Implant A103 can have any desired configuration or be constructed of any desired material. Implant A103 can be rigid, flexible, soft, hard, solid, gel, hinged, unitary, multiple, etc. Implant A103 can also comprise a pair of sliding surfaces like implant 100 in FIG. 1.

Referring to FIGS. 292-294, optical guide unit system 100L can be coupled to or include shaft A101, which extends from proximal end A106 to distal tip T101. In one embodiment, coupler B1 reversible attaches to shaft A101 at portion A105 and at end A106. End A106 is detachable from coupler B1, or post A107 is detachable from coupler B1. In one option, post A107 is configured as coupler B1. The shaft A101 can have a uniform diameter along the entire length. Tip T101 can be inserted into implant A103 or implant A103 can be inserted over end A106. Implant A103 can be advanced, with any suitable instrument, along shaft A101 and inserted into a joint or other location within the body of a patient or animal.

In one embodiment shown as a combination of FIGS. 292-299, proximal end A109 of scope 5101 is reversibly attached to coupler B. Focus ring o1 can be rotated with respect to optical element o2 so as move coupler B1 in the direction of arrows D and to focus an image normally viewed through camera C1 and monitor C2 (see FIGS. 298 and 299) and or an eyepiece (not shown) from a lens (not shown). Output cable C3 can be reversible connected to another viewing monitor and/or computing system as desired. Light cable L1 can be operably coupled to light post A107 of scope 5101 to direct light through shaft A101 and out tip T101. Light cable L1 is operably coupled to light source LS2 by any of various optically coupling configurations. Light source LS1 can contain a halogen bulb, a brighter xenon bulb, or provide light in any desired method or intensity and can contain a dimmer. Power supply PS1 provides current to light source LS1 from a battery or wall outlet in the operating room.

Nearly everything that uses or transmits forces gets hot before it fails. Camera C1 in FIG. 298-299 can be constructed to detect and convert infrared energy (heat) into an electronic signal, which is then processed to produce a thermal image on a video monitor C2 and perform temperature calculations. Heat sensed by infrared camera C1 can be quantified monitoring thermal performance of the body and or implant identifying heat-related problems. Combining visual imaging and infrared software allows thermal analysis within the body. An infrared camera image of an implant can locate a worn mechanical part.

Temperature measurements can be compared with historical operating temperatures, or with infrared readings of similar joints to determine a temperature rise, implant reliability, or implant safety. Finding and fixing a worn, infected, or damaged implant or body part can prevent catastrophic failures.

Digital image storage, available on most infrared cameras, produces calibrated thermal images that contains independent temperature measurements that can be measured at any time with the optical guide system 100L in FIG. 294. Infrared thermography camera C1 can visualize and verify thermal performance. Infrared camera C1 detects thermal problems, quantify them with precise non-contact temperature measurement, and document them automatically in seconds with reports Infrared cameras, software, accessories, can be combined with the optical guide system 100L in FIG. 294.

FIGS. 295-297A includes schematic representations of embodiments of a shaft A101 configured as a cannula having an internal lumen OC1, and shows an end cross sectional view of distal tip T101 of shaft A101 illustrated in FIG. 292. FIG. 295 shows a light source conduit LS2 is optically coupled to any light source and is insulated from image sensor conduit C7 that is optically coupled to an image sensor. Also shown in an optional electrical conductive fiber ST1 that can also be insulated from light source conduit LS2 and image sensor conduit C7. The insulation can be by any optically or electrically isolating material I101. Light source LS2 can originate from any commercially available light emitting diode (LED), such as LS1 or LS3 shown herein. Image sensor conduit C7 can comprise any type of optical fiber, such as single mode or multimode optical fibers, and can be optically coupled to any commercially available charge coupled device (CCD). Electrical fiber ST1 can comprise any electrically conductive material. Open center OC1 can contain additional viewing elements, light sources, electrical conductive materials, lasers, cable, disc preparation instruments, disc removal instruments, provide suction or transmit pressurized saline to the surgical site. Implant A103 can also be delivered through open section OC1 along shaft A101 to the surgical site. While only one light source conduit LS2, one image sensor conduit C7, or electrical conductive fiber ST1, any number and arrangement can be shown. Also, the shapes of these components can be modified in order to be suitable for the use. The light source conduit LS2 and image sensor conduit C7 can be individual optical fibers, where the LS2 fiber is a light transmitting fiber and the C7 fiber is a light receiving fiber, and appropriate optical elements can be associate therewith for shining light and receiving light.

FIG. 296 includes another end cross sectional view of distal tip T101 of shaft A101 illustrated in FIG. 294. Light source conduit LS2 is insulated from image sensor conduit C7 and electrical conductive fiber ST1 by material I101. Open center OC1 can contain additional viewing elements, light sources, electrical conductive materials, lasers, cable, disc preparation instruments, disc removal instruments, provide suction, or transmit pressurized saline to the surgical site. Implant A103 can also be delivered through open section OC1 along shaft A101 to the surgical site.

FIG. 297 includes another end cross sectional view of distal tip T101 of shaft A101 illustrated in FIG. 294. Light source conduit LS2 is insulated from image sensor conduit C7 and electrical conductive fiber ST1 by material I101. Open center OC1 can contain additional viewing elements, light sources, electrical conductive materials, lasers, cable, disc preparation instruments, disc removal instruments, provide suction, or transmit pressurized saline to the surgical site. Implant A103 can also be delivered through open section OC1 along shaft A101 to the surgical site.

With reference to FIGS. 295-297, the end cross sectional view of distal tip T101 of shaft A101 can exclude the electrical conductive fiber ST1 is some embodiments. That is, only the light transmitting fiber (e.g., light shining fiber) and light receiving fiber (e.g., image fiber) can be included. In one embodiment, only one fiber is needed when the light being transmitted and the light being received have different wavelengths and are capable of passing each other in opposite directions without interference. Monochromatic or single wavelength light that down shifts to a lower wavelength when striking tissue may be suitable in some applications with only a single fiber. In one embodiment, one of I101, LS2, ST1, or OC1 can be configured as a coloring agent conduit for applying coloring agent to the site of the medical procedure as described above.

Also, while the cross sectional profile is generally round, other shapes, such as in FIGS. 295A-297CA can be used, as well as others. The non-round cross sectional shapes of the shaft A101 can be used to help rotate the implant when the shaft A101 is being used as a guide wire or a guide cannula. That is, when the non-round shaft A101 rotates, the implant sliding thereon or therein will also rotate.

FIG. 295B illustrates another cross sectional profile of shaft A101, which includes a light source conduit LS2 and an image sensor conduit C7, surrounded by a cladding C9 or other sheath for optical fibers. Since the light source conduit LS2 and an image sensor conduit C7 are adjacent a top recess C11 and bottom recess C12 are formed. The recesses C11, C12 can act as guide rails for an implant A103 that can be slid down the shaft A101. In another aspect, the recesses C11, C12 can be configured into protrusions and also function as guide rails for an implant A103. The function of the guide rails allows the implant to rotate when the shaft A101 is rotated. The other implantation devices described herein can be modified in accordance with the cross sectional profiles of FIGS. 295, 295B, 296A, and 297A.

FIG. 298 includes an end view of another optical guide unit system 200L further illustrated in FIG. 299. Guide unit system 200L is operable to illuminate a surgical site, transmit current, and configured to accept a perforated implant. Guide unit 200L functions like to implant insertion system illustrated in FIG. 184. Shaft A101 of FIG. 292-300 functions similar to wire 780 of FIG. 184 and can be used in with lever or dilator 781, cannula sleeve 783, and or driver 786. Shaft A101, in addition to delivering an implant A103, can illuminate the operative site and transmit images to a camera or video recorder. Delivering an implant along shaft A101 is safer then when delivered to an operative site along wire 780 in image 184. The implant system in FIG. 184 can be orthogonal as shown or be round or oval as illustrated in FIG. 299 as cannula sleeve CA1, or it can be any polygon shape. In FIG. 298 Monitor C2 functions similar any time of monitor, such as an LCD screen. Shaft A101 or guide wire 780 (FIG. 184) slides through handle H1. Pressing Light button C1 with a finger connects current from power supply PS1 (connected to a wall outlet or battery) to shaft A101 or wire 780 (FIG. 184). Pressing Current button ST2 with a finger connects current from power supply PS1 (connected to a wall outlet or battery) to shaft A101 or wire 780, which can provide electrical current to electrical conductive fiber ST1. Tip T101 in FIG. 299 functions similar to end 780A of wire 780 (FIG. 184) and can deliver in implant into a joint intermediate two vertebra or to any desired location within the body.

FIG. 299A illustrates another embodiment of a medical system 305 that can be used in the methods of the present invention, such as for delivering an implant with the elongate light guide as well as grabbing tissue, pulling tissue, or removing tissue. The medical system 305 is illustrated to include a shaft A101 that is received in a cannula sleeve CA1 so as to extend from cannula end CE, and operated by a handle CX. The shaft A101 and cannula sleeve CA1 can be configured as described herein, and modified as now described. The shaft A101 can include a distal tip T101 that is outfitted with a grabbing tip G that has grabbing member G2 that articulates with respect to grabbing member G1, however, both of the grabbing members G1, G2 may be able to articulate with respect to each other and/or with respect to the shaft A101.

One or more of the grabbing members G1, G2 can include one or more teeth T1 to facilitate grabbing tissue, such as grabbing a herniation that extends from a disc. Alternatively grabbing members G1 and G2 can be configured as multiple fingers (FIGS. 46A-47D), a rotating shaver, rasp, with or without an expandable cutting edge (FIG. 213) or any desired configuration. Any of the implants and instruments described herein can be operatively coupled with external traction, or an external suction to create a vacuum intermediate the vertebra to suck material back into the disc. Alternatively the implant can generate negative pressure by separating the vertebra (internal fraction) and draw material away from nerves adjacent the disc (FIGS. 12-15). The shaft A101 and cannula CA1 are both shown to be coupled with a cannula coupler CN, which has a port P1 that can be used for irrigation or sucking of fluids from the distal end T101 and may be able to suck fluids through the cannula CA1, such as sucking tissue bits that have been grabbed with the grabbing tip G, and pulled off or torn into tissue bits. Suction can also provide negative pressure to reduce a disc herniation without directly removing the disc. The cannula coupler CN can be coupled to a membrane M1 that prevents fluid flow from flowing further up the medical system 305, and directs fluid out of the port P1. The shaft A101 may extend through the cannula coupler CN, and may have a portion A105 coupled to an image sensor conduit C7 that extends into the housing of the handle CX. As shown, the shaft A101 can also be operably coupled with a light source L1. A focusing ring C6 may be operably coupled with the sensor conduit C7 and with the shaft A101, and may be positioned to focus light from the shaft A101 fiber optical elements to the sensor conduit C7. The focusing ring C6 can be operated by rotation thereof as shown by arrow R1. The sensor conduit C7 can have a proximal end C 19 that is operably coupled (or remotely coupled) to a camera device C1, which camera device C1 can be operably coupled (or remotely coupled) to a monitor C2 so that a medical practitioner or surgeon can visualize the intervertebral space with the system 305. Visualizing the intervertebral space provides for viewing the retrieval of a disc herniation, placement of an implant, or separation or realignment of the vertebra. Optionally, an optical output cable C3 is operably or remotely coupled with the camera C1 or monitor C2, which output cable can be operably or remotely coupled with any computing system or other visualization device. Alternatively the image can be viewed remotely.

The handle CX can be articulated to as to move and articulate the grabbing tip G, such that one or more mechanical components are associated with both the grabbing tip G and the handle CX. For example, pull wires (not shown) can be operably coupled from the grabbing tip G to the handle CX such that articulation of the handle CX at handle axis CX1 moves the grabbing member G2 with respect to grabbing member G1 so that the grabbing tip G can grab tissue. The handle CX can be articulated so that the grabbing member G1 and grabbing member G2 are closed or together so that an implant can slide over the shaft A101 (similar to implant A103 in FIG. 300), over the grabbing tip G, and off of the shaft A101 and grabbing tip G in order to be deployed. A delivery member or push member can be used to deliver the implant over the shaft A101 and grabbing tip G.

FIG. 300 illustrates another wire 780 or shaft A101 handle reversibly connected to end A105, A106 of shaft A101. Handle H101 has a hollow channel (not shown) for shaft A101 to slide through. Implant A103 can slide along shaft A101. Tip T101 is operable by pressing button ST2 to transmit current via electrical conductive fiber ST1 within the body. The amount of current transmitted through shaft A101 is controlled by thumb wheel W1. Thumb wheel W1 controls the resistance through wire W2 connected to a power source.

Shaft A101 can be used to insert an implant into any region of the body including blood vessels, organs, bones, joints, brain, tumors, and the spinal column. One path for inserting an instrument or implant into the intervertebral disc of the spine is illustrated in FIG. 41 as arrow 319. Shaft A101 can function as instrument 61 in FIG. 7, wire 324 in FIG. 43, apparatus 321 in FIG. 45, hollow cylindrical body 364 in FIG. 47E, wire 324 in FIGS. 50 and 51, member 764 in FIG. 178, instrument 800 in FIGS. 187 and 188, handle A22 of instrument A32 in FIG. 213. Instrument A60A in FIG. 227A can be inserted along shaft A101 through aperture A63A. Implant insertion tool A73 in FIG. 230 can be inserted along shaft A101 as can instrument B60 in FIG. 231A, with implant B66 as shown in FIG. 231C and FIG. 231D. Shaft A101 can be inserted through aperture A81 of instrument A80 in FIG. 232, apertures C61, C62, C63, of instrument C60 in FIG. 235A-D, or through hollow instrument A80B in FIGS. 235E-H as long as shaft A101 transmits light, images, and/or electricity, and assists to deliver an implant.

Instrument 800 in FIGS. 187 and 188 can also be cannulated, perforated, or provided with a channel along the length to slide along shaft A101. Instrument 800 can be electrically insulated along handle 801. Handle 801 and end 802 can be constructed of electrically conductive material such as metal. A current can be delivered through instrument 800 adjacent disc 70. A current can be recorded along principal nerve 316, 317 in FIG. 41 and instrument 800 can be manipulated by a surgical operator as desired.

The shape and dimension of shaft A101 can vary as desired. It is currently preferred that Shaft A101 be cylindrical with a cross sectional diameter in the range of 0.028 to 0.125 inches and a length of 1 to 12 inches. Shaft A101 can contain many or consist of a single fiber optic wire or cable. Shaft A101 can also contain a lens at tip T101.

Shaft A101 can be combined with a cannula configured to attach pressurized irrigation fluids, colored stains, and or radiopaque contrast. Shaft A101 can have an aperture for inserting instruments and for removing materials, such as an intervertebral disc, from the body as shown in FIGS. 295, 296, and 297.

Implant

FIG. 301 illustrates an implant A103 configured to revitalize an intervertebral disc after deposition intermediate two vertebras by an elongate guide unit. Implant A103 comprises a top toothed arcuate surface T1, a bottom toothed arcuate surface T2, a slot Z, placed circumferentially around implant A103, and an aperture 3 through implant A103. Implant A103 can also have a flat top and or bottom, a smooth top and or bottom and may or may not be toothed to function. When implant A103 is smooth and without teeth and inserted intermediate two vertebra, at least one vertebra can slide, glide, or otherwise move about implant A103 in the direction of arrows DA, DB, DC, DD, and in directions intermediate arrows DA-DD. When implant A103 is toothed with teeth T3, implant A103 can fix to tissue such as disc or bone or other tissue intermediate two vertebras and move in the directions DA-DD, in directions intermediate arrows DA-DD, and in the direction DE-DF when compressed intermediate two vertebras. Perforation aperture 3 and or slot Z can accept a guide wire, an optical guide unit, or other elongate guide unit. When a guide unit is inserted into the intervertebral disc, implant A103 can travel along said guide unit into the disc.

Implant A103 can have any shape or dimension and function to fuse two vertebras by joining two vertebras together with teeth T3 on top surface T1 and bottom surface T2. Implant A103 can function to allow movement of one vertebra with respect to another adjacent vertebra by joining two vertebra together with teeth T3 on top T1 and bottom T2 surfaces and by having a compressible slot Z intermediate top T1 surface with distance G, the distance between top T1 and bottom T2 surfaces at one portion of implant A103, greater or less than the distance H, the distance between top T1 and bottom T2 surfaces at another portion of implant A103. It is preferred that slot Z be of a variable configuration along implant A103 and distance G be greater or less than distance H between Top surface T1 and bottom surface T2. The variable shape and dimension of slot Z and surfaces T1 and T2 along the length of implant A103 causes tilting of top T1 surface with respect to bottom surface T2 of implant A103 and of adjacent compressing vertebras. When the top T1 and bottom T2 surfaces at distance G and distance H are loaded equally by adjacent vertebra, the said surfaces at Distance G compress more than said surfaces at distance H (since less support is provided by implant A103 at distance G than at distance H) allowing the compressing vertebra to tilt with respect to each other and move into a more preferred alignment than if slot Z was uniform and compressed. Implant A103 can also assist movement of one vertebra with respect to another adjacent vertebra by either joining to one vertebra but not the other or by not joining to neither of two adjacent vertebra where the vertebra slide along the top and/or bottom of implant A103.

Implant A103 can function to differentially expand in response to forces applied to slot z. Compressing slot z with a constant force such as when applied by an operator or when applied by the adjacent vertebra causes slot z to compress then expand variably along its length. The variable shape and dimension causes slot z to better adapt to movement of the vertebra and to differentially expand in response to a constant load.

FIGS. 302 and 303 illustrate an intervertebral spacer D28. Spacer D28 can be inserted between and contact each of a pair of vertebra, or, can be inserted between and contact a vertebra and/or an intervertebral disc. The top view of FIG. 302 illustrates the generally trapezoidal shape of spacer D28. Spacer D28 includes spaced apart, in-turned, opposing ends D29 and D30, along with outwardly depending leg D31 with aperture D32 formed therethrough. A screw or other fastener can be inserted through aperture D32 to affix spacer D28 to an intervertebral disc or vertebra. Spacer D28 can be size to fit within the annulus of a disc. The opening between ends D29 and D30 diverges inwardly into spacer D28 to permit bone, disc, metals, polymers, and other materials to enter implant D28 and prevent or restrict materials from exiting implant D28 when implant D28 is compressed between two vertebra.

FIGS. 304 to 307 depict a generally orthogonal implant D35 constructed in accordance with another embodiment of the invention. The material utilized to construct this implant, as well as any of the other implants illustrated herein, can vary as desired but typically comprises either a metal or metallic compound or a polymer or polymer compound, textiles, or naturally occurring material such as machined bone. Implant D35 includes side D39, internally threaded aperture D38, and a plurality of parallel, spaced apart grooves D36, D37 formed on the top and bottom of implant D35. The size of each groove preferably, although not necessarily, initially increases or widens as the depth of the groove D36, D37 from the outer surface of implant D35 increases.

Another principal embodiment of the invention provides grooves and inserts that can be hemophillic, hydrophillic, and attract and draw blood, fluids, and solids (using visco-elasticity and/or negative pressure) into the interior of the groove (D36, D37, etc.). The narrower outer opening in a groove creates an environment of lower pressure when a fluid flows through the opening (like a volume of water passing through a narrow opening is under less pressure than the same volume of water traveling through a wider opening).

Bernoulli's Principle states that as the speed of a moving fluid increases, the pressure within the fluid decreases. As fluid or tissue or materials flow faster through the narrower portions of a groove or implant, the pressure actually decreases rather than increases facilitating ingrowth into the implant. Likewise the pressure on the surface on the implant is less than the pressure within the implant reducing subsidence of the implant into the vertebra. The grooves are shaped and dimensioned to also allow faster healing by allowing tissue to flow (in grow) rapidly (through the narrower opening with lower pressure) and slow within the larger opening preventing the tissue from escaping once entering the implant. Likewise materials inserted into the groove or implant are secured within the implant. Less force is also required to insert the implant as pressure is transferred from the surface to the inside of the groove or implant. The wider interior opening of the groove (inside the implant) has a greater volume and higher pressure than the outer opening when a material is flowing through the outer opening into the interior of the groove. When the grooves are sufficiently small, fluid flows into the grooves under capillary action due to a combination of liquid surface tension and the adhesion of the liquid to the surface of the groove.

When materials (disc, vertebral, cement, fluids, solids, etc.) are viscoelastic, the diverging interior opening in a groove allows materials to expand (due to lower pressure) to interlock with the interior of the implants provided herein.

Grooves can be oriented in any direction in implant D35. By way of example, and not limitation, grooves can be vertically, horizontally, obliquely, diagonally, and tangentially oriented and can, with respect to one another, be offset, co-linear, spaced apart, angled, etc.

Inserts within groove D35 can be entirely solid, partially solid, hollow, and can be applied to a groove by any method of manufacturing including spray coating, electrolysis, macro-technology, micro-technology, nano-technology, etc.

Alternatively, the outer opening in a groove can have a constant diameter or width for a distance then widen like a keyhole. Grooves can be formed horizontally along the surface of the implant, can be formed vertically along the surface of the implant, or can be placed in any other desired orientation.

In one embodiment of the invention, grooves D36, D37 remain open when implant D35 is inserted between a pair of opposing vertebra. This permits vertebral tissue, disc tissue, or other materials to move into grooves D36 and D37. Any materials can be applied to alter the surface texture of the grooves. Such materials can be applied by, for example, spraying nano-particles, etching, electrolysis, and or heat treatment.

After implant D35 is in position for a period of time and vertebral tissue has moved into grooves D36 and D37, grooves D36 and D37 tend to anchor implant in place and to oppose, at a minimum, movement of the implant D35 in directions of travel D43, D44 (FIG. 305) that are perpendicular to the longitudinal axes of grooves D36 and D37. The parallel configuration of slots D36 and D37 also facilitate, however, the insertion of implant in the direction of arrow D42 or arrow D41 (FIG. 304). Directions D42 and D41 are parallel to the longitudinal axes of slots D36 and D37.

In another embodiment of the invention illustrated in FIGS. 308 and 309, grooves D36, D37 function to receive elongate cylindrical markers D40 and D50. Marker D40, D50 can be porous, to facilitate the ingrowth of tissue, or can be solid and impermeable.

In one embodiment, each marker, in addition to being solid, can have a smooth outer surface D50A that extends across the opening to a slot D36. For example, in FIGS. 308 and 309 outer surface D50A extends across the opening to slot D36 and is visible in FIGS. 308 and 309. A smooth outer surface D50A facilitates the insertion between a pair of vertebras of implant D35 in the direction of arrow D41 or D42 (FIG. 304).

In another embodiment of the invention, each marker is porous and has a rough surface to facilitate scraping or rasping the vertebral end-plates or disc to encourage vascular ingrowth. In another embodiment of the invention, each marker is resorbable. In still another embodiment each marker is a textile.

The "boat shaped" implant D52 illustrated in FIGS. 310 and 311 includes, as does implant D35, a plurality of parallel spaced apart grooves D54, D56, D61 formed on the top and bottom of implant D52. The parallel configuration of grooves D54, D56, D61, D62 facilitates the insertion of implant D52 between a pair of vertebra in the direction of arrow D 55 (FIG. 310), or in a direction normal to arrow D55. Alternatively, the outer opening of each groove can have a constant diameter or shape for a distance and can thereafter widen like a keyhole. Grooves can be formed horizontally along a surface of the implant, can be formed vertically along a surface of the implant, and/or can be formed in any desired orientation, particularly to facilitate the growth of bone into at least a portion of the grooves. If the density or other physical property of the bone enables it to be distinguished from the implant, radiography can be used to detect the ingrowth of bone in a groove. The size of each groove D54, D56, D61, D62 preferably, although not necessarily, initially increases or widens as the depth of the groove D54, D56, D61 from the outer surface of implant D52 increases. Aperture D58 extends through the tapered tip D57 of the implant and into the aperture that is formed through the center of implant D52. Internally threaded aperture D58 also opens into the aperture that is formed through the center of implant D52 and extends completely through the end D53 of implant D52. As a result, implant D52 can slide along a wire that extends through aperture D58, through the central aperture in implant D52, and through aperture D54. A wire can be constructed of a material similar to or different from that of the implant to help visualize radiographically the position of the implant along the wire. The wire can be optical cable for transmitting light, or can be constructed to conduct electricity to determine the location of a nerve. The section view of FIG. 311 further illustrates the configuration of the aperture D 63 extending through the center of implant D52. Aperture D63 is bounded by generally U-shaped sides D59 and D60 which function to gather, capture and contain materials within aperture D63. Any material or method can be utilized to alter the surface texture of aperture D63. One such material comprises nano-particles. Methods utilized at alter the surface texture include spraying, etching, electrolysis, and heat treatment.

Apertures and grooves can be placed eccentrically in or through the tip D57 to facilitate inserting implant D52 by dissecting or dilating openings in an intervertebral disc (or in adjacent tissue like muscle, skin, or fascia). Such apertures are similar to the eccentric apertures in instrument A81 in FIGS. 232 and C63, and C61 in FIG. 235A-D.

The implant D65 of FIGS. 312 and 313 (and all other implants presented herein), can be inserted in a disc, can be inserted between a pair of vertebra after a disc is removed, or can be positioned to extend around the exterior of an intervertebral disc. Implant D65 includes arms D66 and D67 each with a generally triangularly shaped opening D75 formed therein. Triangular opening D75 at least partially widens as the depth into implant D65 increases. Arm D66 includes upper vertebral support surfaces D71, D70 and lower vertebral support surfaces D76 and D78. Arm D67 includes upper vertebral support surface D69 and includes lower vertebral support surfaces D77. Each of the upper vertebral support surfaces D70 is presently parallel to each of the lower vertebral support surfaces D77, although this need not, if desired, be the case. Said vertebral support surfaces can be shaped and dimensioned to alter the orientation or cant of the vertebra as in FIGS. 35-40. Implant D65 can comprise two springs (arms D66 and D67) pivotally attached at opening D74.

Opening D75 is bounded by triangularly shaped portion D72. Triangularly shaped portion D73 in leg D67 similarly bounds a triangular opening in leg D67. Legs D67 and D66 are pivotally attached by pin D68 (FIG. 312) which extends through opening D74.

Opening D74 extends through each of legs D67 and D66. FIG. 313 illustrated implant D65 in an open configuration. FIG. 312 illustrated implant D65 in a closed configuration. In one embodiment of the invention, implant D65 is inserted in the nucleus of a disc in an open configuration and arms D66 and D67 are then pivoted about in D68 to the closed configuration of FIG. 312. Pivoting arms D66 and D67 from the open to the closed configuration functions to gather nuclear material within arms D66 and D67.

Inserting implant D65 in the open configuration (a smaller surface area reduces friction) requires a smaller surgical incision than if inserting implant D65 in the closed configuration. Articulating implant D65 from the open configuration to the closed configuration better conforms the shape of a normal intervertebral disc.

If, however, excessive nuclear material is gathered within arms D66 and D67, it can escape through openings D75 or beneath portion of implant D65 like the portion on which vertebral support D69 is formed. In another embodiment of the invention, implant D65 is inserted in a disc in the closed configuration of FIG. 312 and arms D67 and D66 are pivoted about pin D68 to an open configuration like that of FIG. 313. In a further embodiment of the invention, implant D65 is manipulated to an open configuration like that of FIG. 313, is positioned on the exterior of a disc, and arms D66 and D67 are pivoted about pin D68 to contact and extend around the exterior of the disc.

Pivoting spring implant D65 (FIGS. 312, 313) and any of the implants disclosed herein provides the operator the ability to position vertebral support surfaces in a specific location intermediate two vertebra. By way of example, but not limitation, vertebral support surface D67 can be positioned to contact the vertebra adjacent the annulus where the vertebra are strongest and away from the disc nucleus and center of the vertebra where subsidence is more likely.

The unitary implant D80 of FIGS. 314 to 317 has a shape and dimension similar to that of implant D65 when D65 is in the closed configuration of FIG. 312, except that implant D80 is provided with a downturned flange or leg D92 with an aperture D82 formed therethrough. A screw or other fastening apparatus can be inserted through, and interlock with, aperture D82 and into a disc or vertebra. Implant D80 includes triangularly shaped openings D89, D83 similar to the triangularly shaped openings D75 formed in implant D65. The size of each opening D89, D83 (as do openings D75 in implant D65) initially increases or widens as the depth of the opening D89, D83 from the outer surface D81 of implant D35 increases.

Implants D80, D65, etc., can be rigid, semi-rigid, or entirely flexible and can be constructed of metal (e.g., titanium, nitinol, etc.), polymer, ceramic to absorb loads intermediate two vertebra.

In another embodiment of the invention, implants are manufactured by combining two or more materials with different densities. By way of example, and not limitation, porous material and solid non-porous materials are blended together to form a density gradient in an implant. The blend gradient can be linear, where the implant density changes gradually at a constant rate across the body of the implant, or can non-linear, where the implant density changes at a non-constant rate across the body of the implant. An exponential rate of density change is an example of a non-constant density rate change.

Another example of blending materials of different densities is combining polymer with metal, polymer with ceramic, polymer with bone, etc. Another example of blending materials of different densities is to layer a material of one density adjacent a material of another density. Moving from a layer of one density to a layer with another density can, in comparison to the density gradients described above, provide an instant, distinct, readily recognizable change in density.

One advantage of the implants disclosed herein is the groove(s) or other opening(s) in the implant reduce the amount of material required to produce and implant and to maintain a desired intervertebral spacing.

In one embodiment of the invention, implant D80 is inserted in the nucleus of a disc such that portion D92A of leg D92 extends intermediate the annulus and a vertebra and portion D92B extends downwardly along the periphery of a vertebra such that a screw can be inserted through and may interlock with, aperture D82 and into the vertebra to secure implant D80 in place. This embodiment of the invention is illustrated in FIG. 319, except that the disc has been omitted from the drawing for purposes of clarity.

In another embodiment of the invention, implant D80 is inserted between a pair of vertebra D100, D101 after the all or a portion of the disc has been removed.

The unitary implant E16 of FIG. 318 has a shape and dimension similar to that of implant D65 when D65 is in the closed configuration of FIG. 312, except that implant E16 is provided with a downturned flange or leg E14 with an aperture E15 formed therethrough. A screw or other fastening apparatus can be inserted through (and/or interlock with) aperture E15 and into a disc or vertebra. Implant E16 also differ from implant D65 in that implant E16 includes a pair of legs E2 and E3 that are each pivotally attached to a base E1 at a pivot point E5, E4, respectively. In contrast, in implant D65, the legs D66 and D67 are pivotally attached to one another.

Implant E16 can be constructed from a rigid (metal, ceramic), semi-rigid (polymer), or flexible (nitinol, etc.) material. The size, shape, and material used to make an implant are chosen according to the quantity of pressure desired to separate the vertebra, to change the shape of the disc, or to perform an indirect de-compression of the adjacent nerves that are compressed by a disc or vertebra. Implant E16 of FIG. 318 preferably but not necessarily functions like a spring. Pivoting implant E16 at pivot points E4 and E5 facilitates positioning implant E16 intermediate two vertebras as shown in FIG. 319 to reduce the intra-discal and nerve pressure. When implant E16 is compressed, arms E8 and E9 squeeze or gather disc or other materials (typically including nuclear material) and move the materials away from nerves adjacent the intervertebral disc. Compressing a spring ordinarily will shorten and widen the spring. In contrast, implant E16 is constructed to shorten and narrow (not widen) when compressed. Accordingly, implant E16 acts as an "intraction (internal traction) spring" which pulls disc and other tissues away from the nerves adjacent the disc. Compressing arms or legs E8 and E9 reduces the width of the disc. Rods inserted into pivot points E8 and E9 can be porous to facilitate tissue ingrowth or can be solid and be the same density of or different density than (function as a marker) implant E16.

Implant E16 includes triangularly shaped openings E6, E7 similar to the triangularly shaped openings D75 formed in implant D65. The size of each opening E6, E7 (as do openings D75 in implant D65) initially increases or widens as the depth of the opening E6, E7 from the outer surface E10, E9, respectively, of implant E16 increases. Implant E16 also includes upper vertebral contact surface E8 and lower vertebral contact surface E11, E13. Implant E16 can be utilized in the manner described for either implant D65 or D80. In particular, in FIG. 318, legs E2 and E3 are depicted in a closed configuration. If desired, when implant E16 is initially inserted in the nucleus of a disc, legs E2 and E3 can be pivoted to an open configuration comparable to that illustrated in FIG. 313 for implant D65. After the implant D16 is inserted in a disc, legs E2 and E3 can then be pivoted to the closed configuration of FIG. 318, which would serve to gather portions of the nuclear material within legs E2 and E3.

The implant illustrated in FIG. 320 is positioned intermediate vertebra E18 and E19 and includes body E20 and wing E21 pivotally attached to at least one end of body E20. Pivoting element (wing E21) can function as a compression plate or cam and provide counter traction against body E20 in order to counter the amount of force and pressure generated by inserting the implant of FIG. 320. Body E20 is similar to implant E70 illustrated in FIGS. 330 to 333. Implant E20 can reside at least partially, or even completely intermediate two verterbra and when wing cam E21 is rotated by turning a recess in wing E21 or by turning set screw E25, wing E21 functions as a cam to either fix implant E20 to bone or disc by pressing into a vertebra or function as a cam to separate two vertebra. Wing E21 can be at least partially toothed, at least partially porous, etched, textured, shot peened, or coated to facilitate bone to bond, ingrow, or attach into implant E20. Rotating cam E21 expands implant E20 vertically separating adjacent vertebra, and can reshape the disc, reduce pressure, and perform indirect decompression of nerves adjacent the disc with internal traction.

Externally threaded screw E25 turns into an aperture that is formed in body E20 in a location and manner comparable to internally threaded aperture E70A formed in one end of implant E70 in FIG. 333, i.e., such that wing E21 can rotate about screw E25 in the directions indicated by arrows E22. Screws E23 and E24 extend through (and may interlock with) apertures formed in wing E21 and are turned into vertebra E18. Screw E25 can be configured as a cam or toothed gear. When screw E25 is rotated as a cam or gear, portions or screw E25 or teeth (not shown) can interfere with or engage with screws E24. Turning screw E25 can engage portions of screw E24 and simultaneously advance screw E24 in wing E21 and vise versa. As is illustrated in FIG. 320, the screws E23 and E24 can angle away from one another so that if the head of one screw E24 turns out a short distance, it function to block the outward movement of screw E23. This makes it more unlikely that both screws E23 and E24 will work completely free from wing E21. Similarly, member E25 can block the outward movement of either screw E23, E24 or of body E20. Similarly, wing E21 can block the outward movement of implant E20 from between vertebra E18 and E19 by functioning as an expandable cam, locking mechanism, or deployable teeth on at least one end or portion of implant E20. The implant of FIG. 320 can be utilized after a disc is completely removed from between a pair of vertebra, or can be utilized after a portion of the annulus and nucleus is removed which is sufficient to permit insertion of the implant. An aperture parallel to the longitudinal axis of body E20 can be formed along the longitudinal axis of screw E25 such that a wire can slidably extend through and along the longitudinal axis of screw E25.

Implant E26 depicted in FIG. 321 has a configuration comparable to that of the implant illustrated in FIG. 320 and includes body E27 and wing E28 pivotable on body E27 in the directions indicated by arrows E29. Screw E30 extending through the top of wing E28 extends into one vertebra E18, while screw E31 extend through the bottom of wing E28 extends into another vertebra E19. Parallel grooves E32, E33, E37 are formed in the top and bottom of the implant and can receive cylindrical members E34, E35. Members E34 and E35 can serve any desirable function such as functioning as markers which facilitate determining the location of implant E26 in the spinal column of a patient and such as facilitating the ingrowth of tissue into members E34, E35. When members E34 and E35 serve as markers, members E34 and E35 have at least one physical property (such as density) which differs from that of body E27. Aperture E39 can be at least partially filled (for example but not limitation, circumferentially filled) with porous bone, metal (titanium, tantalum, etc.), ceramics or other materials for ingrowth of bone or other tissues into aperture E39. When members E34 and E35 serve to facilitate the ingrowth of tissue, members E34 and E35 may be porous or be formed from materials equivalent to those found in a disc or vertebra. Grooves E32, E33, E37 need not be parallel, but, as noted earlier, a parallel configuration of grooves E32, E33, E37 facilitates inserted of implant 26 in a direction parallel to the longitudinal axes of the grooves. Grooves and/or inserts can be formed along the length, height, and/or width of any of the implants described herein and can provide for ingrowth of vertebra E18, E19 (FIG. 320). The width of the grooves can vary, but presently preferably is in the range of 100 microns to 500 microns. Grooves can be linear or arcuate to steer implant E26 along a linear or arcuate path of travel respectively. Aperture E36 extends through implant E26 along the longitudinal axis E42 of implant E26 such that a wire (optical, electrical, guide, or otherwise) can be slidably inserted through aperture E36 to facilitate insertion of the implant E26 between vertebras by sliding the implant along the wire.

FIG. 322 illustrates the tapered implant E26 inserted intermediate a pair of vertebra E40 and E41. The disc intermediate vertebra E40 and E41 has been omitted for sake of clarity. The implant E26 can be utilized after a disc is completely removed from between a pair of vertebra, or can be utilized after a portion of the annulus and nucleus is removed which is sufficient to permit insertion of the implant.

FIG. 323 illustrates the implant E26 inserted intermediate a pair of vertebra E43, E44. In FIG. 323, wing E28 has been rotated ninety degrees from the position of wing E28 in FIGS. 321 and 322, and apertures (not visible) have been formed through wing E28 and the portion of body E27 adjacent wing E28 such that screws E45 and E46 can, after both wing E28 and body E27 are positioned between vertebra E43 and E44, be inserted and extend upwardly and downwardly, respectively, into the bottom of vertebra E43 and the top of vertebra E44 in the manner illustrated in FIG. 323. In the embodiment of the invention illustrated in FIG. 323, both wing E28 and body E27 are between vertebra E43 and E44. In the embodiment of the invention illustrated in FIG. 322, wing E28 is not positioned between vertebra E40 and E41. Positioning wing E28 entirely intermediate two vertebra and within the intervertebral disc space provides for a lower profile of implant E26 and prevents wing E28 from contacting muscles and nerves. In another embodiment of the invention, wing E28 can be at least partially positioned intermediate two vertebra and function as a cam to either fix implant E26 to bone or disc by pressing into a vertebra and/or function as a cam to separate two vertebra. Wing E28 can be at least partially toothed, at least partially porous, etched, textured, shot peened, or coated to facilitate bone to bond, ingrow, or attach into implant E26. Rotating wing cam E28 expands implant E26 vertically separating adjacent vertebra E43, E44, and can reshape the disc, reduce pressure, and perform indirect decompression of nerves adjacent the disc with internal traction. Wing E21 can block the outward movement of implant E20 from between vertebra E40 and E41 by functioning as an expandable cam, locking mechanism, or deployable tooth on at least one end or portion of implant E26. Wing E28 can be fully recessed (within the disc space), partially recessed, or not recessed (outside the disc space).

Implant E50 is illustrated in FIGS. 324 to 326 and includes parallel grooves E52, E53, E54, E55 formed in the bottom and top of implant E50. Grooves can be in any orientation along or through the length, width, or height of the implant E50. The size of each groove E52, E53, E54, E55 preferably, although not necessarily, initially increases or widens as the depth of the groove E25, E53, E54, E55 from the outer surface of implant D35, D52, E50, etc. increases. Apertures E56 and E57 (FIG. 325) are sized to slidably receive a wire which can extend through aperture E56, through oval aperture E51, and through aperture E57 to enable implant E50 to slide, if desired, along a wire during insertion of implant E50 intermediate a pair of adjacent vertebra. A wire through aperture E51, E57 functions to maintain in registration with implant E50 material (bone graft, etc.) that is placed in aperture E5. Aperture E57 extends through the nose E58 of implant E50 and can also be positioned to extend eccentrically through implant E50. Aperture E56 extends through the rear E59A of implant E50. Aperture E51 extends completely through the central area of implant 50. Implant E50 can, as can the other implants described herein, be shaped and dimensioned to be inserted in a disc or to be inserted intermediate a pair of vertebra after the disc is at least partially removed. Cylinders E59, E60 of any material can each be slidably laterally inserted in a groove E52, E53, E54, E55 in the manner indicated by arrow E50A, or, if a cylinder E59, E60 or the implant E50 is sufficiently deformable, the cylinder E59, E60 can be pressed into a groove E52, E53, E54, E55 in the direction indicated by arrow E50B (FIG. 326). Inserts E59, E60 are shown as cylinders but can be of any shape and dimension (triangular, square, hexagonal, star shaped, etc.). Inserts E59, E60 can, for example, be hollow tubes formed within implant E50 using spray coating, nano-technology, electrolysis, or other desired techniques Any aperture described herein can be at least partially filled (for example but not limitation, at least partially circumferentially filled) with porous bone, porous metal (titanium, tantalum, etc.), porous ceramics or other materials for ingrowth of bone or other.

Implant E61 illustrated in FIGS. 327 to 329 is essentially equivalent to implant E50, except that an additional first pair of parallel longitudinal grooves E62, E63 are formed in the nose implant E61, and an additional second pair of parallel longitudinal grooves E68, E69 are formed in the rear of the implant. The longitudinal axis of groove E62 is coincident with the longitudinal axis of groove E68. The longitudinal axis of groove E63 is coincident with the longitudinal axis of groove E69. Grooves E62, E63, E68, E69 are normal (but can be in any shape, dimention, or direction) to parallel grooves E64, E65, E66, E67. The arrangement in implant E61 of a checkerboard matrix of grooves E62, E63, E68, E69, E64, E65, E66, E67 functions to engage a vertebral surface, anchor implant E61 in place, and prevent implant E61 from traveling away from the original position in which it is placed between a pair of vertebra. Implant E70 in FIG. 330 utilizes a similar checkboard matrix of perpendicular grooves. Grooves E62, E63, E68, E69 are omitted from the top view of FIG. 329. The overall shape of the grooved matrix can be circular, oval, square, hexagonal, star shaped, etc., and can extend in any direction along or within the length, width, and height of implant E70. Grooves can be equally spaced, randomly spaced, or non-linearly spaces along the surfaces of implants disclosed herein.

Implant E50 is illustrated in FIGS. 324 to 326 and includes parallel grooves E52, E53, E54, E55 formed in the bottom and top of implant E50. The size of each groove E52, E53, E54, E55 preferably, although not necessarily, initially increases or widens as the depth of the groove E52, E53, E54, E55 from the outer surface of implant D35 (FIG. 308) increases. Apertures E56 and E57 (FIG. 325) are sized to slidably receive a wire which can extend through aperture E56, through opening E51, and through aperture E57 to enable implant E50 to slide, if desired, along a wire, or cable, or string during insertion of implant E50 intermediate a pair of adjacent vertebra. Aperture E57 extends through the nose E58 of implant E50. Aperture E56 extends through the rear E59A of implant E50. Aperture E51 extends completely through the central area of implant 50.

Apertures E57, E51, and E56 can be centrally (as illustrated) or eccentrically placed (not illustrated) along either the length, width, or height of implant E50. A wire (stainless steel, titanium, nitinol, polymer), cable, spring, string or any desired means can be used to insert implant E50 along a straight or curvilinear path of travel. Articulated implant 540 in FIG. 110-112 provides the original method of articulating an implant along a wire without kinking or deforming the implant or wire. Cylindrical apertures 503, 504 permit portions 501 and 502 to move or rotate relative to one another based on the widening configuration of the apertures.

Implant E70 is illustrated in FIGS. 330 to 333 and includes parallel grooves E74, E76 formed in the top and bottom, respectively, implant E70. Parallel grooves E75, E 77 are also formed in the top and bottom, respectively, of implant E70. Grooves E75 are normal to grooves E74. Grooves can be formed in any direction along the length, width, or height of the implant. The preferred maximum interior width of the grooves is in the range of 100 microns to 500 microns. Grooves E77 are normal to grooves E76. The size of each groove E74, E75, E76, E77 preferably, although not necessarily, initially increases or widens as the depth of the groove from the outer surface of implant D70 increases. Apertures E71 and E72 (FIG. 330) are sized to slidably receive a wire which can extend through aperture E71, through aperture E73, and through internally threaded aperture E72 to enable implant E70 to slide, if desired, along a wire during insertion of implant E70 intermediate a pair of adjacent vertebra. Aperture E71 extends through the nose of implant E70. Aperture E72 extends through the rear of implant E70. Oval aperture E73 extends completely through the central area of implant 50.

Apertures E71, E72, E73 can be offset from each other in the manner that cylindrical apertures 503, 504 are offset in FIG. 110-112 (of articulated implant portions 501, 502) to allow a non-articulated implant E50 to travel in a non-linear path. One advantage of offset channels within an implant is that a solid (non-articulating) implant can travel along an arcuate path of travel.

FIGS. 334 and 335 illustrate telescoping, winged implant E80. Implant E80 includes first E83 and second E84 body portions which telescope toward and away from each other in the directions indicated by arrow E94 (FIG. 335) along cylindrical pins E92 and E93. Body portion E83 includes parallel grooves E90, E91 formed in the top and bottom of portion E83. Similarly, body portion E84 includes parallel grooves E88, E89 formed in the top and bottom of portion E84. Oval aperture E95 extends completely through portion E84. Oval aperture E96 extends completely through portion E83. Wing E81 is pivotally mounted on portion E83 for rotation in the directions indicated by arrows E87. Wing E81 can rotate at least ninety degrees from the orientation illustrated in FIGS. 334 and 335, as can wing E82 mounted on portion E84. Apertures E85 are formed through wings E82 and E81 to receive a screw or other fastener that engages a vertebra or disc and anchor implant E80 in a desired position.

Telescoping implant E80 by moving portions E83 and E84 together with a reversibly threaded member (FIG. 1.) or any other means functions to separate, draw, or otherwise move wing E81 and wing E82 further, closer together respectively. Drawing wings E81 and E82 together while either wing is positioned inside or outside a vertebra functions to draw disc, vertebral, or other tissues back into the disc. Drawing wings E81 and E82 together while either wing is positioned outside a vertebra also functions to change to orientation of a vertebra or draw two vertebra into alignment. Implant E80 can consist of more than two portions. Parallel pins E92, E93 can be tapered to limit or control the amount of telescoping of implant E80. Parallel pins E92, E93 can be configured to allow body portions E83, E84 to separate or collapse linearly or eccentrically allowing implant E80 to maintain a linear shape or to assume an arcuate shape. Body portions E83, E84 can be wedge shaped wherein collapsing said body portions E83, E84 produces an implant E80 with an arcuate shape.

Portions E83 and E84 can be symmetric or asymmetric in shape. For example, portion E83 can be larger, smaller, or equal in size or shape to portion E84 in shape or size so that implant E80 (1) functions like a pivot to alter the cant or alignment of the vertebra in FIGS. 34-40, (2) expands the implant (spreads apart two adjacent shells in FIGS. 1-5), (3) alters the shape and dimension of the disc, or (4) changes the pressure intermediate two vertebra. Portions E83 and E84 can also be linear, offset, or angled from one another. An implant E80 with linear shape facilitates inserting implant E80 (or any of the implants described herein) along a straight guide unit. An implant E80 with an angular configuration can facilitate inserting implant E80 (or any of the implants described herein) (1) along a curvilinear path, (2) along a flexible guide unit, or (3) into the lower lumbar and sacral areas of the spine (that typically are blocked by the pelvis). An implant E80 with an angular configuration could better (1) conform to or change the shape of the disc or (2) alter the orientation of the vertebra. The angular shape of an implant E80 can extend along the height, length, or width of the implant.

As noted, the grooves E90, E91 preferably formed in many of the implants described herein diverge, or widen, as the depth of the groove increases. Forming such grooves in an implant via a molding process is difficult, if not impractical. A preferred method of forming, for example, an implant E50 (FIG. 325) comprises first molding the implant without the grooves E54, E55, E52, E53 formed therein. The grooves E54, E55, and the like are them formed by first securing the implant in fixed position with a chuck or other apparatus, and by then utilizing a rotating drill bit or lazer to cut through the implant in the direction indicated by arrow E50A. In another embodiment of the invention, after the implant is secured in fixed position, a drill bit is not utilized. Instead, a laser is utilized to cut a groove in the direction of arrow E50A. In a further embodiment of the invention, implant E50 is molded, however, before the mold is injected with a polymer or other material for form implant E50, sacrificial cylindrical members E59 are positioned in the mold such that when the mold is injected, implant E50 forms around members E59. After implant E50 solidifies and is removed from the mold, and an acid solution, temperature, electricity, nano-technology or other means is utilized to remove sacrificial members E59 from implant E50, leaving the implant E50 that is illustrated in FIG. 324. Grooves function as frictional textures for tissue attachment. Grooves can also function as teeth to secure the implant. Grooves can also function as frictionless or variable frictional surfaces for steering the implant. In one preferred embodiment the invention, grooves on the leading portion E83 of implant E80 are directional and frictionless to insert implant E80. Grooves on trailing portion E84 are toothed, textured, or filled porous materials increasing the friction by increasing the effective surface area of portion E84 with respect to portion E83 thereby fixing portion E84 to expand implant E80, and vice versa. Likewise a portion each portion of implant E80 can have variable textures or grooves for simultaneously steering, expanding, and/or fixing the implant. When a first portion of an implant described herein is configured, textured, or grooved differently from at least a second portion, the implant can be articulated or moved with respect to the first portion and vice versa. For example, but not limitation, implant E80 expands linearly, implant B80 in FIGS. 276-281 expands arcuately, and implant 100 in FIG. 1 expands polyaxially.

Grooves can be formed in the surface of an implant E50, E80, etc. in any desired direction, spacing, or size. One preferred method of manufacture is forming linear, parallel, evenly spaced grooves on the surface or portion of an implant E50. Another preferred method of manufacture is spacing the grooves un-evenly (for instance, logarithmically) along the surface or at least another portion of implant E50. Unevenly spacing grooves provides for increased (or decreased) ingrowth at specific areas on an implant E50. For example, logarithmically spacing grooves on an implant incrementally distributes the pressure along an implant to reduce friction, stress, and strain on the implant. The shape and dimension of a groove can also vary along the length of a single groove. While the shape and dimension of grooves E50, E80, etc. can vary as desired, the grooves preferably have outer surface openings with a width in the range of 1 micron to 5000 microns, and can also have an maximum interior width of 1 micron to 500 microns, or greater.

Grooves are preferably oriented linearly, or arcuately, or configured as sequential arcs, ellipses, circles (FIG. 62-68) with similar or variable densities, parallel or undulating, or in any desired configuration to steer the implant along any desired path of travel. Any shaped wire or elongate guide (with or without light) can be operably coupled to a groove or grooves to steer the implant along a desired path of travel. In another embodiment in at least one portion of the implant the grooves are parallel (either linear or arcuatley formed) and then change orientation. For example but not limitation, the grooves can be at the leading edge of the implant directing the implant to a desired location intermediate two vertebra and with teeth deployable by a cam (FIGS. 1-3) or otherwise or fixed at a trailing portion of the implant to insert the nose of the implant and stop and fix the tail of the implant intermediate two vertebra. One preferred embodiment includes an implant with a smooth low friction portion and a grooved higher friction portion and/or a toothed highest friction portion. The implant can also consist of portions joined by a hinge (FIGS. 131-149, 273-278). Another embodiment provides an implant with a low friction leading portion or nose that is smooth or with grooves parallel to the direction of insertion, a second portion with grooves similar or different than the first portion to redirect the second portion with regard to the first portion and can also include a third portion with teeth (deployable or fixed) to hold the implant in position. Implant portions can also include at least one smooth low friction surface and at least one higher friction surface either grooved and/or a toothed higher friction surface. Likewise, an implant with a smooth portion functions as a low friction moveable surface, An implant with a grooved surface functions as a slightly higher friction moveable surface (compared to the smooth surface) when the groove is parallel to the direction of travel, An implant with a grooved surface functions as an even higher friction moveable surface (compared to the parallel grooved surface) when the groove is angled to the direction of travel, An implant with a grooved surface functions as an even higher friction immoveable surface (compared to the angled grooved surface) when the groove is normal to the direction of travel An implant with a toothed portion functions as an even higher friction surface (compared to the grooved surface that is normal to the direction of travel) to hold or fix the implant and prevent the implant from moving.

Another embodiment of the invention provides an implant for deposition intermediate two vertebra wherein said implant can include at least one recess, or aperture, or tooth, or wing, that is textured to provide for tissue attachment. The recess can be part of a tooth, adjacent a tooth, on the surface of the implant, through at least a portion of the implant, or completely through the implant. The recess, tooth, aperture, or wing can be textured by any desired method. Some preferred methods include chemical (acid) etching, laser etching, grit or sand blasting, electrolysis, etc. Texturing can be an additive coating or a subtractive process as described. Texturing is believed to aid in tissue attachment to the implants surface as well as to the interior of the implant where materials such as bone graft is packed or placed within the apertures. Texturing the implant provides for a bioactive surface to attract tissue inside the implant by providing a favorable charge or altering the pressure within the implant as is the case with openings that diverge inwardly and providing a scaffold for tissue migration inside the implant. Combining textures with teeth and or apertures that diverge inwardly provides an immediate, (on growth) and delayed (in growth) element to stably fix an implant. Teeth can be deployable, fixed, resorbable, porous, etc. The implant can be expandable, contractable, articulated, flexible, or fixed. Apertures can be variable or fixed, variable as the implant opens or closes. The implant or any elements described herein can be flexible, like a spring, rigid, or otherwise. Any material can be used to construct the implant but presently preferred materials include but not limited to polymers, metals (titanium, alloys, etc.), composites, hybrids, ceramics, bone, or other suitable materials.

One element of the invention is that texturing implant interiors may not be easily performed with lasers or blasting. Therefore, chemical etching is presently preferred. Texturing the interior of apertures also provides a locking mechanism for a screw and fastener when inserted within the aperture. Plates, screws, rods, cages, are other examples of implants with features that can be textured for enhanced performance.

In one embodiment, the textures described in connection to the implant can be gradual, gradient, partial, full, and be applied randomly, evenly, or in any desired distribution.

A further embodiment of the invention provides an implant that is easy to insert and once inserted is stable by offering varying porosity portions. As porosity increases the surface area increases and therefore friction increases. Altering the porosity of an implant changes the mobility, stability, and steerability of the implant. For example but not limitation, an implant portion with a low porosity portion functions as a smooth surface and is more mobile due to less friction than a higher porosity portion with a greater surface area functioning as a higher friction immobile or less steerable portion to prevent the implant from migrating after insertion.

In the event an implant E50 utilizes a cylindrically shaped piece of material E59 (FIG. 326) as a marker to facilitate location of an implant E50 in the spine (or in any location) of a patient, any desired means can be utilized to locate material E59. Presently preferred, however, are non-invasive external detection methodologies utilizing, for example, ultra sound equipment, X-ray equipment, radio-frequency, thermography, endoscopy, immunologic system, magnetic (resonance) equipment, and the like.

FIGS. 6 and 7 illustrate an implant being laterally inserted in a disc. The discussion herein concerning FIGS. 6 and 7 notes that one method for inserting device 100 in the interior of disc 50 inserts device 100 in the front, back, or one of the sides of a disc. 50 without separating the pair of vertebra between which disc 50 is sandwiched. Device 100 can also, of course, be inserted to separate the pair of vertebra. The parallel configuration of grooves E52 to E54 in an implant E50 can, for example, promote such an insertion in a direction E50A (FIG. 326) that is generally parallel to (can also be normal or diagonal to) the longitudinal axes of grooves E52 to E54. The formation of additional grooves E62 which are perpendicular to grooves E52 to E54 would tend to minimize or eliminate any advantage gained in this respect. Similarly, filling a groove E54 with a cylindrical member E59 having a smooth surface that extends across and is flush with the parallel edges bounding the upper opening of groove E54 tends to facilitate the insertion of an implant. If every one of the grooves E52, etc. in an implant E50 is filled, the exposed smooth surfaces of members E59 also facilitate the insertion of implant E50 laterally between a pair of vertebra in a direction normal to (or at some other angle with respect to) direction E50A and parallel to the longitudinal axes of apertures E56 and E57.

Separating a pair of vertebra with device 100 provides a method if indirect decompression of nerves and structures adjacent or remote from disc 50A in FIG. 6.

As noted above, before a disc is treated, an original pressure, $P_O$, exists in the nucleus of the disc. When an implant is inserted in the nucleus of a disc, the implant occupies a volume and produces an increased new pressure, $P_P$, in the disc. In many cases, when the implant is inserted in the nucleus it will displace nuclear material and produce an increase in the pressure acting outwardly against the disc annulus and against the vertebra bounding the disc and acting inwardly against the implant. An implant can, as noted, have apertures which have surface openings and which have inner portions which diverge as the distance from the surface of the implant increases. The surface openings are smaller than the wider diverging inner portions of the apertures. Nuclear material passes through the surface openings and expands into the diverging inner portions of the apertures to reduce the pressure acting inwardly against the implant. The implant can also directly contact the annulus or vertebra and generate forces acting to outwardly expand or inwardly contract the annulus or to separate the vertebra to indirectly decompress the nerves adjacent the annulus. The amount, ▲P, that the implant initially increases the pressure in the disc is indicated by Equation 1.

$$\blacktriangle P = P_P - P_O \quad [1]$$

If there is a rupture or nuclear herniation in the disc, the pressure increase, ▲P, may increase the severity of the rupture or herniation by forcing additional nuclear material out through the herniation. As also noted above, one ideal implant for, in accordance with various of the embodiments disclosed herein, producing a quantity of negative pressure sufficient to draw a nuclear herniation back into the nucleus of a disc utilizes an implant with an outer surface (438) configured with tissue interlocking openings 436 in FIG. 69 (or openings E54) that diverge away from the outer surface, that receive vertebral, or nuclear, or other tissue, and that therefore function to minimize the pressure increase when the implant is inserted in the nucleus of a disc. When negative pressure is generated in a disc, the width of the disc tends to be reduced, which indirectly decompresses nerves and nerve coverings that are adjacent to, or even remote from, the disc and the vertebra bounding the disc. Similarly, if the herniation drawn back into the disc was generating pressure against nerves, drawing the herniation back into the disc indirectly accomplishes a decompression of such nerves and their coverings.

Other implants that function to minimize the pressure increase when the implant is inserted in the nucleus of a disc are hinged implants B60 in FIGS. 273 and B80 in FIG. 279 illustrated herein. However, the manner in which implants B60 and B80 minimized the pressure increase differs from that of the mechanism associated with openings 436 in FIG. 69. In particular, in FIG. 279, implant B80 is in an "open" arcuate orientation, and the pie-shaped surface area or space B83 extending between the opposing pair of surfaces C22 and C23 is larger than the pie-shaped surface area or space extending between the opposing pair of surfaces C24 and C25 in FIG. 276. In FIG. 276, implant B80 is in a "closed", linear orientation. Since the pie-shaped surface area B83 extending between opposing surface pair C22 and C23 (and other comparable pie-shaped surface areas in articulating implant B80) in FIG. 279 is larger than the pie-shaped surface area between opposing surface pair C24 and C25 (and other comparable pie-shaped surface areas in implant B80) in FIG. 276, when implant B80 is in the non-linear arcuate orientation of FIG. 279, the cumulative upper (and lower) surface area of implant B80 increases in comparison to when implant B80 is in the linear orientation of FIG. 276. Consequently, when implant B80 is in the arcuate orientation of FIG. 279, the cumulative upper (and lower) surface area of implant B80 extends over a greater surface area of a vertebra than when implant B80 is in the linear orientation of FIG. 276. The cumulative upper, or top, surface area of implant B80 in the arcuate orientation of FIG. 279 includes the exposed pie-shaped areas B81, B82, B83 of the joints that join the articulating members, and includes the upper, or top, surface area of each separate articulating member B81, B82, B83, B84. The upper surface area of each articulating member B81, etc. is visible in the top views of FIGS. 276, 279. The lower, or bottom, view of implant B80 is identical to the top view of FIG. 276, although this need not be the case. The cumulative upper surface area of implant B80 in the linear orientation of FIG. 276 includes the exposed pie-shaped areas (for example the pie-shaped area that is visible in FIG. 276 and extends intermediate surfaces C24 and C25) of the joints that join the articulating members, and includes the upper, or top, surface area of each separate articulating member B81, B82, B83, B84. The cumulative upper surface area of implant B80 is equivalent to the cumulative lower surface area of implant B80 when implant B80 in the linear configuration of FIG. 276, although this need not be the case. Similarly, the cumulative upper surface area of implant B80 is equivalent to the cumulative lower surface area of implant B80 when implant B80 is in the arcuate configuration of FIG. 279, although this need not be the case. Pie shaped area B83 is a portion of the upper surface of the male joint or tongue that extends from member B83 into a slot formed in member B84. Pie shaped area B82 is a portion of the upper surface of the male joint or tongue that extends from member B82 into a slot formed in member B83. A comparable male joint or tongue extends from member B81 into a slot formed in member B82. As can be seen in FIG. 277, each of said male joints or tongue includes a lower surface area that is parallel and equivalent in size to the lower surface area of the joint.

The increase in the upper (and lower) surface area when the implant B80 is in the arcuate orientation of FIG. 279 is important because it reduces the force per unit area generated by implant B80 against a vertebra and reduces the tendency of implant B80 to deform the vertebra and sink into the vertebra. Minimizing the amount that implant B80 deforms and sinks into a vertebra is important because it maximizes the distance that implant B80 separates one vertebra from another and maximizes the likelihood that the implant will reduce the pressure in a disc sufficiently to overcome the ▲P noted above, will reduce the intra-discal pressure to less than $P_O$, and/or will produce a negative intra-discal pressure sufficient to draw herniated nuclear material back into a disc. As noted above, generating negative intra-discal pressure and drawing herniated nuclear material back into a disc can indirectly decompress the nerves adjacent to, or remote from, the disc. Further, increasing the surface area of the implant can be used to offset features of the implant—like grooves E54—which perform other useful function but which tend to promote the ingress of vertebral tissue into an implant.

As described herein, "indirect decompression" pertains to methods and apparatus described herein for reducing the pressure generated by discs (bulges, tears, hernias, etc.), vertebra (fractures, osteophytes, tumors, etc.), facets, ligaments, capsules, etc., on the nerves and nerve coverings (meninges, arachnoid, dura, etc.) of the spine and nervous system without directly removing (or by minimally removing) the offending structure from a patient's body. The apparatus and methods described herein are especially useful for indirect decompression of nerves or vessels when direct access to a disc herniation is not possible or is risky.

In another preferred embodiment of the invention an implant is provided sterile or sterilizable either separate or in a kit as a peel pack or other packaging along with insertion instruments described herein that can be disposable or multiple use. Such instruments described herein include one of a group but not limited to a light guide, elongate guide unit, implant delivery unit, dilator, tissue separation instrument, tissue removal instruments and/or instruments or implants to alter the tilt or rotation of the vertebra or change the shape of the disc. (FIGS. 34-40). The implant can be tapered, expandable, flexible, or rigid.

The components of the invention, including the implants, elongate light guides, delivery systems, and others, can be prepared by standard techniques in the arts of manufacturing medical devices and implant. The processes of manufacture will vary depending on the material being used. For example, standard manufacturing techniques used to make micro scale optical fibers can be used to manufacture the elongate light guide, which can include sheathing optical waveguides with sheaths of variable stiffness or flexibility in order to obtain suitable bending characteristics. Also, metal implants can be prepared from molding, casting, sintering, or otherwise prepare a metal object that is solid or porous. Porous materials prepared by sintering can have variable particle size in order to select porosity and to provide texture to the implant surface. Additionally, laser sintering can be used to sinter particles of various material ranging from polymer to ceramic to metal. Methods of texturing of the implant material can be performed to provide for texture by electron beam melting.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. Also, all embodiments of implants described herein can include features, such as shape, recesses, materials, apertures, or the like, which can be applied to any other implant described herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. An intervertebral implant comprising:
 a body having a tapered arcuate shape comprising:
  a base end having a first arced cross sectional profile and area;

a tip end having a second arced cross sectional profile that is smaller than the first cross sectional profile and area; and a body portion that tapers and arcs between the base end and tip end, the body portion having a third arced cross sectional profile and area that tapers from the first cross-sectional profile and area to the second cross-sectional profile and area.

2. The implant of claim 1, wherein the tapered arcuate shape has a first arc in a first plane and a second arc in a second plane orthogonal to the first plane, wherein the first plane is parallel to the first arced cross sectional profile, second arced cross sectional profile, and third arced cross sectional profile.

3. The implant of claim 2, wherein the tapered arcuate shape tapers in a third plane orthogonal with the first plane and second plane.

4. The implant of claim 3, wherein the tapered arcuate shape tapers in the second plane.

5. The implant of claim 1, comprising a solid non-elastic portion.

6. The implant of claim 1, wherein the body portion extends from a first end to a second end to define the third arced cross sectional profile.

7. The implant of claim 6, wherein the substantially flat surface is configured to be mounted on a surface of a vertebra of two adjacent vertebras.

8. The implant of claim 6, wherein the rounded surface is configured to contact a surface of a vertebra of two adjacent vertebras.

9. The implant of claim 7, wherein the implant is configured to be secured to and only contact the surface of the vertebra.

10. The implant of claim 6, wherein the substantially flat surface is configured to be secured to a surface of a vertebra of two adjacent vertebras such that the other vertebra is capable of pivoting and rotating about the rounded surface.

11. The implant of claim 1, comprising a spring that is configured to generate force between two adjacent vertebras when the spring is loaded.

12. The implant of claim 1, wherein the tapered arcuate shape extends from a substantially flat base to a tip.

13. The implant of claim 1, comprising the body having the tapered arcuate shape extending from a substantially flat base end to the tip end, the body portion having the rounded surface and the flat surface opposite of the rounded surface, the surfaces extending between the base and tip.

14. The implant of claim 1, wherein the implant is configured for implantation between two adjacent vertebras.

15. The implant of claim 14, wherein the implant is dimensioned to be implanted between and edge portion and center of the two adjacent vertebras.

16. The implant of claim 1, wherein the tapered arcuate shape is configured to align two adjacent vertebras by rotating the two adjacent vertebras around the tapered arcuate shaped implant in three axes of rotation, wherein the at least two axes of rotation are relative to the sagittal and coronal planes and one of the axes is the vertical axis of rotation.

17. The implant of claim 1, wherein the tapered arcuate shape is configured to align two adjacent vertebras by:
rotating surfaces of the two adjacent vertebras around the tapered arcuate implant in at least one axis of rotation; and/or
rotating the surfaces of the two adjacent vertebras around a vertical axis of rotation.

18. The implant of claim 1, wherein the tapered arcuate shape is configured to provide rotation about a vertical axis of rotation from a wide portion to a tip of the tapered arcuate shape in the direction of its arc.

19. The implant of claim 1, wherein the tapered arcuate shape includes a surface configured to be secured to a surface of a vertebra between two adjacent vertebras.

20. The implant of claim 1, wherein the tapered arcuate shape includes a surface configured to pivotally contact a surface of a vertebra between two adjacent vertebras.

21. The implant of claim 1, wherein the tapered arcuate shape includes a surface configured to pivotally and rotatably contact a surface of a vertebra between two adjacent vertebras.

22. The implant of claim 1, wherein the implant is at least partially porous.

23. The implant of claim 1, comprising a hybrid of at least two implant-suitable materials.

24. A method of treating adjacent vertebras, the method comprising:
providing the implant of claim 1; and
inserting the implant between two adjacent and misaligned vertebras so as to align the two adjacent vertebras.

25. The method of claim 24, wherein the two adjacent vertebras include a vertical axis of rotation, a first vertebra having a bottom surface, and a second vertebra having a top surface, the method comprising one of the following:
contacting the implant with the top surface of the second vertebra, and securing the implant to the top surface of the second vertebra;
contacting the implant with the top surface of the second vertebra without contacting the bottom surface of the first vertebra, and securing the implant to the top surface of the second vertebra; or
contacting the implant with the top surface of the second vertebra without contacting the bottom surface of the first vertebra or securing the implant to the top surface of the second vertebra; or
contacting the implant with the top surface of the second vertebra without securing the implant to the top surface of the second vertebra; or
contacting the implant with the bottom surface of the first vertebra, and securing the implant to the bottom surface of the first vertebra; or
contacting the implant with the bottom surface of the first vertebra without contacting the top surface of the second vertebra, and securing the implant to the bottom surface of the first vertebra; or
contacting the implant with the bottom surface of the first vertebra without contacting the top surface of the second vertebra or securing the implant to the bottom surface of the first vertebra; or
contacting the implant with the bottom surface of the first vertebra without securing the implant to the bottom surface of the first vertebra; or
contacting the implant with the bottom surface of the first vertebra and top surface of the second vertebra.

26. A method of treating adjacent vertebras, the method comprising:
selecting the tapered arcuate implant of claim 1;
identifying two adjacent vertebras having a vertical axis of rotation and adjacent surfaces being nonparallel; and
inserting the tapered arcuate implant between the vertebras at a location between the vertical axis of rotation and edge portions of the two adjacent vertebras; and
rotating the two adjacent vertebras around the tapered arcuate implant in at least one axis of rotation.

27. The method of claim 26, comprising rotating the two adjacent vertebras so as to be about parallel.

28. The method of claim 26, comprising rotating the two adjacent vertebras around the implant in at least two axes of rotation, wherein the at least two axes of rotation are relative to at least one of the sagittal, coronal planes, and vertical axis of rotation.

29. The method of claim 26, comprising rotating the two adjacent vertebras around the implant in at least three axes of rotation.

30. The method of claim 26, comprising:
locating the implant to be closer to the edge portions of the two adjacent vertebras than the vertical axis of rotation.

31. The method of claim 26, comprising:
locating the implant to be closer to the vertical axis of rotation than the edge portions.

* * * * *